United States Patent
Tak et al.

(10) Patent No.: US 12,259,331 B2
(45) Date of Patent: Mar. 25, 2025

(54) URINE TEST DEVICE DESIGNED TO BE EASILY MOUNTED AND OPERATION METHOD THEROF

(71) Applicant: YELLOSIS, INC., Seoul (KR)

(72) Inventors: Yu Kyung Tak, Seoul (KR); Jong Gun Lee, Gyeonggi-do (KR)

(73) Assignee: YELLOSIS, INC., Seoul (KR)

( * ) Notice: Subject to any disclaimer, the term of this patent is extended or adjusted under 35 U.S.C. 154(b) by 0 days.

(21) Appl. No.: 18/001,502

(22) PCT Filed: Nov. 30, 2022

(86) PCT No.: PCT/KR2022/019280
§ 371 (c)(1),
(2) Date: Dec. 12, 2022

(87) PCT Pub. No.: WO2023/249178
PCT Pub. Date: Dec. 28, 2023

(65) Prior Publication Data
US 2024/0230541 A1    Jul. 11, 2024

(30) Foreign Application Priority Data

Jun. 20, 2022  (KR) .................. 10-2022-0074893
Jun. 20, 2022  (KR) .................. 10-2022-0074894
(Continued)

(51) Int. Cl.
*G01N 21/78* (2006.01)
*G01N 21/77* (2006.01)
*G01N 21/84* (2006.01)

(52) U.S. Cl.
CPC ......... *G01N 21/78* (2013.01); *G01N 21/8483* (2013.01); *G01N 2021/7796* (2013.01);
(Continued)

(58) Field of Classification Search
CPC ............... G01N 21/78; G01N 21/8483; G01N 2021/7796; G01N 2201/121; G01N 2201/126; G01N 2201/12746
See application file for complete search history.

(56) References Cited

U.S. PATENT DOCUMENTS

| 4,636,474 A | 1/1987 | Ogura et al. |
| 5,424,545 A * | 6/1995 | Block .................. A61B 5/1455 250/341.7 |

(Continued)

FOREIGN PATENT DOCUMENTS

| JP | H08-171640 A | 7/1996 |
| JP | H08-235359 A | 9/1996 |

(Continued)

OTHER PUBLICATIONS

International Search Report for corresponding International Application No. PCT/KR2022/019280 mailed Mar. 17, 2023.
(Continued)

*Primary Examiner* — Lisa M Caputo
*Assistant Examiner* — Cynthia L Davis
(74) *Attorney, Agent, or Firm* — Chrisman Gallo Tochtrop LLC

(57) ABSTRACT

According to various embodiments, there is provided an electronic device including a first housing having a bottom surface formed to be disposed on a specific portion of a top surface of a toilet, a second housing connected to one side of the first housing, a third housing connected to another side of the first housing and having a shape extending from a point connected to the first housing by a specific length in a direction associated with a first curvature, and a detection unit having a shape of a second curvature corresponding to the first curvature, and the detection unit is rotatably coupled to at least a portion of the third housing.

9 Claims, 83 Drawing Sheets

(30) Foreign Application Priority Data

| | | |
|---|---|---|
| Jun. 20, 2022 | (KR) | 10-2022-0074895 |
| Jun. 20, 2022 | (KR) | 10-2022-0074896 |
| Sep. 5, 2022 | (KR) | 10-2022-0111930 |
| Sep. 19, 2022 | (KR) | 10-2022-0118120 |
| Sep. 19, 2022 | (KR) | 10-2022-0118121 |
| Sep. 19, 2022 | (KR) | 10-2022-0118122 |
| Sep. 19, 2022 | (KR) | 10-2022-0118123 |
| Sep. 19, 2022 | (KR) | 20-2022-0002247 |
| Nov. 29, 2022 | (KR) | 10-2022-0163363 |

(52) U.S. Cl.
CPC . *G01N 2201/121* (2013.01); *G01N 2201/126* (2013.01); *G01N 2201/12746* (2013.01)

(56) References Cited

U.S. PATENT DOCUMENTS

| | | | | |
|---|---|---|---|---|
| 5,745,229 A | * | 4/1998 | Jung | G01J 3/0218 |
| | | | | 356/417 |
| 5,817,475 A | * | 10/1998 | Gibbs | G01N 21/253 |
| | | | | 435/287.1 |
| 6,572,564 B2 | | 6/2003 | Ito et al. | |
| 2013/0016356 A1 | * | 1/2013 | Kendall | G01N 21/314 |
| | | | | 356/445 |
| 2016/0269693 A1 | | 9/2016 | Moriguchi et al. | |
| 2019/0087945 A1 | | 3/2019 | Lee | |
| 2020/0015791 A1 | * | 1/2020 | Mccord | A61B 5/207 |

FOREIGN PATENT DOCUMENTS

| | | |
|---|---|---|
| JP | 2015-106889 A | 6/2015 |
| KR | 10-2010-0002802 A | 1/2010 |
| KR | 10-2018-0041441 A | 4/2018 |
| KR | 10-2022-0058406 A | 5/2022 |
| WO | 2016/135735 A1 | 9/2016 |
| WO | 2020/018232 A1 | 1/2020 |

OTHER PUBLICATIONS

Written Opinion for corresponding International Application No. PCT/KR2022/019280 dated Mar. 17, 2023.
Written Decision on Preferential Examination dated Dec. 13, 2022 for corresponding Korean Application No. 2022-0163363 and English translation.

* cited by examiner

FIG. 5A
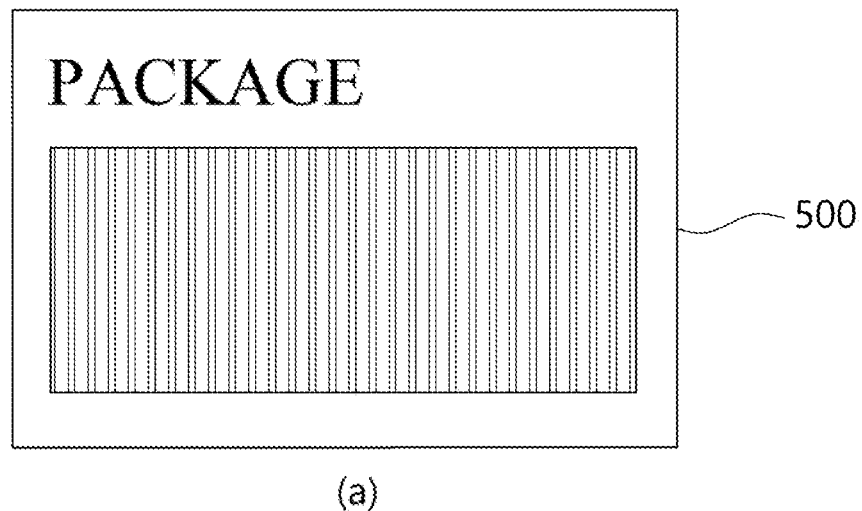
(a)
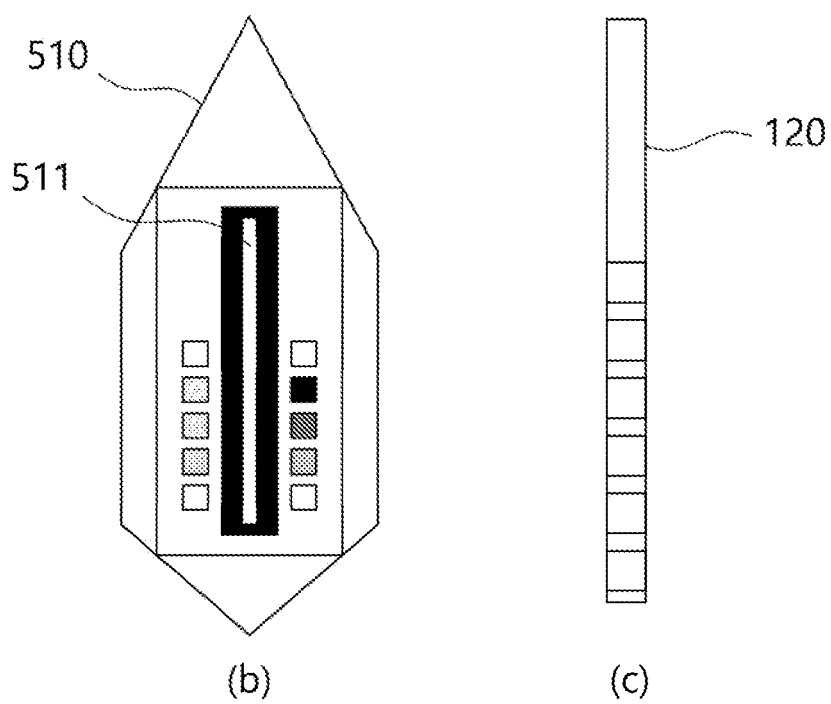
(b)　　　　　　(c)

FIG. 6
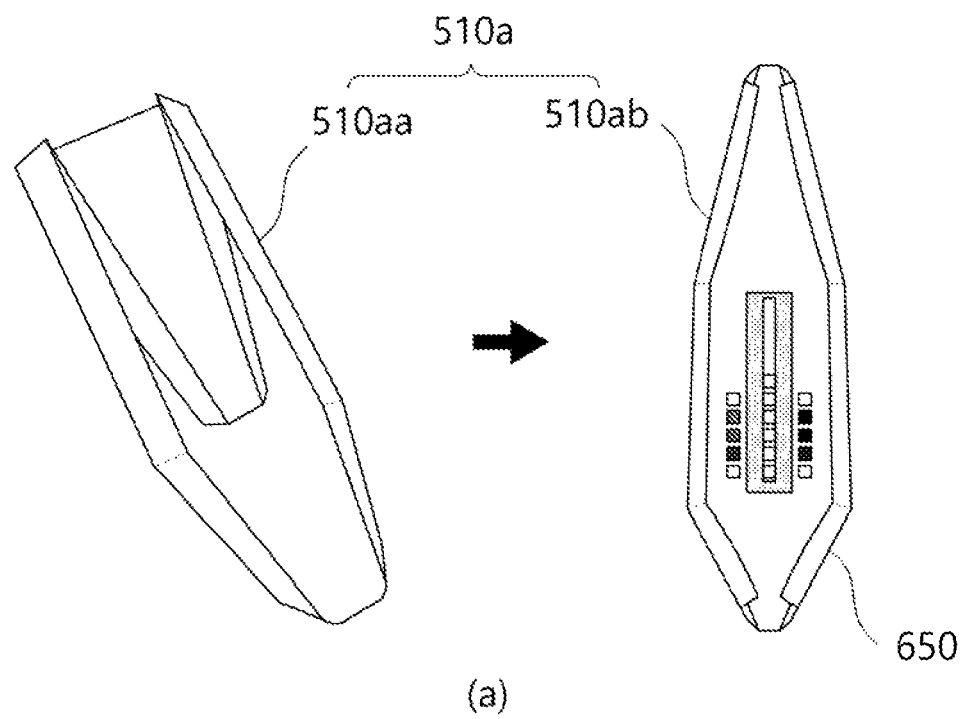
(a)
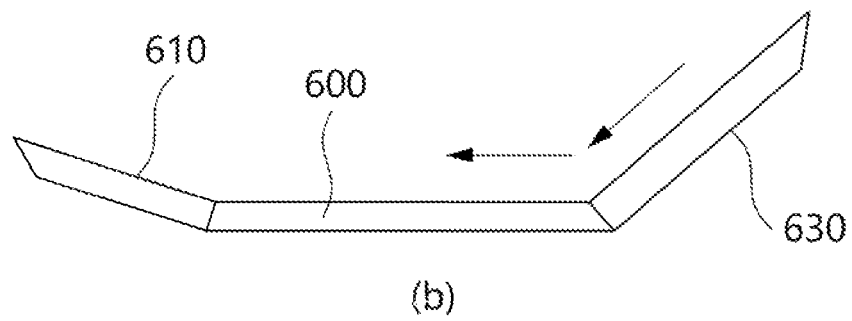
(b)

FIG. 12
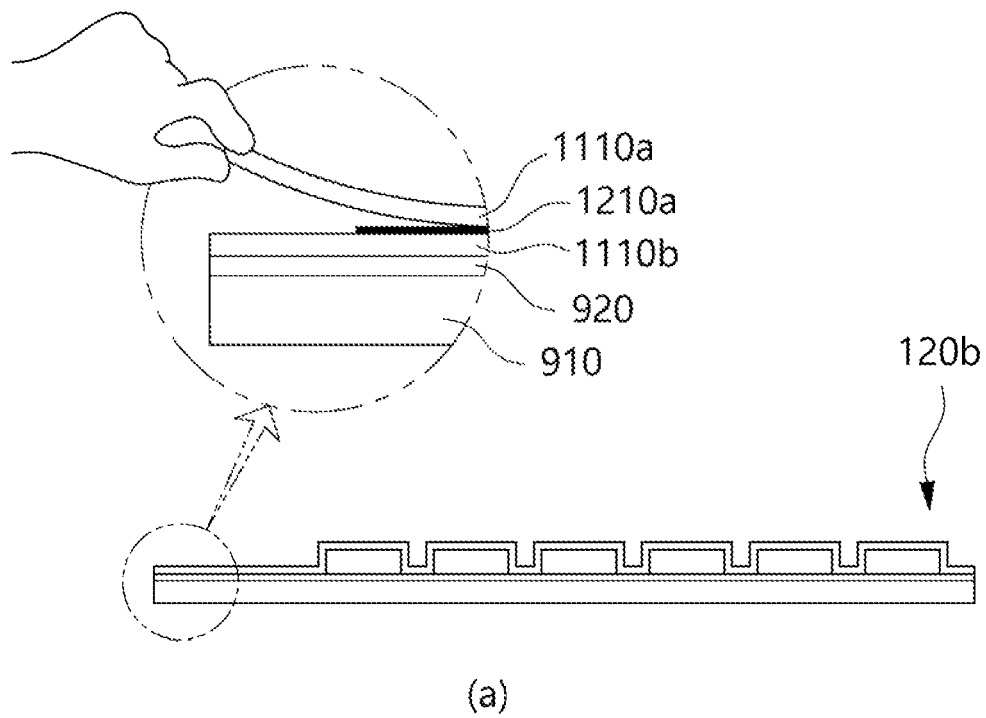
(a)
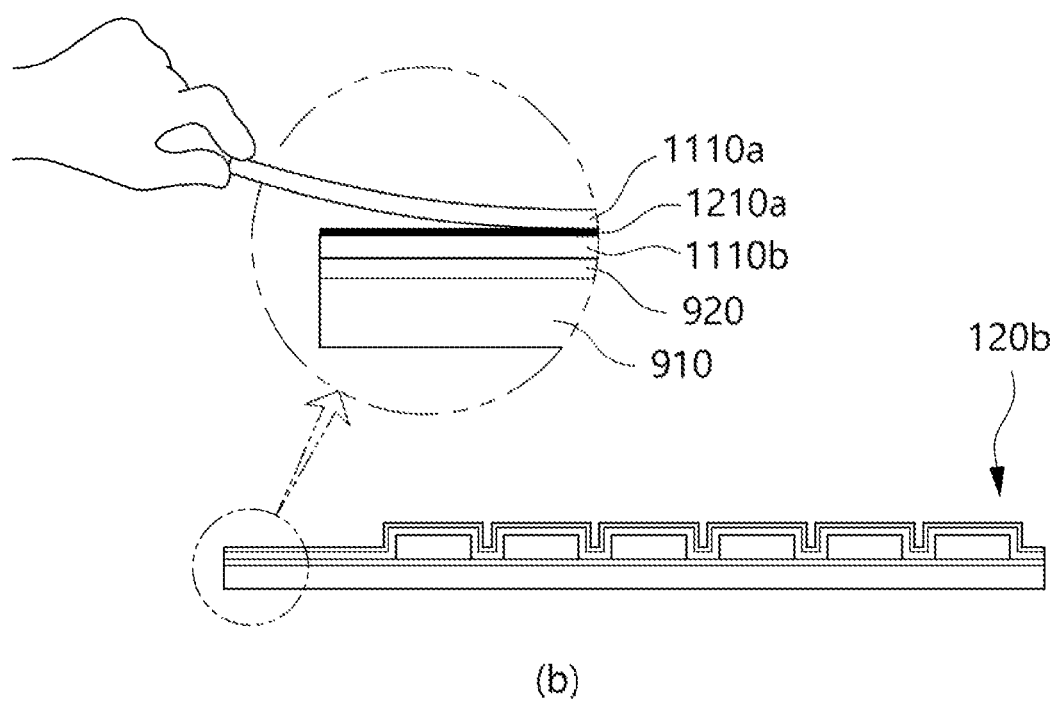
(b)

FIG. 16A
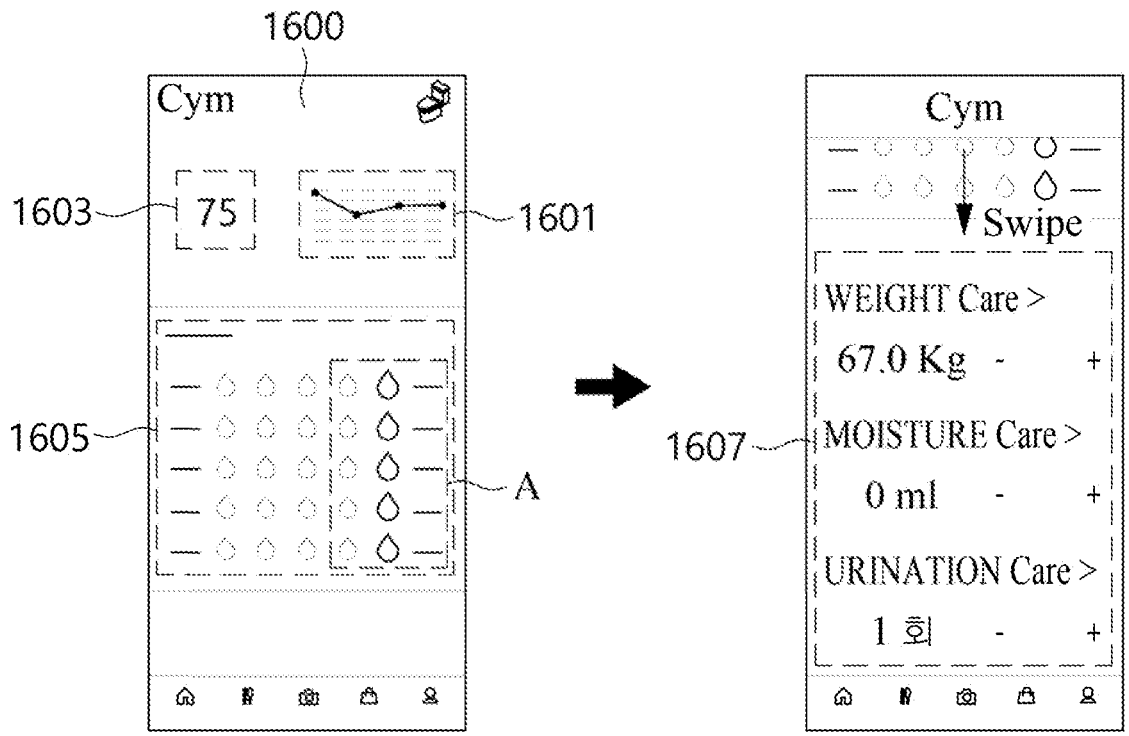
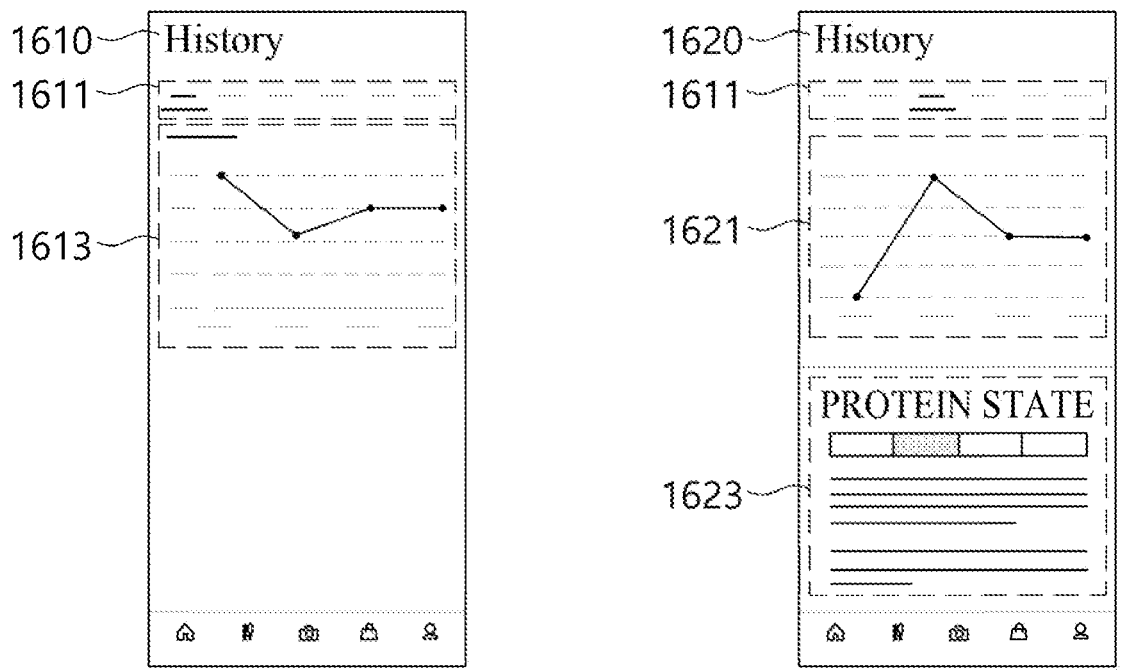

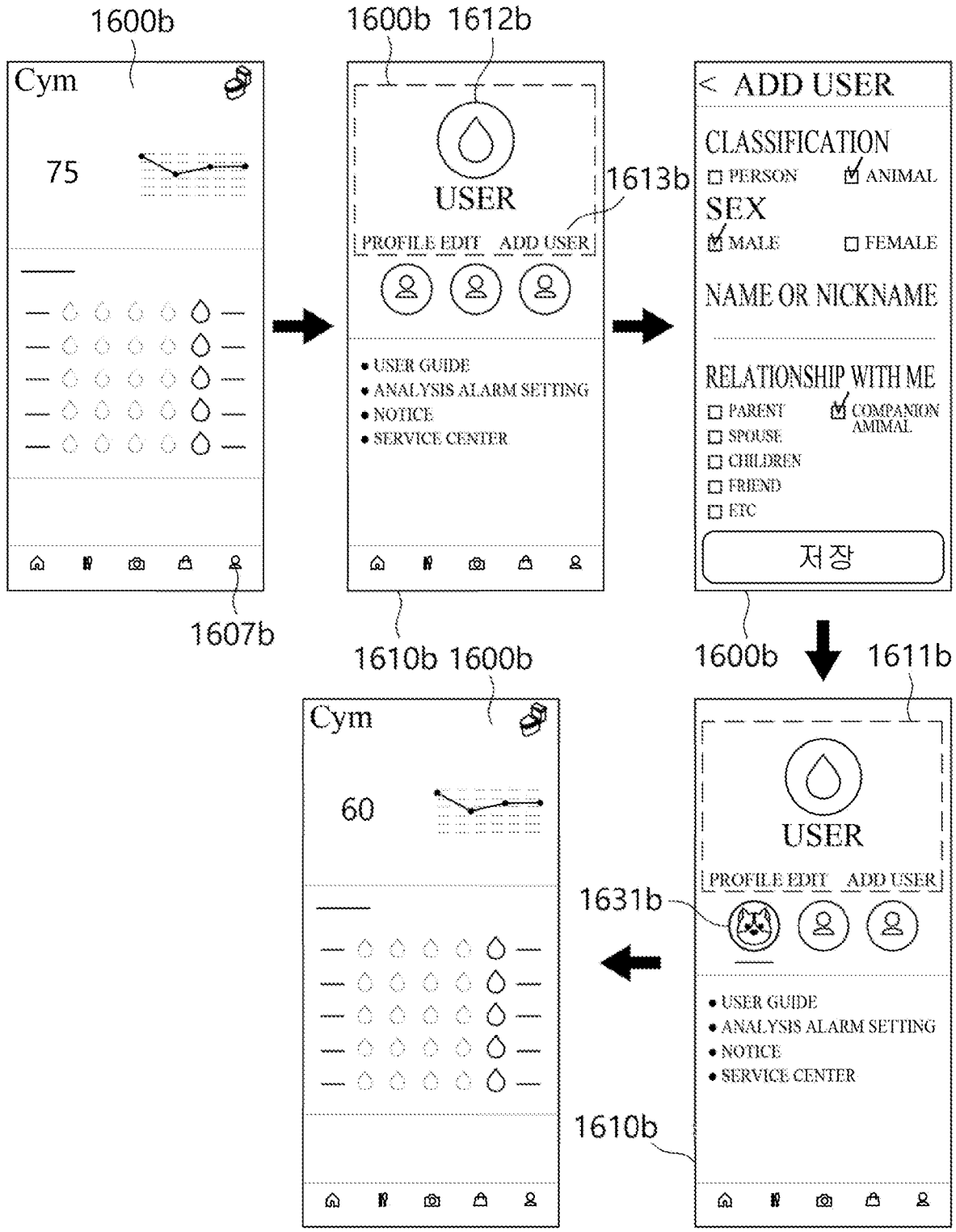

FIG. 20
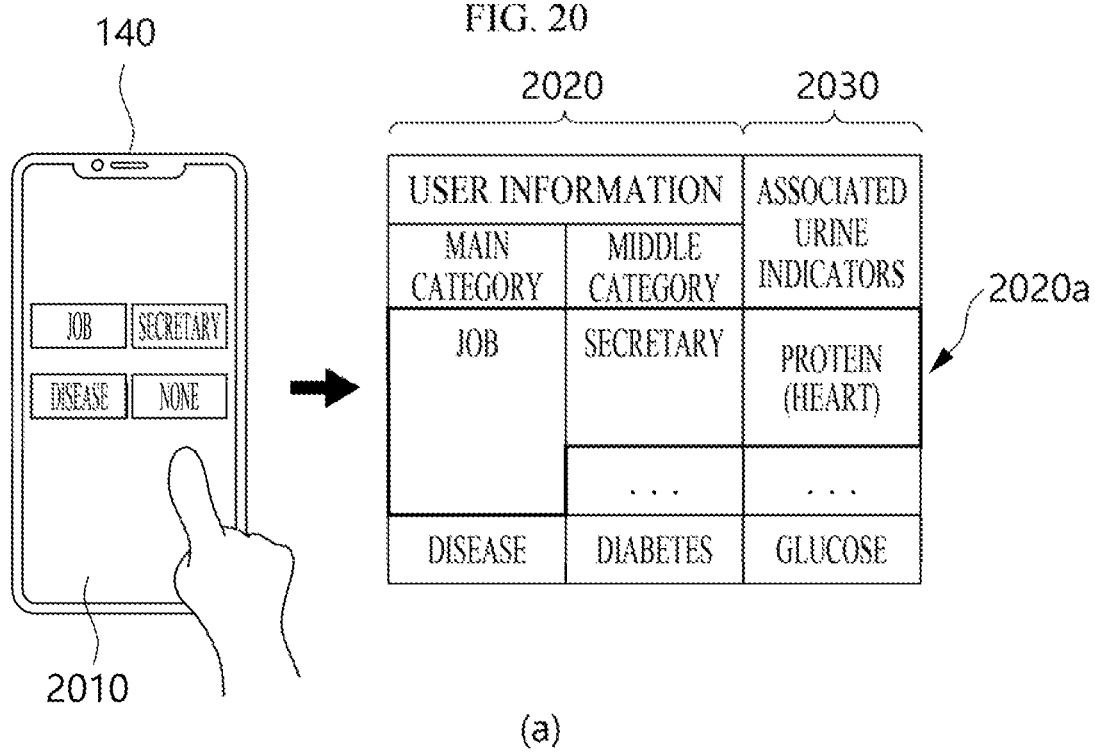
(a)
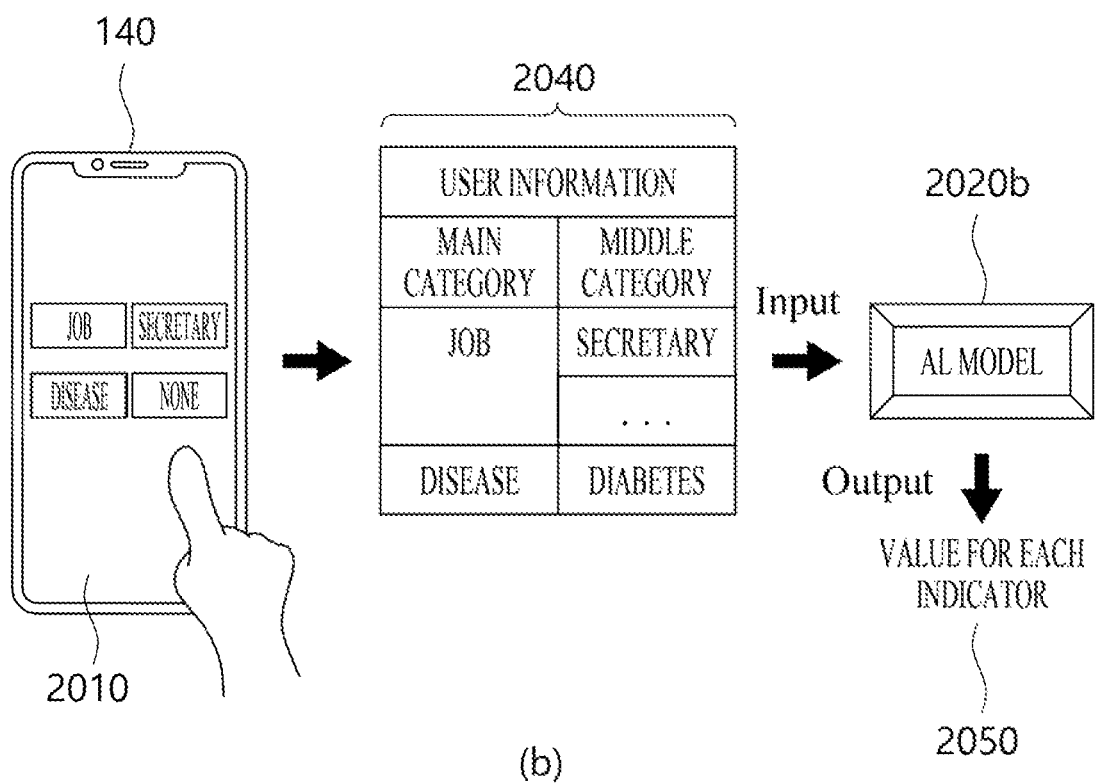
(b)

FIG. 29
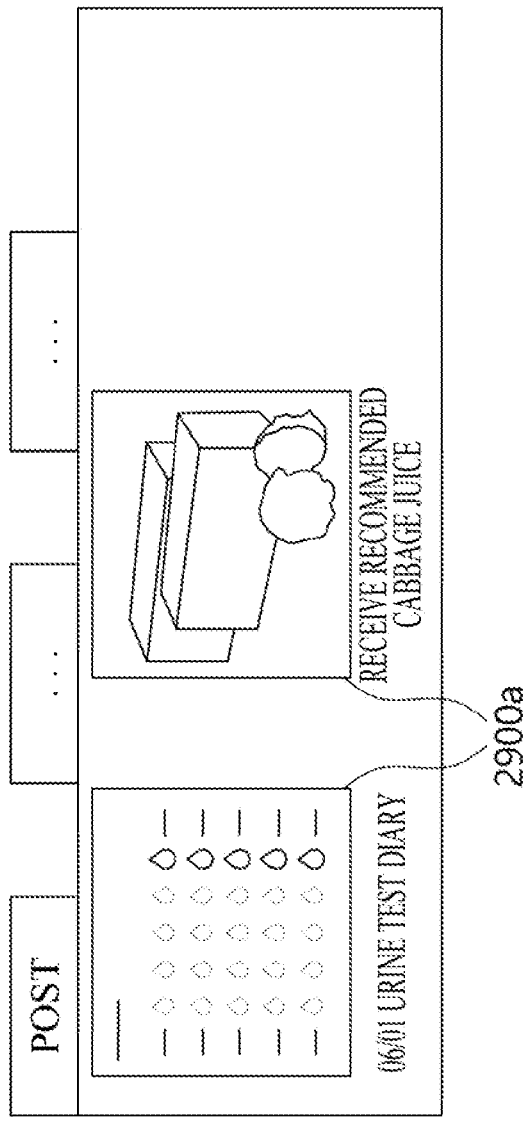
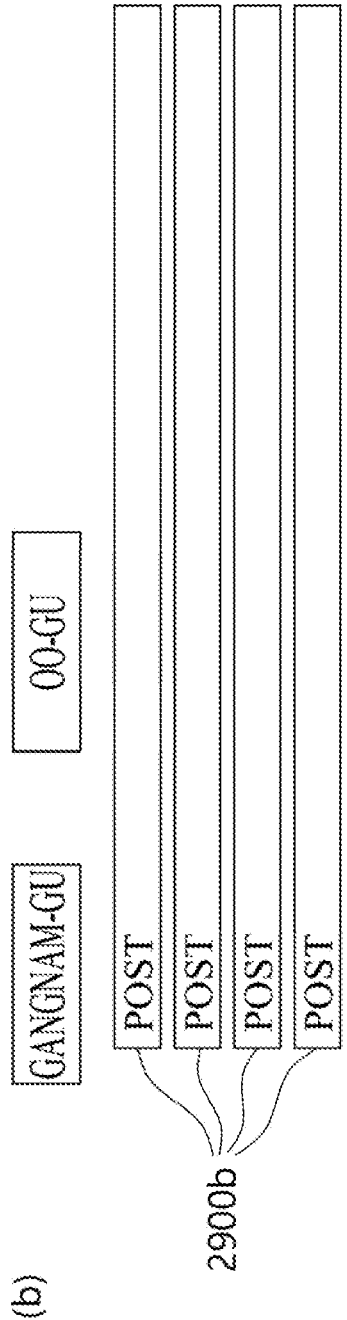

FIG. 30
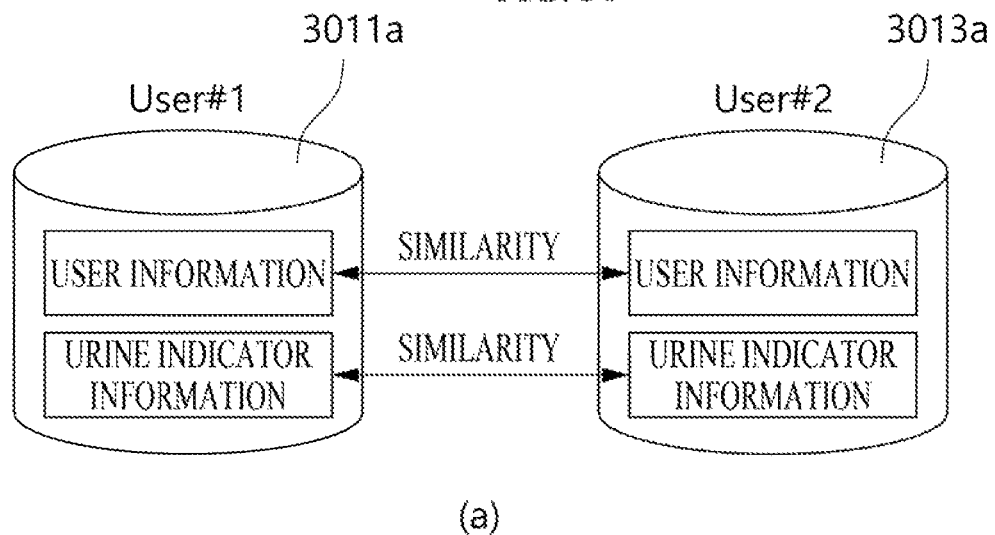
(a)
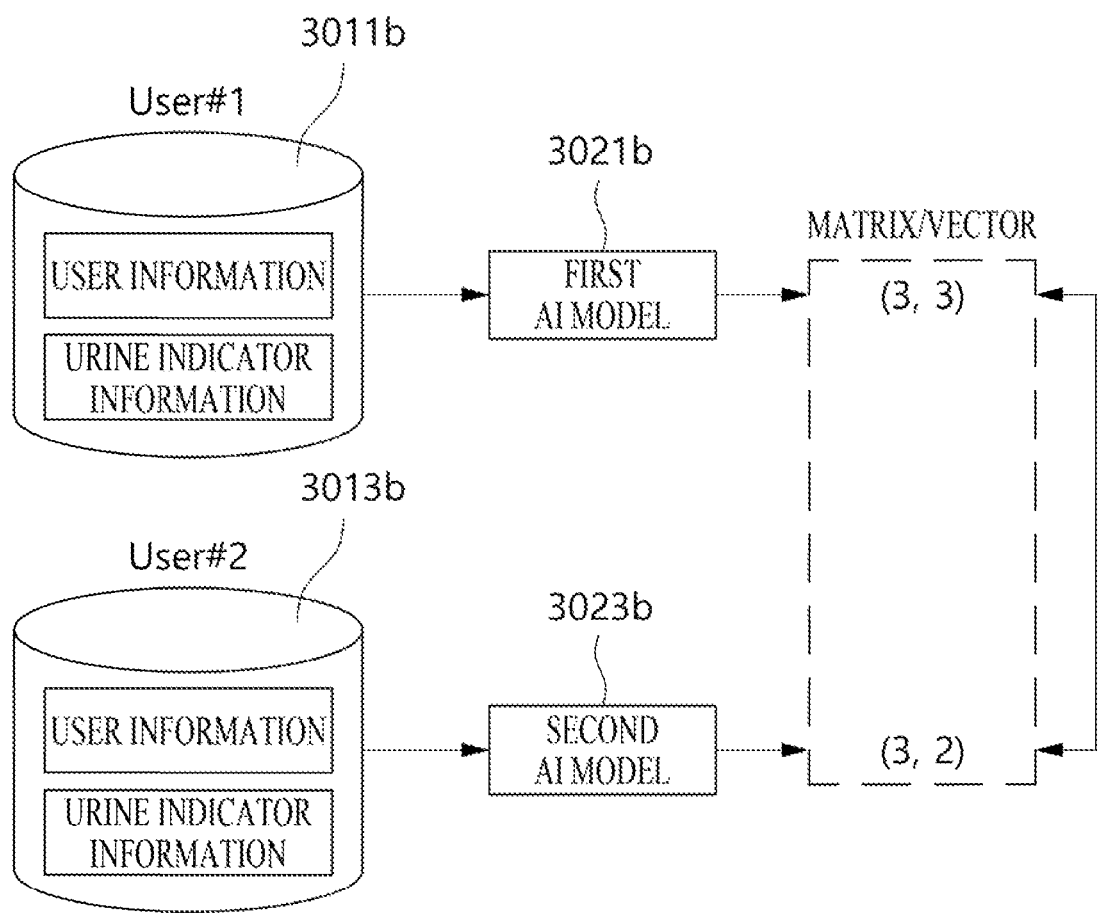
(b)

FIG. 39
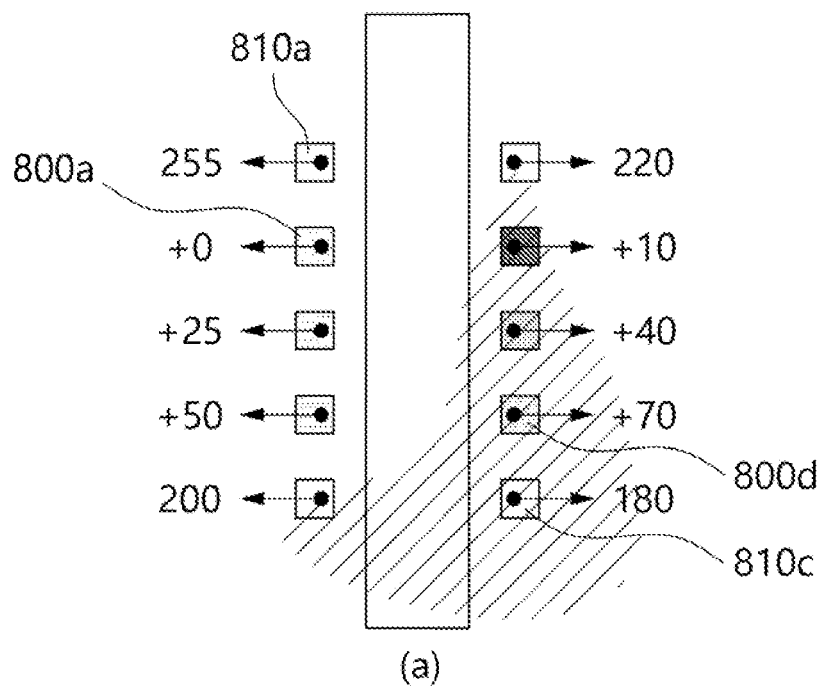
(a)
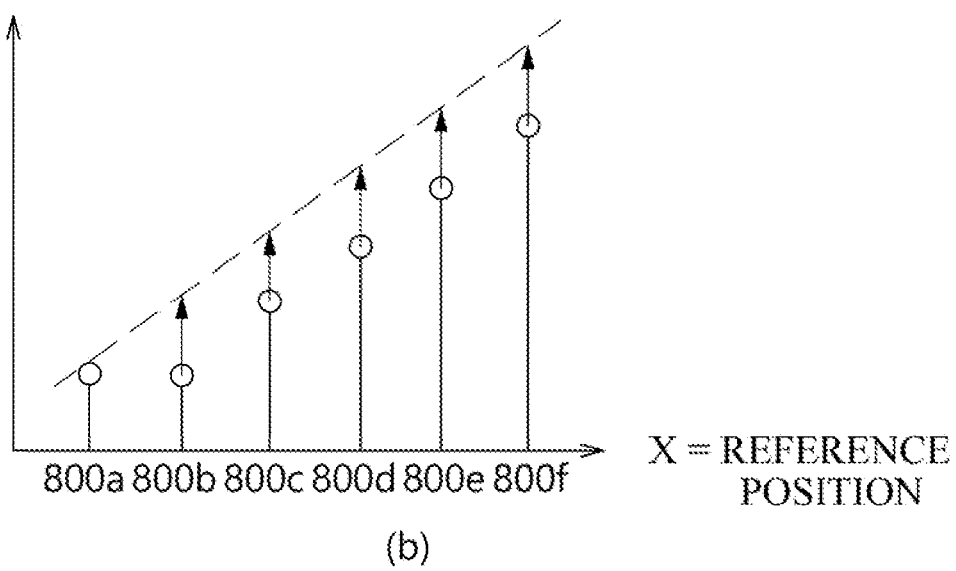
(b)

FIG. 44
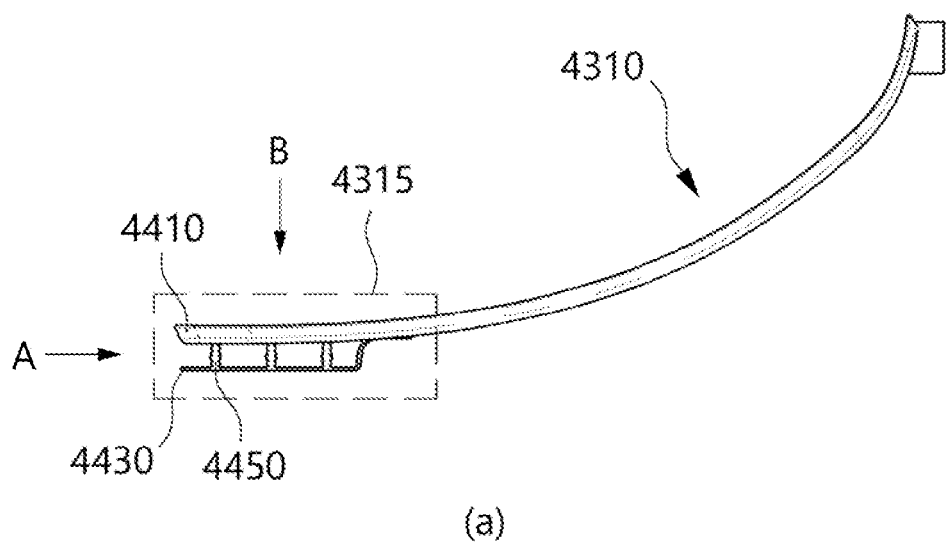
(a)
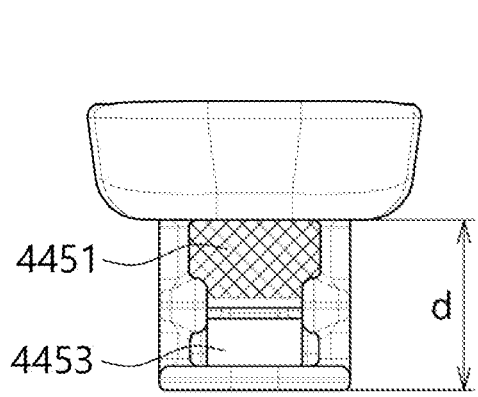
(b)
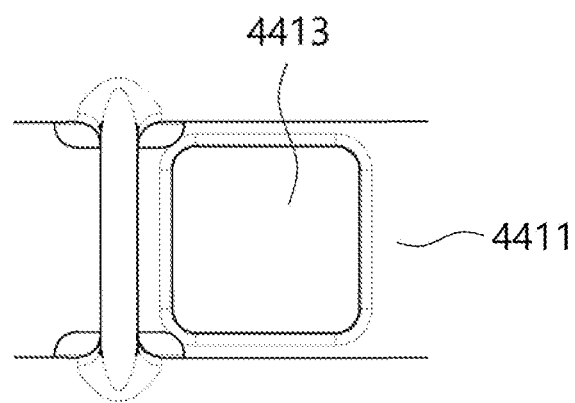
(c)

FIG. 51
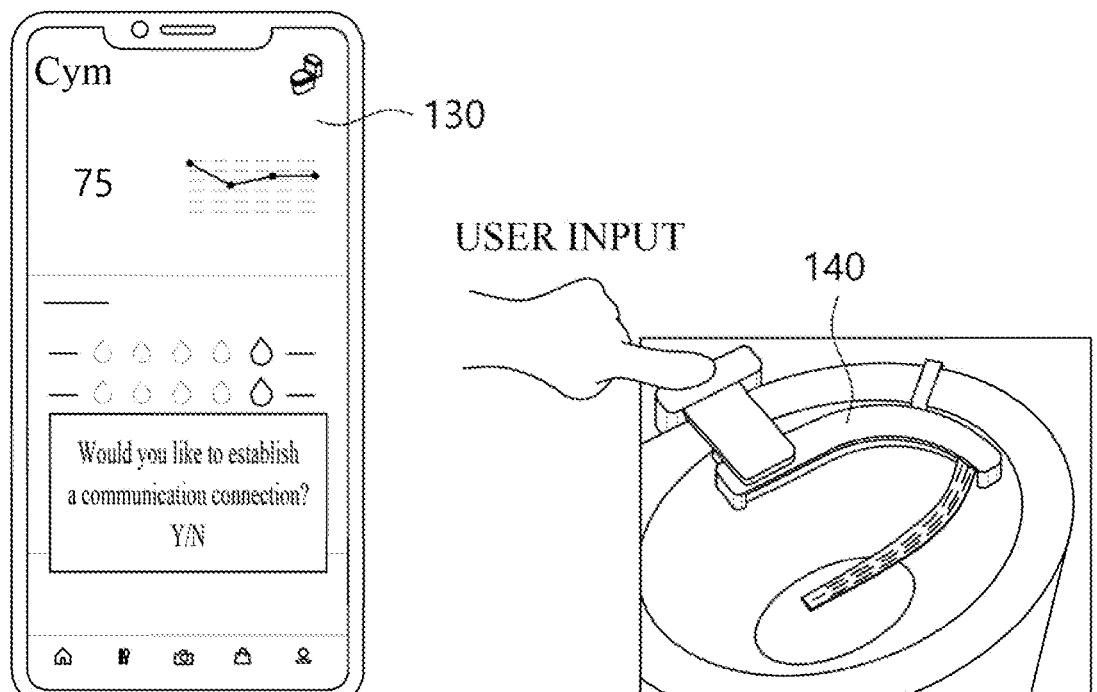
(a)  (b)
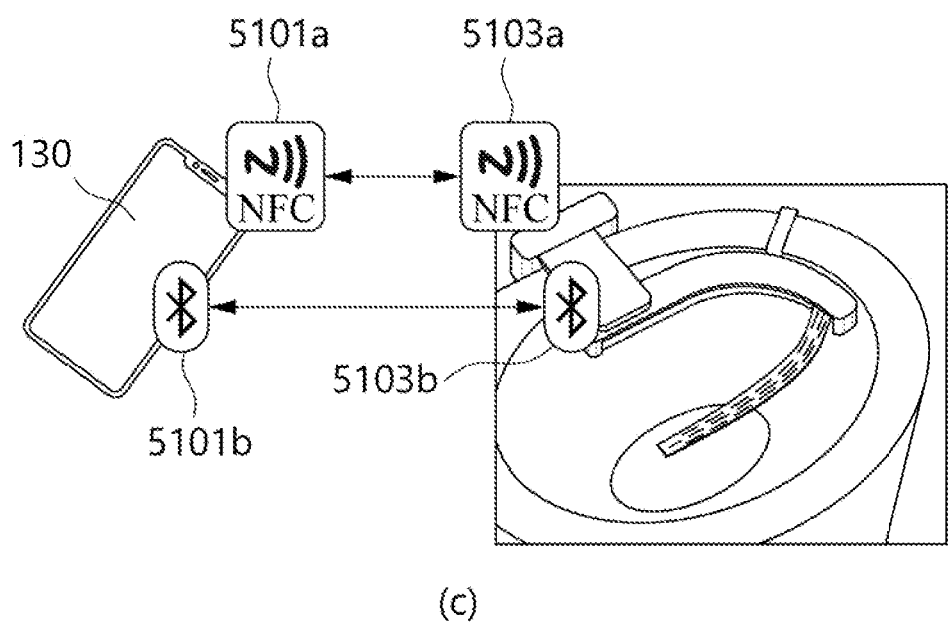
(c)

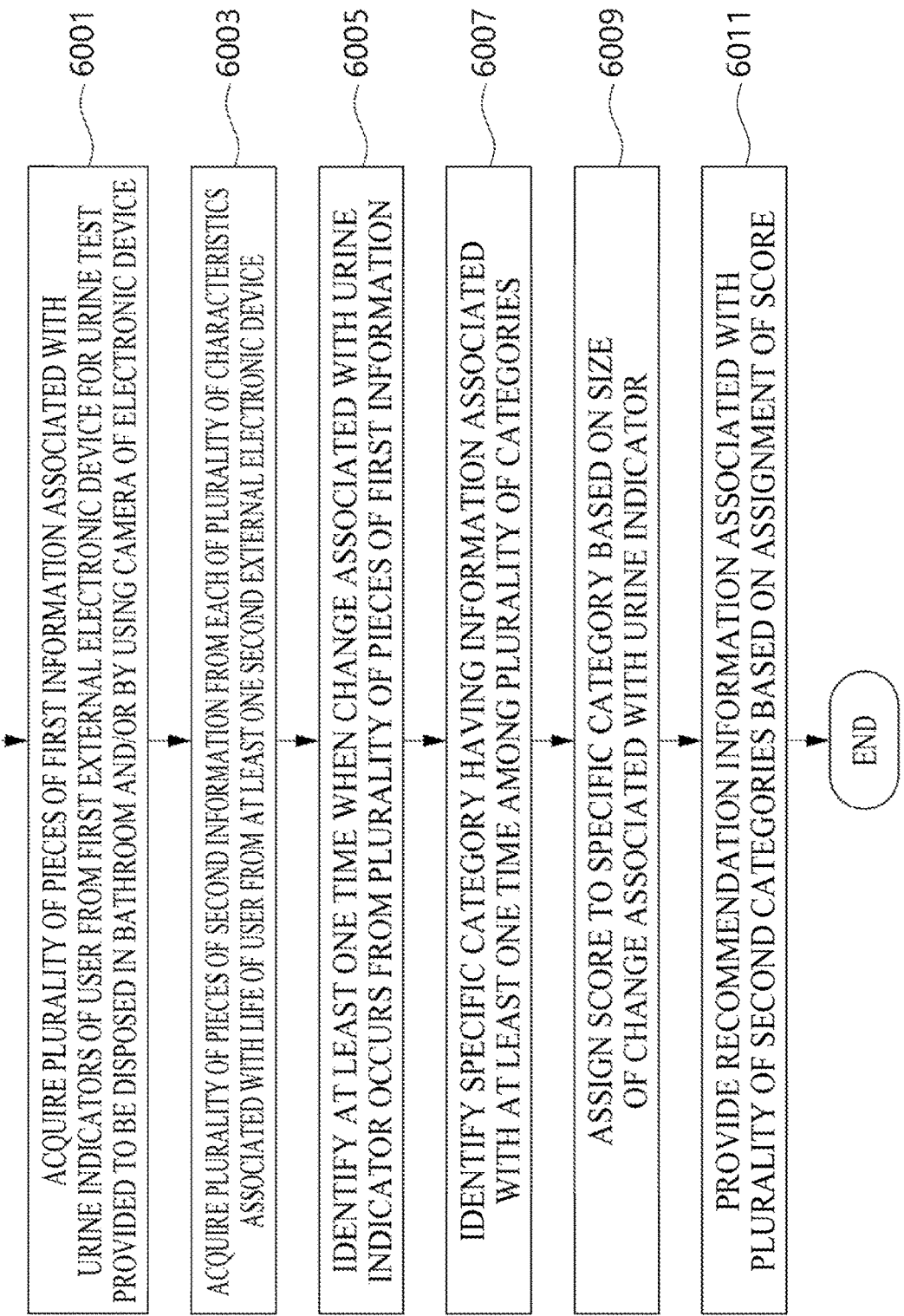

FIG. 61
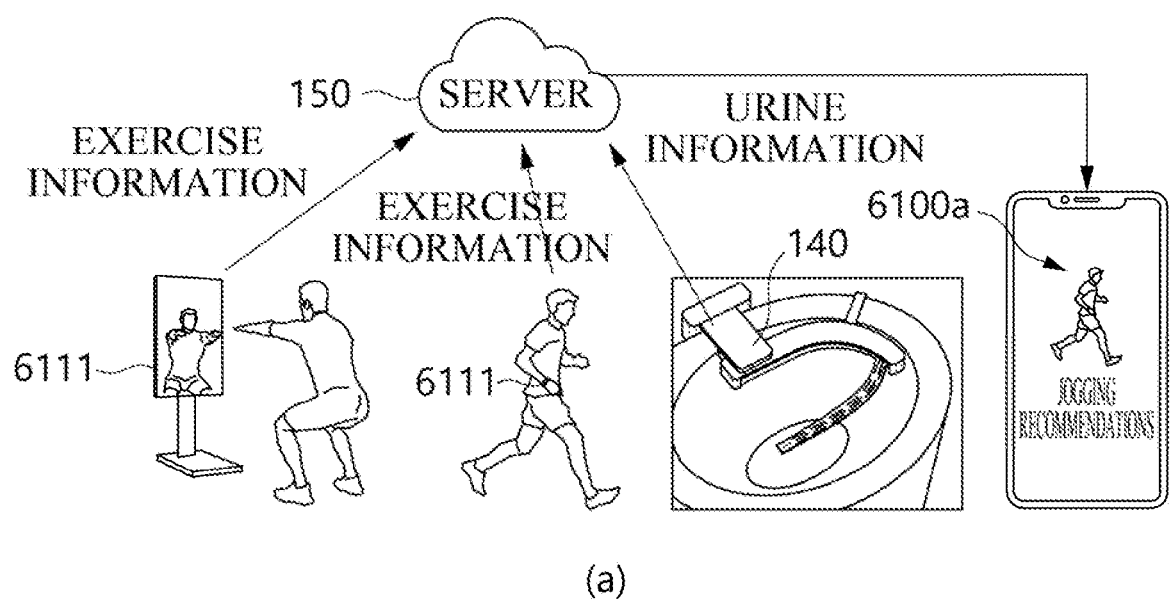
(a)
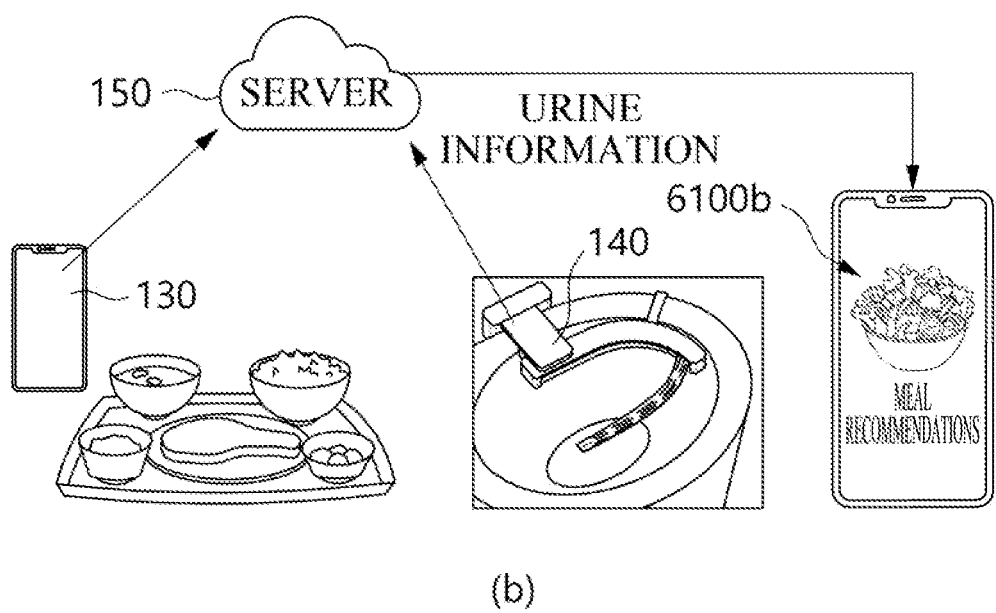
(b)

FIG. 65
(a)
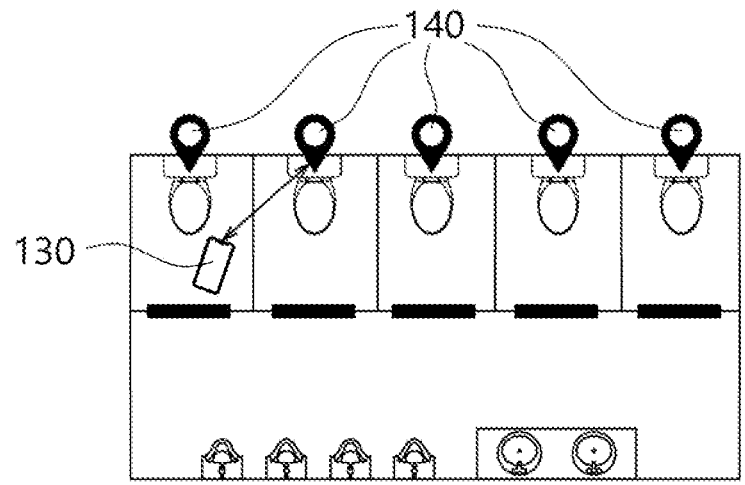
(b)
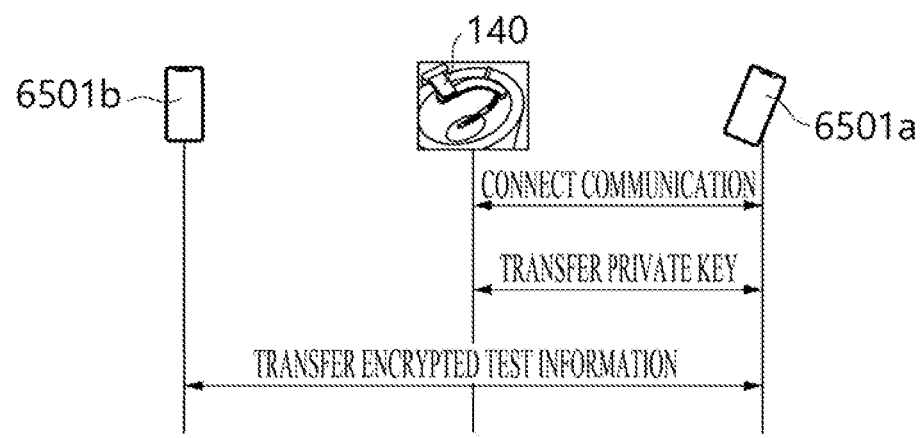
(c)
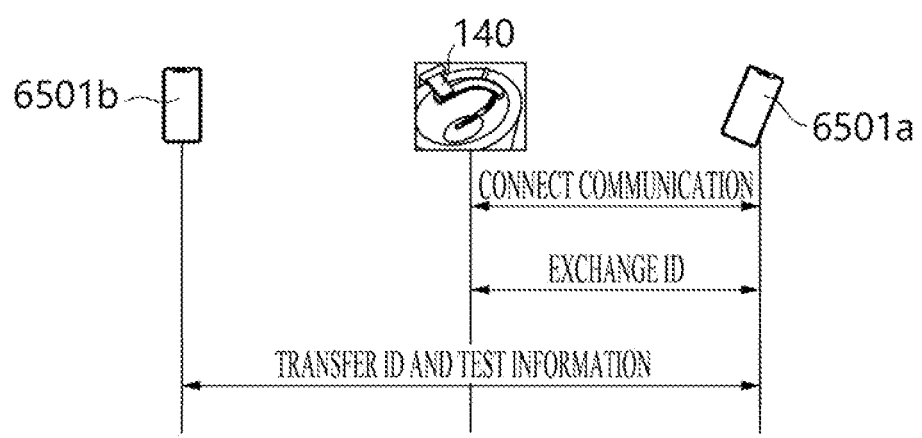

FIG. 78
FIRST ENVIRONMENT
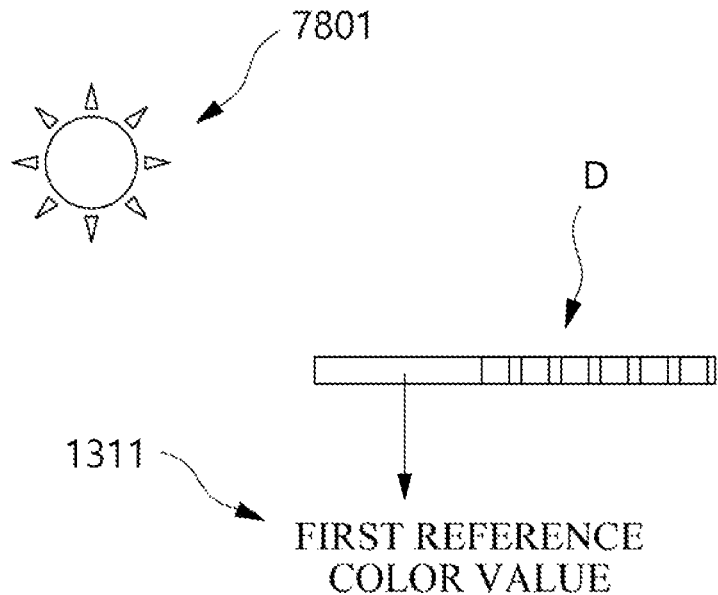
SECOND ENVIRONMENT
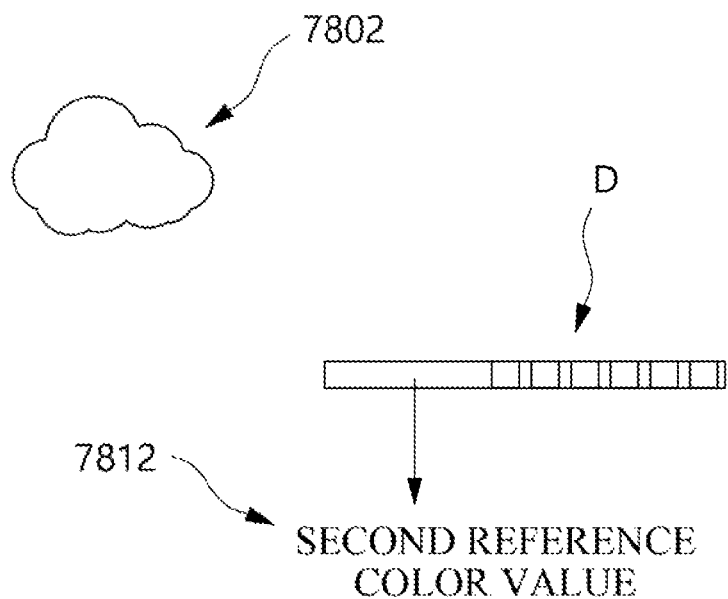

URINE TEST DEVICE DESIGNED TO BE EASILY MOUNTED AND OPERATION METHOD THEROF

CROSS-REFERENCE TO RELATED APPLICATIONS

This is a National Stage Application of PCT Application Number PCT/KR2022/019280 filed Nov. 30, 2022, which claims the priority of Korean Patent Application Nos. KR10-2022-0074893 filed Jun. 20, 2022, KR10-2022-0074894 filed Jun. 20, 2022, KR10-2022-0074895 filed Jun. 20, 2022, KR10-2022-0074896 filed Jun. 20, 2022, KR10-2022-0111930 filed Sep. 5, 2022, KR10-2022-0118120 filed Sep. 19, 2022, KR10-2022-0118121 filed Sep. 19, 2022, KR10-2022-0118122 filed Sep. 19, 2022, KR10-2022-0118123 filed Sep. 19, 2022, KR20-2022-0002247 filed Sep. 19, 2022 and KR10-2022-0163363 filed Nov. 29, 2022, all of which are incorporated herein by reference in their entirety.

TECHNICAL FIELD

The present disclosure relates to a urine test device designed to be easily mounted and an operation method thereof.

BACKGROUND ART

Urine is a liquid in the form of an aqueous solution, which allows waste products in blood filtered out while the blood passes through the kidneys to be stored and then excreted, and typically plays a role in regulating the amount of water in the body and excreting waste products.

By examining the components of urine, it is possible to primarily screen the risk of various diseases such as endocrine diseases and metabolic diseases as well as urinary diseases, and the urine test is simpler than other types of tests, and accordingly, is one of the essential tests in the checkup process to check the health of the body.

The urine test in the related art is conducted in such a way that the examinee manually collects urine or excretes urine from a designated location; however, this way has problems with foreign matter inflow, test strip damage, and poor hygiene that occur during the collection and examination process, and there are limitations caused by different collection ways according to gender.

Therefore, although the urine test is a simple test, it is difficult to perform the urine test not only for patients suffering from urine-related diseases, but also for the general public, and as a consequence, it is a time when it is necessary to build a system that provides a service so as to perform a urine test regardless of time and place.

DISCLOSURE

Technical Problem

Various products may be provided to perform a urine test by using a urine strip for the urine test. For example, a cup-shaped housing may be provided to support the urine strip in a state in which the collected urine is received. However, the cup-shaped housing is not only inconvenient to carry, but also has significant usability due to the inconvenience of containing urine. Further, for example, a kit may be provided having a predetermined groove into which the urine strip is inserted. However, the kit having the groove is difficult for a user to grip for photographing and is made of a material that is easily deformed to make photographing difficult, and thus, usability may be significant. According to various embodiments, a board for urine test strips may be provided that is made of a biodegradable material, easily carried by a user for the urine test, and formed to have a unique physical structure such as a wing structure and/or a urine guide structure to be photographed in a gripped state.

In addition, a urine strip for the urine test may be made to include a base substrate and a plurality of reagent pads formed on the base substrate. The plurality of reagent pads may cope with occult blood, bilirubin, bilogen, ketone bodies, protein, nitrite, glucose, PH, specific gravity, and/or leukocytes. In this case, when the urine strip is stored in the bathroom for urine test, the test accuracy of the reagent pads may be reduced due to the effect of humidity. According to various embodiments, a urine strip made of a biodegradable material and including at least one filter layer to improve the accuracy of a urine test may be provided. Further, according to various embodiments, a urine strip made to include a unique structure for facilitating the urine test when mounted on a toilet-mounted urine test device may be provided.

In addition, according to various embodiments, in order to meet the technical requirements for a urine test device capable of simply collecting urine and sanitarily performing the test, a urine test device including a gutter for collecting urine and guiding it to a strip and a driving device for rotating the gutter and an operation method thereof may be provided.

In addition, an application for the urine test is simply built to provide information on urine indicators, and as a consequence, in many cases, the urine test is limited to a simple primary urine test due to insufficient provision of customized functions for users using the application. According to various embodiments, an electronic device that provides user-customized functions and various types of services for improving health associated with urine tests and an operation method thereof may be provided.

In addition, while there are various issues for each environment (e.g., private environment and public environment) in which the urine test is performed, the urine test system is being built without sufficient consideration for the issues. According to various embodiments, an electronic device and an operation method thereof may be provided that enhance usability by resolving various issues for each environment (e.g., a private environment and a public environment).

Technical Solution

According to an aspect of the present invention, there is provided an electronic device including: a first housing having a bottom surface formed to be disposed on a specific portion of a top surface of a toilet; a second housing connected to one side of the first housing; a third housing connected to another side of the first housing and having a shape extending from a point connected to the first housing by a specific length in a direction associated with a first curvature; and a detection unit having a shape of a second curvature corresponding to the first curvature, in which the detection unit is rotatably coupled to at least a portion of the third housing.

According to another aspect of the present invention, there is provided an electronic device including: at least one processor; at least one motor; a first housing having a bottom surface formed to be disposed on a specific portion of a top surface of a toilet; a second housing connected to one side of the first housing; a third housing connected to another side of the first housing and having a shape extending from a point connected to the first housing by a specific length in a direction associated with a first curvature; and a gutter having a shape of a second curvature corresponding to the first curvature, in which the gutter includes a strip mounting portion having an inner space for mounting a strip, and the at least one processor provides power to the strip mounting portion by using the at least one motor to move the strip mounted on the strip mounting portion.

Aspects of various embodiments are not limited to those mentioned above, and other aspects not mentioned will be clearly understood by those skilled in the art from the present specification and the accompanying drawings.

Advantageous Effects

According to various embodiments, a board for urine test strips may be provided that is made of a biodegradable material, easily carried by a user for the urine test, and formed to have a unique physical structure such as a wing structure and/or a urine guide structure to be photographed in a gripped state.

According to various embodiments, a urine strip made to include a unique structure for facilitating the urine test when mounted on a toilet-mounted urine test device may be provided.

According to various embodiments, a urine test device including a gutter for collecting urine and guiding it to a strip and a driving device for rotating the gutter and an operation method thereof may be provided.

According to various embodiments, an electronic device that provides user-customized functions and various types of services for improving health associated with urine tests and an operation method thereof may be provided.

According to various embodiments, an electronic device and an operation method thereof that enhance usability by resolving various issues for each environment (e.g., a private environment and a public environment) may be provided.

BRIEF DESCRIPTION OF DRAWINGS

FIG. 5a is a diagram for describing packaging of a urine test board, according to various embodiments.

FIG. 6 is a diagram illustrating a first embodiment of a test board, according to various embodiments.

FIG. 12 is a diagram for describing another example of the urine strip, according to various embodiments.

FIG. 16a is a diagram for describing examples of execution screens of an application, according to various embodiments.

FIG. 16b is a diagram for describing examples of execution screens of an application for user add, according to various embodiments.

FIG. 20 is a diagram for describing an example of an operation of determining a priority of a urine indicator based on user information about the user terminal, according to various embodiments.

FIG. 29 is a diagram for describing an example of a social service to be provided by a urine test system, according to various embodiments.

FIG. 30 is a diagram for describing an example of an operation of determining a user similar to a specific user of the urine test system, according to various embodiments.

FIGS. 39 and 40 are diagrams illustrating an example in which the method according to FIG. 38 is performed.

FIG. 44 is a diagram for describing a strip mounting portion of a gutter which is an embodiment of a detection unit included in an electronic device, according to various embodiments.

FIG. 51 is a diagram for describing an example of an operation of establishing and/or releasing the communication connection between the user terminal and the electronic device, according to various embodiments.

FIG. 60 is a flowchart illustrating an example of operations of a server (150), according to various embodiments.

FIG. 61 is a diagram for describing an example of an operation of collecting information about life characteristics for each life category by a server, according to various embodiments.

FIG. 65 is a diagram for describing an example of performing a urine test in an environment in which a plurality of electronic devices are provided, according to various embodiments.

FIG. 78 is a flowchart for explaining an example of an operation of measuring a reference value for each environment of the electronic device according to various embodiments.

MODE FOR CARRYING OUT INVENTION

Figure 1:
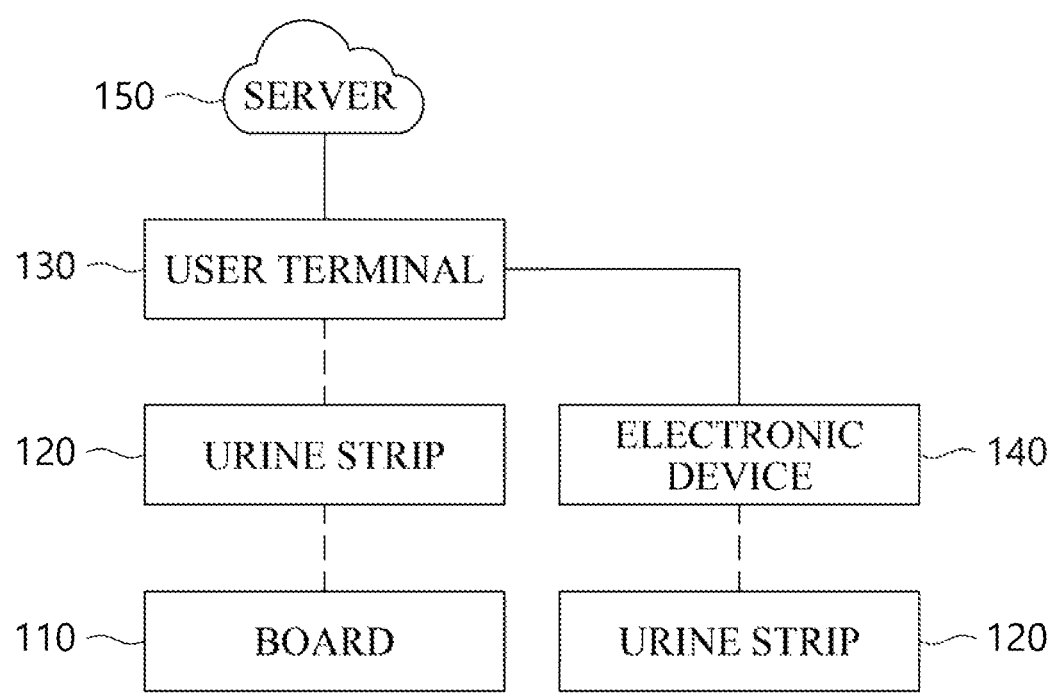
FIG. 1 is a diagram for describing an example of a urine test system, according to various embodiments.

The electronic device according to various embodiments disclosed herein may be one of various types of electronic devices. The electronic devices may include, for example, a portable communication device (e.g., a smartphone), a computer device, a portable multimedia device, a portable medical device, a camera, a wearable device, or a home appliance. According to an embodiment of the present disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar or related reference numerals may be used to refer to similar or related elements. It is to be understood that a singular form of a noun corresponding to an item may include one or more of the things, unless the relevant context clearly indicates otherwise. As used herein, each of phrases such as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. Terms such as "1st" and "2nd," or "first" and "second" may be used to simply distinguish a corresponding component from another, and do not limit the components in other aspects (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., wiredly), wirelessly, or via a third element.

As used in various embodiments disclosed herein, the term "module" may include a unit implemented in hardware, software, or firmware, and may interchangeably be used with other terms, for example, logic, logic block, part, or circuitry. A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., a program) including one or more instructions that are stored in a storage medium (e.g., an internal memory or an external memory) that is readable by a machine (e.g., the electronic device). For example, a processor (e.g., the processor) of the machine (e.g., the electronic device) may invoke at least one of the one or more instructions stored in the storage medium, and execute it. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments disclosed herein may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smartphones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the plurality of entities may be disposed separately from other components. According to various embodiments, one or more of the above-described components may be omitted, or one or more other components may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Hereinafter, urine test systems according to various embodiments will be described.

According to various embodiments, the urine test systems may be defined as systems for providing services (or performing functions) to allow a user to perform a urine test regardless of the location and/or time for improving the user's health in daily life. The urine test may include a chemical test for test items contained in and associated with urine (e.g., occult blood, bilirubin, bilogen, ketone bodies, protein, nitrite, glucose, PH, specific gravity, and/or leukocytes), a physical test for urine characteristics (e.g., color, turbidity, odor), and/or a urine sediment test, and urine test systems may be implemented to primarily diagnose the physical abnormality and/or further provide the user's disease, health condition, wellness information, and the like associated therewith. The urine test systems may provide various types of urine test instruments and/or urine test devices provided in a form that allows the user to carry them and/or provided in a form of being equipped in various environments (e.g., a private environment or a public environment) in which the user lives. Accordingly, the user using the urine test systems performs the urine test in various locations and at various times to obtain various information (e.g., disease-related information, health condition, wellness information) along with the primary physical abnormality check. The urine test systems may improve overall health by guiding not only kidney-related disease patients who need regular urine tests at short time intervals, but also the general public to perform urine tests naturally in daily life.

Figure 2:
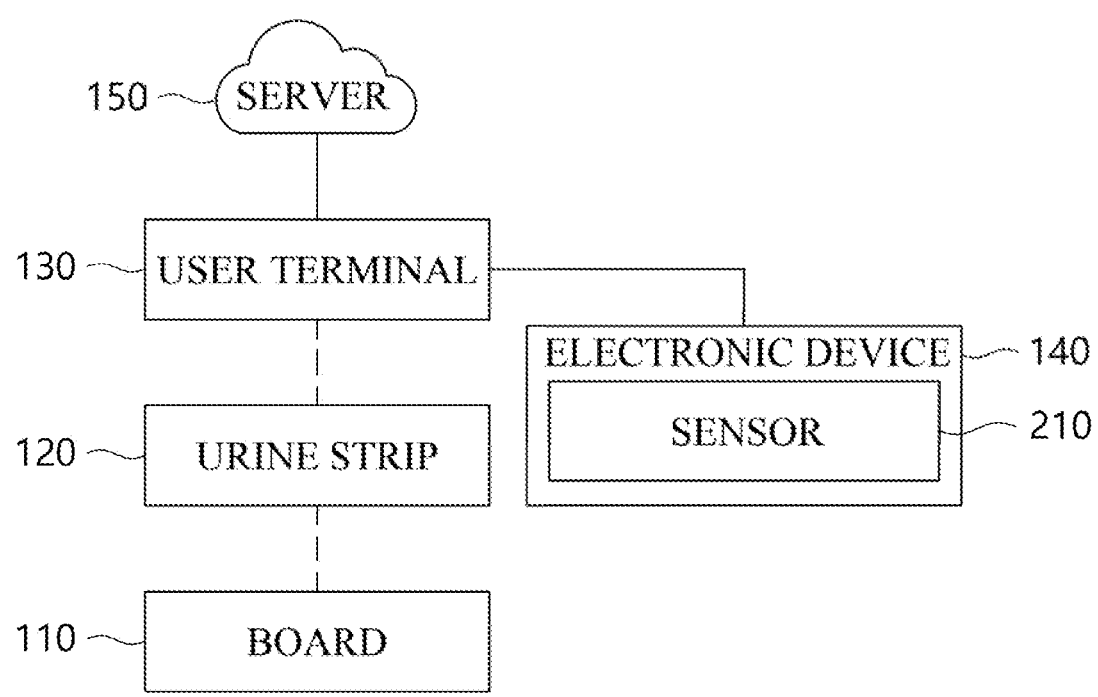
FIG. 2 is a diagram for describing another example of the urine test system, according to various embodiments.

FIG. 1 is a diagram for describing an example of the urine test system, according to various embodiments. FIG. 2 is a diagram for describing another example of the urine test system, according to various embodiments. Hereinafter, a further description of FIGS. 1 and 2 will be given below with reference to FIGS. 3 and 4.

Figure 3:
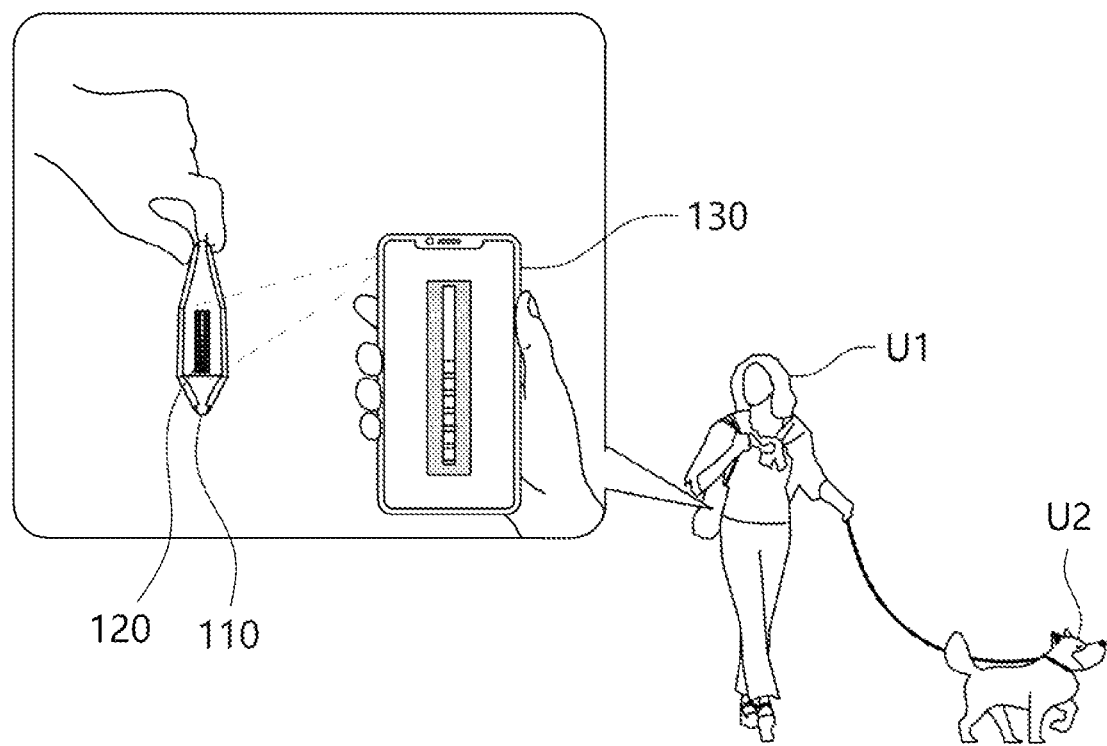
FIG. 3 is a diagram for describing an example of a urine test using a board on which a urine strip is disposed and an electronic device, according to various embodiments.
Figure 4:
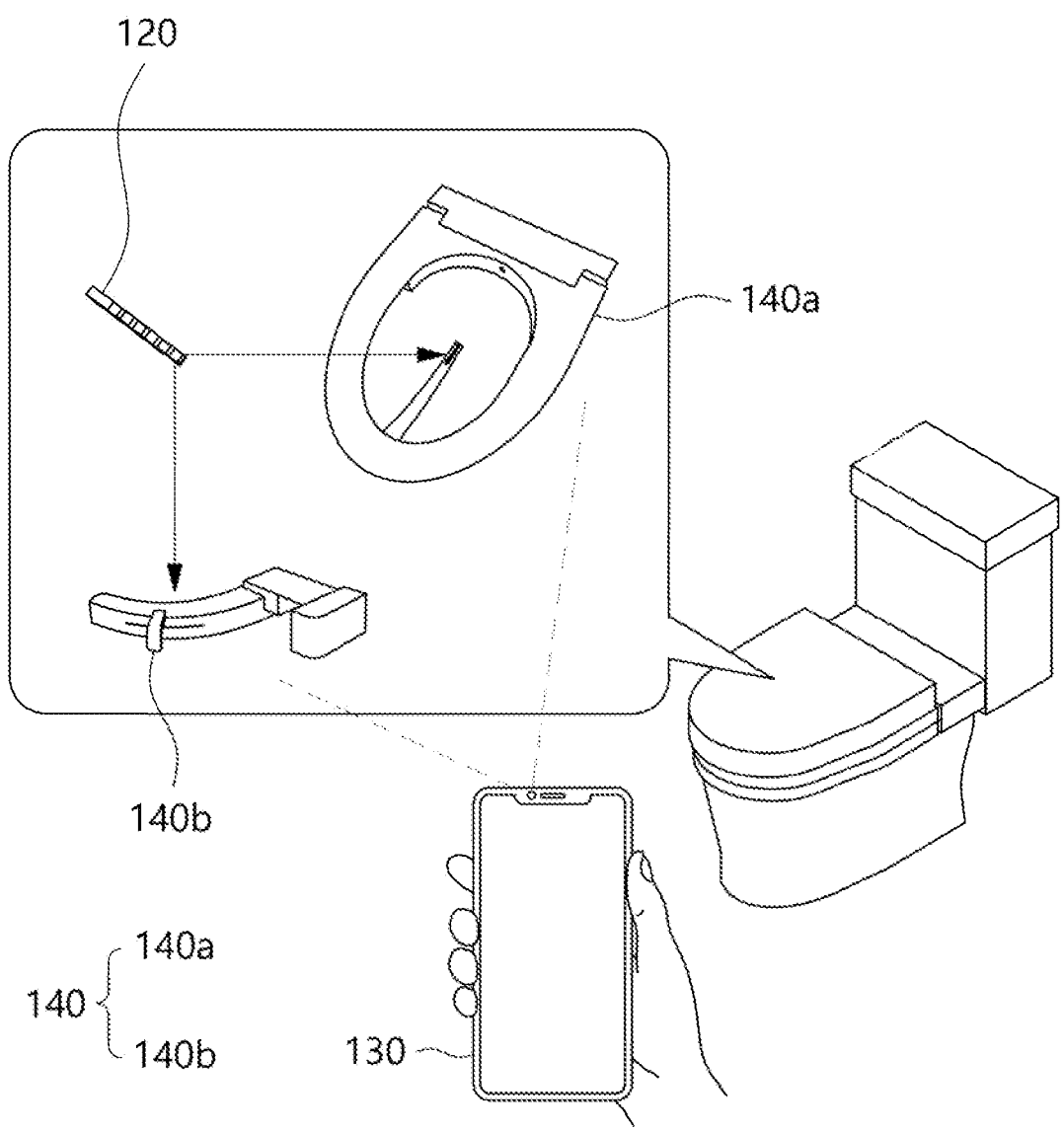
FIG. 4 is a diagram for describing an example of a urine test using a urine test device provided to be disposed in a space in a bathroom, according to various embodiments.

FIG. 3 is a diagram for describing an example of a urine test using a board 110 on which a urine strip 120 is disposed and a user terminal 130, according to various embodiments. FIG. 4 is a diagram for describing an example of a urine test using a urine test device 140 provided to be disposed in a space in a bathroom, according to various embodiments.

According to various embodiments, referring to FIG. 1, the urine test system may include a board 110, a urine strip 120, a user terminal 130, a user terminal 130, and a server 150, but is not limited to the example described and/or illustrated, and may be implemented to include more instruments and/or electronic devices, or fewer instruments and/or electronic devices.

According to various embodiments, the board 110 may be an instrument made so as to use the urine test service of the urine test system in a state of being gripped by a user's hand. For example, referring to FIG. 3, in the board 110, a specific region may be formed to attach the urine strip 120 to the board, and/or to include the urine strip 120, which makes it possible to guide the urine to the urine strip 120 on the specific region in the state in which the user U1 gripping the board 110 with his or her hand. The user terminal 130 may provide a result of the urine test that has been performed using the urine strip 120 based on photographing the urine strip 120 on the board 110, based on the execution of an application (or a urine test application) built to provide the urine test and a service linked thereto. The user U1 may perform a urine analysis about another user (e.g., animal U2, family) associated with the user U1.

According to various embodiments, the urine strip 120 (or a urine test kit) may include at least one reagent pad (or reagent item, or reagent paper) for urine test. For example, the at least one reagent pad may be provided so that color is changed in response to a specific test item in urine among test items, such as occult blood, bilirubin, bilogen, ketone body, protein, nitrite, glucose, PH, specific gravity, and/or white blood cells, in order to test the specific item, but is not limited to the aforementioned examples, and may be provided to test more various test items. Based on the color change of the reagent pad being visually recognized by the user (or medical personnel) and/or optical analysis based on the urine test application of the user terminal 130, a test on a specific item in urine responding to the reagent pad may be conducted. In the following various embodiments, a case where the number of reagent pads is five will be described as an example, but the number described and/or shown is not limited, and unless otherwise stated, it is obvious to those skilled in the art that various numbers (e.g., ten) of reagent pads may be provided.

According to various embodiments, the board 110 and the urine strip 120 may be provided (or made) so that the user is able to carrying (or holding) the board 110 and the urine strip 120, which makes it possible for the user to perform the urine test by using the board 110 and the urine strip 120 regardless of the location and/or time. For example, the board 110 and the urine strip 120 may be accommodated in one packaging material (or packaging case) and provided (or sold) to the user. Here, the board 110 and the urine strip 120 each may be packaged in different packaging materials, and the packaging materials may be provided in a form of being accommodated in one packaging material described above, but the packaging method is not limited to the described example. In this case, in the packaging material for packaging the urine strip 120, materials and/or members (e.g., a dehumidifier) that inhibit the reaction of the reagent pad of the urine strip 120 may be further included.

According to various embodiments, the user terminal 130 may be an electronic device that is usable by the user and is implemented to include an electronic component (or device) (e.g., a camera and/or an image sensor) for photographing. For example, the user terminal 130 may include a smartphone, a wearable device, a head mounted display (HMD) device, or the like, but is not limited to the aforementioned examples and may include various types of electronic devices usable by the user. As will be described later, the user terminal 130 may store an application built to provide a urine test function (e.g., download and store the application from an application distribution server (not shown)), and may be implemented to provide a function of photographing and analyzing the urine strip 120 on the board 110 and/or a function of establishing a communication connection with the electronic device 140 for the urine test, based on the execution of the application. As described above, the result of the urine test provided based on the application may include not only information for each of a plurality of urine indicators, but also results related to diagnosis and prognosis of a disease, determination of a health condition, determination of a disease treatment effect, and/or prevention of a disease, but is not limited to the aforementioned examples, and may include information in the form of processing and/or analysis of the described examples (e.g., hourly in vitro diagnostic results (history), information for health promotion, wellness recommendation information, digital vaccine, digital medicine). In addition, the application may be built to store history information on the result of the urine test, and may perform a function of providing at least one piece of information for health promotion based on the stored history information.

According to various embodiments, the electronic device 140 may be a urine test device implemented to be provided (or placed) in a toilet for the urine test. For example, the electronic device 140 may be implemented so that the urine strip 120 is mounted and the urine of the user is analyzed through the urine strip 120, and/or may be implemented to include a urine test sensor (e.g., a Raman sensor or a urine test electrode) to perform the urine test based on the sensor. Although described later, the electronic device 140 may include a portable type electronic device and a bidet type electronic device.

According to various embodiments, the server 150 may be various types of external electronic devices provided outside the user terminal 130 and/or the electronic device 140. The server 150 may include at least one of a distribution server for providing an application (or program) built to provide a service for the urine test to the user terminal 130, an analysis server for providing in vitro diagnostic results based on information for the urine test (e.g., an image, a color value) received through the user terminal 130, a storage server implemented to store various types of information (e.g., user account information, result information about the urine test for each user account information), or a learning server for performing learning based on various types of stored information. When the server 150 is provided, the user terminal 130 to be described below may perform a urine test function of the user terminal 130 in collaboration with the server 150, and/or all image/color analysis functions for the urine test may be performed in the server 150 and the user terminal 130 may receive information about the in vitro diagnosis results from the server 150.

Hereinafter, examples of a urine test board according to various embodiments will be described.

Figure 5B:
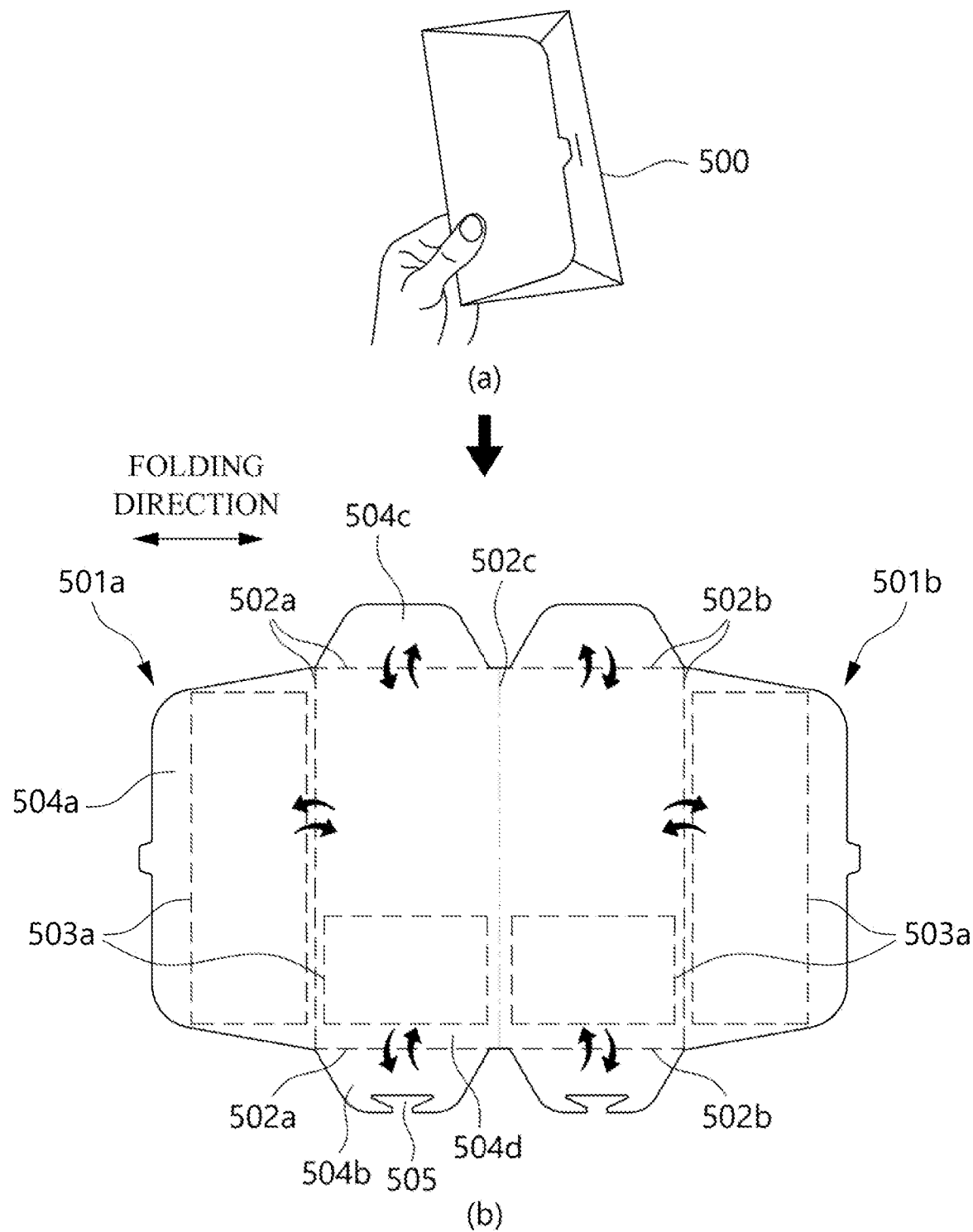
FIG. 5b is a diagram for describing an example of a package, according to various embodiments.

FIG. 5a is a diagram for describing packaging of a urine test board, according to various embodiments. Hereinafter, a further description will be given with reference to FIGS. 5b and 5c.

Figure 5C:
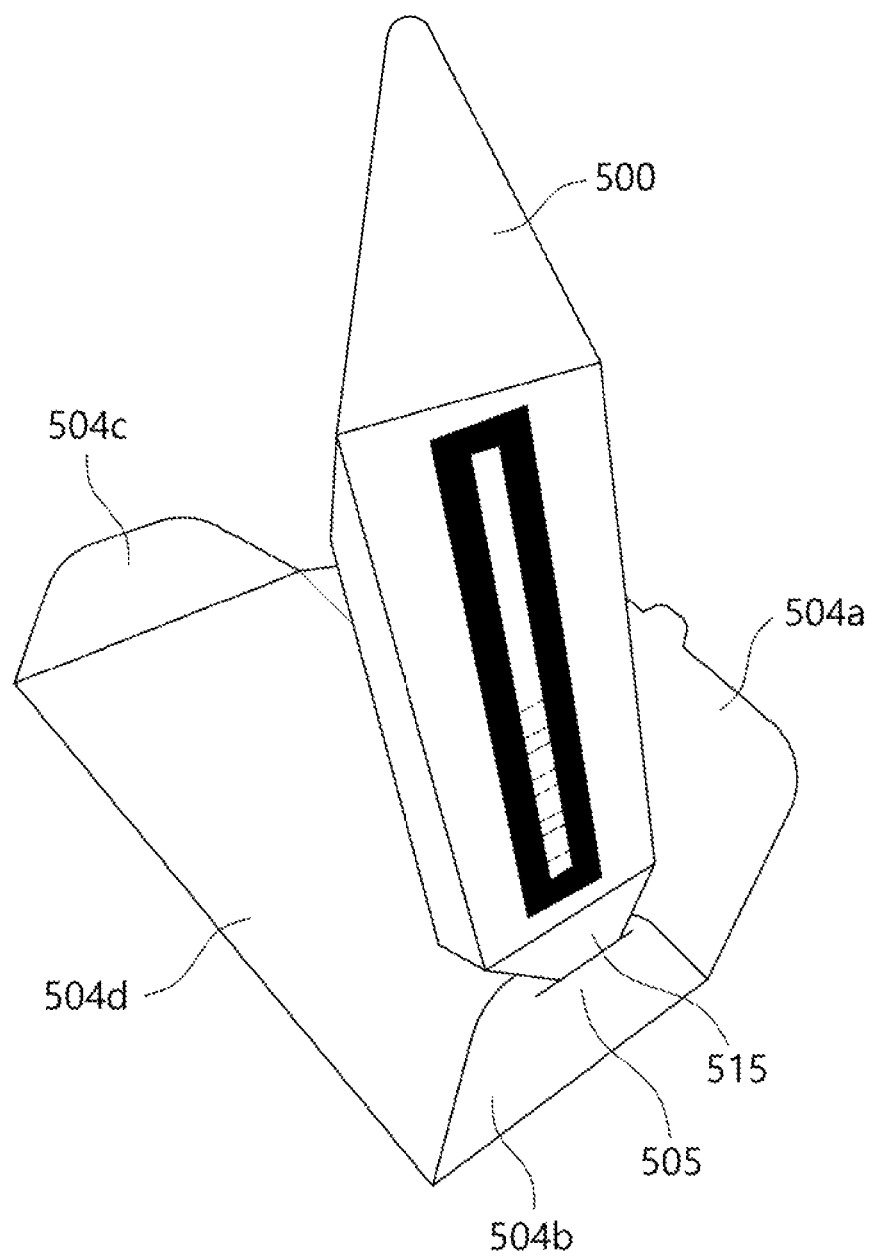
FIG. 5c is a diagram for describing an example of an operation of performing the urine test by using a package to mount the urine test board, according to various embodiments.

FIG. 5b is a diagram for describing an example of a package, according to various embodiments. FIG. 5c is a diagram for describing an example of an operation of performing the urine test by using a package to mount the urine test board, according to various embodiments.

Referring to FIG. 5a, the urine test board may include a package (see reference numeral 500 in (a) of FIG. 5a), a test board (see reference numeral 510 in (b) of FIG. 5a) (e.g., the board 110 described above) including at least one mark (see FIG. 8) used for image analysis for the urine test to be described later (see FIGS. 32 to 41), and a strip (see reference numeral 120 in (c) of FIG. 5a) including a reagent item for detecting a specific substance.

In this case, the package 500 may be a component for packaging the test board 510 and the strip 120. The package 500 may be provided to prevent contamination of internal components during distribution to users. For example, the test board 510 and the strip 120 may be packaged to be surrounded by the package 500, but the packaging is not limited thereto, and the test board 510 and/or the strip 120 may be packaged so that at least a portion thereof is exposed to the outside. In addition, the test board 510 and/or the strip 120 may be attached to at least a portion (e.g., an inner surface) of the package 500. In this case, an adhesive material having weak adhesiveness may be applied to at least a portion of the package 500, whereby separation of the test board 510 and/or the strip 120 in the state of being attached to the package 500 may be easily achieved by the user.

In an embodiment, as shown in (a) of FIG. 5b, the package 500 may be provided in an envelope form for accommodating the test board 510 and the strip 120. However, the form of the package is not limited to the examples described and/or illustrated, and may be provided in the form of a box other than the envelope form. As shown in (b) of FIG. 5b, a plurality of surfaces 504a, 504b, 504c, and 504d included in the package 500 (or constituting the package 500) may be unfolded based on specific portions 502a, 502b, and 502c) (or a specific line, or a specific region). As the unfolding, the inner surface of the package 500 may be exposed to the outside. Instructions for a urine test may be described and/or shown on at least some region 503a of the inner surface, but the embodiment is not limited thereto.

In an embodiment, at least a portion of the unfolded package 500 may be used as a portion for mounting (or supporting) the urine test board 510. For example, referring to (b) of FIG. 5b, one of the plurality of portions 501a and 501b of the package 500 divided based on the perforated line 502c may be used as a portion for mounting the urine test board 510. Each of the plurality of portions 501a and 501b may be provided to include a plurality of portions 504a, 504b, 504c and 504d. Referring to FIG. 5c, in a state in which a disposing portion 504d, which is a portion separated from among a plurality of portions 501a and 501b divided based on the perforated line 502c by a user, is disposed on the ground, the mounting portion 504b, which is formed to include an insertion hole 505 into which a portion (e.g., an end portion 515) of the urine test board 510 is capable of being inserted, may be folded to form a specific angle with the disposing portion 504d. In a state in which the urine test board 510 is mounted in the insertion hole 505 of the disposing portion 504d, the urine test may be performed by the user photographing the urine strip 120 on the urine test board 510 using the user terminal 130.

In an embodiment, the mounting portion 504b may be provided such that the portion 502a thereof connecting to the disposing portion 504d may be folded to form a specific angle, but the embodiment is not limited to the example described and/or illustrated.

In addition, the test board 510 and/or the strip 120 may be provided to be integrated with the package 500. Specifically, at least a portion of the package 500 (e.g., the inner surface of the package) may have components included in the above-described test board 510 (see description of FIG. 8) and/or reagent items included in the strip 120 integrally formed. For example, on at least a portion of the package 500, at least one correction (reference) mark may be visually printed, and at least one reagent item (or a color mark including the reagent item) may be attached.

The packaging method for the test board 510 and the strip 120 using the package 500 is not limited to the above method, and a packaging method commercialized in a sample detection kit may be used.

In addition, the test board 510 may include a strip attachment region 511 to which the strip 120 is attached. In this case, the strip attachment region 511 may include a visual display (e.g., a character display such as "strip attachment region") for guiding the user to attach the strip 120. Further, an adhesive material (not shown) for attaching the strip 120 is attached may be applied on the strip attachment region 511. In addition, a cover (not shown) may be additionally applied on the adhesive material to prevent the adhesive material from being exposed to the outside. In this case, the user removes the cover and attaches the strip 120 to the test board 510 using the adhesive material applied to the strip attachment region 511 to perform the test.

According to various embodiments, the test board 510 and the strip 120 may be integrally formed. Specifically, the test board 510 may include at least one reagent item (or a color mark including the reagent item) included in the strip 120. For example, at least one reagent item (or color mark including the reagent item) included in the strip 120 may be provided in at least a portion of the test board 510 (e.g., a portion corresponding to the strip attachment region 511), but the embodiments are not limited thereto.

According to various embodiments, the test board 510 and/or the strip 120 may be made of a biodegradable material.

FIG. 6 is a diagram illustrating a first embodiment of a test board, according to various embodiments.

Referring to (a) of FIG. 6, a test board 510*a* according to the first embodiment may have a packaging form 510*aa* and a use form 510*ab* that are different from each other. Specifically, the test board 510*a* may be packaged in a state in which at least a portion (e.g., both ends) is folded, and at least a portion thereof may be unfolded for use. In (a) of FIG. 6, the packaging form 510*aa* of the test board is illustrated with only one end of the test board folded, but is not limited thereto, and both ends may be folded. Accordingly, the test board 510*a* may include a folded portion (e.g., a groove formed along the folded part) for implementing the packaging form 510*aa*.

The test board 510*a* according to the first embodiment may be designed as a physical structure for guiding urine toward the reagent item.

The test board 510*a* may include a plurality of components for guiding urine for test. Specifically, the test board 510*a* may include a main board 600 on which reagent items are disposed, at least one region 610 or 630, and a guide portion 650 for preventing leakage of urine.

In this case, the main board 600 may be a region including the above-described strip attachment region (see 511 in FIG. 5) to which the strip including at least one reagent item is attached. The main board 600 may include the at least one reagent item and at least one color mark for image analysis, and a detailed configuration of the main board 600 will be described in detail with reference to FIG. 8.

The test board 510*a* may include at least one region 610 or 630 that is formed to be inclined with respect to the main board 600. Specifically, the test board 510*a* may be designed so that urine supplied to the at least one region 610 or 630 flows toward the main board 600.

As an example, referring to (b) of FIG. 6, the test board 510*a* may be connected to one side of the main board 600, and may include a first region 610 formed to be inclined with respect to the main board 600. Furthermore, referring to (b) of FIG. 6, the test board 510*a* may be connected to the other side of the main board 600, and may include a second region 630 formed to be inclined with respect to the main board 600.

The length of the first region 610 of the test board 510*a* may be shorter than the length of the second region 630. This is because the second region 630 is formed to guide urine supplied from the user to the main board 600. The length of the first region 610 of the test board 510*a* is not limited thereto, and may be provided to be the same as or longer than that of the second region 630.

In addition, the inclination of the first region 610 with respect to the main board 600 may be smaller than the inclination of the second region 630 with respect to the main board 600. The inclination of the first region 610 with respect to the main board 600 is not limited thereto, and may be provided to be the same as or greater than that of the second region 630 with respect to the main board 600.

Referring back to (a) of FIG. 6, the test board 510*a* according to the first embodiment may include the guide portion 650 formed along the circumference of the test board 510*a*. In this case, the guide portion 650 may be provided to be inclined with respect to the test board 510*a*. For example, the guide portion 650 may have a predetermined width along the circumference of the test board 510*a* and may be formed in a upwardly folded state. The guide portion 650 may be configured to serve as a shield to prevent urine supplied to the test board 510*a* from leaking out. Accordingly, the guide portion 650 may be formed along the circumferences of the main board 600, the first region 610, and the second region 630.

According to the above-described physical structure of the test board, the test board 510*a* according to the first embodiment may be designed to guide urine to the main board, thereby facilitating the urine test of the user.

Figure 7:
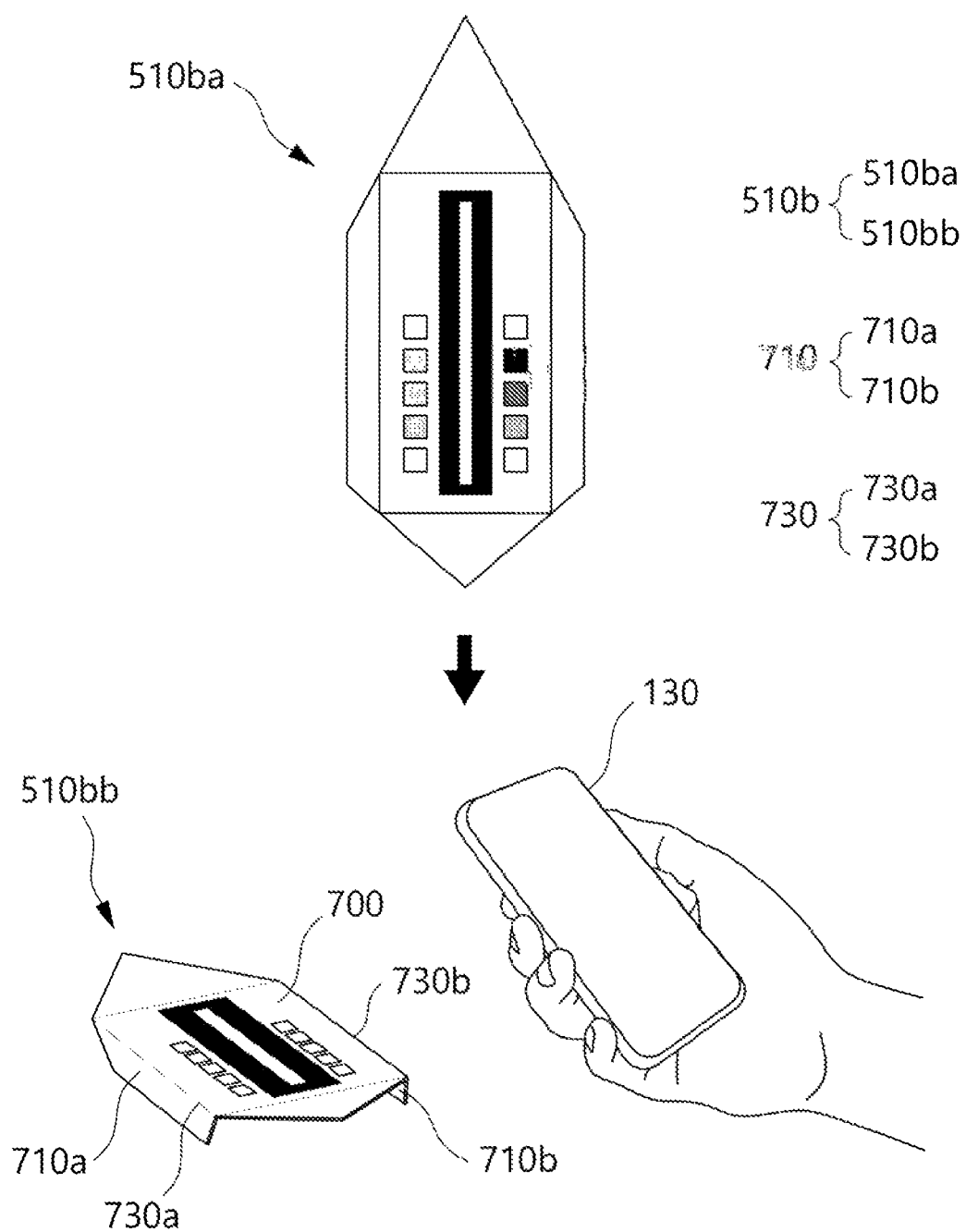
FIG. 7 is a diagram illustrating a second embodiment of a test board, according to various embodiments.

FIG. 7 is a diagram illustrating a second embodiment of a test board, according to various embodiments.

A test board 510*b* according to a second embodiment may include a plurality of components for stably supporting the test board. Specifically, the test board 510*b* may include a main board 700, at least one support portion 710, and at least one fold portion 730.

In this case, the at least one support portion 710 may be a component for supporting the test board 510*b*. Specifically, the support portion 710 may be provided to be folded toward the ground with respect to the main board 700, thereby forming a bridge structure. In addition, the at least one support portion 710 may be integrally formed with the main board 700. Specifically, the at least one support portion 710 may be formed to extend along one side of the main board 700. The at least one support portion 710 may be formed by folding a portion extending along one side of the main board 700 toward the ground. For example, the test board 510*b* may include a first support portion 710*a* formed along a first side of the main board 700 and a second support portion 710*b* formed along a second side of the main board 700. In this case, the first support portion 710*a* and the second support portion 710*b* may be disposed in directions for facing each other. In addition, the first support portion 710*a* and the second support portion 710*b* may be provided to be symmetrical to each other. In this case, the first support portion 710*a* and the second support portion 710*b* may be folded toward the ground as shown by reference numeral 510*bb* in FIG. 6 to form a leg structure, and thus, the test board 510*b* may be supported stably.

In addition, the test board 510*b* may include the at least one fold portion 730 corresponding to the at least one support portion 710. In this case, the at least one fold portion 730 may be provided between the main board 700 and the at least one support portion 710. In addition, the at least one fold portion 730 may be integrally formed with the main board 700 and the at least one support portion 710. Specifically, the at least one fold portion 730 may refer to a guide structure for folding the at least one support portion 710 with respect to the main board 700. For example, the at least one fold portion 730 may have, but is not limited thereto, a curved shape (e.g., a protruding groove) formed extending along one side of the main board 700 and may have a shape for guiding the at least one support portion 710 to be easily folded by the user.

Referring to FIG. 7, the test board 510*b* according to the second embodiment may have a use form 510*ba* and a photographing form 510*bb* that are different from each other. In this case, the photographing form 510*bb* of the test board may refer to a form required when an image of the test board 510*b* is captured by the user terminal 130. Specifically, by folding the at least one support portion 710 in order to maintain the main board 700 horizontally with respect to the ground during photographing, the photographing form 510*bb* in which the leg structure is formed may be made. Of course, depending on the user, there may be cases in which an image is captured in the use form 510*ba*, but since the photographing form 510*bb* is intended as a form necessary at the time of imaging by design, for convenience of description, the photographing form is expressed as reference numeral 510*bb*.

Accordingly, the user may stably capture an image of the test board by the photographing form 510*bb* of the test board stably supported by the at least one support portion 710.

Below, the configuration of the test board, which is the basis of the board image analysis (photography analysis) function of the electronic device according to FIGS. 32 to 41, will be described.

Figure 8:
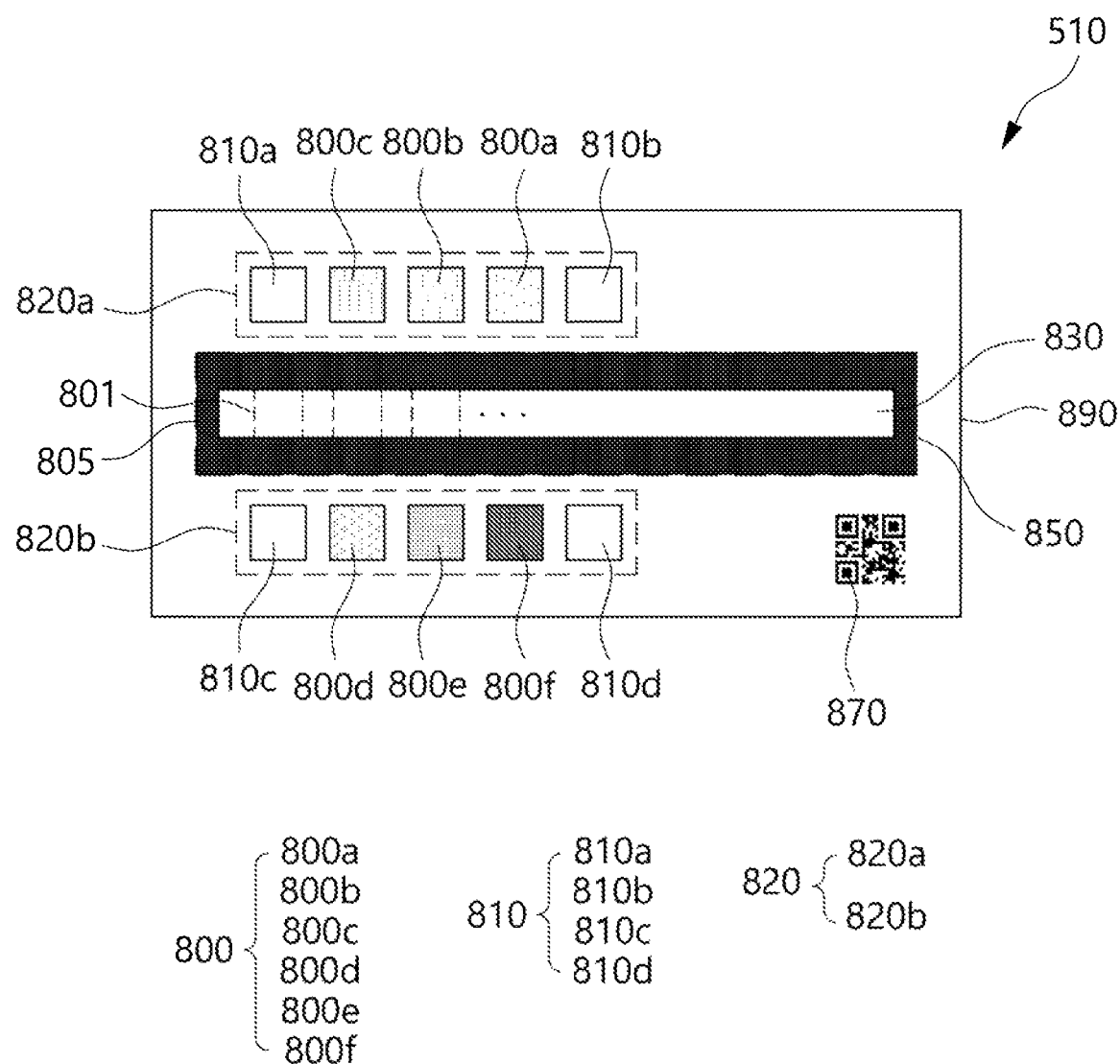
FIG. 8 is a diagram for describing in detail components related to image analysis of the test board, according to various embodiments.

FIG. 8 is a diagram for describing in detail components related to image analysis of the test board, according to various embodiments.

Referring to FIG. 8, the test board 510 according to various embodiments may include a plurality of regions each including different components used for image analysis. For example, the test board 510 may include a test paper region 805 on which at least one color mark including at least one reagent item is disposed and a correction paper region 820 including at least one reference mark for image analysis.

In this case, the test paper region 805 of the test board 510 may be a region provided so that at least one reagent item (or a color mark 801 including the reagent item) is disposed. Specifically, the test paper region 805 may include a main region 830 for disposing the at least one reagent item (or a color mark including the reagent item) and a peripheral region 850 provided to surround the main region 830.

As an example, the main region 830 of the test paper region 805 may correspond to the strip attachment region 511 of FIG. 5. In this case, a strip including at least one reagent item (or a color mark including the reagent item) may be attached to the main region 830 of the test board 510, and the main region 830 may be provided to attach the strip. As another example, the main region 830 of the test paper region 805 may include at least one reagent item (or a color mark including the reagent item). Specifically, the at least one reagent item (or the color mark including the reagent item) may be provided to be integrally attached to the main region 830 of the test paper region 805.

The peripheral region 850 included in the test board 510 according to various embodiments may be a region for providing a region of interest (ROI) during image analysis. In addition, the peripheral region 850 may be a region disposed to more clearly identify or distinguish color values (e.g., RGB) of the main region 830 during image analysis. In this case, the peripheral region 850 may be formed of a low-scale color (e.g., black), and in contrast, the main region 830 may be formed of a high-scale color. Accordingly, the position of at least one reagent item (or a color mark or strip including the reagent item) included in the main region 830 may be easily distinguished based on a color difference from the peripheral region 850. In addition, the peripheral region 850 may be formed to set an interval between at least one reagent item 801 included in the main region 830 and at least one reference mark 800 or 810 included in at least one reference mark region 820 to be described below.

At least one correction paper region 820 included in the test board 510 according to various embodiments may be positioned around the test paper region 805. Specifically, the at least one correction paper region 820 may be a region including at least one reference (or correction) mark 800 or 810 positioned to have a predetermined distance from one side of the test paper region 805.

The at least one correction paper region 820 may include a first correction paper region 820*a* and a second correction paper region 820*b* which are positioned on both sides of the test paper region 805. In this case, the first correction paper region 820*a* and the second correction paper region 820*b* may be provided symmetrically with the test paper region 805 interposed therebetween. In other words, at least one reference mark included in the first correction paper region 820*a* and at least one reference mark included in the second correction paper region 820*b* may be disposed symmetrically with each other. Of course, the disposition is not limited thereto, and at least one reference mark included in the first correction paper region 820*a* and at least one reference mark included in the second correction paper region 820*b* may be disposed asymmetrically with each other (for example, in a zigzag form).

At least one reference mark 800 or 810 included in at least one correction paper region 820 may include a first reference mark group 800 including at least one of the correction marks 800*a* to 800*f* and a second reference mark group 810 including at least one of the reference marks 810*a* to 810*d* (for a clear description of the invention, the terminology is adopted differently as the reference mark and correction mark, but this is for convenience of description, and the two terms may be used interchangeably).

In this case, at least one correction mark included in the first reference mark group 800 may be provided in gray scale, but is not limited thereto. In addition, at least one correction mark included in the first reference mark group 800 may be provided to have different scale values, but is not limited thereto, and may be provided to have the same scale, or such that some have the same scale and the rest have different scales. In addition, at least one correction mark included in the first reference mark group 800 may be provided so that the scale value is increased (or decreased) in a clockwise (or counterclockwise) direction. For example, referring to FIG. 8, the first reference mark group 800 may include, but is not limited to, a second correction mark 800*b*, a third correction mark 800*c*, a fourth correction mark 800*d* (in this case, the fourth correction mark 800*d* may be disposed to face the third correction mark), a fifth correction mark 800*e*, and a sixth correction mark 800*f*, which are sequentially disposed in a counterclockwise direction from the first correction mark 800*a*. In this case, the plurality of correction marks 800*a* to 800*f* may be provided such that a gray scale value decreases in the counterclockwise disposition order. In this case, a difference in scale values between two adjacent (or facing in the case of the third correction mark and the fourth correction mark) correction marks may be made to be constant. Alternatively, the difference in scale values between two adjacent (facing in the case of the third correction mark and the fourth correction mark) correction marks may be selected as an optimal value determined experimentally. The disposition of the plurality of correction marks included in the above-described first reference mark group 800 may be designed to effectively correct the color mark of the strip. A detailed description thereof will be continued with FIGS. 38 and 40.

In addition, at least one reference mark included in the second reference mark group 810 may be provided to have a standard white color, but is not limited thereto. Further, the second reference mark group 810 may be composed of reference marks positioned at the edge of the correction paper region 820. Specifically, the second reference mark group 810 may include a first reference mark 810*a* and a second reference mark 810*b* positioned at both ends of the first correction paper region 820*a*, and a third reference mark 810*c* and a fourth reference mark 810*d* positioned at both ends of the second correction paper region 820*b*. The disposition of the reference marks included in the aforementioned second reference mark group 810 may be designed to effectively compensate for shading effects (shading compensation) caused by lighting. A detailed description thereof will be continued with FIGS. 38 and 39.

The test board 510 according to various embodiments may include at least one QR code 870 including various information about the test board 510. In other words, the at least one QR code 870 may be provided to provide various information about the test board 510 to the user. At least one QR code 870 formed in the test board 510 may be applied to a generally used technology related to the QR code as it is.

In addition, the at least one QR code 870 may be a component for distinguishing a region of interest during image analysis, which will be described in detail below.

In addition, the test board 510 according to various embodiments may further include a visual landmark 890 for setting a boundary between the main board and a surrounding structure.

The components included in the above-described test board 510 may be formed by visually printing on the test board 510, and according to an embodiment, may be provided as separated objects in the form of being attached to the test board 510.

An image analysis operation performed in an electronic device (e.g., at least one processor) based on the test board according to the above configuration will be described in detail with reference to FIGS. 32 to 41.

Hereinafter, examples of the urine strip 120 according to various embodiments will be described.

Figure 9:
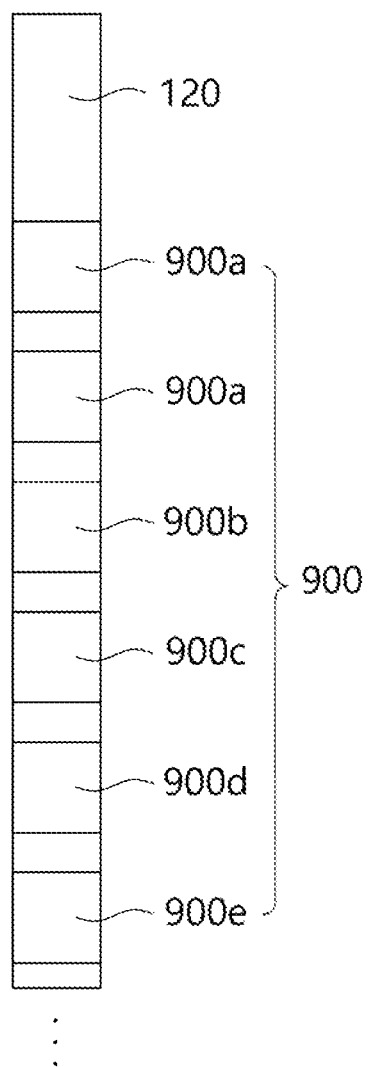
FIG. 9 is a diagram for describing an example of a configuration of a urine strip, according to various embodiments.

FIG. 9 is a diagram for describing an example of a configuration of the urine strip 120, according to various embodiments.

According to various embodiments, referring to FIG. 9, the urine strip 120 may be configured to include at least one reagent pad 900 (or reagent item, or reagent paper) and a base substrate 910 on which the reagent pad 900 is disposed, but is not limited to the example described and/or illustrated, and may include more components or include fewer components. For example, an adhesive layer (or adhesive member or adhesive material) may be disposed between the reagent pad 900 and the base substrate 910. The adhesive layer may be formed on the entire region of the base substrate 910, but may also be formed on a partial region of the base substrate 910 without being limited to the aforementioned example; for example, the adhesive layer may be formed only on a corresponding partial region of the base substrate 910 between the base substrate 910 and the reagent pad 900 (or a region that is larger or smaller than the partial region by a certain size).

According to various embodiments, the at least one reagent pad 900 may be provided so that its color is changed in response to a specific test item in urine among test items, such as occult blood, bilirubin, bilogen, ketone body, protein, nitrite, glucose, PH, specific gravity, and/or white blood cells, in order to test the specific item, but is not limited to the aforementioned examples, and may be provided to test more various test items. Based on the color change of the reagent pad 900 being visually recognized by the user (or medical personnel) and/or optical analysis based on the urine test application of the user terminal 130, a test on a specific item in urine responding to the reagent pad 900 may be conducted. In the following various embodiments, a case where the number of reagent pads 900*a*, 900*b*, 900*c*, 900*d*, and 900*e* is five will be described as an example, but the number described and/or shown is not limited, and unless otherwise stated, it is obvious to those skilled in the art that various numbers (e.g., ten) of reagent pads may be provided.

According to various embodiments, the base substrate 910 may be made of an eco-friendly and biodegradable material. For example, the biodegradable material is a material that is decomposed by the intervention of fungi and/or other microorganisms existing in nature, and may include the materials shown in [Table 1] below, but is not limited to the described examples.

TABLE 1

| Classification | Material type |
|---|---|
| Natural polymer | Sugar cane, bamboo, corn, starch, paper, pulp, lignin, natural fibers, lignin, forestry by-products, seaweed, industrial by-products (e.g., corn hull, wheat hull, soybean husk, rice hull), support fungi, etc. |
| Natural product synthetic system (or plastic) | PLA(poly latic acid), TPS(thermos plastics starch), AP(aliphatic polyester), CA(cellulose ecetate), CDA(cellulose di acetate) |
| Petrochemical synthetic system (or plastic) | PBS(Poly btylene buccinate), PCL(Poly capro lactone), PEU(Poly ester urethane), PGA (Ploy glycolic acid), PBAT(Poly butylene adipate-co-terephthalate) |
| Microbial synthetic system (or plastic) | PHA(Poly hydroxy alkanoic acid), PHB(Poly 3-hydroxybutyrate), PHV(Poly 3-hydroxy valerate), Pullulan |

Accordingly, the urine strip 120 that may be discarded by the user after the urine test has been completed (e.g., discarded in toilet water) is biodegraded, thereby reducing environmental pollution. In addition, among the biodegradable materials, a natural polymer may be a hydrophilic material, but a synthetic material (e.g., a natural product synthetic material) may be a hydrophobic material. Accordingly, inflow of urine into the base substrate 910 may be prevented, and folding of the base substrate 910 due to urine may be prevented.

Hereinafter, examples of the urine strip 120 according to various embodiments will be described.

Figure 10:
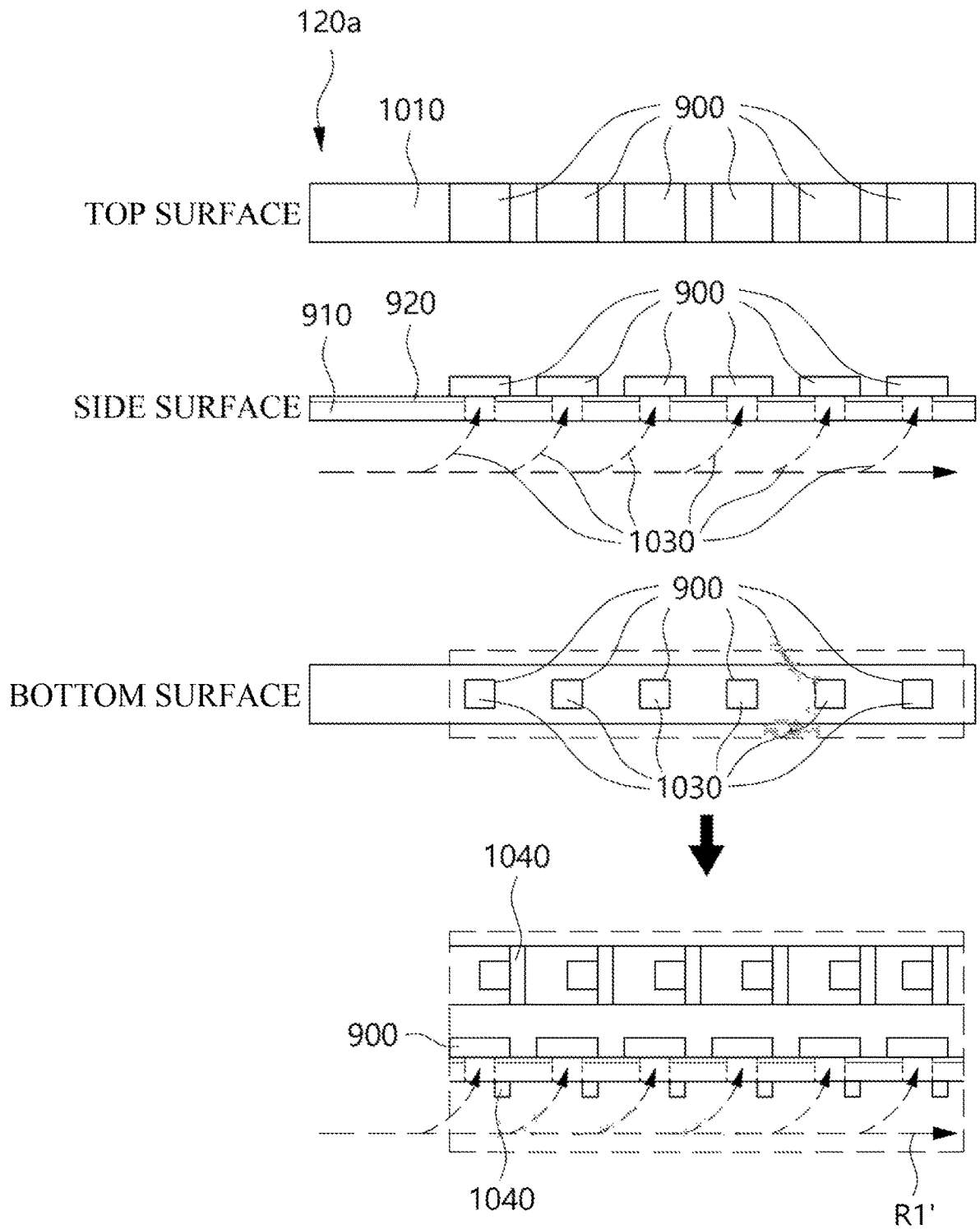
FIG. 10 is a diagram for describing an example of a urine strip, according to various embodiments.

FIG. 10 is a diagram for describing an example of a urine strip 120*a*, according to various embodiments.

According to various embodiments, referring to FIG. 10, the urine strip 120*a* may include at least one reagent pad 900, the base substrate 910, and an adhesive layer 920 between the at least one reagent pad 900 and the base substrate 910, and may include at least one hole 1030 passing through the base substrate 910 and the adhesive layer 920.

According to various embodiments, the at least one hole 1030 may be formed at a position of the base substrate 910 and the adhesive layer 920 corresponding to position of the at least one reagent pad 900. For example, positions of the center point of the at least one reagent pad 900 and the center point of the at least one hole 1030 may correspond to each other. Accordingly, as observed in a direction perpendicular to the bottom surface of the urine strip 120a, the at least one reagent pad 900 may be observed through the at least one hole 1030. As will be described later, when the urine test is performed in the state in which the urine strip 120a is mounted in the gutter of the user terminal 130 provided (or mounted) in the toilet, urine passes may be smoothly guided through the at least one hole 1030 to the reagent pad 900, and thus the urine test may proceed smoothly. The disposition is performed so that, in a portion of the gutter of the electronic device 140, the top surface of the urine strip 120a (e.g., the surface on which the reagent pad 900 is disposed) faces the bottom of the toilet, and the bottom surface of the urine strip 120a (e.g., the surface opposite to the surface on which the reagent pad 900 is disposed) faces the top of the toilet, and in this case, as shown in FIG. 10, the urine R1 guided along the gutter may be transferred to the corresponding reagent pad 900 through the at least one hole 1030, which may make the reaction between the reagent pad 900 and the urine R1 smooth.

According to various embodiments, as the urine strip 120a is observed in a direction perpendicular to the top and/or bottom surfaces, the shape of the at least one hole 1030 may be made in a square shape as shown, but the shape is not limited to the example described and/or illustrated and may be made in various types of shapes such as a circular shape and a triangular shape.

According to various embodiments, the width (or area, or size) of the at least one hole 1030 may be formed to be smaller than the corresponding width (or area, or size) of the reagent pad 900, but the width is not limited to the example described and/or illustrated. In addition, for example, the width of the at least one hole 1030 in each of the base substrate 910 and the adhesive layer 920 may be formed to be the same, but the widths are not limited to the example described and/or illustrated and may be different from each other.

According to various embodiments, the urine strip 120a may be provided to further include at least one protruding portion 1040, but is not limited to the example described and/or illustrated. Referring to FIG. 10, the at least one protruding portion 1040 may be formed to protrude downward from the urine strip 120a in a region adjacent to the at least one hole 1030 on the bottom surface of the urine strip 120a. The at least one protruding portion 1040 may be formed in a region corresponding to a specific direction among regions adjacent to the region where the at least one hole 1030 of the base substrate 910 of the urine strip 120a is formed. For example, referring to FIG. 10, among regions adjacent to the hole 1030 on the bottom surface of the base substrate 910, the protruding portion 1040 may be formed in a region corresponding to a direction in which urine R1' flows.

According to various embodiments, the height of the at least one protruding portion 1040 may be formed to be smaller than the thickness of the base substrate 910, but is not limited to the example described and/or illustrated.

Figure 11:
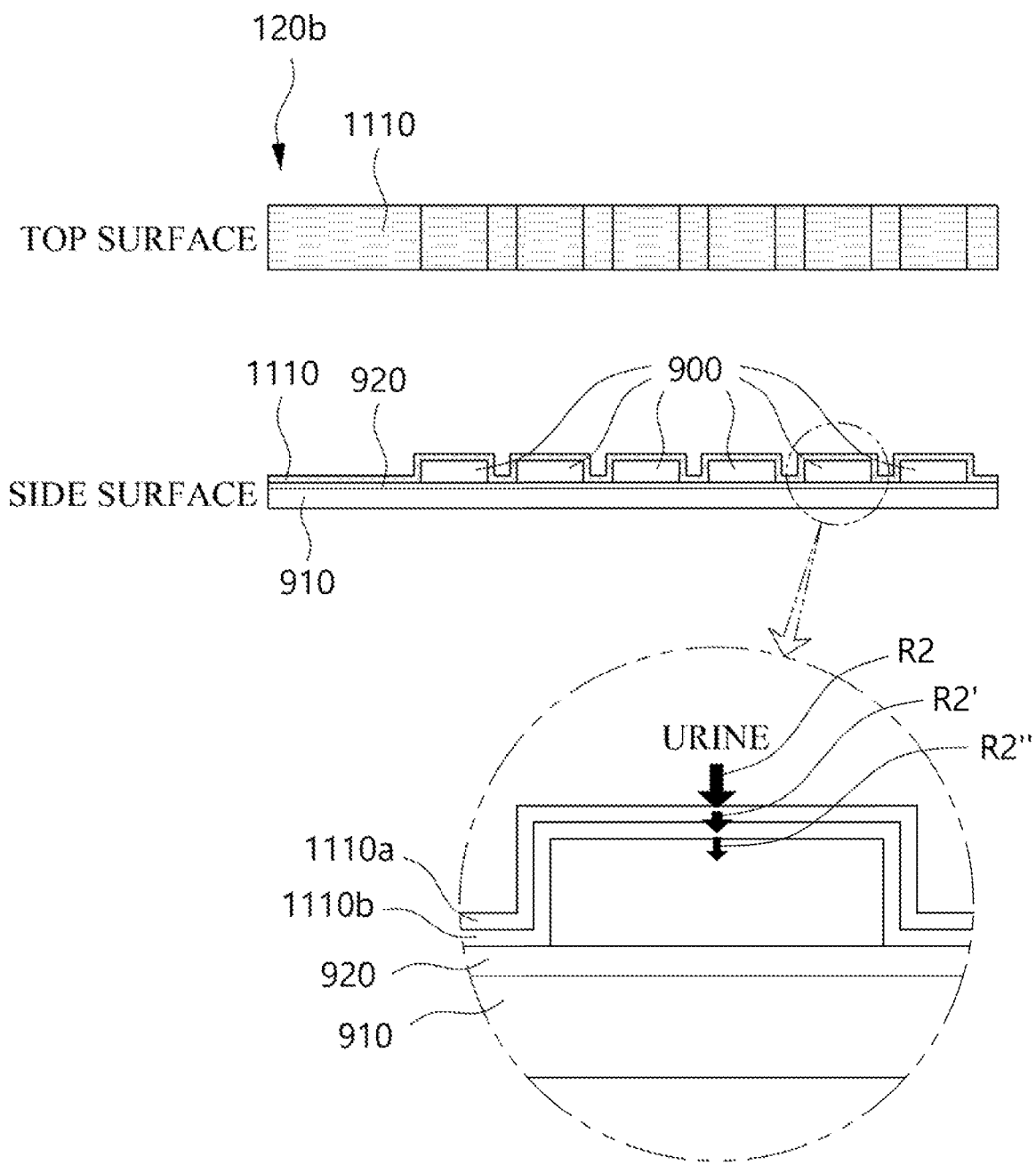
FIG. 11 is a diagram for describing another example of a urine strip, according to various embodiments.

FIG. 11 is a diagram for describing another example of a urine strip 120b, according to various embodiments. FIG. 12 is a diagram for describing another example of the urine strip 120b, according to various embodiments.

According to various embodiments, referring to FIG. 11, the urine strip 120b may include at least one reagent pad 900, the base substrate 910, an adhesive layer 920 between the at least one reagent pad 900 and the base substrate 910, and at least one filter layer 1110.

According to various embodiments, at least one filter layer 1110 may be provided to prevent substances that inhibit the urine test from being transferred to the reagent pad 900. For example, the at least one filter layer 1110 may include at least one of a first filter layer 1110a for preventing substances in the bathroom such as moisture (or water vapor) from being transferred to the reagent pad 900, or a second filter layer 1110b for preventing substances in the urine from being transferred to the reagent pad 900. Referring to FIG. 11, the at least one filter layer 1110 may be formed to include the first filter layer 1110a and the second filter layer 1110b, but is not limited to the example described and/or illustrated, and may be formed to include a single filter layer (e.g., the first filter layer 1110a or the second filter layer 1110b). The at least one filter layer is a biodegradable hydrophilic material, and for example, the material of the filter layer (e.g., the first filter layer 1110a or the second filter layer 1110b) may include at least one of corn starch (poly vinyl alcohol (PVA), poly latic acid, polycaprolactone), cellulose (sodium carboxymethyl cellulose), polyhydroxyalkanoates (PHAs), polybutylene adipate terephthalate (PBAT), polycaprolactone (PCL), or polybutylene succinate (PBS). Accordingly, urine permeated into the filter layer may be diffused in a horizontal direction along the filter layer and transferred to the reagent pad 900.

According to various embodiments, the first filter layer 1110a may be formed to include at least one pore hole (not shown) having a first size for blocking (filtering out) moisture at normal times, and allowing fluid such as urine to be smoothly transferred in the direction toward the reagent pad 900 when the urine enters and allowing the urine to be applied in a horizontal direction in the first filter layer 111a. The pore hole (not shown) is a hole that simulates a pore structure, and may protect the reagent pad 900 from humidity at normal times, but may allow liquid such as urine to be transferred to the reagent pad 900 rapidly and quickly when the urine comes in contact with it. The diameter of the pore hole 110 may be formed to be 1.0 mm or less as a first size. For example, the diameter of the pore hole 110 may be formed to be 0.5 mm, 0.65 mm or 0.75 mm. By forming the pore hole 110 as described above, it is possible to maintain a reagent paper 300 for a long time without discoloration even when the reagent paper 300 is left for a long time in a bathroom, which is a high-humidity environment where the urine test strip is mainly used.

Accordingly, the urine strip 120b may be prevented from being contaminated by substances (e.g., steam) in the bathroom when the urine strip 120b is provided in the bathroom.

According to various embodiments, the second filter layer 1110b may be formed to include at least one pore (not shown) (or hole) having a second size different from the first size of the pore hole of the first filter layer 1110a described above so as to filter out substances (e.g., contaminants) different from the test items in the urine, and so as to allow the urine excluding the contaminants to be smoothly transferred toward the reagent pad 900. For example, the contaminant may refer to a substance that is possible to be contained in urine when the urine test is performed. For example, the second size may be formed to be different from the aforementioned first size, but is not limited to the described example and may be formed to correspond to the aforementioned first size. The second filter layer 1110b may be formed in a nano fiber structure and/or a mesh structure to include at least one pore having the second size described above.

According to various embodiments, when at least one filter layer 1110 is formed to include both the first filter layer 1110a and the second filter layer 1110b, the second filter layer 1110b may be disposed on the base substrate 910 and the reagent pad 900, and the first filter layer 1110a may be disposed on the second filter layer 1110b. Accordingly, referring to FIG. 11, when urine R2 passes through the first filter layer 1110a, substances (e.g., water vapor) in the bathroom may be first filtered out (R2') and, when the urine R2 passes through the second filter layer 1110b, substances in the urine (e.g., contaminants) may be filtered out (R2").

According to various embodiments, referring to FIG. 12, the first filter layer 1110a may be formed to be removable (or peelable) from the second filter layer 1110b. For example, as shown in (a) of FIG. 12, an adhesive layer 1210a may be formed only on at least a portion between the first filter layer 1110a and the second filter layer 1110b, so that the first filter layer 1110a may be separated from the second filter layer 1110b by an external force (e.g., by force of hand for removing) from the second filter layer 1110b. For example, the region where the adhesive layer 1210a is not formed between the first filter layer 1110a and the second filter layer 1110b is a corner region of the urine strip 120b, for example, may be the end region of the urine strip 120 as shown in FIG. 12, but the region is not limited to the example described and/or illustrated. In addition, for example, as shown in (b) of FIG. 12, the first filter layer 1110a may be formed to have a larger size than that of the second filter layer 1110b, so that a portion of the first filter layer 1110a that is not positioned on the second filter layer 1110b and the first filter layer 1110a may be separated from the second filter layer 1110b by external force (e.g., by force of hand for removing). Accordingly, by using the urine strip 120b from which the first filter layer 1110a is removed for the urine test, the inflow of urine into the reagent pad 900 may be smoother and as a result, an effect of filtering out substances in the urine by the second filter layer 1110b may be produced.

Figure 13:
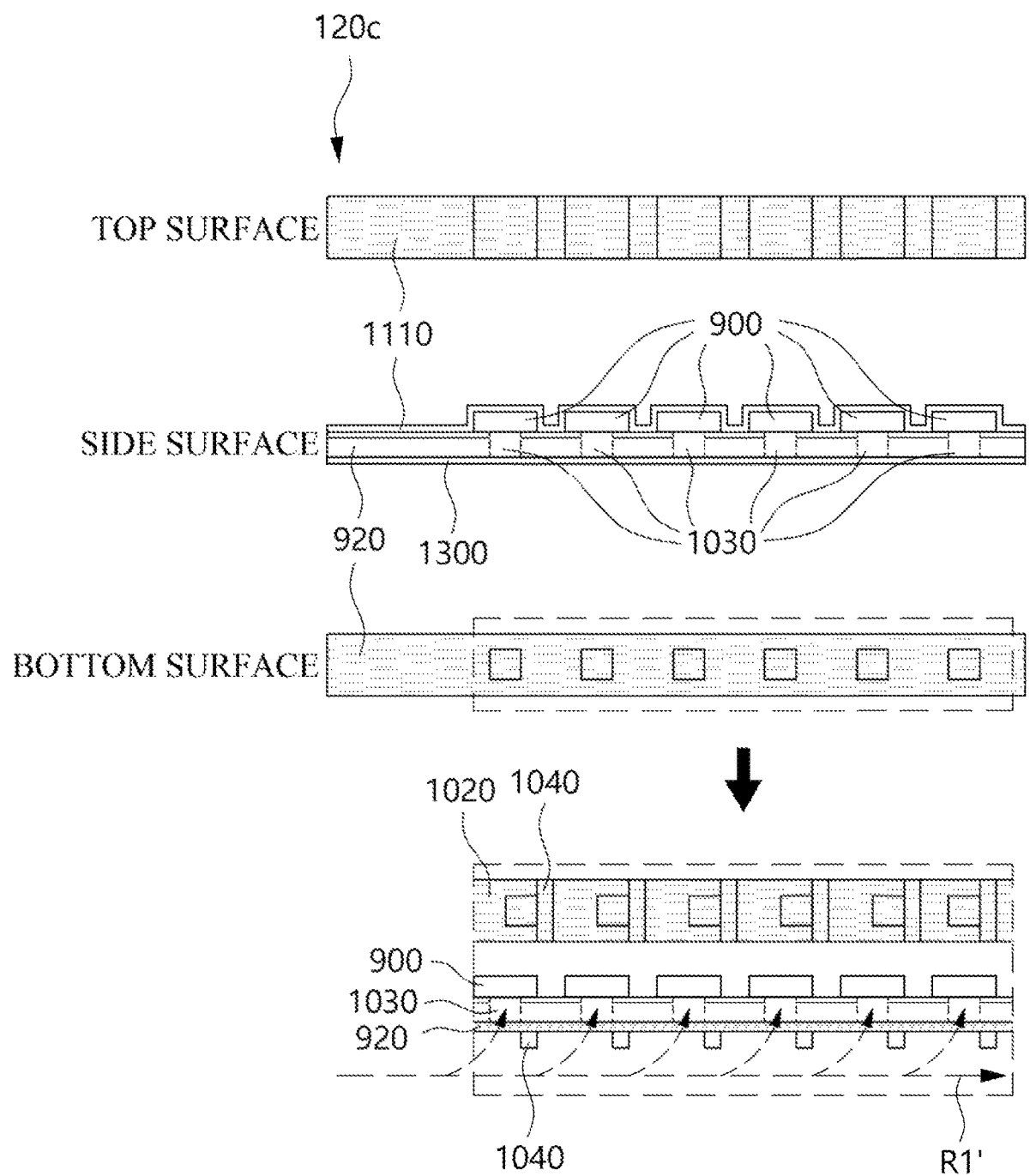
FIG. 13 is a diagram for describing another example of a urine strip, according to various embodiments.

FIG. 13 is a diagram for describing another example of a urine strip 120c, according to various embodiments.

According to various embodiments, referring to FIG. 13, the urine strip 120c may include at least one reagent pad 900, the base substrate 910, an adhesive layer 920 between the at least one reagent pad 900 and the base substrate 910, at least one first filter layer 1300a, at least one second filter 1300b, and at least one hole 1030 passing through the base substrate 910 and the adhesive layer 920. In addition, the bottom surface of the urine strip 120c may be formed to further include at least one protruding portion 1040 described above.

According to various embodiments, the at least one first filter layer 1300a and the at least one second filter layer 1300b may be formed like the filter layer 1110 described above, and thus a detailed description thereof will be omitted.

When the urine test is performed in the state in which the urine strip 120a is mounted in the gutter of the electronic device 140 provided (or mounted) in the toilet, urine may be smoothly guided to the reagent pad 900 through at least one hole 1030, and substances that inhibit the urine test may be filtered out by the second filter layer 1300b on the bottom surface, and thus more accurate urine test may be performed.

Hereinafter, examples of the configuration of the user terminal 130 and the application executed in the user terminal 130 according to various embodiments will be described.

Figure 14:
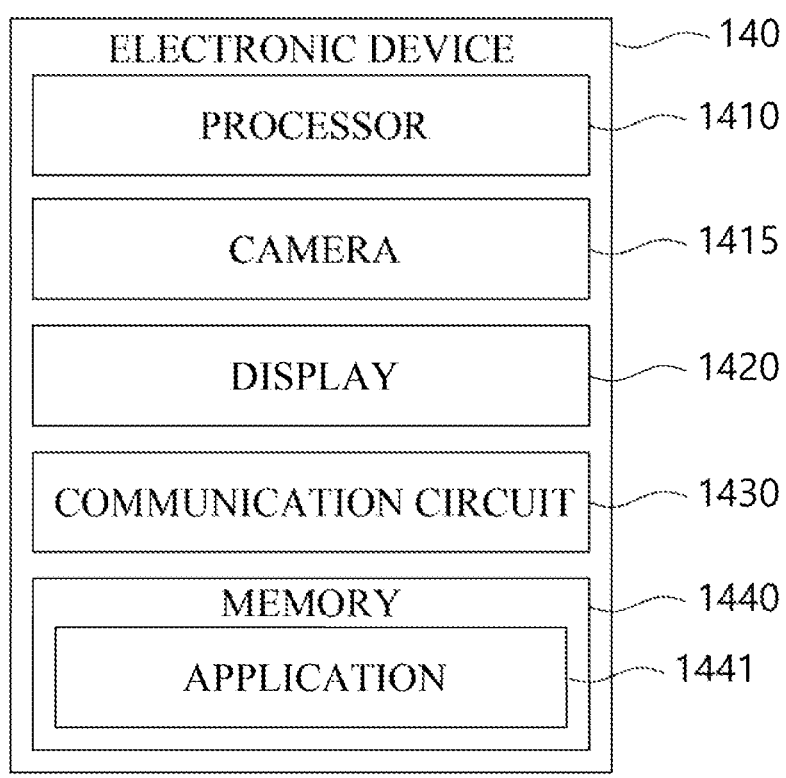
FIG. 14 is a diagram for describing an example of a configuration of a user terminal, according to various embodiments.

FIG. 14 is a diagram for describing an example of a configuration of the user terminal 130, according to various embodiments. Meanwhile, the configuration of the server 150 may be implemented in the same way as the configuration of the user terminal 130 described below, and thus the repeated description thereof will be omitted.

Referring to FIG. 14, according to various embodiments, the user terminal 130 may include a processor 1410, a display 1420, a communication circuit 1430, and a memory 1440 for storing an application 1441 (or program, computer code, or instructions).

According to various embodiments, the processor 1410 may include at least one processor, at least some of which are implemented to provide different functions. The processor 1410 may execute, for example, software (e.g., a program) to control at least one other component (e.g., a hardware or software component) of the user terminal 130 coupled with the processor 1240, and may perform various data processing or computation. According to an embodiment, as at least part of the data processing or computation, the processor 1410 may store a command or data received from another component (e.g., a sensor (not shown) or the communication circuit 1430) in the memory 1411 (volatile memory), process the command or the data stored in the volatile memory, and store resulting data in a non-volatile memory. According to an embodiment, the processor 1410 may include a main processor (e.g., a central processing unit (CPU) or an application processor (AP)), or an auxiliary processor (e.g., a graphics processing unit (GPU), a neural processing unit (NPU), an image signal processor (ISP), a sensor hub processor, or a communication processor (CP)) that is operable independently from, or in conjunction with the main processor. For example, when the user terminal 130 includes a main processor and an auxiliary processor, the auxiliary processor may be configured to use less power than the main processor or to be specialized for a specified function. The auxiliary processor may be constructed as separate from, or as part of the main processor. The auxiliary processor may control at least some of functions or states related to at least one component (e.g., the display 1420 or the communication circuit 1430) among the components of the user terminal 130, instead of the main processor while the main processor is in an inactive (e.g., sleep) state, or together with the main processor while the main processor is in an active state (e.g., executing an application), for example. According to an embodiment, an auxiliary processor (e.g., an image signal processor or a communication processor) may be provided as part of another component (e.g., a camera 1415 or the communication circuit 1430) functionally related to the auxiliary processor. According to an embodiment, the auxiliary processor (e.g., a neural network processing device) may include a hardware structure specialized for processing an artificial intelligence model. The artificial intelligence model may be generated through machine learning. Such learning may be performed, for example, in the user terminal 130 itself on which an artificial intelligence model is performed, or may be performed through a separate server (e.g., the server 150). The learning algorithm may include, for example, supervised learning, unsupervised learning, semi-supervised learning, or reinforcement learning, but is not limited to the above-mentioned examples. The artificial intelligence model may include a plurality of artificial neural network layers. The artificial neural network may be one of a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-networks, or a combination of two or more of the above networks, but is not limited to the above examples. The artificial intelligence model may additionally or alternatively include a software structure, in addition to the hardware structure. Meanwhile, operations of the user terminal 130 described below may be understood as an operation of the processor 1410.

According to various embodiments, the display 1420 may visually provide information to the outside (e.g., the user) of the user terminal 130. The display 1420 may include, for example, a display, a hologram device, or a projector and control circuitry to control a corresponding one of the display, hologram device, and projector. According to an embodiment, the display 1420 may include a touch sensor adapted to detect a touch, or a pressure sensor adapted to measure the strength of force incurred by the touch.

According to various embodiments, the communication circuit 1430 may support establishing a direct (e.g., wired) communication channel or a wireless communication channel between the user terminal 130 and the external electronic device (e.g., the server 150 of FIG. 1) and performing communication via the established communication channel. The communication circuit 1407 may include one or more communication processors that are operable independently from the processor 1410 (e.g., the application processor (AP)) and support a direct (e.g., wired) communication or a wireless communication. According to an embodiment, the communication circuit 1407 may include a wireless communication module (e.g., a cellular communication module, a short-range wireless communication module, or a global navigation satellite system (GNSS) communication module) or a wired communication module (e.g., a local area network (LAN) communication module or a power line communication (PLC) module). A corresponding one of these communication modules may communicate with an external electronic device (e.g., the server 150) via a first network (e.g., a short-range communication network, such as Bluetooth™, wireless-fidelity (Wi-Fi) direct, or infrared data association (IrDA)) or a second network (e.g., a long-range communication network, such as a legacy cellular network, a 5G network, a next-generation communication network, the Internet, or a computer network (e.g., LAN or wide area network (WAN)). These various types of communication modules may be integrated into a single component (e.g., a single chip), or may be implemented as multi components (e.g., multi chips) separate from each other. The wireless communication module may identify or authenticate the user terminal 130 in a communication network, such as the first network or the second network, using subscriber information (e.g., international mobile subscriber identity (IMSI)) stored in a subscriber identification module. The wireless communication module may support a 5G network after a 4G network and a next-generation communication technology, for example, a new radio access technology (NR). NR access technology may support a high-speed transmission of high-capacity data (enhanced mobile broadband (eMBB)), minimization of terminal power and access to multiple terminals (massive machine type communications (mMTC)), or high reliability and low latency (ultra-reliable and low-latency communications (URLLC)). The wireless communication module may support a high frequency band (e.g., mmWave band) to achieve a high data rate, for example. The wireless communication module may support various techniques for securing performance in a high frequency band, for example, beamforming, massive multiple-input and multiple-output (MIMO), full dimensional MIMO (FD-MIMO), array antenna, analog beamforming, or large-scale antenna. The wireless communication module may support various requirements defined in the user terminal 130, an external electronic device (e.g., the server 150), or a network system (e.g., the second network). According to an embodiment, the wireless communication module may support a peak data rate (e.g., 20 Gbps or more) for achieving the eMBB, loss coverage (e.g., 164 dB or less) for achieving the mMTC, or U-plane latency (e.g., 0.5 ms or less each for downlink (DL) and uplink (UL), or 1 ms or less for the round trip) for achieving the URLLC.

According to various embodiments, the memory 1440 may store various data to be used by at least one component (e.g., the processor 1410) of the user terminal 130. The various data may include, for example, software (e.g., the program) and input data or output data for a command related thereto. The memory 1440 may include a volatile memory or a non-volatile memory. The memory 1440 may be implemented to store an operating system, middleware or applications, and/or the aforementioned artificial intelligence model.

According to various embodiments, the application 1441 may be built to provide a function for the urine test. For example, the application 1441 may be built to provide a function of receiving a urine test result by the user terminal 130 (e.g., the processor 1410) photographing the urine strip 120 and providing it to the server 150, or receiving the urine test result by the user terminal 130 providing a color value received from the electronic device 140 to the server 150. In addition to the examples described above, the operation of the user terminal 130 based on the application 1441 will be described below.

Hereinafter, an example of operations of the user terminal 130 according to various embodiments will be described.

According to various embodiments, the urine test system 1 may acquire information for acquiring different types of result information about the urine test, convert the different types of urine test information into one piece of result information about the urine test (e.g., a graphic object representing the urine test result), and provide the converted result information about the urine test to an execution screen. Accordingly, even if the user using the urine test system 1 performs the urine test in various ways, such as photographing the urine strip 120 on the board 110 and using the electronic device 140, the result information about the urine test may be managed in an integrated manner.

Figure 15:
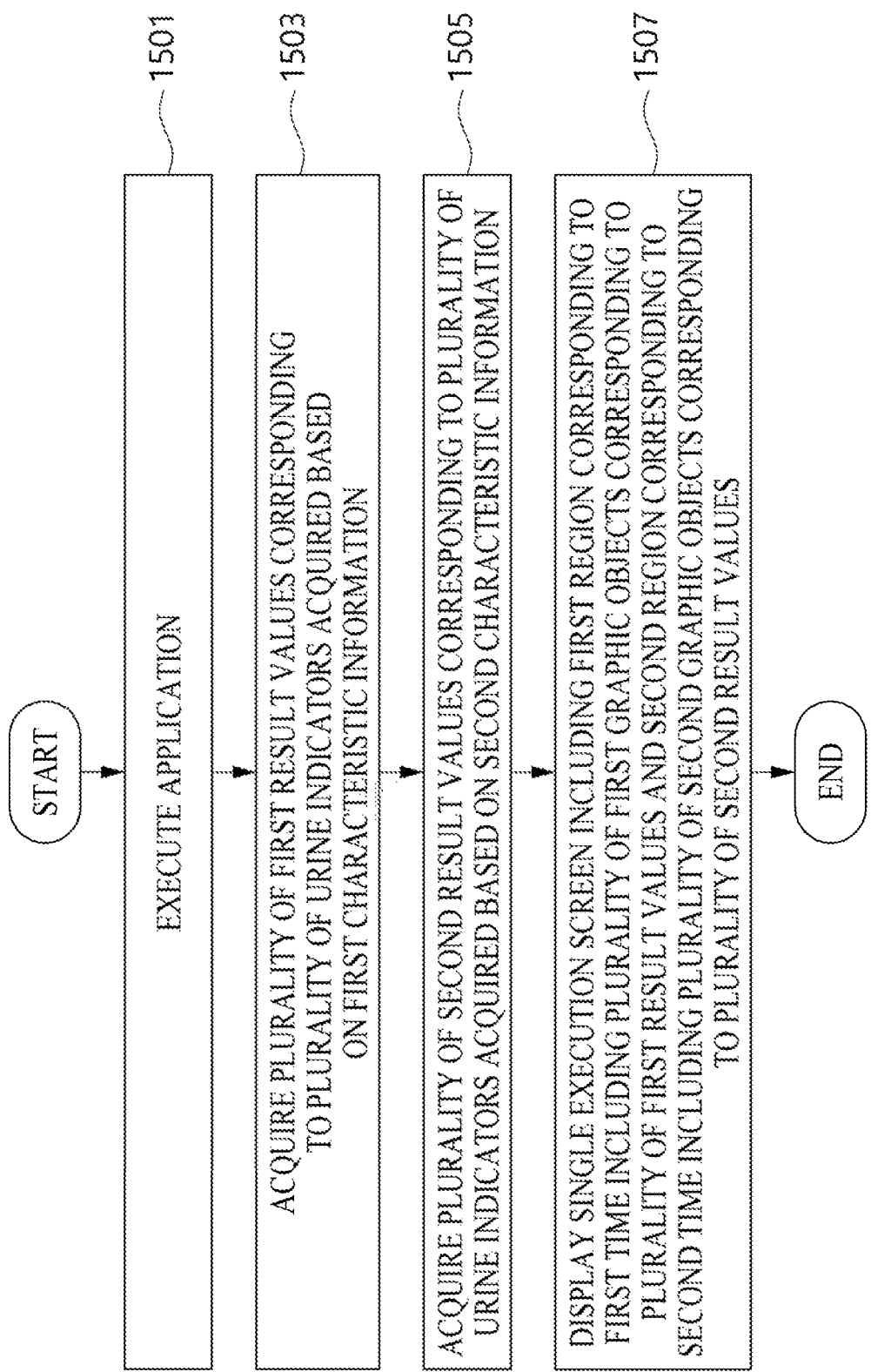
FIG. 15 is a flowchart illustrating operations of a user terminal, according to various embodiments.

FIG. 15 is a flowchart illustrating operations of the user terminal 130, according to various embodiments. According to various embodiments, the operations shown in FIG. 15 are not limited to the order shown and may be performed in various orders. Further, according to various embodiments, at least one operation, but more than the operations shown in FIG. 15 or less than those shown in FIG. 15 may be performed. Hereinafter, a further description will be given with reference to FIGS. 16 to 18.

Figure 17:
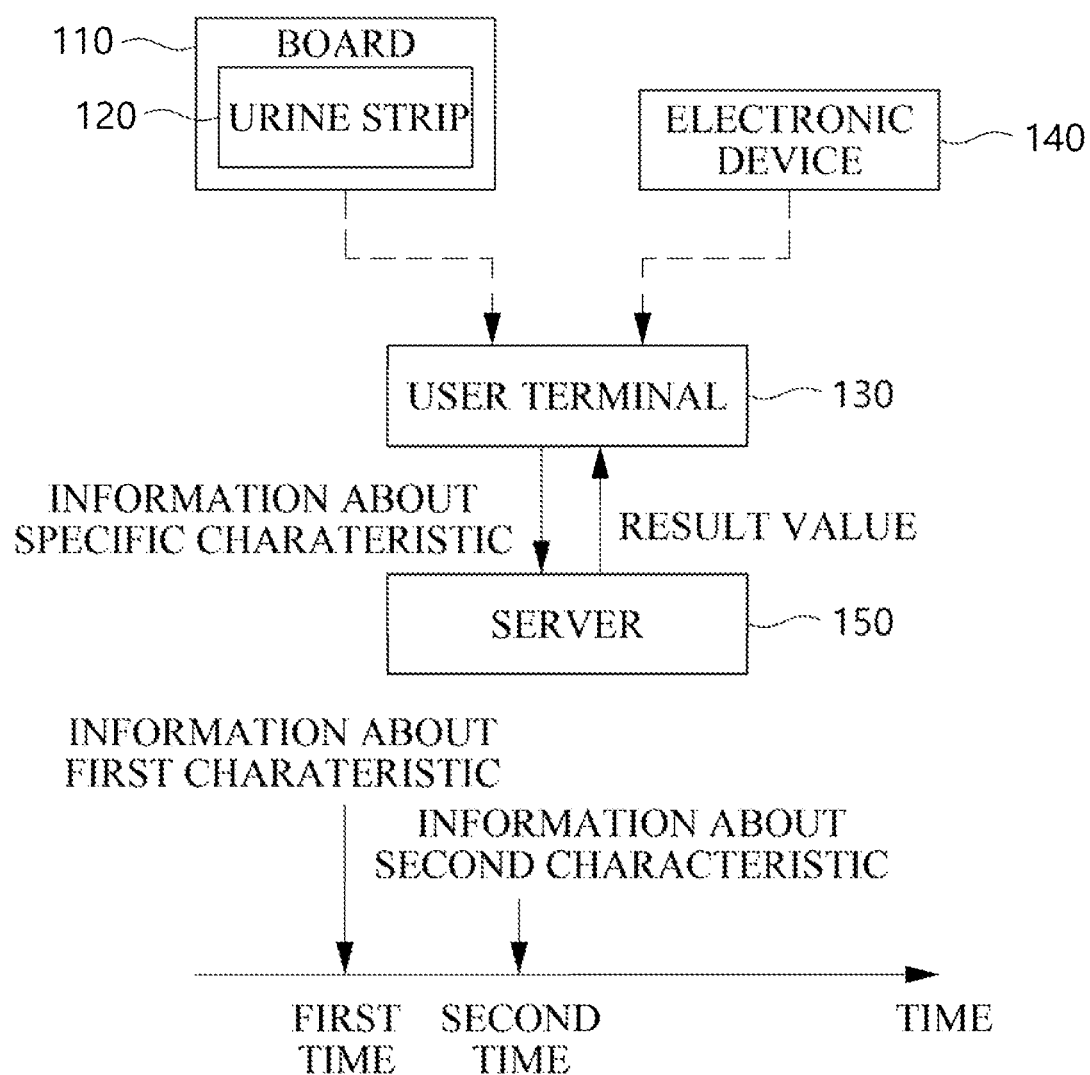
FIG. 17 is a diagram for describing an example of an operation of displaying urine test information based on an application of a user terminal, according to various embodiments.
Figure 18:
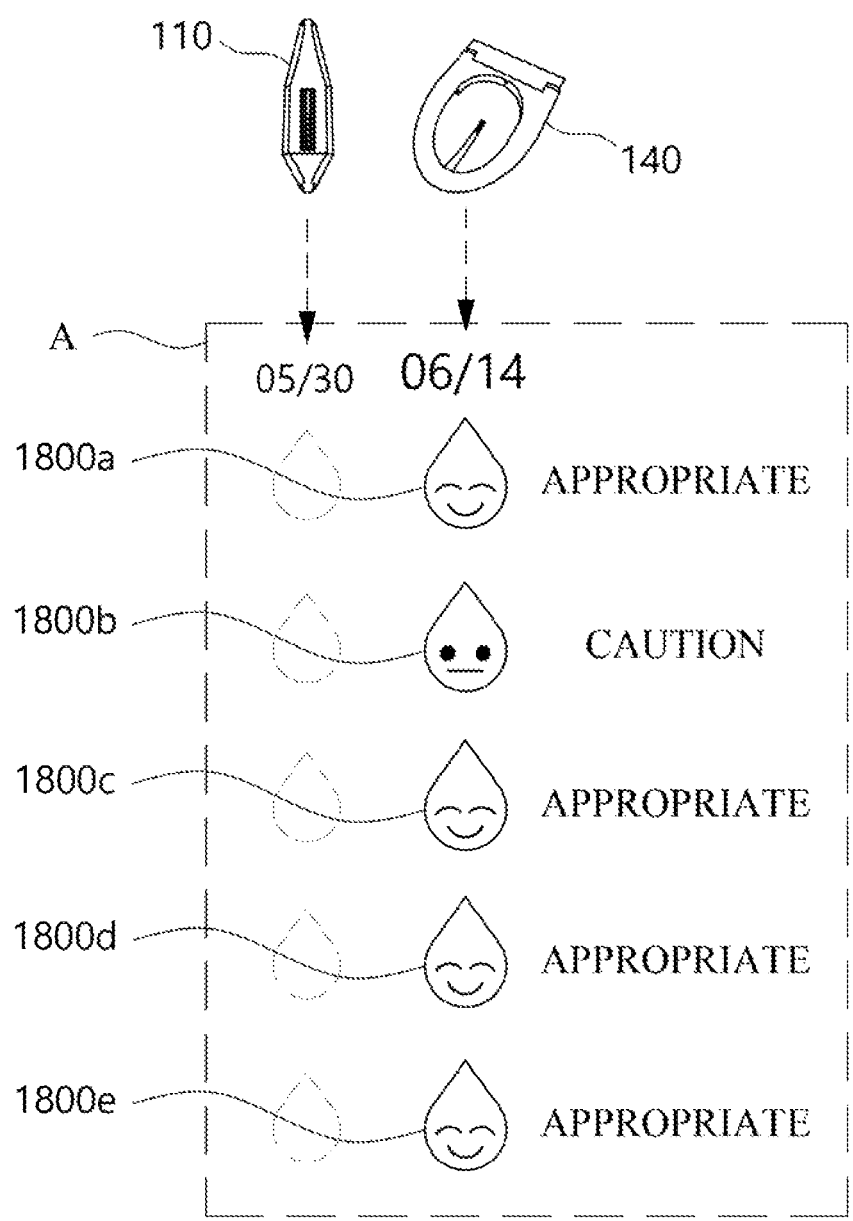
FIG. 18 is a diagram for describing an example of an execution screen of an application including comprehensive urine test information (e.g., a urine test information based on photographing of the urine strip, and urine test information based on an electronic device) of a user terminal, according to various embodiments.

FIG. 16a is a diagram for describing examples of execution screens of the application 1441, according to various embodiments. FIG. 16b is a diagram for describing examples of execution screens of an application for user add, according to various embodiments. FIG. 17 is a diagram for describing an example of an operation of displaying urine test information based on the application 1441 of the user terminal 130, according to various embodiments. FIG. 18 is a diagram for describing an example of an execution screen of the application 1441 including comprehensive urine test information (e.g., urine test information based on photographing of the urine strip 120, and urine test information based on the user terminal 130) of the user terminal 130, according to various embodiments.

According to various embodiments, the user terminal 130 (e.g., the processor 1410) may execute an application (e.g., the application 1441 of FIG. 14) in operation 1501. For example, referring to FIG. 16a, the user terminal 130 may display a first execution screen 1600 of the application 1441 including information associated with the urine test result of the user. The execution screen 1600 may be a screen initially displayed based on the application 1441 (e.g., a main screen), but is not limited thereto. The first execution screen 1600 may include a first region 1601 including a history of a score corresponding to the urine test result (e.g., a graph representing scores per date), a second region 1603 including an average score corresponding to the urine test result, and a third region 1605 including a plurality of objects per date for displaying the urine test result for a plurality of urine indicators (e.g., occult blood, protein, glucose, pH, ketone). In this case, the user terminal 130 may display an execution screen including other information based on the user input identified on the first execution screen 1600. For example, the user terminal 130 may display the first execution screen 1600 by converting to a fourth region 1607 including health information associated with other users (e.g., weight, water intake, and the number of times of urination) based on the user input (e.g., swipe input, drag input) in the downward direction identified on the first execution screen 1600. Further, for example, the user terminal 130 may display the second execution screen 1610 adapted to provide a graph representing a history of a score for each of a plurality of urine indicators, based on the user input for selecting a graphic object (e.g., a graph representing scores per date) representing the history of the score corresponding to the urine test result of the first region 1601. The second execution screen 1610 may be implemented to provide a graph 1613 of a comprehensive average score, a graph 1621 of a comprehensive average score for each of a plurality of urine indicators selected from a menu 1620, and health information 1623 associated therewith.

According to various embodiments, the user terminal 130 (e.g., the processor 1410) may manage information related to urine test results for a plurality of users and display the information. For example, referring to FIG. 16B, the user terminal 130 (e.g., the processor 1410) provides a function of adding at least two or more users 1612b and 16331b, and outputs a urine test result for each of the added users. An operation of storing information related to and providing an execution screen 1600b for a urine test result may be performed. In an embodiment, the user terminal 130 (e.g., the processor 1410) may display an execution screen of an application 1441 including information related to a urine test result associated with a specific user (e.g., the first user 1612b). When an icon 1607b for calling an execution screen 1610b providing account information is selected on 1600b, information on a user (eg, a first user 1612b) registered in a specific area 1611b may be displayed. It is possible to provide an execution screen 1610b including At this time, the user terminal 130 (eg, the processor 1410), when the icon 1613b for adding a user is selected, may display an execution screen 1620b for registering an additional user and inputting information on a user to be additionally registered. In this case, the additionally registerable users may include not only people (e.g., family members) associated with a specific user (e.g., the first user 1612b), but also pets such as pet dogs and pet cats. When an additional user (e.g., pet dog 1631b) is registered through the execution screen 1620b, the user terminal 130 (e.g., the processor 1410) may provide information about the registered user 1631b on a specific area. The user terminal 130 (e.g., the processor 1410) may display an execution screen 1610b by highlighting an object representing the user selected from the plurality of users 1612b and 1631b, and may display an execution screen for the urine test result (1600b, 1640b), it may be implemented to provide urine test result information for the selected user. Meanwhile, the user terminal 130 (e.g., the processor 1410) is not limited to the described and/or illustrated examples, and although not mentioned, the user terminal 130 (e.g., the processor 1410) not only provides urine test result information for the changed user, but also it is obvious to those skilled in the art that various operations (e.g., provision of health information, etc.) described in may be provided.

According to various embodiments, the user terminal 130 (e.g., the processor 1410) may acquire a plurality of first result values corresponding to a plurality of urine indicators acquired based on information about a first characteristic in operation 1503, and acquire a plurality of second result values corresponding to a plurality of urine indicators acquired based on information about a second characteristic in operation 1505. For example, referring to FIG. 17, the user terminal 130 may acquire information about different characteristics (e.g., the information about the first characteristic and the information about the second characteristic) generated from the performance of the urine test at different times (e.g., first time and second time). As an example, when the user performs the urine test by using the urine strip 120 on the board 110, at the first time, the user terminal 130 may acquire an image of the urine strip 120 based on the application 1441. As another example, when the user performs the urine test by using the electronic device 140 at another time, the user terminal 130 may receive data for the urine test from the electronic device 140 at the second time. The user terminal 130 may transmit information about different characteristics (e.g., the information about the first characteristic and the information about the second characteristic) to the server 150, and the server 150 may transmit information on the urine test result to the user terminal 130 based on analyzing the information about the different characteristics (e.g., the information about the first characteristic and the information about the second characteristic) based on each different analysis algorithm (which will be described later). The result information about the urine test may include respective values (or states) for a plurality of urine indicators, and/or information about a graphic object for representing respective values (or states) for the plurality of urine indicators. Meanwhile, the user terminal 130 is not limited to the examples described and/or illustrated, and may be implemented to, without performing a cooperative operation with the server 150, analyze information about different characteristics (e.g., the information about the first characteristic and the information about the second characteristic) on its own and acquire the result information about the urine test.

According to various embodiments, the information about the first characteristic and the information about the second characteristic may refer to information of different formats (or types, or types). In an embodiment, the information about the first characteristic may refer to image type information (e.g., pixel data), and the information about the second characteristic may refer to a type of data (e.g., color data associated with the urine strip 120) to be identified by a sensor (not shown) for the urine test of the electronic device 140. In another embodiment, the information about the first characteristic may refer to an image acquired by the user terminal 130, and the information about the second characteristic may refer to a communication signal including data acquired by a sensor (not shown) of the electronic device 140 that is received through the communication circuit 1430.

According to various embodiments, in operation 1507, the user terminal 130 (e.g., the processor 1410) may display a single execution screen including a first region corresponding to the first time including a plurality of first graphic objects corresponding to the plurality of first result values and a second region corresponding to the second time including a plurality of second graphic objects corresponding to the plurality of second result values. As shown in FIG. 18, the user terminal 130 may display an execution screen including a plurality of objects 1800a, 1800b, 1800c, 1800d, and 1800e for representing respective values for the plurality of urine indicators (or state) based on the acquired result information about the urine test. Each of the plurality of graphic objects 1800a, 1800b, 1800c, 1800d, and 1800e may represent result information about the urine test acquired by urine tests performed in different ways. Accordingly, even if the user performs the urine test in various ways, such as photographing the urine strip 120 on the board 110 and using the electronic device 140, the result information about the urine test may be managed in an integrated manner.

According to various embodiments, although not shown, a graphic object (not shown) (e.g., an object representing the board 110 or an object representing the electronic device 140) representing a urine test method corresponding to the plurality of graphic objects 1800a, 1800b, 1800c, 1800d, and 1800e may be further provided on the execution screen 1600.

According to various embodiments, although not shown, in the case of the plurality of graphic objects 1800a, 1800b, 1800c, 1800d, and 1800e representing urine test results on the same day, a graphic object (not shown) (e.g., text) representing the test time in a specific region may be further provided on the execution screen 1600.

Hereinafter, an example of operations of the user terminal 130 according to various embodiments will be described.

According to various embodiments, the urine test system 1 may be implemented to provide result information about the urine test based on user information. For example, the urine test system 1 may allow the user to more intuitively check the result information about the urine test by setting the display position of the result information about the urine test that is most useful to the user based on the user information.

Figure 19:
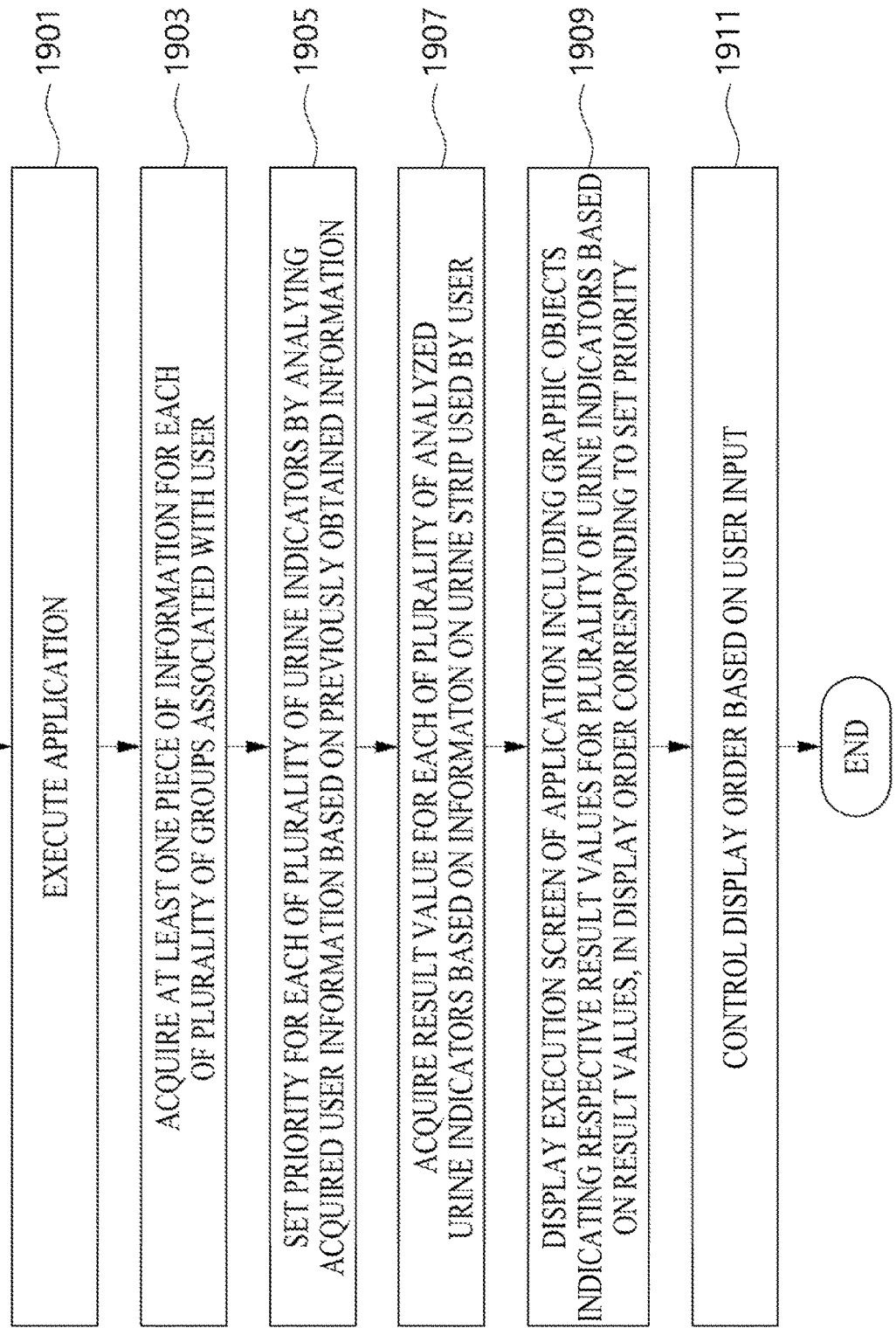
FIG. 19 is a flowchart illustrating operations of a user terminal, according to various embodiments.

FIG. 19 is a flowchart illustrating operations of the user terminal 130, according to various embodiments. According to various embodiments, the operations shown in FIG. 19 are not limited to the order shown and may be performed in various orders. Further, according to various embodiments, at least one operation, but more than the operations shown in FIG. 19 or less than those shown in FIG. 19 may be performed. Hereinafter, a further description will be given with reference to FIGS. 20 and 21.

Figure 21:
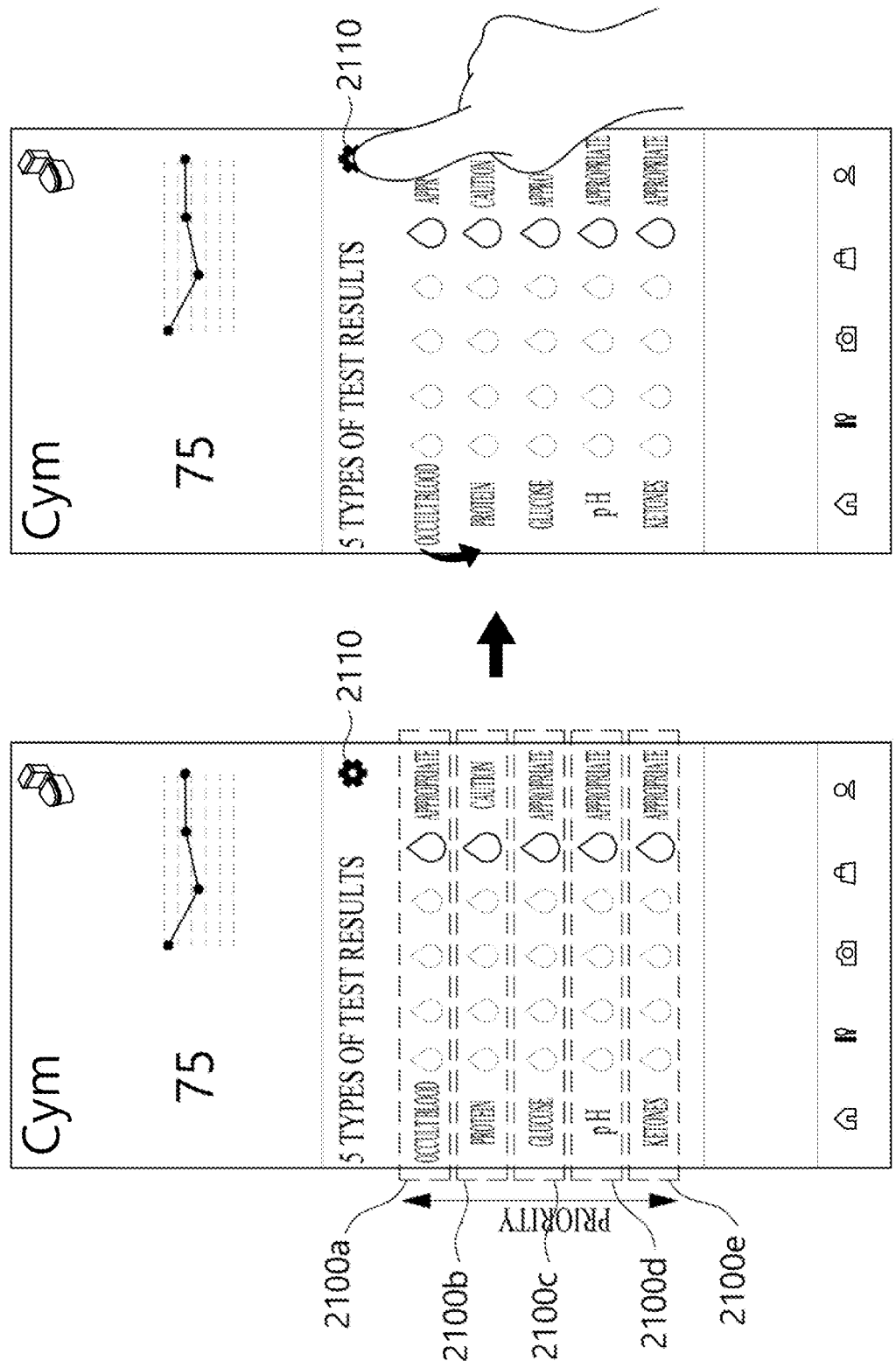
FIG. 21 is a diagram for describing an example of an operation of determining a display order of respective graphic objects for the urine indicators based on the priority of the determined urine indicator of the user terminal, according to various embodiments.

FIG. 20 is a diagram for describing an example of an operation of determining a priority of a urine indicator based on user information about the user terminal 130, according to various embodiments. FIG. 21 is a diagram for describing an example of an operation of determining a display order of respective graphic objects for the urine indicators based on a priority of the determined urine indicator of the user terminal 130, according to various embodiments.

According to various embodiments, the user terminal 130 (e.g., the processor 1410) may execute an application (e.g., the application 1441 of FIG. 14) in operation 1901.

According to various embodiments, the user terminal 130 (e.g., the processor 1410) may acquire at least one piece of information for each of a plurality of groups associated with the user in operation 1903, and may set priorities of the plurality of urine indicators by analyzing the acquired user information based on the previously obtained information, in operation 1905. For example, the group associated with the user may refer to various types of information for specifying the user, such as job, disease, age, weight, and height. As shown in FIG. 20, the user terminal 130 may provide an execution screen 2010 for acquiring information associated with the user for each group (e.g., job, disease, and age) based on the application 1441. The execution screen 2010 may include an input field for receiving information for each group (e.g., job, disease, and age) from the user.

In an embodiment, as shown in (a) of FIG. 20, the user terminal 130 may store information 2020a (e.g., a look-up table) on the urine indicator 2030 corresponding to information 2020 about the user for each group in advance, and may determine the priorities of urine indicators based on the pre-stored information and user information acquired based on the execution screen 2010. For example, the information 2020a may be obtained in advance based on information on the urine indicator that have been investigated as requiring management corresponding to a specific job, specific disease, specific age, or the like, through experiments and research, and may be provided to the user terminal 130 together with the application 1441. The user terminal 130 may identify urine indicators corresponding to the input user information, and determine priorities of the urine indicators such that the higher the number of the identified urine indicators, the higher the priority.

In another embodiment, as shown in (b) of FIG. 20, the user terminal 130 may make a determination such that the higher the value for each urine indicator, the higher the priority of the corresponding urine indicator, based on an artificial intelligence model 2020b implemented to output a value 2050 (e.g., a weight value) for each urine indicator in response to receiving the input user information 2040. The artificial intelligence model 2020b may be constructed by performing training based on various types of learning algorithms by using user information 2040 as input data and the value 2050 for each urine indicator as output data, and may include various types of well-known machine learning and deep learning algorithms, and thus a detailed description thereof will be omitted.

According to various embodiments, in operation 1907, the user terminal 130 (e.g., the processor 1410) may acquire respective result values for the plurality of urine indicators analyzed based on the information on the urine strip used by the user. For example, as described above, the user terminal 130 may acquire the respective result values for urine indicators by performing the urine test in various ways, such as photographing the urine strip 120 on the board 110 and using the electronic device 140, and repeated description thereof will be omitted.

According to various embodiments, in operation 1909, the user terminal 130 (e.g., the processor 1410) may display the execution screen of the application including graphic objects indicating the respective result values for the plurality of urine indicators based on the result values, in a display order corresponding to the set priority. For example, as shown in FIG. 21, the user terminal 130 may determine the display order of the respective graphic objects 2100a, 2100b, 2100c, 2100d, and 2100e for the plurality of urine indicators in order of highest priority. As shown, the display order refer to a row in which each of the graphic objects 2100a, 2100b, 2100c, 2100d, and 2100e is displayed, and as the graphic object 2100a, 2100b, 2100c, 2100d, or 2100e has a higher priority, it may be displayed in a higher row.

However, the display order is not limited to the example illustrated and/or described; the display order may merely refer to displayed columns, or may be set such that as the graphic object has a higher priority, it is displayed in a lower row.

Meanwhile, according to various embodiments, the corresponding graphic object 2100a, 2100b, 2100c, 2100d, or 2100e of the urine indicator is not limited to the examples illustrated and/or described, and may be visually emphasized instead of the display order. For example, a graphic object of a urine indicator having the highest priority may be provided to have a larger size and/or a different color than graphic objects of other urine indicators.

According to various embodiments, in operation 1909, the user terminal 130 (e.g., the processor 1410) may control the display order based on user input. For example, when an object 2110 for changing the display order is selected, the user terminal 130 may control the display order of the respective graphic objects 2100a, 2100b, 2100c, 2100d, and 2100e for the plurality of urine indicators to be in a changeable state.

According to various embodiments, the user information may be updated based on the respective test results for the urine indicators that are acquired as the urine test progresses, and in this way, the priority of the urine indicator may be determined. For example, a specific urine indicator that is included in a risk range and/or has a close value to the risk range may be set to have a higher priority.

Hereinafter, an example of operations of the user terminal 130 according to various embodiments will be described.

Figure 22:
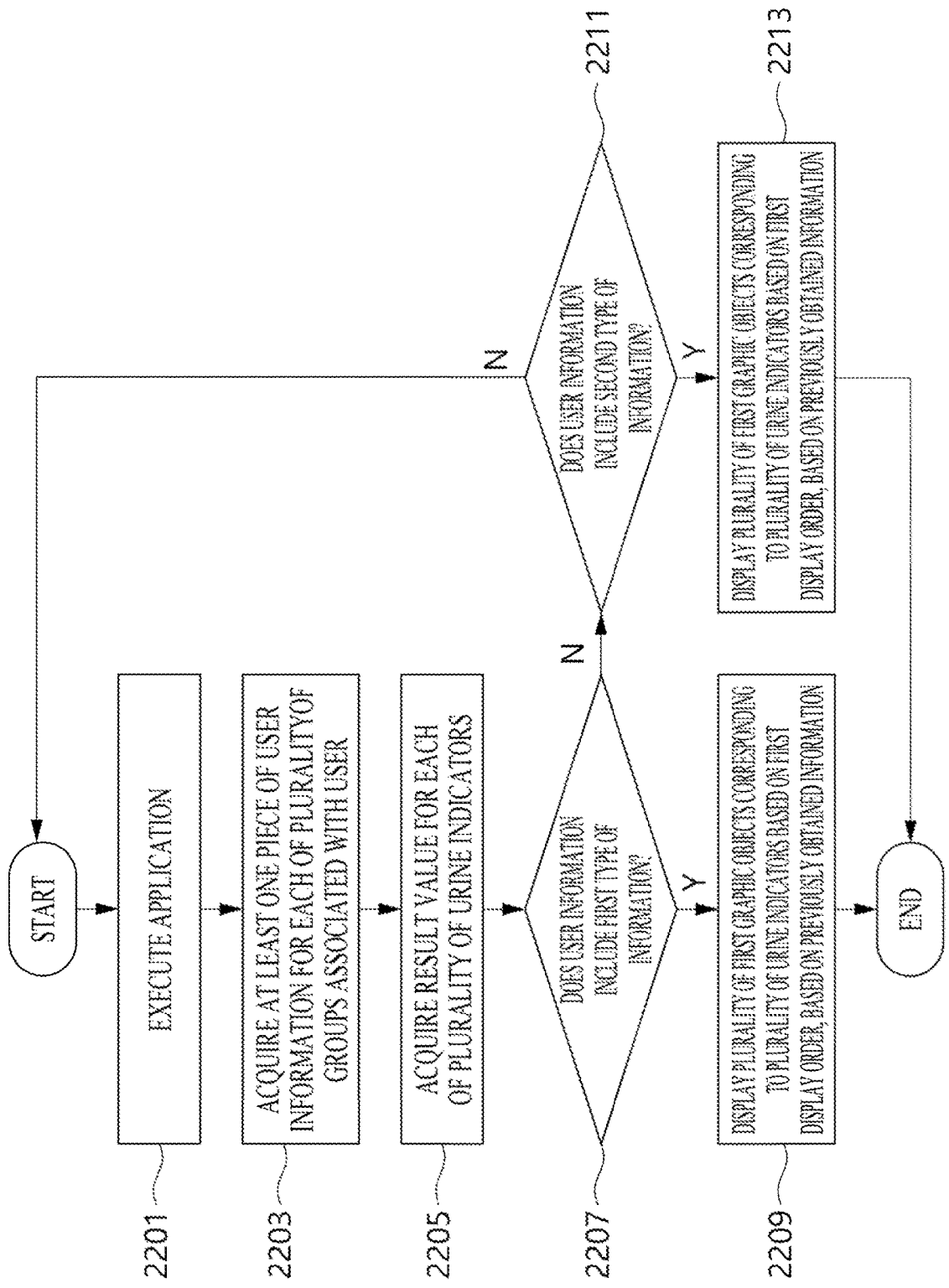
FIG. 22 is a flowchart illustrating operations of a user terminal, according to various embodiments.

FIG. 22 is a flowchart illustrating operations of the user terminal 130, according to various embodiments. According to various embodiments, the operations shown in FIG. 22 are not limited to the order shown and may be performed in various orders. Further, according to various embodiments, at least one operation, but more than the operations shown in FIG. 22 or less than those shown in FIG. 22 may be performed.

According to various embodiments, the user terminal 130 (e.g., the processor 1410) may execute an application (e.g., the application 1441 of FIG. 14) in operation 2201 and, may acquire at least one piece of user information for each of a plurality of groups (e.g., job and age) associated with the user in operation 2203.

According to various embodiments, in operation 2205, the user terminal 130 (e.g., the processor 1410) may acquire respective result values for a plurality of urine indicators.

According to various embodiments, the user terminal 130 (e.g., the processor 1410) may determine whether the user information includes a first type of information in operation 2207, and when the user information includes the first type of information (Yes in operation 2207), may display a plurality of first graphic objects corresponding to the plurality of urine indicators based on a first display order, based on previously obtained information (e.g., information 2020a and 2020b of FIG. 20) in operation 2209. For example, when the user information includes "secretary" as the job of the user, the user terminal 130 may set highest the priority corresponding to the display order of the graphic object representing the urine test result for "protein", which is a urine indicator associated with heart disease the secretary is more likely to have, the priority is not limited to the described example.

According to various embodiments, the user terminal 130 (e.g., the processor 1410) may determine whether the user information includes a second type of information when the user information does not include the first type of information (No in operation 2207), in operation 2211, and the user terminal 130 may display a plurality of second graphic objects corresponding to the plurality of urine indicators based on a second display order based on previously obtained information (e.g., information 2020a and 2020b of FIG. 20) when the user information includes the second type of information (Yes in operation 2211), in operation 2213. For example, when the user information includes "cook" as the job of the user, the user terminal 130 may set highest the priority corresponding to the display order of the graphic object representing the urine test result for "glucose", which is a urine indicator associated with diabetes the cook is more likely to have, the priority is not limited to the described example.

Hereinafter, an example of operations of the server 150 according to various embodiments will be described.

According to various embodiments, the urine test system 1 may acquire health information other than urine indicators from various IOT devices provided in the home and/or an external server, and may be implemented to provide various types of services associated with the health management of the user based on selecting and using information on urine indicators and health information other than urine indicators that is linked to the urine indicators.

Figure 23:
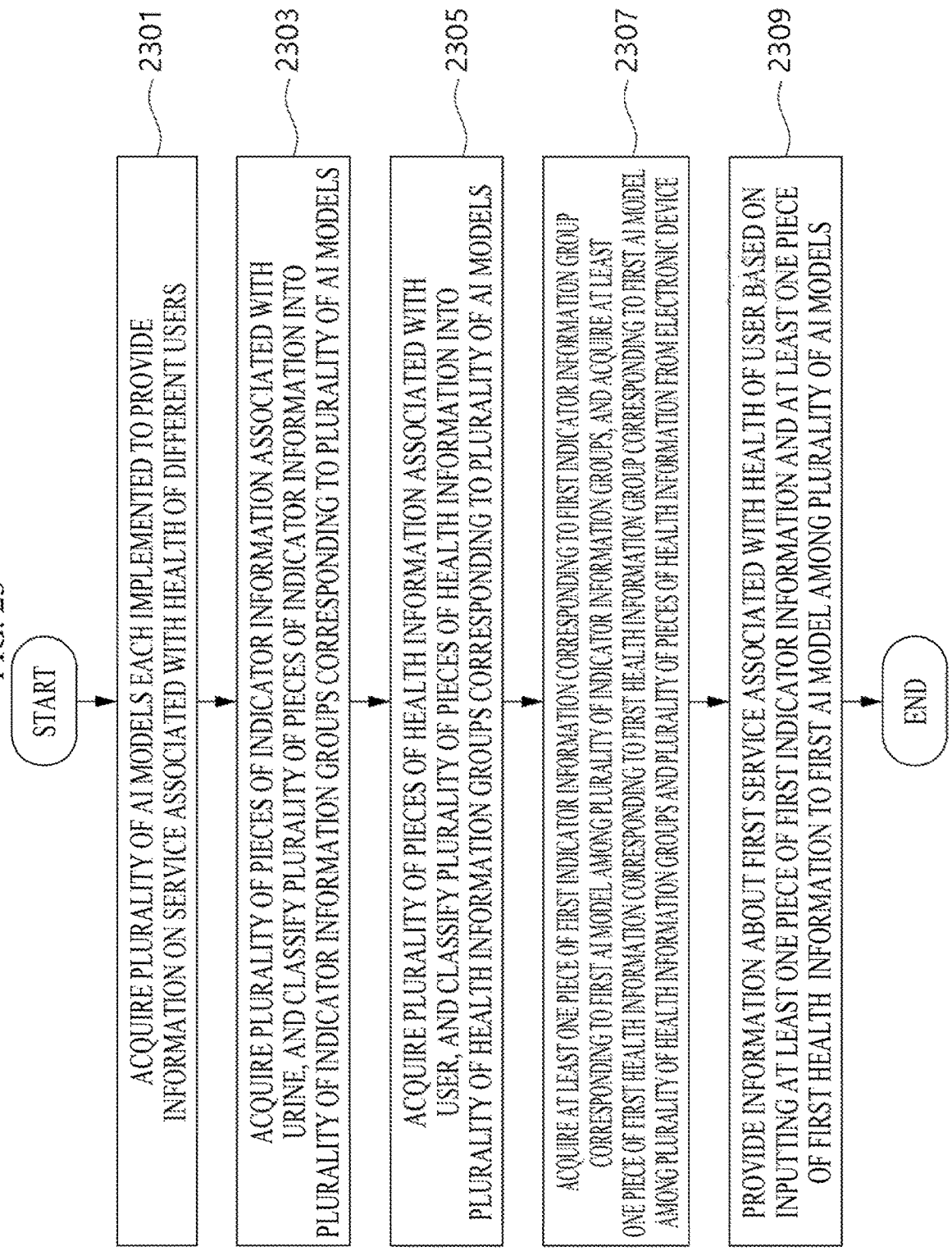
FIG. 23 is a flowchart illustrating operations of a server, according to various embodiments.

FIG. 23 is a flowchart illustrating operations of the server 150, according to various embodiments. According to various embodiments, the operations shown in FIG. 23 are not limited to the order shown and may be performed in various orders. Further, according to various embodiments, at least one operation, but more than the operations shown in FIG. 23 or less than those shown in FIG. 23 may be performed. Hereinafter, a further description of FIG. 23 will be given with reference to FIGS. 24 and 25.

Figure 24:
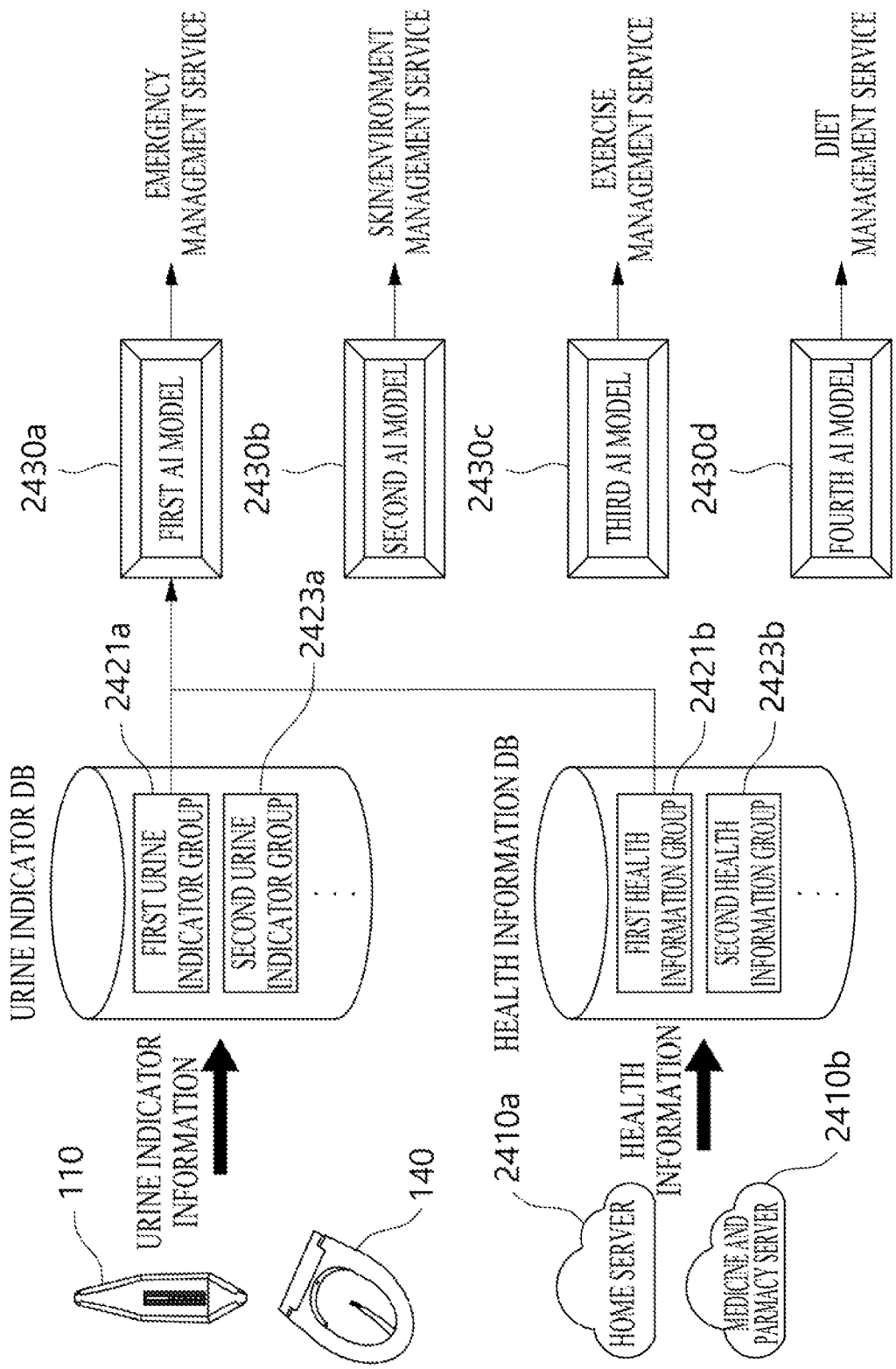
FIG. 24 is a diagram for describing an example of an operation of providing various types of services associated with health management of a user based on information on urine indicators of a server and health information other than the urine indicators that is associated therewith, according to various embodiments.
Figure 25:
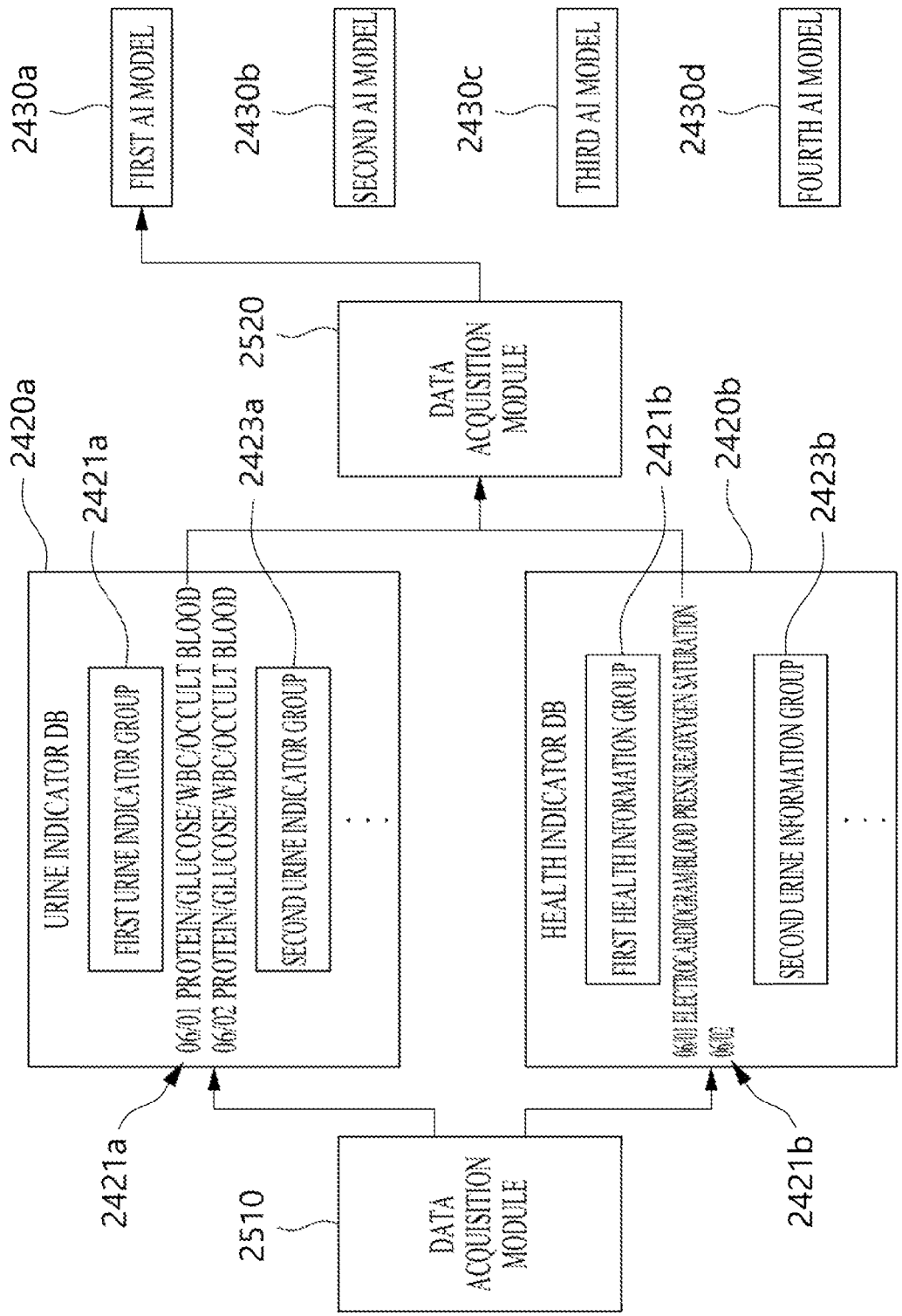
FIG. 25 is a diagram for describing an example of an operation of selecting information on urine indicators of the server and health information other than the urine indicators that is associated therewith, according to various embodiments.

FIG. 24 is a diagram for describing an example of an operation of providing various types of services associated with health management of a user based on information on urine indicators of the server 150 and health information other than the urine indicators that is associated therewith, according to various embodiments. FIG. 25 is a diagram for describing an example of an operation of selecting information on urine indicators of the server 150 and health information other than the urine indicators that is associated therewith, according to various embodiments.

According to various embodiments, in operation 2301, the server 150 (e.g., the processor) may acquire a plurality of AI models 2430 each implemented to provide information on a service associated with health of different users. Referring to FIG. 24, each of the plurality of AI models 2430 (e.g., a first AI model 2430a, a second AI model 2430b, a third AI model 2430c, and a fourth AI model 2430d) may be an artificial intelligence model trained to provide different health services associated with the user. For example, the health service may include an emergency management service, a skin/environment management service, an exercise management service, and a diet management service, and are not limited to the examples described above, and more artificial intelligence models may be constructed to include more types of management services.

For example, as described in [Table 2] below, in order to construct an artificial intelligence model for providing a specific health management service, a plurality of AI models 2430 (the first AI model 2430a, the second AI model 2430b, the third AI model 2430c, and the fourth AI model 2430d) may be constructed based on training being performed by using the urine indicator and health information corresponding to the specific health management service as input data and the specific health management service as output data.

TABLE 2

| Health management service | Urine indicator | Health information |
| --- | --- | --- |
| Emergency management service | Protein, glucose, WBC, occult blood | Electrocardiogram, blood pressure, oxygen saturation |
| Skin/environment management service | pH, vitamin C, specific gravity | Image, moisture |
| Exercise management service | Bilirubin, urobililogen, occult blood | Exercise type, exercise strength |
| Diet management service | pH, ketone | Calorie, meat-vegetable ratio |

The emergency management service may be a service for detecting a situation in which the health management is urgently required and/or a call for medical personnel is required based on information acquired based on urine indicators and health information and providing an alarm (e.g., the user terminal 130 or an associated medical facility (not shown)), but is not limited to the described examples. The skin/environment management service may be defined as a service for acquiring evaluation information associated with the skin based on information acquired based on urine indicators and health information and providing information for improving skin health corresponding to the evaluation information.

The exercise management service may be defined as a service for recommending an exercise by identifying an exercise suitable for the user based on information acquired based on urine indicators and health information.

The diet management service may be defined as a service for recommending a diet by identifying a diet suitable for the user based on information acquired based on urine indicators and health information.

According to various embodiments, in operation 2303, the server 150 (e.g., the processor) may acquire a plurality of pieces of indicator information associated with urine, and classify the plurality of pieces of indicator information into a plurality of indicator information groups corresponding to the plurality of AI models (e.g., the first AI model 2430a, the second AI model 2430b, the third AI model 2430c, and the fourth AI model 2430d). For example, as shown in FIG. 24, the server 150 may acquire (e.g., acquire from the user terminal 130) information for each of a plurality of urine indicators of the user based on the urine test performed using the board 110 and the user terminal 130. The server 150 may classify the acquired information for each urine indicator into a corresponding group for each health management service (e.g., a first urine indicator group 2421a and a second urine indicator group 2423a), and store classified groups (e.g., in a database 2420a). For example, as shown in FIG. 25, the server 150 (e.g., a data classification module 2510) may classify protein, glucose, WBC, and/or occult blood corresponding to the emergency management service as a specific urine indicator group (e.g., the first urine indicator group 2421a) and store it.

According to various embodiments, in operation 2305, the server 150 (e.g., the processor) may acquire a plurality of pieces of health information associated with the user, and classify the plurality of pieces of health information into a plurality of health information groups corresponding to the plurality of AI models. For example, as shown in FIG. 24, the server 150 may acquire health information from IOT devices (not shown) used by the user at home and/or a home server 2410a that manages the IOT devices (not shown), a medicine and pharmacy server 2410b that manages information such as a hospital or pharmacy visited by the user, and/or a wearable device (not shown) worn by the user. The health information may include the aforementioned health information in [Table 2]. As an example, the server 150 may acquire, from a wearable device (not shown) (e.g., smart watch or electrocardiogram patch) worn by the user, electrocardiogram, blood pressure, and/or oxygen saturation measured by the wearable device. As another example, the server 150 may acquire information associated with an RGB image of the user captured by the user terminal 130 and/or an IOT device (e.g., a smart mirror) in the home or the user's moisture acquired by a moisture sensor. As yet another example, the server 150 may acquire information about exercise type and/or exercise strength acquired by a wearable device (not shown) (e.g., a smart watch, or an electrocardiogram patch) and/or an IOT device in the home (e.g., a smart mirror). As yet another example, the server 150 may acquire information such as calories and meat/vegetable ratio of the diet input by the user terminal 130 and/or acquired by an IOT device (e.g., a smart mirror) in the home.

The server 150 may classify the acquired information for each urine indicator into groups corresponding to each health management service (e.g., a first health information group 2421b and a second health information group 2423b), and store the groups (e.g., in a database 2420b). For example, as shown in FIG. 25, the server 150 (e.g., a data classification module 2510) may classify electrocardiogram, blood pressure, and/or oxygen saturation corresponding to the emergency management service as a specific urine indicator group (e.g., the first urine indicator group 2421a) and store it.

Meanwhile, the above-described operation of acquiring information on the urine indicator of the server 150 may be performed when the urine test is performed, but the operation of acquiring the health information may be performed periodically and/or non-periodically (e.g., when a request for a specific health service is received).

According to various embodiments, as shown in FIG. 25, the server 150 may also manage time information (e.g., date/hour/second when information has been acquired) about information stored for each information group (e.g., urine indicator group or health information group).

According to various embodiments, in operation 2307, the server 150 (e.g., the processor) may acquire at least one piece of first indicator information corresponding to a first indicator information group corresponding to the first AI model among the plurality of indicator information groups, and may acquire at least one piece of first health information corresponding to a first health information group corresponding to the first AI model among the plurality of health information groups from the electronic device. According to various embodiments, in operation 2309, the server 150 (e.g., the processor) may provide information about a first service associated with health of the user based on inputting the at least one piece of first indicator information and the at least one piece of first health information to the first AI model among a plurality of AI models. As shown in FIG. 24, in order to provide a specific health service (e.g., the emergency management service), the server 150 may acquire information about a specific health management service (e.g., emergency management service) output from an AI model (e.g., the first AI model 2430a) in response to inputting, into the AI model (e.g., the first AI model 2430a) corresponding to the specific health service information, information included in the specific urine indicator group (e.g., the first urine indicator group) corresponding to the specific health service and information included in the health information group (e.g., the first health information group) corresponding to the urine indicator group. The server 150 provides information on the specific health management service (e.g., emergency management service) to the user terminal 130, thereby allowing the user to use the information on the specific health management service through the user terminal 130. The information on the specific health management service may include information processed so as to be provided by the aforementioned specific health management service. In this case, for example, the server 150 may perform an operation of acquiring the aforementioned information on the specific health management service (e.g., emergency management service) based on a determination to receive a request for the specific health service (e.g., emergency management service) based on the application 1441 of the user terminal 130, and/or periodically provide the information on the specific management service. The server 150 may acquire the most recent information stored in the database in order to acquire the information on the specific health management service.

According to various embodiments, referring to FIG. 25, the server 150 (e.g., a data acquisition module 2520) may perform an operation of acquiring information including pieces of time information associated with each other (or satisfying a specific condition), as at least part of an operation of acquiring information included in a specific urine indicator group (e.g., the first urine indicator group) and information included in a health information group (e.g., the first health information group) corresponding to the specific urine indicator group. For example, the server 150 (e.g., the data acquisition module 2520) may acquire information included in a difference of a specific time from each other among information included in a specific urine indicator group (e.g., the first urine indicator group) and information included in a health information group (e.g., the first health information group) corresponding to the specific urine indicator group. The specific time may be different for each type of provided management service. For example, the server 150 may be implemented to acquire information included in the difference by a first time in the case of a first health service (e.g., the emergency management service), and acquire information included in the difference by a second time in the case of a second health service (e.g., skin/environment management service). Accordingly, a more accurate health management service may be provided based on pieces of information related to each other.

According to various embodiments, in order to acquire pieces of information associated with each other, the server 150 (e.g., the data acquisition module 2520) may be implemented to acquire other information within a difference by a specific time needed to respond to the specific health service when information about one of the urine indicator group and the health information group corresponding to the specific health service is acquired. For example, the server 150 may be configured to, when the server 150 acquires information on at least one urine indicator (e.g., Ph) corresponding to the skin/environment management service, acquire information on an image by requesting the information on the image through a wearable device (not shown) within the specific time needed to respond to the service.

According to various embodiments, the server 150 (e.g., the data acquisition module 2520) may provide, to the user terminal 130, a message indicating that it is not possible to provide the specific health service when there is no information having pieces of time information associated with each other (or satisfying a specific condition) for each group.

The message may be set to display information indicating that it is not possible for user terminal 130 to provide the specific health service.

Hereinafter, an example of operations of the user terminal 130 according to various embodiments will be described.

According to various embodiments, the user terminal 130 may acquire health information other than urine indicators from various IOT devices provided in the home and/or an external server, and may be implemented to provide various types of services associated with the health management of the user based on selecting and using information on urine indicators and health information other than urine indicators that is linked to the urine indicators.

Figure 26:
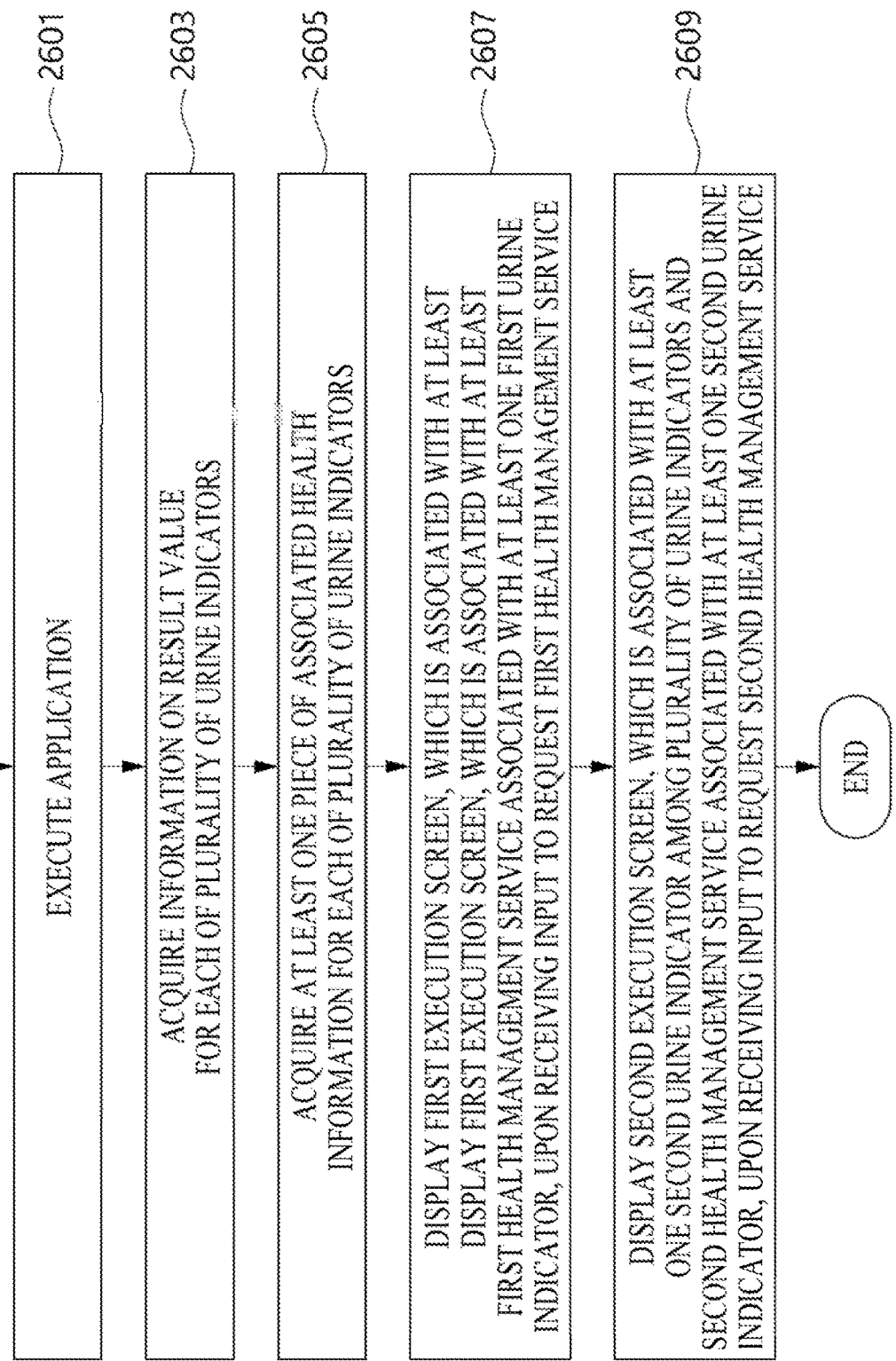
FIG. 26 is a flowchart illustrating operations of a user terminal, according to various embodiments.

FIG. 26 is a flowchart illustrating operations of the user terminal 130, according to various embodiments. According to various embodiments, the operations shown in FIG. 26 are not limited to the order shown and may be performed in various orders. Further, according to various embodiments, at least one operation, but more than the operations shown in FIG. 26 or less than those shown in FIG. 26 may be performed. Hereinafter, a further description of FIG. 26 will be given with reference to FIG. 27.

Figure 27:
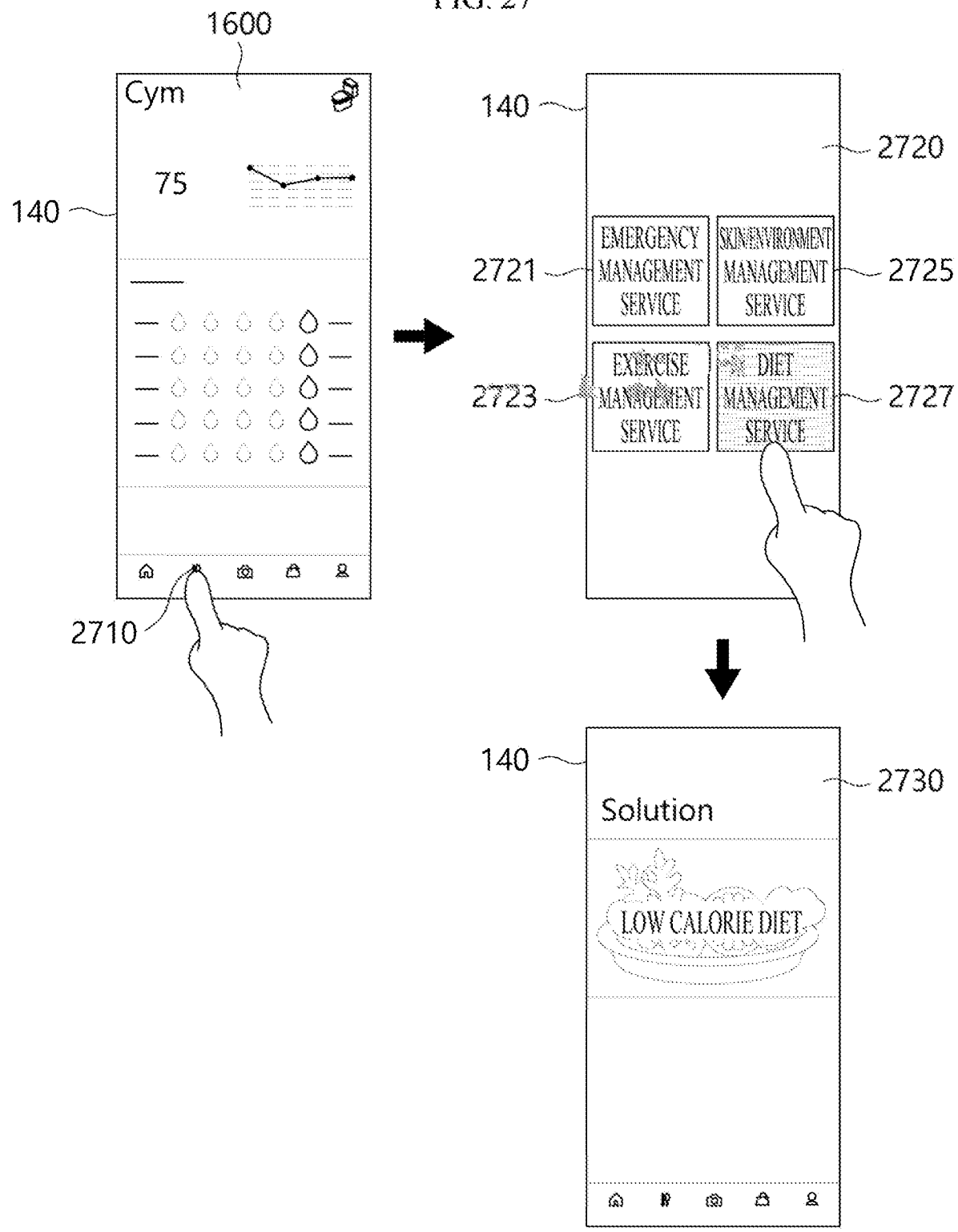
FIG. 27 is a diagram for describing an example of an operation of providing information on a specific health management service by a user terminal, according to various embodiments.

FIG. 27 is a diagram for describing an example of an operation of providing information on a specific health management service by the user terminal 130, according to various embodiments.

According to various embodiments, the user terminal 130 (e.g., the processor 1410) may execute an application (e.g., the application 1441 of FIG. 14) in operation 2601, acquire information on a result value for each of a plurality of urine indicators (e.g., information on the urine indicators in [Table 2]) in operation 2603, and acquire at least one piece of associated health information (e.g., health information in [Table 2]) for each of the plurality of urine indicators in operation 2605.

According to various embodiments, the user terminal 130 (e.g., the processor 1410) may display a first execution screen, which is associated with at least one first urine indicator among the plurality of urine indicators and a first health management service associated with the at least one first urine indicator, upon receiving an input to request the first health management service, in operation 2607, and may display a second execution screen, which is associated with at least one second urine indicator among the plurality of urine indicators and a second health management service associated with the at least one second urine indicator, upon receiving an input to request the second health management service, in operation 2609. For example, as shown in FIG. 27, the user terminal 130 may provide a menu 2710 for providing the health management service on the execution screen 1600 of the application 1441, and when the menu 2710 is selected, may provide an execution screen 2720 including a plurality of objects (e.g., objects corresponding to an emergency management service 2721, an exercise management service 2723, a skin/environment management service 2725, and a diet management service 2727) corresponding to a plurality of health management services. When the specific service (e.g., the diet management service 2727) is selected, the user terminal 130 may provide an execution screen 2730 including information corresponding to the specific management service.

Hereinafter, an example of operations of the user terminal 130 according to various embodiments will be described.

According to various embodiments, the urine test system 1 may be implemented to provide a social service for sharing various types of information related to the user's health promotion, such as the urine test, with other users. This makes it possible for patients with a specific disease (e.g., kidney) to smoothly communicate their experiences with each other, which in turn, makes it possible to the patients to share helpful information between each other.

Figure 28:
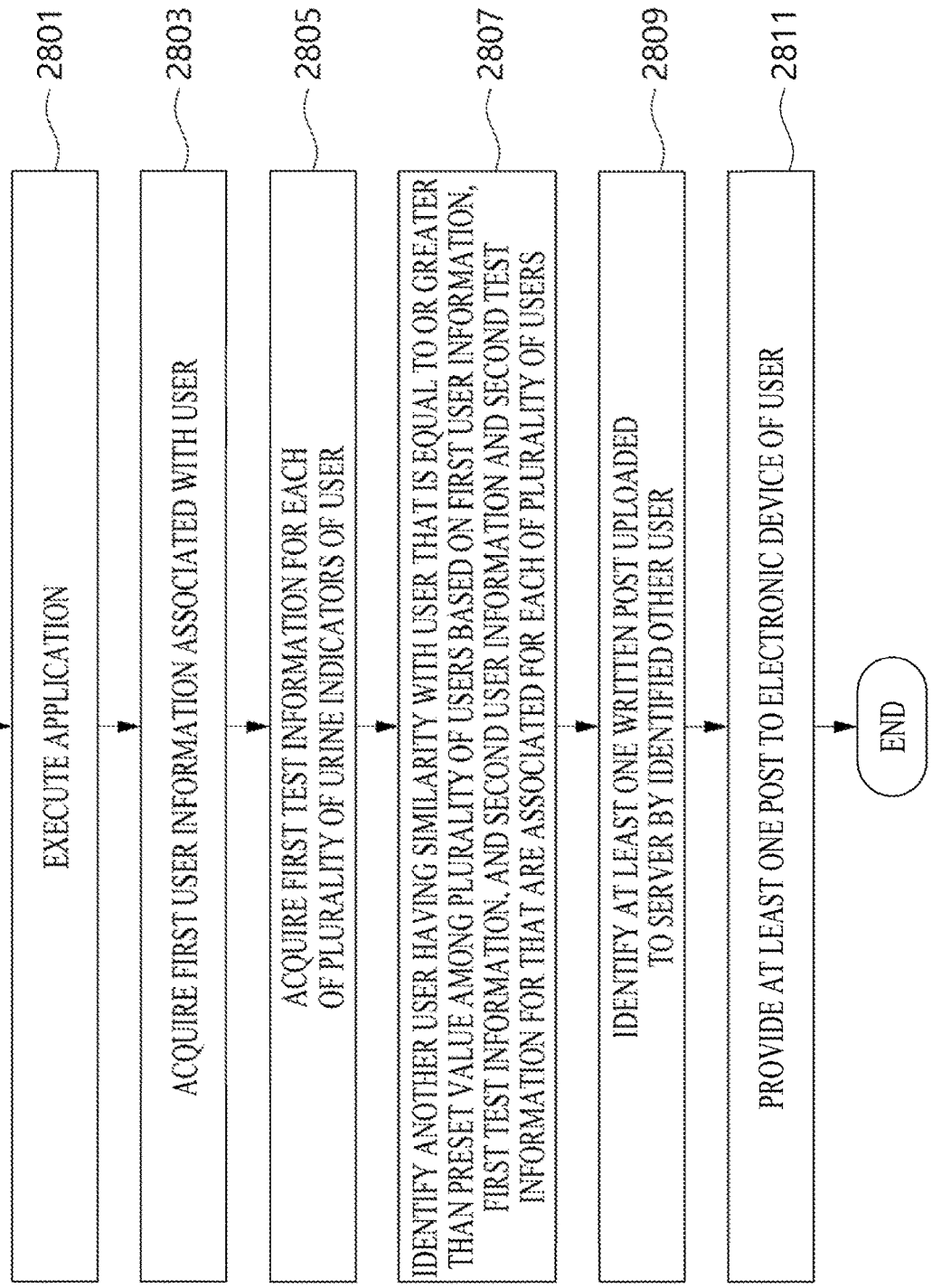
FIG. 28 is a flowchart illustrating operations of a user terminal, according to various embodiments.

FIG. 28 is a flowchart illustrating operations of the user terminal 130, according to various embodiments. According to various embodiments, the operations shown in FIG. 28 are not limited to the order shown and may be performed in various orders. Further, according to various embodiments, at least one operation, but more than the operations shown in FIG. 28 or less than those shown in FIG. 28 may be performed. Hereinafter, a further description of FIG. 28 will be given below with reference to FIGS. 29, 30 and 31.

Figure 31:
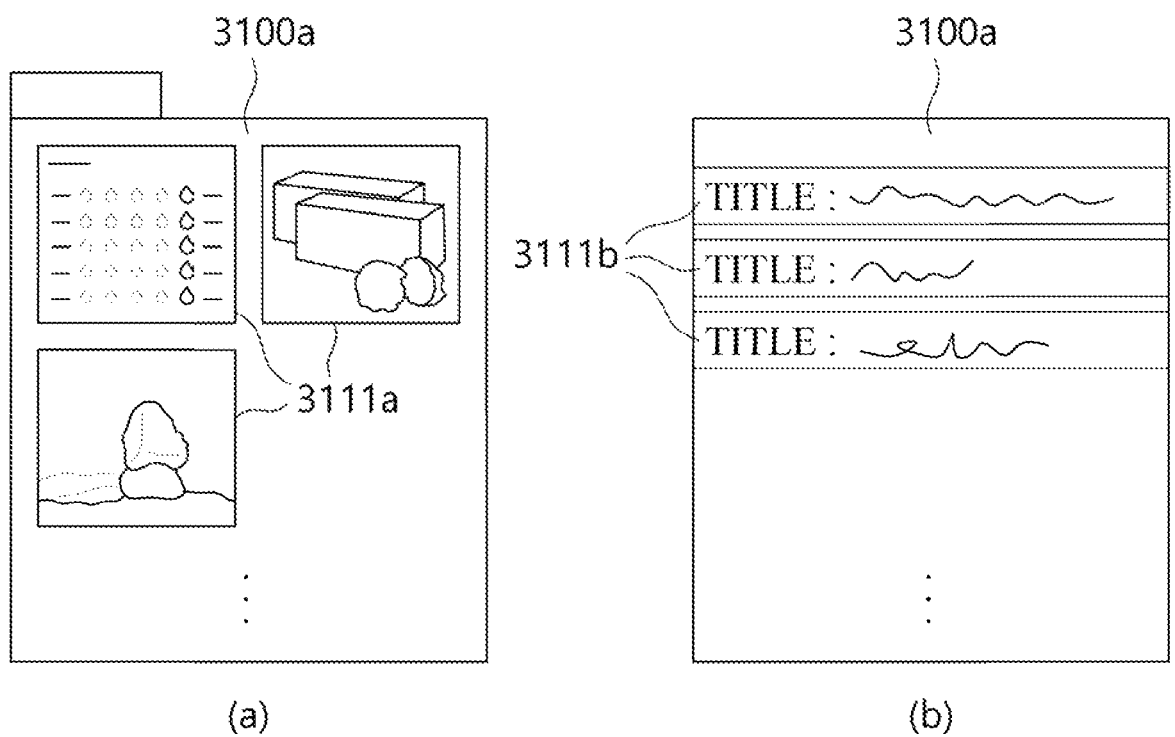
FIG. 31 is a diagram for describing an example of a post upload service and a post recommendation service of the urine test system, according to various embodiments.

FIG. 29 is a diagram for describing an example of a social service to be provided by the urine test system 1, according to various embodiments. FIG. 30 is a diagram for describing an example of an operation of determining a user similar to a specific user of the urine test system 1, according to various embodiments. FIG. 31 is a diagram for describing an example of a post upload service and a post recommendation service of the urine test system 1, according to various embodiments.

According to various embodiments, the user terminal 130 (e.g., the processor 1410) may execute the application 1441 in operation 2801. For example, referring to FIG. 29, the application (or server 150) of the user terminal 130 may provide an SNS type service in which it is possible for posts 2900a to be registered for each user, as shown in (a) of FIG. 29, and a bulletin board type service in which it is possible for posts to be registered, as shown (b) in FIG. 29. Users using the urine test system 1 are able to register various types of posts associated with the urine test and view posts of other users by using the service.

According to various embodiments, the user terminal 130 (e.g., the processor 1410) may acquire first user information associated with the user in operation 2803, may acquire first test information for each of a plurality of urine indicators of the user in operation 2805, and may identify another user having the similarity with the user that is equal to or greater than preset value among the plurality of users based on the first user information, the first test information, and second user information and second test information that are associated for each of a plurality of users in operation 2807. For example, referring to FIG. 30, the server 150 may accumulate information associated with each user (user information) (e.g., job, age, or disease) and information associated with the urine indicator (urine indicator information), and identify the similarity between users based on the accumulated information. As an example, as shown in (a) of FIG. 30, the server 150 may identify the similarity based on comparing second user information (e.g., user information or urine indicator information) different from the first user information (e.g., user information or urine indicator information). As an example, as shown in (b) of FIG. 30, the server 150 may identify the similarity based on comparing values (e.g., matrix/vector) output in response to inputting second user information (e.g., user information or urine indicator information) different from the first user information (e.g., user information or urine indicator information) into an artificial intelligence model (e.g., the first AI model 3021b or the second AI model 3023b). The server 150 may determine that users having the similarity equal to or greater than a threshold value are similar users, and provide posts 3111a and 3111b of similar users for the specific user on the execution screen 3100a as shown in (a) of FIG. 31 and (b) of FIG. 31. Accordingly, the user may refer to posts of other users similar to himself or herself to acquire various information and use the information for health promotion activities.

According to various embodiments, the user terminal 130 (e.g., the processor 1410) may identify at least one written post uploaded to the server by the identified other user in operation 2809, and provide at least one post to the electronic device of the user in operation 2811.

Hereinafter, examples of an image analysis (photographing analysis) function of an electronic device according to various embodiments will be described.

Figure 32:
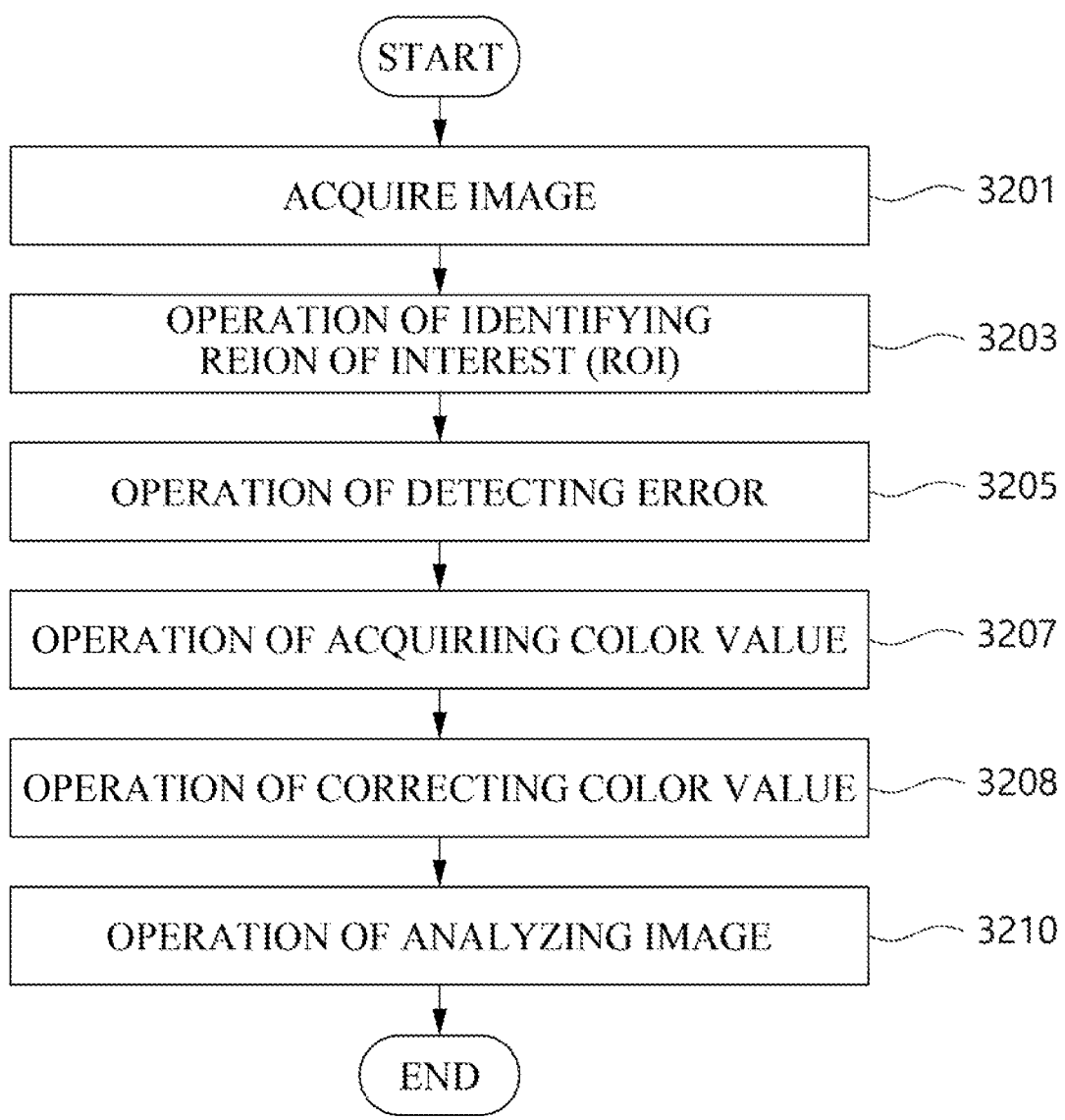
FIG. 32 is a diagram illustrating an operation sequence of image analysis for a urine test board that is performed by an electronic device (e.g., a user terminal or a processor of a server) according to various embodiments.

FIG. 32 is a diagram illustrating an operation sequence of image analysis for a urine test board that is performed by an electronic device (e.g., a processor of the user terminal 130 or the server 150) according to various embodiments.

Referring to FIG. 32, an electronic device (e.g., the processor of the user terminal 130 or the server 150) according to an embodiment may acquire an image of a test board (e.g., see 510 of FIG. 5) (3201). In this case, the image may be acquired using at least one camera included in the user terminal.

In addition, the electronic device (e.g., the processor of the user terminal 130 or the server 150) may perform operation 3203 of identifying a region of interest (ROI) for image analysis based on the image. In this case, the region of interest may refer to a region corresponding to at least a portion of the test board that needs to be actually analyzed on the image, and the operation 3203 may be performed according to a predetermined method (see FIG. 33).

In addition, the electronic device (e.g., the processor of the user terminal 130 or the server 150) may perform operation 3205 of detecting an error based on the acquired image. The error described in the present specification may refer to a situation in which an unexpected result may occur during an image analysis process. Details of the operating 3205 of detecting an error are described in FIG. 34.

In addition, the electronic device (e.g., the processor of the user terminal 130 or the server 150) may perform operation 3207 of acquiring at least one color value based on the acquired image. Specifically, the electronic device may acquire color values of at least one color mark and at least one reference mark included in the test board. Details of the operation 3207 of acquiring a color value will be described with reference to FIG. 36.

In addition, the electronic device (e.g., the processor of the user terminal 130 or the server 150) may perform operation 3208 of correcting the color value based on the at least one acquired color value. The operation of correcting may be an operation for removing external factors such as the surrounding environment in order to always perform operation 3210 of analyzing the image, which will be described below, under similar conditions. Details of the operation 3208 of correcting the color value will be described with reference to FIGS. 38 to 40.

In addition, the electronic device (e.g., the processor of the user terminal 130 or the server 150) may perform operation 3210 of analyzing the image having the corrected color value as described above. In this case, the electronic device may provide result information about the urine test to the user upon performing the image analysis. Specifically, the electronic device may estimate the extent to which a specific substance exists in urine by comparing the color value of at least one color mark included in the test board, which has been acquired based on the above-described operations, with a previously stored test indicator, and generate result information about the urine test based on the estimated result and provide it to the user.

Hereinafter, a detailed operation method (or algorithm) for the electronic device shown in FIG. 32 will be described.

Figure 33:
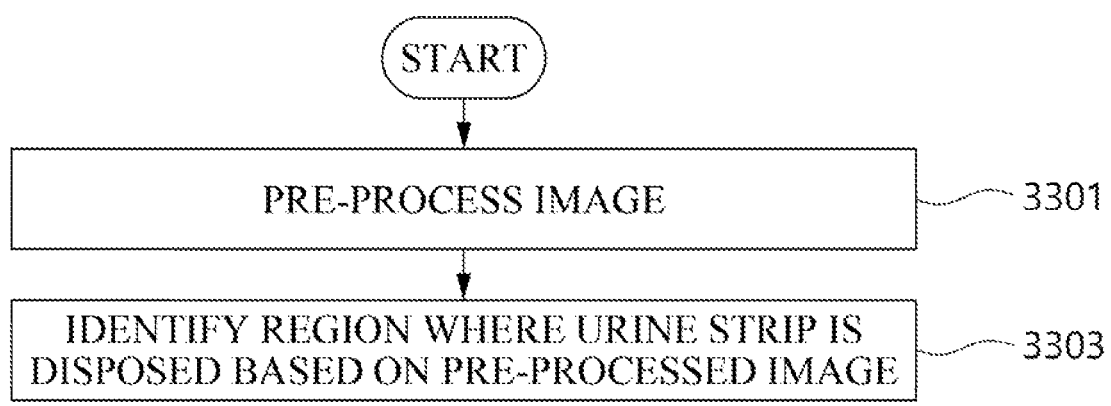
FIG. 33 is a flowchart illustrating operations for identifying a region of interest based on an image acquired by an electronic device, according to various embodiments.

FIG. 33 is a flowchart illustrating operations for identifying a region of interest based on an image acquired by an electronic device (e.g., a processor of the user terminal 130 or the server 150), according to various embodiments.

Referring to FIG. 33, the electronic device (e.g., a processor of the user terminal 130 or the server 150) may pre-process an image acquired in operation 3201 in a preset manner (3301). Specifically, the electronic device may pre-process the image by determining whether visual information about the test board included in the acquired image is appropriate for image processing. As an example, the electronic device may be configured to check whether the image is set in a preset direction, and rotate the image in a preset direction when the image is out of alignment. For example, when the horizontal length of the acquired image is longer than the vertical length, the electronic device may determine that the direction is out of alignment, and rotate the image in a preset direction. As another example, the electronic device may perform adjustment when the length of the test board at the top of the acquired image and the length of the test board at the bottom of the image differ by more than a preset threshold. In addition, the electronic device may change the acquired image to black and perform blurring on it. For the above-described image processing method, techniques commonly used in the related art may be applied.

In addition, the electronic device (e.g., the processor of the user terminal 130 or the server 150) may identify a region where the urine strip 120 is disposed based on the preprocessed image according to the above method (3303). Specifically, the electronic device may identify, from the image, a region having a shape corresponding to the shape of the region (e.g., test paper region 805 of the test board 510, described in FIG. 8) where the urine strip 120 is disposed as the region of interest, based on pixel values included in the image.

Figure 34:
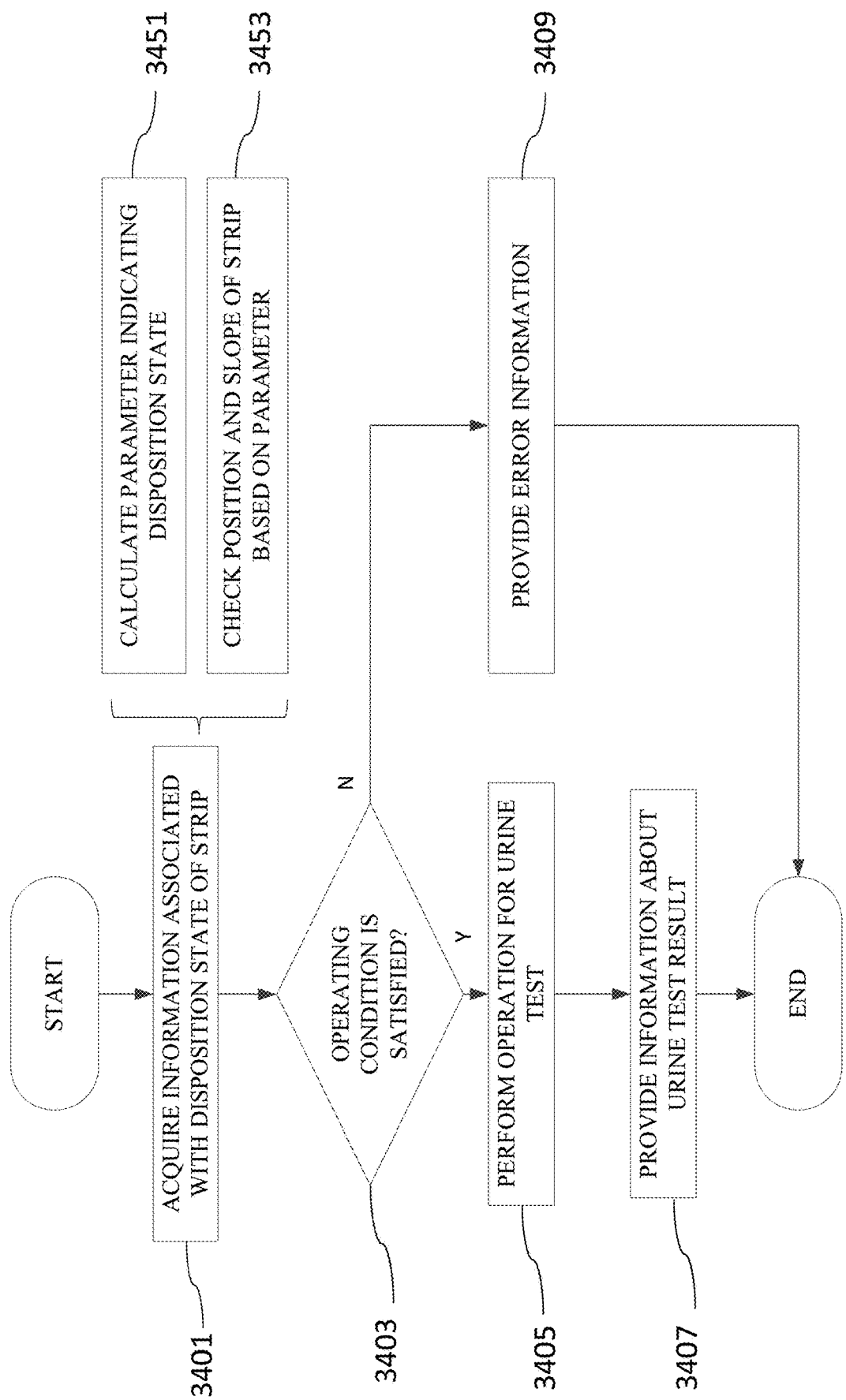
FIG. 34 is a flowchart illustrating a method of performing a urine test operation based on information associated with a disposition state of a urine strip by an electronic device, according to various embodiments.

FIG. 34 is a flowchart illustrating a method of performing a urine test operation based on information associated with a disposition state of the urine strip 120 by an electronic device (e.g., the processor of the user terminal 130 or the server 150), according to various embodiments.

Figure 35:
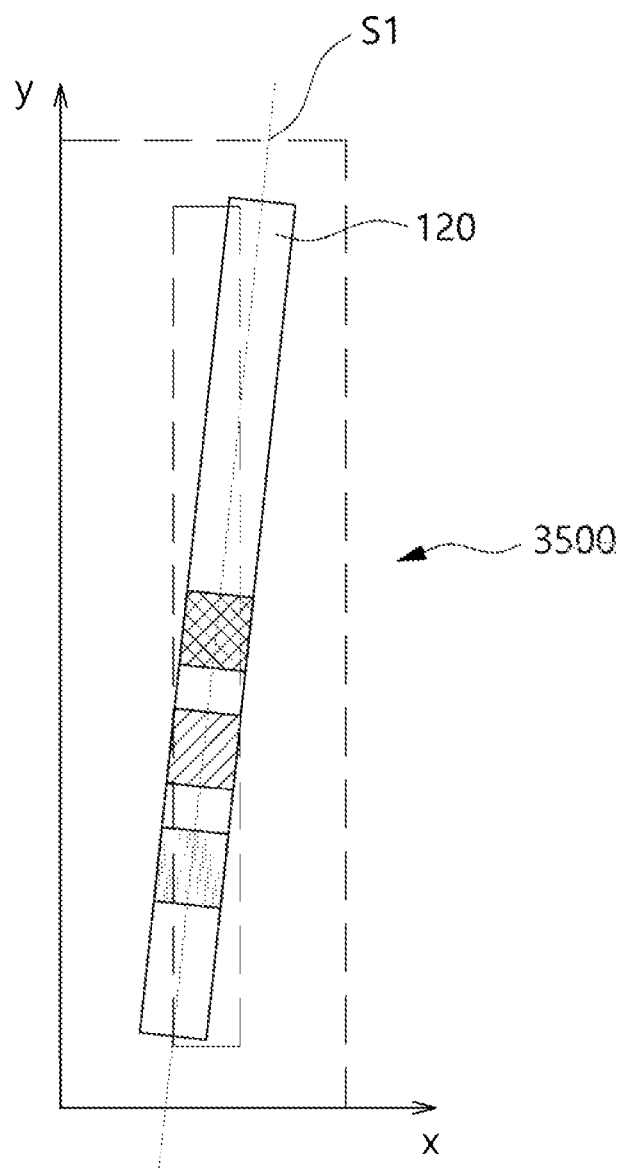
FIG. 35 illustrates an example of information associated with a disposition state of a urine strip acquired by an electronic device, according to various embodiments.

FIG. 35 shows an example of the information associated with the disposition state of the urine strip 120 acquired by an electronic device (e.g., the processor of the user terminal 130 or the server 150), according to various embodiments.

Referring to FIG. 34, the electronic device (e.g., the processor of the user terminal 130 or the server 150) may acquire the information associated with the disposition state of the urine strip 120 based on the acquired image (more specifically, the region of interest in the image identified according to FIG. 33) (3401). In this case, the information associated with the disposition state of the urine strip 120 may include relative position information or slope information of the urine strip 120 disposed on the test board 110.

The above operation 3401 may be performed with the following detailed operations.

Specifically, the electronic device (e.g., the processor of the user terminal 130 or the server 150) may calculate a parameter indicating a disposition state S1 of the urine strip 120 based on a first coordinate space corresponding to the region of interest of the acquired image (3451). In this case, the first coordinate space may refer to a virtual coordinate space created by software in the electronic device and may be defined based on position coordinates. Specifically, the electronic device may define the first coordinate space based on the region of interest. For example, referring to FIG. 35, the electronic device may define a first coordinate space 3500 corresponding to the scale of the identified ROI. In this case, the horizontal scale of the first coordinate space 3500 may correspond to the horizontal scale of the region of interest, and the vertical scale of the first coordinate space 3500 may correspond to the vertical scale of the region of interest. In addition, the electronic device may calculate a mathematical parameter indicating the disposition state S1 of the urine strip 120 based on pixel coordinates of a plurality of pixels corresponding to the urine strip 120 on the first coordinate space. For example, referring to FIG. 35, the electronic device may check a plurality of data points corresponding to the urine strip 120 on the first coordinate space 3500. In this case, the plurality of data points corresponding to the urine strip may be defined based on positions of pixels with the pixel value equal to or greater than a threshold value (a value used as a criterion for determining the urine strip), among pixels included in the region of interest of the image. In this case, the electronic device may provide error information associated with the presence of a strip when the number of data points obtained by checking by the above-described definition condition is less than or equal to a threshold value (a value used as a criterion for determining a strip existence error).

In addition, the electronic device (e.g., the processor of the user terminal 130 or the server 150) may acquire information associated with the disposition state S1 of the strip that indicates the position and slope of the strip, based on the parameter (3453).

In addition, the electronic device (e.g., the processor of the user terminal 130 or the server 150) may check whether a preset operating condition for the urine test is satisfied (3403). The above operation 3403 may be an operation for additionally checking error information associated with the disposition state of the urine strip 120, in addition to the above-described operation of checking error information associated with non-recognition of the QR code and the process of checking error information associated with the presence of the urine strip 120.

Specifically, the electronic device (e.g., the processor of the user terminal 130 or the server 150) may check whether the preset operating condition is satisfied based on information associated with the disposition state of the urine strip 120. For example, the electronic device may determine that the preset operating condition is not satisfied, when the slope value of the urine strip 120 obtained by checking based on the slope information about the strip included in the information associated with the disposition state of the urine strip 120 is less than a predetermined threshold value (a value used as a criterion for strip disposition error). This means that the slope value of the urine strip 120 is small, which means that the urine strip 120 is attached with an excessive inclination with respect to the preset strip attachment region, and accordingly, this is useful for detecting conditions that are not appropriate for analyzing such images. For example, referring to FIG. 35, it may be checked whether the preset operating condition is satisfied based on a slope m of a first linear regression line corresponding to the urine strip 120 defined on the first coordinate space 3500.

As described above, when the information associated with the disposition state S1 of the urine strip 120 does not satisfy a preset operating condition, the electronic device (e.g., the processor of the user terminal 130 or the server 150) may provide error information associated with the disposition of the urine strip 120 (3409).

In addition, the electronic device (e.g., the processor of the user terminal 130 or the server 150) may perform the operation for the urine test when the preset operating condition is satisfied (3405).

The above-described operation 3405 may be performed by comparing a color value identified based on the ROI of the acquired image with a pre-stored test indicator, which will be described in detail below.

In addition, the electronic device (e.g., the processor of the user terminal 130 or the server 150) may provide information about the urine test result to the user according to the result of the above-described operation (3407).

Figure 36:
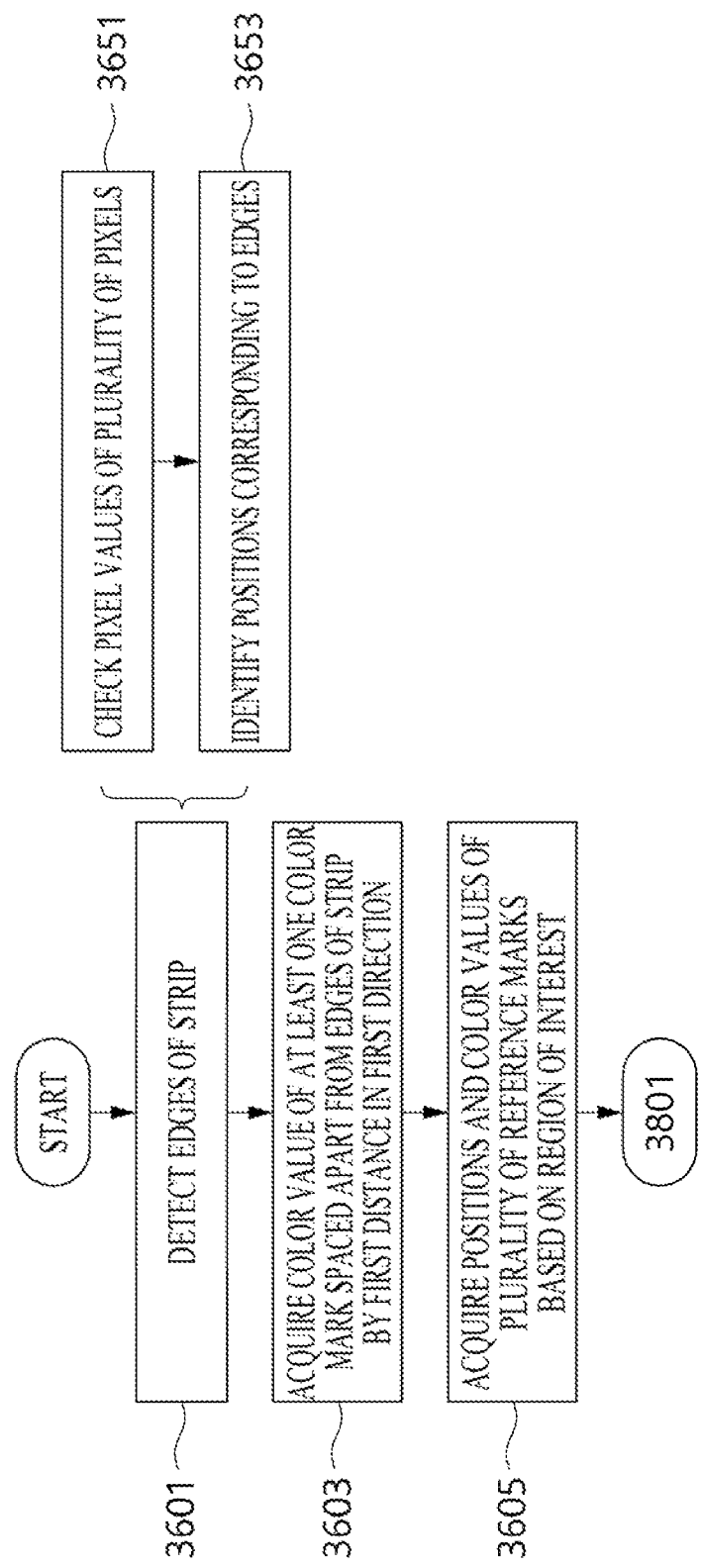
FIG. 36 is a flowchart illustrating a method of acquiring at least one color value by detecting a reference position by an electronic device, according to various embodiments.

FIG. 36 is a flowchart illustrating a method of acquiring at least one color value associated with the reagent pad 900 by detecting a reference position by an electronic device (e.g., the processor of the user terminal 130 or the server 150), according to various embodiments.

Figure 37:
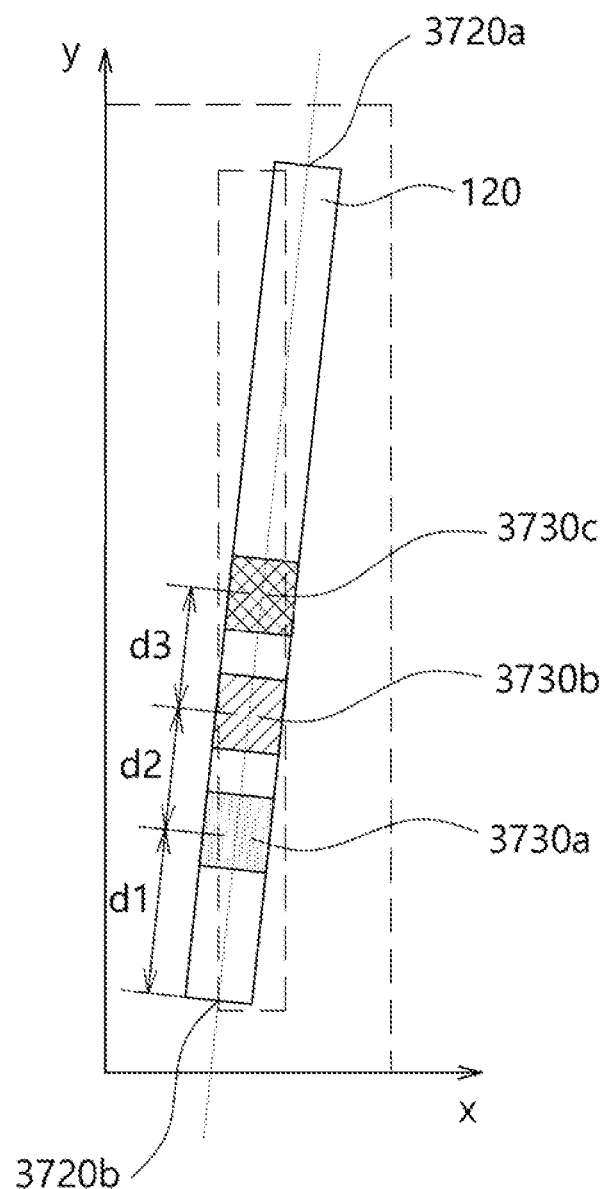
FIG. 37 illustrates information associated with a disposition state of a urine strip acquired by an electronic device to detect a reference position, according to various embodiments.

FIG. 37 shows another example of the information associated with the disposition state of the urine strip 120 acquired by an electronic device (e.g., the processor of the user terminal 130 or the server 150) to detect the reference position, according to various embodiments.

Referring to FIG. 36, the electronic device (e.g., the processor of the user terminal 130 or the server 150) may acquire information associated with the reference position of the urine strip 120 attached to the test board 110 in an acquired image based on the region of interest included in the image (3601). Specifically, the reference position may be acquired by calculating position coordinates associated with the urine strip 120 on the first coordinate space. For example, the reference position may include edges 3720a and 3720b of the urine strip 120.

In this case, the above-described operation 3601 may be performed with the following detailed operations.

Specifically, the electronic device (e.g., the processor of the user terminal 130 or the server 150) may check pixel values of a plurality of pixels included in the image (3651). In this case, the plurality of pixels may be pixels corresponding to the position of the strip, which are obtained by checking according to the method of FIG. 34. In this case, the electronic device may represent the plurality of pixels in the form of data points on a second coordinate space defined based on the positions of the plurality of pixels.

The electronic device (e.g., the processor of the user terminal 130 or the server 150) may identify positions corresponding to the edges 3720a and 3720b of the urine strip 120 (3653). For example, the at least one identified pixel may include at least one first pixel corresponding to a top edge 3720a and at least one second pixel corresponding to a bottom edge 3720b. The distance between the first pixel and the second pixel may correspond to the length of the urine strip 120, and the slope between the first pixel and the second pixel may correspond to the slope of the urine strip 120 included in the information associated with the disposition state S1. For example, the electronic device may identify the positions of the edges 3720a and 3720b among a plurality of pixels, based on the position of at least one pixel representing the reagent pads 3730a, 3730b, and 3730c of the urine strip 120, and/or the position of at least one pixel representing the base substrate 910. The electronic device may identify a pixel having a color value corresponding to the reagent pads 3730a, 3730b, and 3730c and a pixel having a color value corresponding to the base substrate 910 based on the values of the plurality of pixels.

In addition, the electronic device may acquire information associated with the reference position according to the above-described method (3601), and then acquire a color value of at least one color mark spaced apart from the reference position by a first distance in a first direction (3603). In this case, the first direction may be a longitudinal direction of the strip. Specifically, the electronic device may set, as the first direction, the slope direction of the strip obtained by checking. Further, the electronic device may preliminarily recognize (e.g., store in advance in the memory) information on the distance (e.g., the first distance) from the edge of the strip to the color mark, and may detect the position of at least one color mark based on information associated with the edge of the strip (e.g., slope information) and the information on the distance to acquire the color value of the at least one color mark. In addition, the above-described operation 3603 may be performed a number of times corresponding to the number of color marks included in the strip. In this case, the electronic device may acquire color values of color marks adjacent to the initially detected color mark by checking pixel values of pixels spaced apart from the initially detected color mark by a specific distance (an interval between pre-stored color marks, which may be the same as or different from the first distance) in the direction of slope of the strip. For example, referring to FIG. 37, the electronic device may determine that a pixel value of at least one pixel corresponding to the first color mark 3730a spaced apart from the second edge 3720b by a first distance d1 in the longitudinal direction considering the slope of the strip is the color value of the first color mark. In addition, the electronic device may determine that a pixel value of at least one pixel corresponding to the second color mark 3730b spaced apart from the first color mark 3730a by the second distance d2 is the color value of the second color mark, and may determine that a pixel value of at least one pixel corresponding to the third color mark 3730c spaced apart from the second color mark 3730b by a third distance d3 is the color value of the third color mark. In this case, the first distance d1 and the second distance d2 may be different from each other, but are not limited thereto and may be the same. In addition, the second distance d2 and the third distance d3 may be the same, but are not limited thereto and may be different from each other.

In addition, the electronic device is not limited thereto, and may acquire position information about the color mark based on a minimum point of pixel values (scales) corresponding to a plurality of pixels extending in the longitudinal direction of the strip. In this case, the electronic device may determine a pixel coordinate corresponding to the minimum point of the plurality of pixel values as the position of the color mark, and may determine that a pixel value corresponding to the minimum point is a color value of the color mark.

In addition, the electronic device may acquire positions of a plurality of reference marks based on the region of interest and, accordingly, acquire color values of the reference marks (3605). In this case, the electronic device may preliminarily recognize (e.g., store in advance in the memory) information about relative positions of the plurality of reference marks with respect to the region of interest. Accordingly, the positions and color values of the plurality of reference marks may be acquired by checking pixel coordinates and values of pixels corresponding to the plurality of reference marks based on the information about relative positions of the plurality of reference marks with respect to the region of interest.

After acquiring the color values according to operations 3603 and 3605, the electronic device may be configured to perform operation 3801 to be described below in order to correct the color values to values suitable for image analysis.

Figure 38:
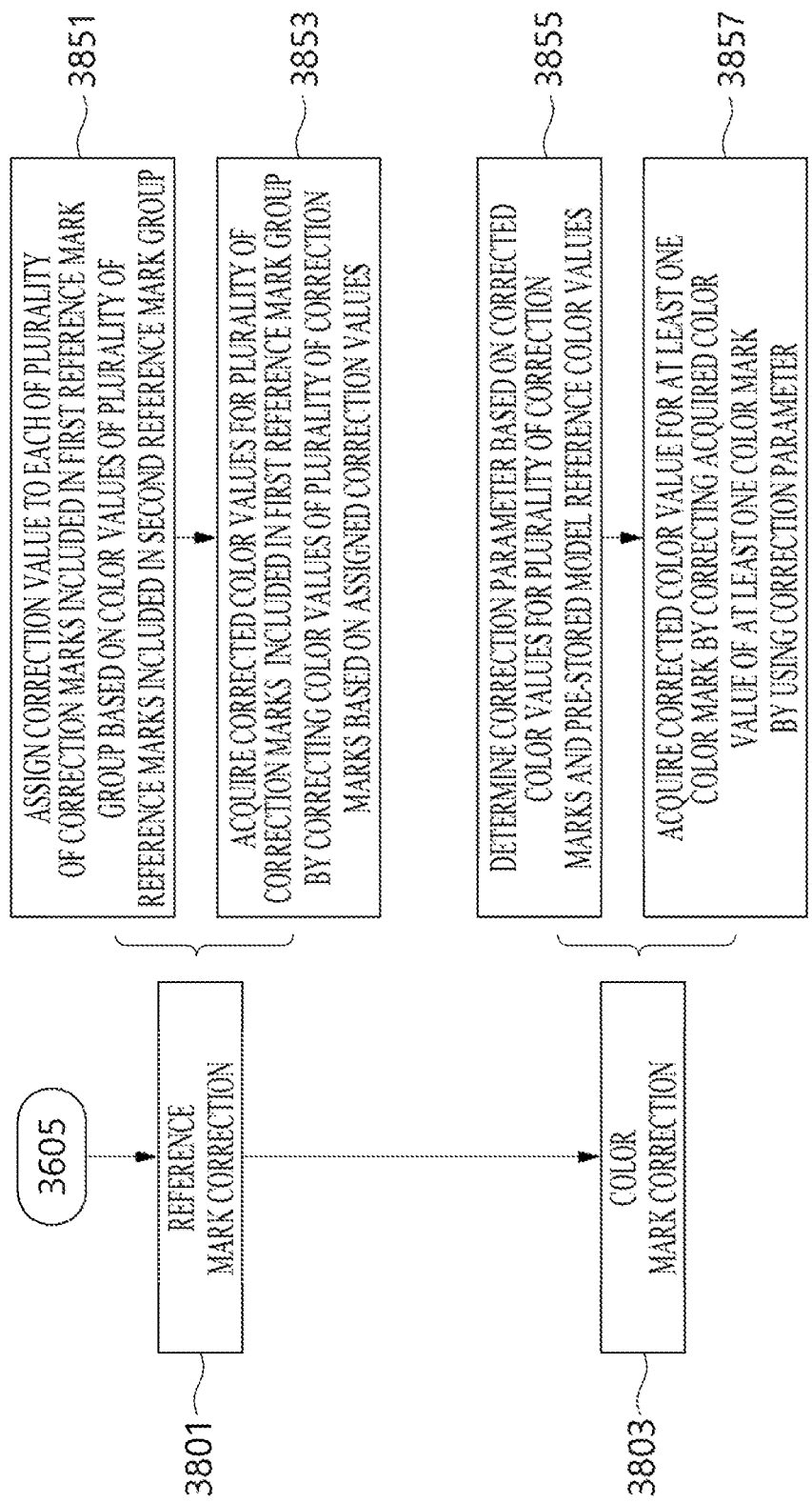
FIG. 38 is a flowchart illustrating a specific method for correcting a color value by an electronic device, according to various embodiments.

FIG. 38 is a flowchart illustrating a specific method for correcting a color value by an electronic device, according to various embodiments.

Figure 40:
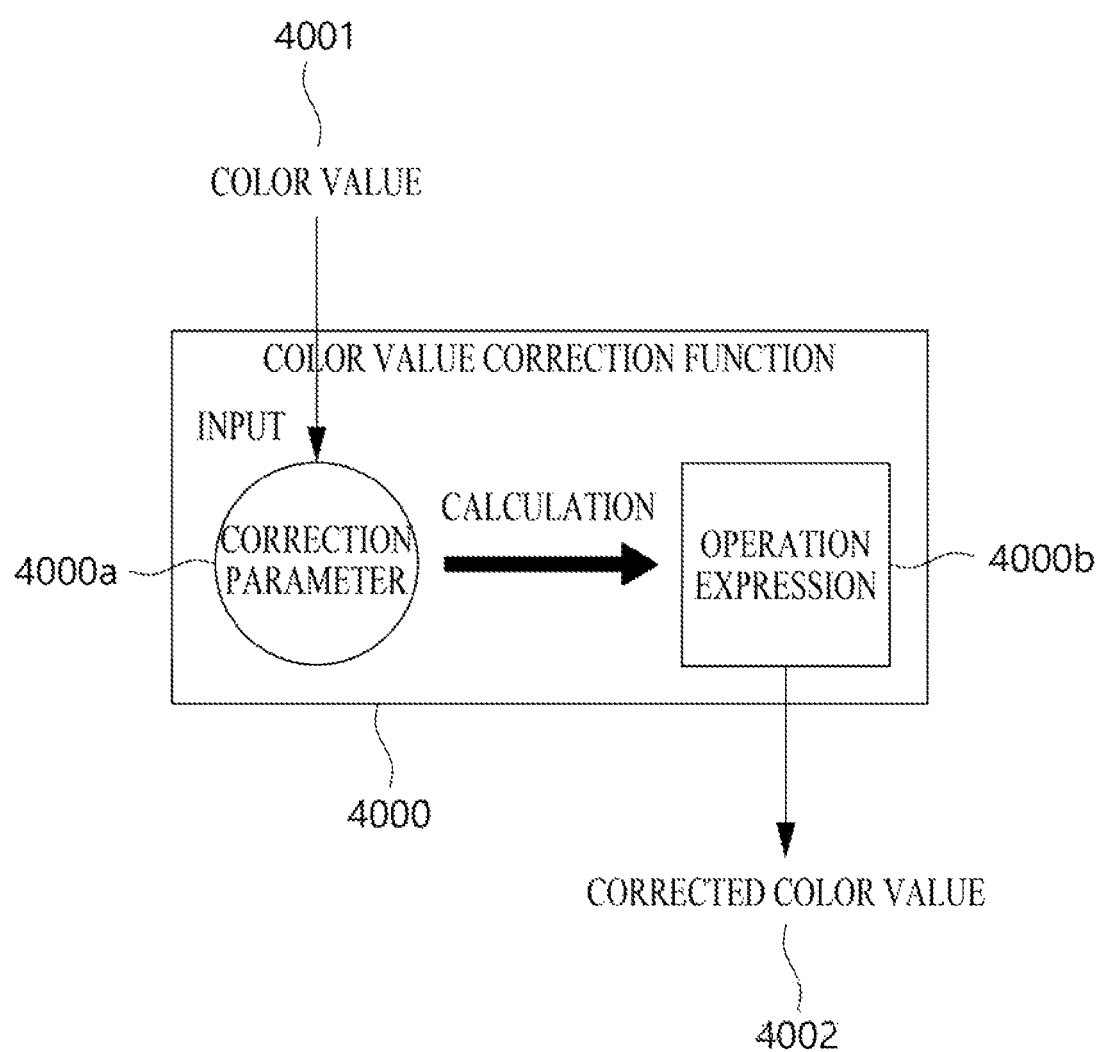

FIGS. 39 and 40 are diagrams illustrating an example in which the method according to FIG. 38 is performed.

Referring to FIG. 38, the electronic device may perform a correction operation 3801 on a reference mark included in an image. In this case, the reference mark correction operation 3801 may refer to an operation of correcting color values of a plurality of correction marks included in the test board on the image in a predetermined manner. Specifically, the reference mark correction operation 3801 may be performed for the purpose of compensating for color value errors caused by shading (shading compensation) in order to perform image analysis in the same lighting environment.

The detailed method is as follows.

An electronic device according to various embodiments may assign a correction value to each of the plurality of correction marks (see reference numerals 800a to 800f in FIG. 8) included in the first reference mark group (see reference numeral 800 in FIG. 8), based on the color values of the plurality of reference marks (see reference numerals 820a to 820d in FIG. 8) included in the second reference mark group (see reference numeral 810 in FIG. 8) acquired by the method described above (the method according to FIG. 36) (3851). Since the plurality of reference marks are formed in standard white color (e.g., gray scale: 255) and positioned at the edge of the correction paper region, color values of the reference marks identified through image processing may reflect the direction of lighting and/or the degree of shade. In this case, the electronic device may determine correction values to be assigned to each of the plurality of correction marks based on a difference between the color values of the plurality of reference mark. Specifically, the electronic device may determine the correction values based on a difference between a maximum value and a minimum value of color values of the plurality of reference marks. Further, the electronic device may determine the correction values based on a distance from each of the correction marks to the reference mark with the maximum (or minimum) color value. For example, the electronic device may assign a smaller correction value to a correction mark as the distance to the reference mark having the maximum value (or minimum value) is closer (or farther), but the assignment is not limited thereto. As a specific example, in FIG. 39 (a) (some reference numerals of FIG. 8 are borrowed for convenience of description), it is assumed that the first reference mark 810a has a maximum color value (e.g., 255) and the third reference mark 810c has a minimum color value (e.g., 180). The electronic device may assign a minimum correction value (e.g., 0) to a first correction mark 800a that is closest to the first reference mark 810a and farthest from the third reference mark 810c, and may assign a maximum compensation value (e.g., 70) to the fourth correction mark 800d that is furthest from the first reference mark 810a and closest to the third reference mark 810c. In addition, here, the maximum correction value and the minimum correction value may be determined based on a difference between a maximum value and a minimum value of the color values.

In addition, the electronic device may acquire corrected color values for a plurality of correction marks included in the first reference mark group by correcting color values of the plurality of correction marks based on the assigned correction values (3853). Specifically, the electronic device may acquire corrected color values for the correction marks by calculating the assigned correction values and the color values of the correction marks based on a predetermined calculation method. For example, referring to FIG. 39(b), the corrected color value for each of the correction marks shown in FIG. 39(a) may be acquired by adding the assigned correction value to each of the correction marks.

In addition, the electronic device may perform a color mark correction operation 3803 after performing the reference mark correction operation 3801 (regardless of whether or not the reference mark correction operation is performed according to the embodiment). In this case, the color mark correction operation 3803 may refer to an operation of correcting the color value of at least one color mark included in the test board on the image in a predetermined manner. Specifically, the color mark correction operation 3803 may be performed for the purpose of matching the color values to the environment in which the model reference color values are photographed by utilizing pre-stored model reference color values in order to perform image analysis in the same photographing environment. In this case, the model reference color values may refer to data on color values of a plurality of correction marks in a specific environment that the electronic device stores in advance (e.g., color values of correction marks acquired by photographing with a mobile phone of company A). For example, the electronic device may set color values acquired by photographing a strip with six levels of reagents under a predetermined lighting using each of mobile phones of company A and company B as different model references and store the different model references in advance.

The detailed method is as follows.

The electronic device according to various embodiments may determine a correction parameter 4000a based on the corrected color values for the plurality of correction marks acquired in operation 3801 and the pre-stored model reference color values (3855). For example, referring to FIG. 40, the electronic device may store a color value correction function 4000 for correcting a specific color value in advance. The color value correction function 4000 may include the correction parameter 4000a and a predetermined operation expression 4000b. In this case, the correction parameter 4000a may be a parameter for correcting an input color value. For example, the correction parameter may include a parameter of a parametric function defined based on a correspondence between corrected color values for the plurality of correction marks and the model reference color values. That is, since the operation expression 4000b is determined in advance, the correction parameter 4000a may be varied. Accordingly, when the electronic device inputs corrected color values for a plurality of correction marks as input values 4001 of the correction function 4000, the electronic device may set (or determine) the correction parameter 4000a so that model reference color values stored in advance are output as output values 4002.

In addition, the electronic device may acquire the corrected color value for at least one color mark by correcting the acquired color value of the at least one color mark by using the correction parameter (3857). Specifically, the electronic device may acquire the output (4002) corrected color value for at least one color mark by inputting (4001) the color value of the at least one color mark to the color value correction function (4000) defined based on the correction parameter.

According to the above-described reference mark correction operation 3801 and color mark correction operation 3803, the electronic device may acquire the corrected color value. In this way, the degree to which a specific substance exists in urine may be estimated by comparing the color values for which color correction has been completed with the test indicators stored in advance, and result information about the urine test may be generated and provided to the user based on the estimated result (image analysis operation 3210 of FIG. 32). Specifically, the electronic device may analyze the image using a machine learning algorithm such as a support vector machine (SVM) or a K-nearest neighbor (KNN), but the analysis method is not limited thereto and a machine learning algorithm commonly used in the related art may be selectively utilized.

Figure 41:
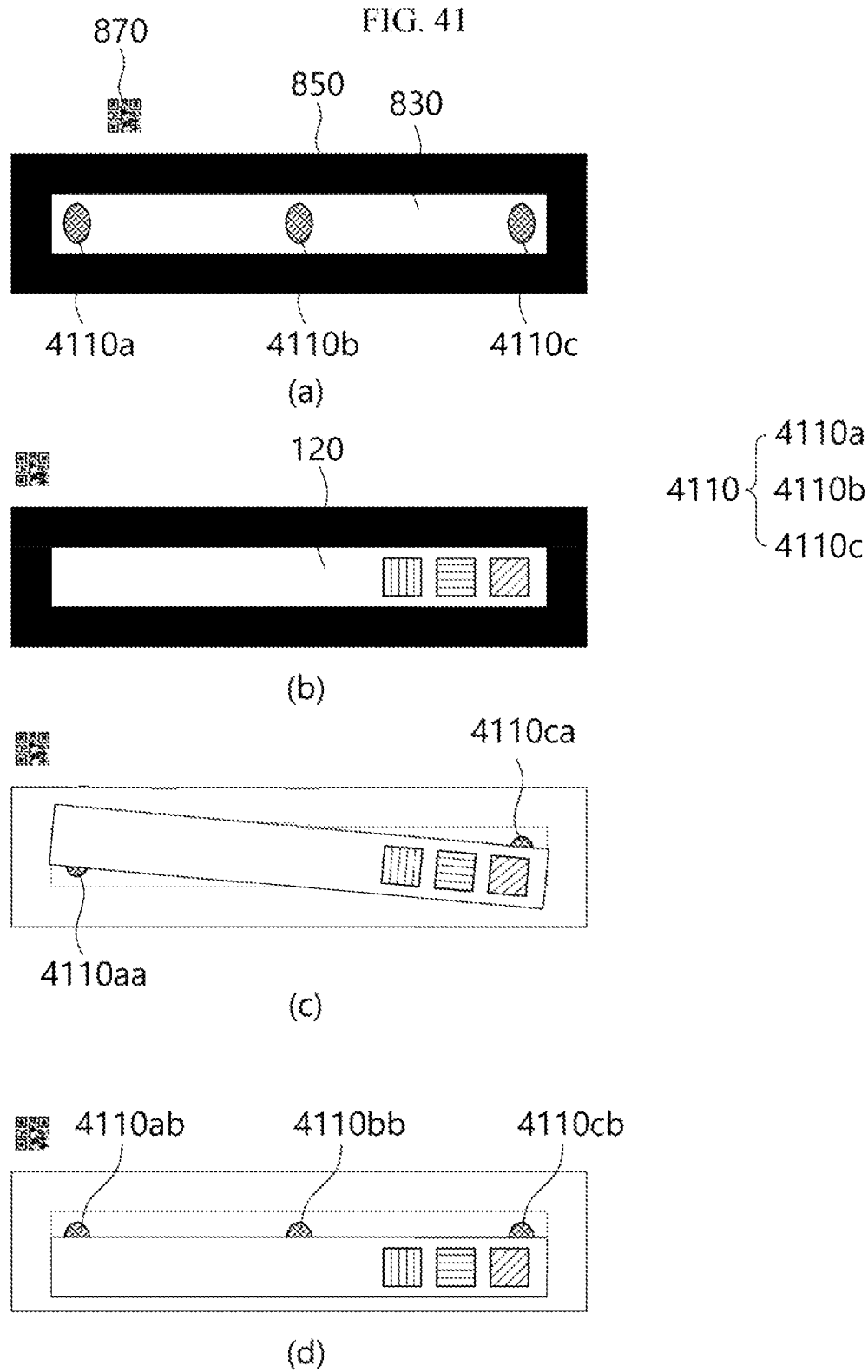
FIG. 41 is a diagram illustrating another example of a method of acquiring information associated with a disposition state of a strip by an electronic device, according to various embodiments.

FIG. 41 is a diagram illustrating another example of a method of acquiring information associated with a disposition state of a strip by an electronic device, according to various embodiments.

A test board (e.g., the board 110) according to another embodiment may include at least one marker 4110 visually displayed on the test board (e.g., the board 110). For example, referring to FIG. 41(a), the test board (e.g., the board 110) according to the embodiment may include a main region 830 (or strip attachment region) for attaching a reagent item (or a color mark including the reagent item) and a peripheral region 850 provided to surround the main region 830, and a QR code 870 provided adjacent to the peripheral region 850. In this case, at least one marker 4110 may be visually provided on at least a portion of the main region 830. Specifically, the main region 840 may include a first marker 4110a, a second marker 4110b, and a third marker 4110c that are sequentially formed along the longitudinal direction of the strip attachment region.

In this case, the at least one marker 4110 may be a component for checking whether the strip is properly attached to the test board during the urine test based on the image of the test board (e.g., the board 110).

Specifically, the electronic device (e.g., the user terminal 130) according to various embodiments may check whether the strip is properly attached to the test board by detecting information about the at least one marker 4110 in the image of the test board. In this case, the electronic device may generate and provide error information associated with the strip attachment state, which means that the strip 120 is not properly attached, when a predetermined error condition is achieved with respect to the at least one marker 4110. More specifically, when the electronic device (e.g., the user terminal 130) may generate and provide error information associated with the strip attachment state when visual information on at least one marker 4110 of a certain level or higher is detected in the image of the test board to which the strip 120 is attached.

As an example, when the strip 120 is properly attached to the strip attachment region of the test board (e.g., the board 110) as shown in FIG. 41(b), the at least one marker 4110 may be completely covered. In this case, the electronic device (e.g., the user terminal 130) may not acquire visual information on the at least one marker 4110, and accordingly, may determine that the strip is properly attached.

As another example, as shown in FIG. 41(c), when the strip 120 is obliquely attached to the strip attachment region of the test board (e.g., the board 110), at least a portion of the at least one marker 4110 may be exposed. For example, the image of the test board (e.g., the board 110) to which the strip is attached may include visual information on a portion 4110aa of the first marker and visual information on a portion 4110ca of the third marker. In this case, since the electronic device (e.g., the user terminal 130) does not detect visual information on the second marker 4110b, the electronic device may determine that the strip 120 is attached obliquely. In addition, the electronic device may generate error information on the degree of inclination of the strip by determining whether the exposure ratio of the visual information on the portion 4110aa of the first marker and the visual information on the portion 4110ca of the third marker is equal to or greater than a predetermined level.

As another example, as shown in FIG. 41(d), when the strip 120 is attached to the strip attachment region of the test board (e.g., the board 110) in a misaligned state, at least a portion of the at least one marker 4110 may be exposed. For example, the image of the test board (e.g., the board 110) to which the strip 120 is attached may include visual information on a portion 4110ab of the first marker, visual information on a portion 4110bb of the second marker, and visual information on a portion 4110cb of the third marker. In this case, since the electronic device (e.g., the user terminal 130) acquires visual information for all markers 4110a, 4110b, and 4110c, the electronic device may determine that the strip is attached in a misaligned state. The electronic device (e.g., the user terminal 130) may generate error information on the degree of misalignment of the strip by determining whether the exposure ratio of the visual information on the portion 4110ab of the first marker, the visual information on the portion 4110bb of the second marker, and the visual information on the portion 4110cb of the third marker is equal to or greater than a predetermined level.

As an additional example, the electronic device (e.g., the user terminal 130) may use character information for guide to the strip attachment region as the above-described marker. Specifically, the electronic device (e.g., the user terminal 130) may determine the attachment state of the strip based on the degree to which characters for guide to the strip attachment region are covered. Further, in this case, the electronic device (e.g., the user terminal 130) may generate and provide error information associated with the strip attachment when the degree to which the characters for guide to the strip attachment region are covered exceeds a preset threshold.

Hereinafter, examples of electronic devices for the urine test according to various embodiments will be described.

According to various embodiments, an electronic device for the urine test (e.g., the electronic device 140) may include a portable type electronic device and a bidet type electronic device.

In this case, the bidet type electronic device (not shown) may be provided integrally attached to a toilet cover. In addition, the bidet type electronic device may be implemented so that the urine strip is mounted and the urine of the user is analyzed through the urine strip, and/or may be implemented to include a urine test sensor (e.g., a Raman sensor or a urine test electrode) to perform the urine test based on the sensor.

Examples of the electronic device for the urine test will be described based on a portable type electronic device through FIGS. 42 to 49, but it goes without saying that some of the features disclosed through the embodiments will be applied regardless of the form of the device.

Figure 42:
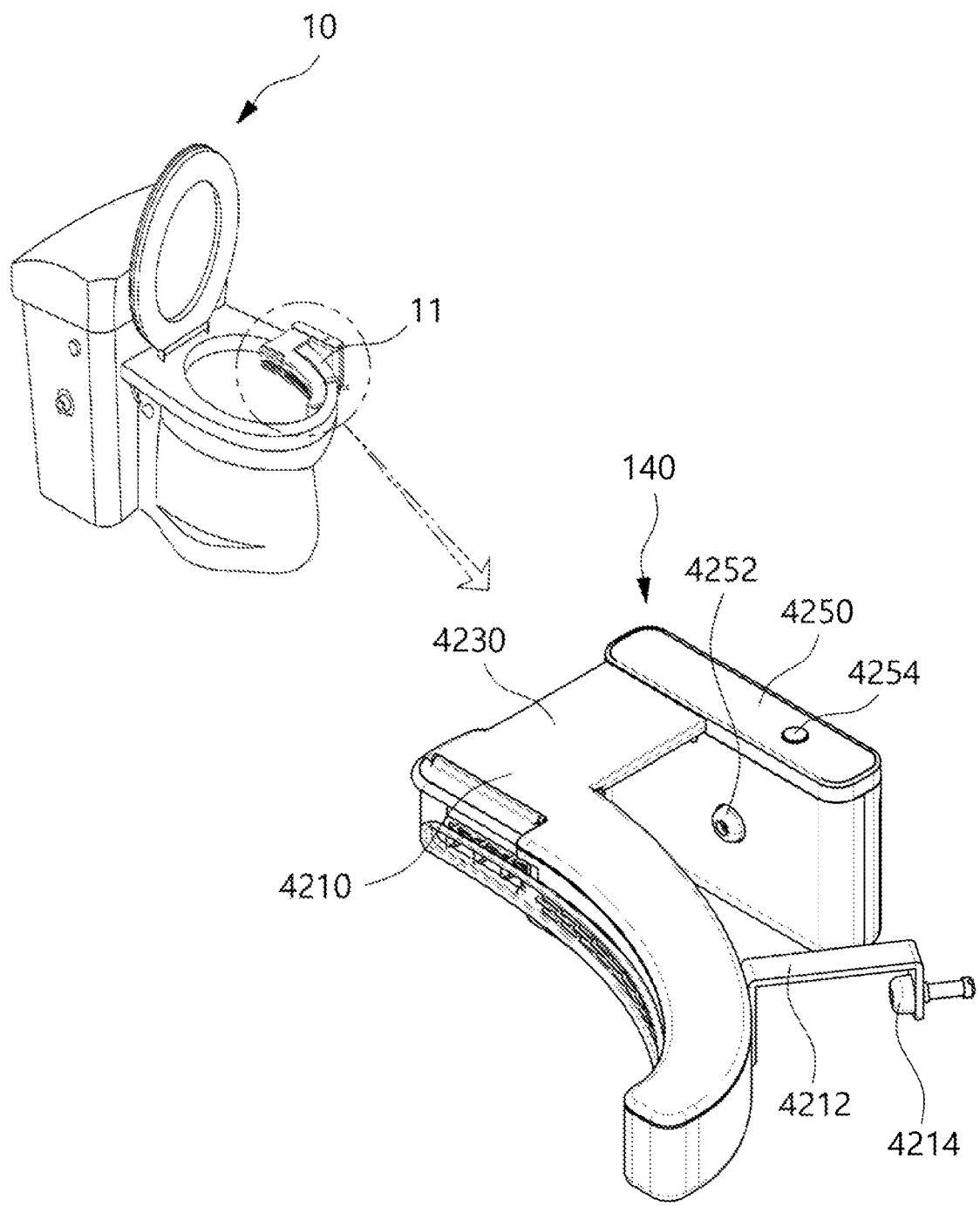
FIG. 42 is a diagram illustrating an appearance of an electronic device for a urine test, according to various embodiments.

FIG. 42 is a diagram illustrating an appearance of an electronic device for a urine test (hereinafter, referred to as "electronic device"), according to various embodiments.

Referring to FIG. 42, the electronic device 140 according to an embodiment may be mounted on at least a portion 11 of a toilet 10. In this case, at least a portion 11 of the toilet may be a portion of pottery or a portion of the toilet cover.

Further, although not shown in FIG. 42, the electronic device 140 according to another embodiment may be provided so that some components included in the electronic device are mounted on at least the portion 11 of the toilet, and other components are not mounted on the toilet. For example, the electronic device 140 may be provided so that a first portion including physical components for the urine test is mounted on at least a portion of the toilet and a second portion including at least one processor for instructing an operation for the urine test is provided separately, or is integrated into the user terminal. In this case, the second portion may be provided in the form of a controller that may be attached to the wall of the bathroom, but is not limited thereto.

The electronic device 140 may be configured to be stably mounted on at least a portion 11 of the toilet, may have an internal space, and may include at least one housing 4210, 4230, or 4250 having a predetermined shape. For example, the electronic device 140 may include a first housing 4210, a second housing 4230, and a third housing 4250 that are connected to each other but have different shapes and different functional components.

In this case, the first housing 4210 may be provided in a curved shape. Specifically, the first housing 4210 may have a shape extending from a first point connected to the second housing 4230 by a specific length in a direction associated with a first curvature. In this case, the first curvature may correspond to the curvature of the top surface of the toilet on which the electronic device 140 is mounted. Since the shape is different depending on the curvature of the top surface of each toilet, the first housing 4210 may be provided to have a shape corresponding to the curved shape of a generally used toilet. In addition, since the curvature of the first housing 4210 may not be constant, the first housing 4210 may have a shape extending by a specific length in a direction associated with the first curvature (e.g., example, a direction accompanying a change in curvature at a predictable level).

In addition, the second housing 4230 may have a bottom surface to be disposed on at least a portion 11 of the toilet (e.g., a specific position on the top surface of the toilet). Specifically, the second housing 4230 may have a flat bottom surface corresponding to a flat shape of a specific portion of the top surface of the toilet. At least a portion of the toilet on which the second housing 4230 is disposed may be understood as a concept that it includes not only a portion of a component (e.g., a body constituting the toilet) of the toilet (e.g., a portion of the top surface of the body), but also a portion of a component mounted on the toilet (e.g., a toilet seat cover, a bidet device).

In addition, the first housing 4210 and the second housing 4230 may be connected so that the top surface of the first housing 4210 and the top surface of the second housing 4230 are connected without a step. In addition, the connection is not limited thereto, and as the electronic device 140 is designed to be stably mounted on the toilet, the top surface of the second housing 4230 may be connected to the top surface of the first housing 4210 with a step. For example, the second housing 4230 and the first housing 4210 may be connected so that the top surface of the second housing 4230 is formed at a lower position than the top surface of the first housing 4210. Through the above-described stepped structure, it is possible to solve the problem of a step that occurs when the electronic device 140 is mounted and the toilet cover is additionally mounted on the toilet.

Further, the third housing 4250 may be connected from a specific point opposite to a point where the second housing 4230 is connected to the first housing 4210. Accordingly, when the electronic device 140 is mounted on a specific portion of the toilet, the third housing 4250 may be disposed in a direction away from the outer surface of the toilet.

Meanwhile, although not shown, at least some of the housings (e.g., the first housing 4210, the second housing 4230, and the third housing 4250) may not be integrally formed. For example, the third housing 4250 provided to include electronic components (e.g., a processor) may be provided separately from the electronic device 140. The third housing 4250 may be provided to communicate with wireless communication circuits of remaining components (e.g., first housing 4210 and/or second housing 4230) of the electronic device 140 using wireless communication circuit (e.g., short-range communication circuit), and control electronic components (e.g., a sensor and a motor) associated with the remaining components through the communication. In this case, fixing members for fixing to the toilet may be further provided in the remaining components (e.g., the first housing 4210 and/or the second housing 4230). Meanwhile, the configuration is not limited to the described example, and the second housing 4230 may not be provided.

According to various embodiments, the electronic device 140 may include components to be firmly fixed to a specific portion of the toilet.

As an example, the electronic device 140 may include at least one mounting member 4212 connected to at least a portion of the first housing 4210. In this case, the at least one mounting member 4212 may be connected to at least a portion of an outer curved surface of the first housing 4210. In addition, the at least one mounting member 4212 may be designed to cover a portion of the top surface of the toilet, and thus may be formed to fix the electronic device 140 to the toilet by applying force from both sides of the portion of the toilet to which the electronic device is mounted.

Further, as another example, the electronic device 140 (or the first housing 4210 or the at least one mounting member 4212) may include a first member 4214. In this case, the first member 4214 may be a screw type member, and may be used to fix the electronic device 140 to a portion of the toilet by applying force to the outer surface of the toilet.

Further, as another example, the third housing 4250 of the electronic device 140 may include a second member 4252. In this case, the second member 4252 may be component that comes into contact with the outer surface of the toilet when the electronic device 140 is mounted on a specific portion of the toilet. In addition, the second member 4252 may be made of an elastic material with the shape that may be deformed in order to prevent an impact applied to components accommodated in the third housing 4250.

Additionally or alternatively, electronic device 140 may include at least one function button 4254. In this case, the at least one function button 4254 may be provided on at least a portion of the third housing 4250 and may allow a predetermined function to be operated when an input is performed. For example, the at least one function button 4254 may include a power button for controlling power of the electronic device 140. However, a method for controlling the power is not limited to the button method and may include a method based on a communication connection with the user terminal. In addition, the at least one function button 4254 may include a function button for performing or ending driving for the electronic device 140 to perform the test and/or a function button for performing or ending a sensing function of a sensor. However, the above-described function performing method is not limited to the button control method, and may be performed automatically according to a preset driving algorithm or based on an input received from a user terminal.

Figure 43:
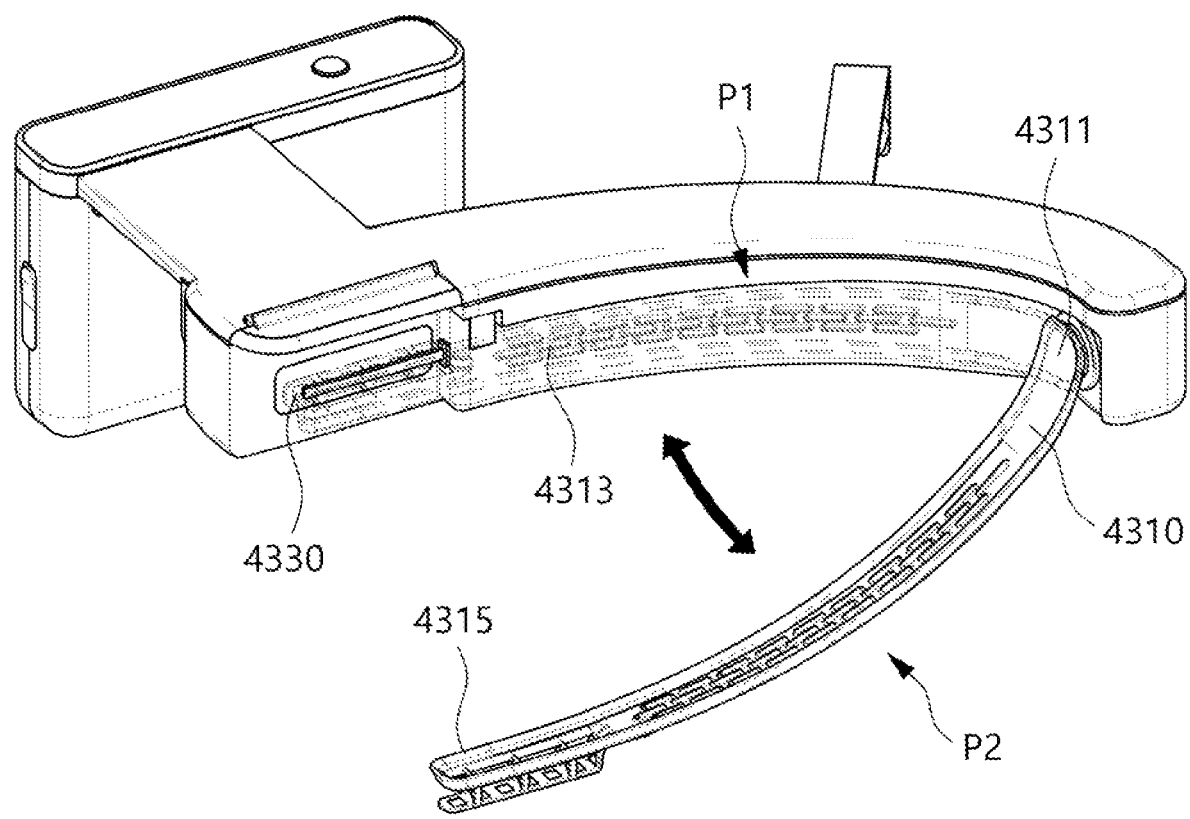
FIG. 43 is a diagram for describing components included in or mounted in the electronic device of FIG. 42.

FIG. 43 is a diagram for describing components included in or mounted in the electronic device of FIG. 42.

According to various embodiments, the electronic device may include a detection unit for detecting a sample such as urine and a sensing unit for acquiring information about the sample using at least one sensor.

Specifically, the detection unit may be implemented as a gutter 4310 provided with a space in which a urine test strip is mounted. In this case, although the detection unit is illustrated in the shape of the gutter shape in FIG. 43, the detection unit is not limited thereto, and FIG. 43 is merely a diagram illustratively shown to describe an embodiment of an electronic device including a gutter-shaped detection unit.

In this case, the gutter 4310 may be formed to be rotatably driven. Specifically, the gutter 4310 may be formed to be rotatably driven between a first position P1 for sensing detected urine and a second position P2 for collecting urine. The operation of the electronic device at the first position P1 and the second position P2 will be described in more detail below.

In addition, the radius of rotation of the gutter 4310 is not limited to between the first position P1 and the second position P2, and may be determined to rotatably driven to a required position according to an embodiment. For example, in order to guide the user to conveniently mount the gutter, the gutter 4310 may be driven to be rotated by 180 degrees with respect to the second position P2 to a third position (not shown) where the gutter is exposed above the toilet. As a specific example, when a communication connection is established between the user terminal and the electronic device, at least one processor of the electronic device may rotatably drive the gutter to the third position (not shown) where it is possible for the user to easily mount the strip.

In addition, the gutter 4310 may be coupled to a specific portion of the first housing to be rotatably driven with respect to the first housing (see 4210 in FIG. 42). Further, in this case, the gutter 4310 may have a curvature corresponding to the curvature of the first housing.

The gutter 4310 may include a coupling portion 4311 for connecting the gutter to the first housing (see 4210 in FIG. 42), a flow path portion 4313 for guiding urine toward the strip, and a strip mounting portion 4315 for mounting the urine test strip.

As described above, the coupling portion 4311 may be formed such that the gutter 4310 is rotatably driven with respect to the housing.

In addition, the flow path portion 4313 may include at least one protruding structure for guiding the urine provided in at least a portion of the gutter 4310 toward the strip mounting portion 4315 to lead the urine to at least one reagent item included in the strip.

In addition, the strip mounting portion 4315 may include a space in which the urine test strip is mounted. The strip mounting structure of the strip mounting portion 4315 will be described in detail with reference to FIG. 44.

In addition, according to an embodiment, the strip mounting portion 4315 may be formed to be detachable from the gutter 4310. In this case, the user may mount the strip on the detached strip mounting portion 4315, attach the strip mounting portion to the gutter again, and then perform the urine test.

In addition, the sensing unit included in the electronic device may be at least one sensor 4330 for acquiring information on reagent items included in the urine test strip. In this case, the at least one sensor 4330 may be implemented to include a color sensor provided to acquire color values. A method of acquiring information on a reagent item by using at least one sensor 4330 will be described in detail with reference to FIG. 49.

Further, in the electronic device according to another embodiment, the detection unit may be provided in the form of a sensing probe. Specifically, the electronic device may be implemented to analyze components of urine using electrodes by bringing a probe into contact with urine. For example, the detection unit of the electronic device may include a Raman scattering-based biosensor, and in this case, may better detect a specific component in urine by detecting an electrical signal with high sensitivity. Also, the detection unit of the electronic device is not limited thereto, and may include a component that generates heat by reacting with urine components, and in this case, detect the urine components based on detected heat information.

FIG. 44 is a diagram for describing a strip mounting portion of a gutter which is an embodiment of a detection unit included in an electronic device, according to various embodiments.

Referring to FIG. 44(*a*), the strip mounting portion 4315 of the gutter 4310 may include a plurality of components for providing a space for mounting the strip. For example, the strip mounting portion 4315 of the gutter 4310 may include a first portion 4410 extending from the coupling portion toward one end of the gutter and constituting the strip mounting portion, a second portion 4430 spaced apart from the first portion 4410 to form a strip mounting space, and at least one third portion 4450 connecting the first portion 4410 and the second portion 4430. In this case, the third portion 4450 may be a component for providing a space in which the strip is mounted, and may be configured in multiple numbers (e.g., three) to stably mount the strip.

Further, the strip mounting portion 4315 may be formed so that the user may mount the strip along an A direction. Regarding the mounting method of the strip, the user mounts the strip so that the reagent item included in the strip faces the at least one sensor 4330 when the gutter is positioned at the first position (position P1 in FIG. 43), and the user mounts the strip so that the reagent item included in the strip faces the bottom when the gutter is positioned at the second position (position P2 in FIG. 43).

Referring to FIG. 44(*b*) showing the gutter according to FIG. 44(*a*) in the A direction, the third portion 4450 may include a fourth portion 4451 provided to limit the space in which the strip is mounted and may include at least one strip hole 4453 formed depending on the size of the fourth portion 4451 and providing a passage through which a strip passes. For example, the strip mounting portion 4315 may be formed so that the strip is mounted in a space formed by a plurality of strip holes formed in a plurality (e.g., three) of third portions 4450. Further, at least one strip hole 4453 may be defined along a length of the fourth portion 4451 extending toward the second portion 4430. In this case, the length at which the fourth portion 4451 extends may be set to a length at which the strip provided in the space formed through the at least one strip hole 4453 may be stably mounted and separated by a driving force.

In addition, a distance d between the first portion 4410 and the second portion 4430 (that is, the length of the third portion 4450) may define a distance between at least one sensor and at least one reagent item on the strip. Accordingly, the distance d between the first portion 4410 and the second portion 4430 may be set in consideration of a distance required for the at least one sensor 4330 shown in FIG. 43 to sense at least one reagent item mounted in the gutter positioned at the first position P1.

Referring to FIG. 44(c) showing the gutter according to FIG. 44 (a) in a direction B, the second portion 4430 (the first portion 4410 according to the embodiment) may include a fifth portion 4411 and at least one reagent hole 4413 corresponding to at least one reagent item of the strip. In this case, physical characteristics of the at least one reagent hole 4413 may correspond to physical characteristics of at least one reagent item included in the mounted strip. For example, the position of the at least one reagent hole 4413 may correspond to the position of at least one reagent item included in the strip, the number of the at least one reagent hole 4413 may correspond to the number of at least one reagent item included in the strip, and a size of the at least one reagent hole 4413 may correspond to a size of at least one reagent item included in the strip.

In addition, the strip mounting portion may include a urine guide structure formed so that, when the gutter is positioned at the second position P2 of FIG. 43, the urine guided to the strip mounting portion along the flow path portion is guided to at least one reagent item included in the strip mounted toward the bottom surface. As an example, the urine guide structure may be formed along the circumference of the at least one reagent hole 4413 and formed to be inclined toward the center of the at least one reagent hole 4413. As another example, the urine guide structure may be formed at a position (for example, a formed hole) where the urine is guided from the first portion 4410 to the strip, and formed to be inclined toward the strip so that the urine is guided to at least one reagent item.

In addition, the structure for the electronic device to hold the urine test strip is not limited to the structure shown in FIG. 44 and may be modified according to embodiments. For example, the electronic device may include a strip storage unit for storing a plurality of strips in advance. Further, for example, the electronic device may include a mounting structure for horizontally inserting the strip in a direction perpendicular to both the A direction and the B direction (the direction protruding from the screen in FIG. 44(a)).

Figure 45:
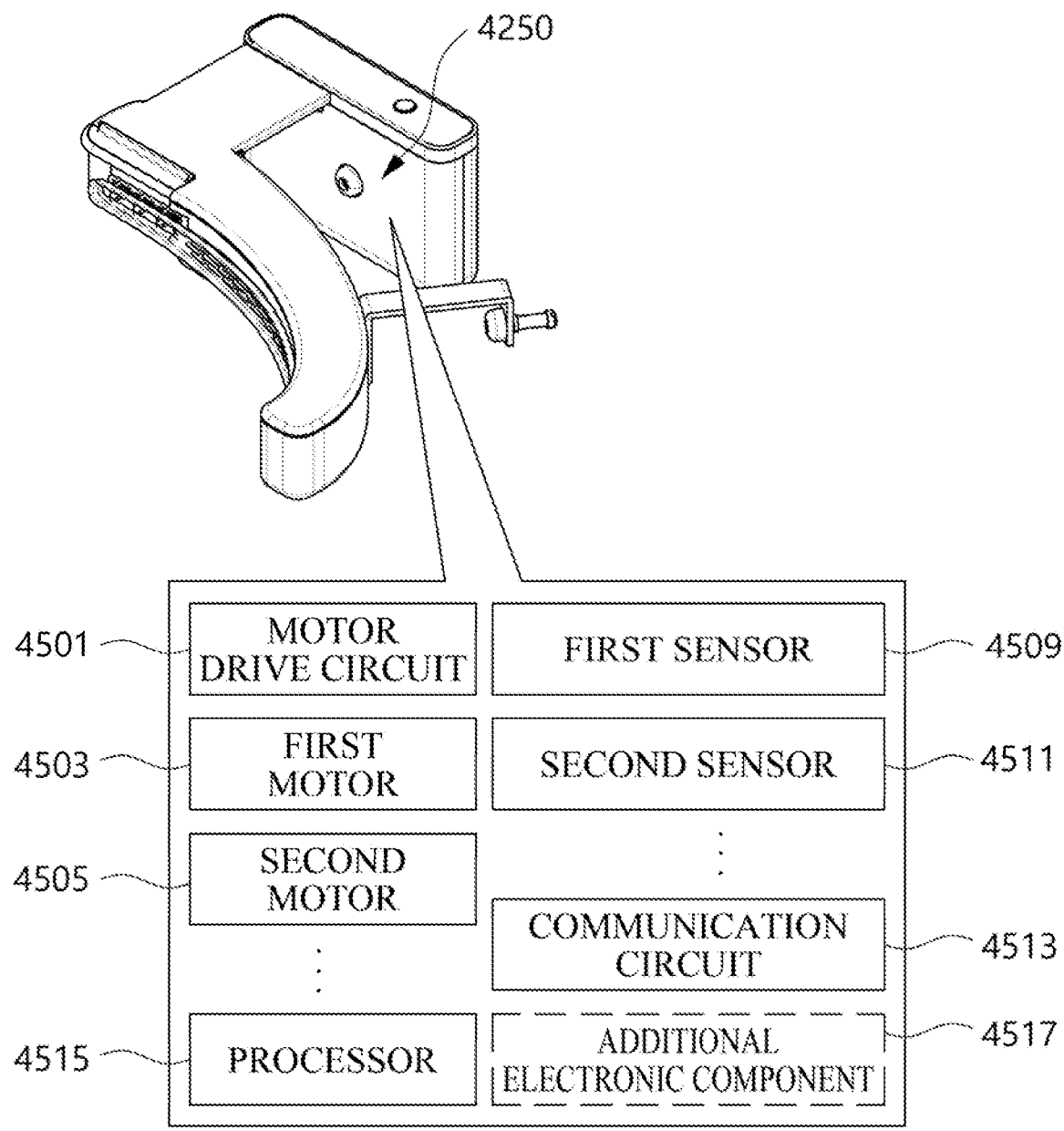
FIG. 45 is a diagram for describing electronic components included in the electronic device of FIG. 42.

FIG. 45 is a diagram for describing electronic components included in the electronic device of FIG. 42.

Referring to FIG. 45, the electronic device may include a motor drive circuit 4501 for driving a motor, at least one motor 4503 or 4505, at least one sensor 4509 or 4511, a communication circuit 4513 for establishing a communication connection with an external device, and at least one processor 4515 for controlling the electronic device and components of the electronic device.

Specifically, the electronic device may include a first motor 4503 for supplying power to drive the rotation of the gutter and a second motor 4505 for supplying power to move the mounted strip, but is limited thereto, and may further include additional motors including a third motor for driving at least one sensor.

In addition, the electronic device may include a first sensor 4509 for acquiring information on reagent items and a second sensor 4511 for detecting a rotation state of the gutter. However, the electronic device is not limited thereto, and the electronic device according to an embodiment may further include additional sensors disposed for a predetermined purpose, such as a sensor for sensing the pressure of excreted urine, a sensor for sensing the temperature of excreted urine, a sensor for sensing the sound of excreted urine, and a sensor for acquiring an image of urine that is excreted and accommodated in the toilet.

Further, the at least one processor may be configured to perform an operation of controlling the electronic device according to received instructions.

In addition, the electronic device may further include a memory (not shown) configured to store instructions to be transferred to the at least one processor and to store various data including sensing data.

In addition, the electronic device may further include an additional electronic component 4517 normally required for the electronic operation of the above-described electronic components.

In addition, various electronic components shown in FIG. 45 may be included in at least one printed circuit board (PCB) accommodated in at least one housing shown in FIG. 42. In this case, the at least one PCB may be accommodated inside the third housing 4250, but is not limited thereto, and some may be accommodated inside the first housing 4210. The respective PCBs included inside housings may be electrically and/or operatively connected to each other by wires, PCBs, or flexible printed circuit boards (FPCBs) provided in the second housing 4230 connecting the first housing 4210 and the third housing 4250. In this case, in order to protect electrical components, a design for a waterproof structure may be made.

Figure 46:
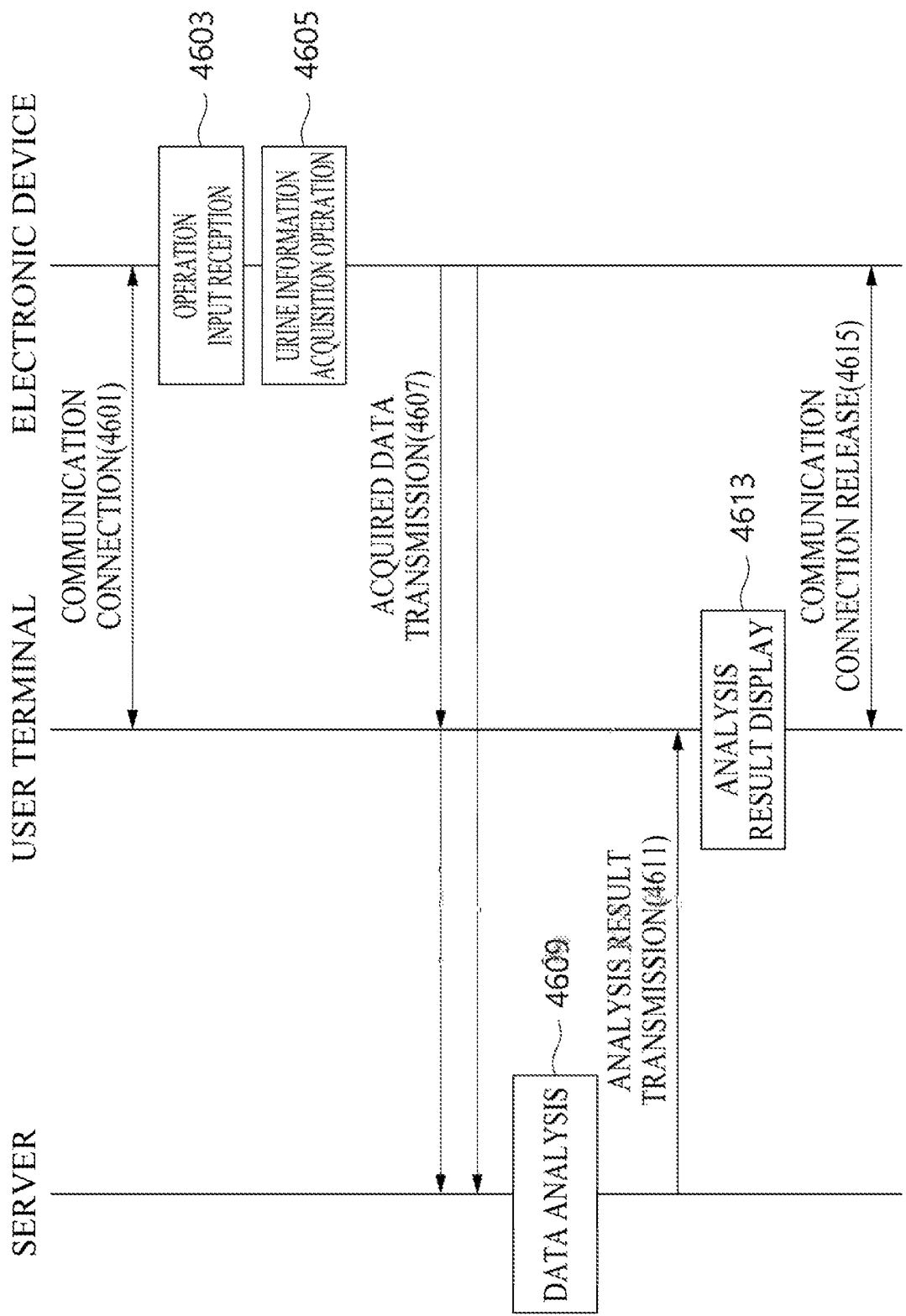
FIG. 46 is a flowchart illustrating operations performed by an electronic device, a server, and a user terminal to perform urine analysis by using the electronic device, according to various embodiments.

FIG. 46 is a flowchart illustrating operations performed by an electronic device, a server, and a user terminal to perform urine analysis by using the electronic device, according to various embodiments.

Referring to FIG. 46, a communication connection between the electronic device and the user terminal may be established in order for the electronic device to operate (4601). In addition, after the communication connection is established, the electronic device may receive a user input for an operation (4603). In this case, operation 4603 may be an optional operation. Specifically, the electronic device may recognize an event in which the communication connection is established with the user terminal as an operation input, and perform a urine information acquisition operation 4605 to be described later. Based on the reception of the operation input, the electronic device may perform the preset urine information acquisition operation 4605. In addition, the electronic device may transmit data acquired by the urine information acquisition operation to the user terminal and/or the server (4607). Upon receiving the data associated with the sensing information about urine, the server may analyze the data (4609). Further, the server may transmit an analysis result to the user terminal (4611). In addition, at least one processor of the user terminal may display the analysis result through a display (4613). In addition, when urine analysis is completed, the communication connection between the user terminal and the electronic device may be released (4615).

Figure 47:
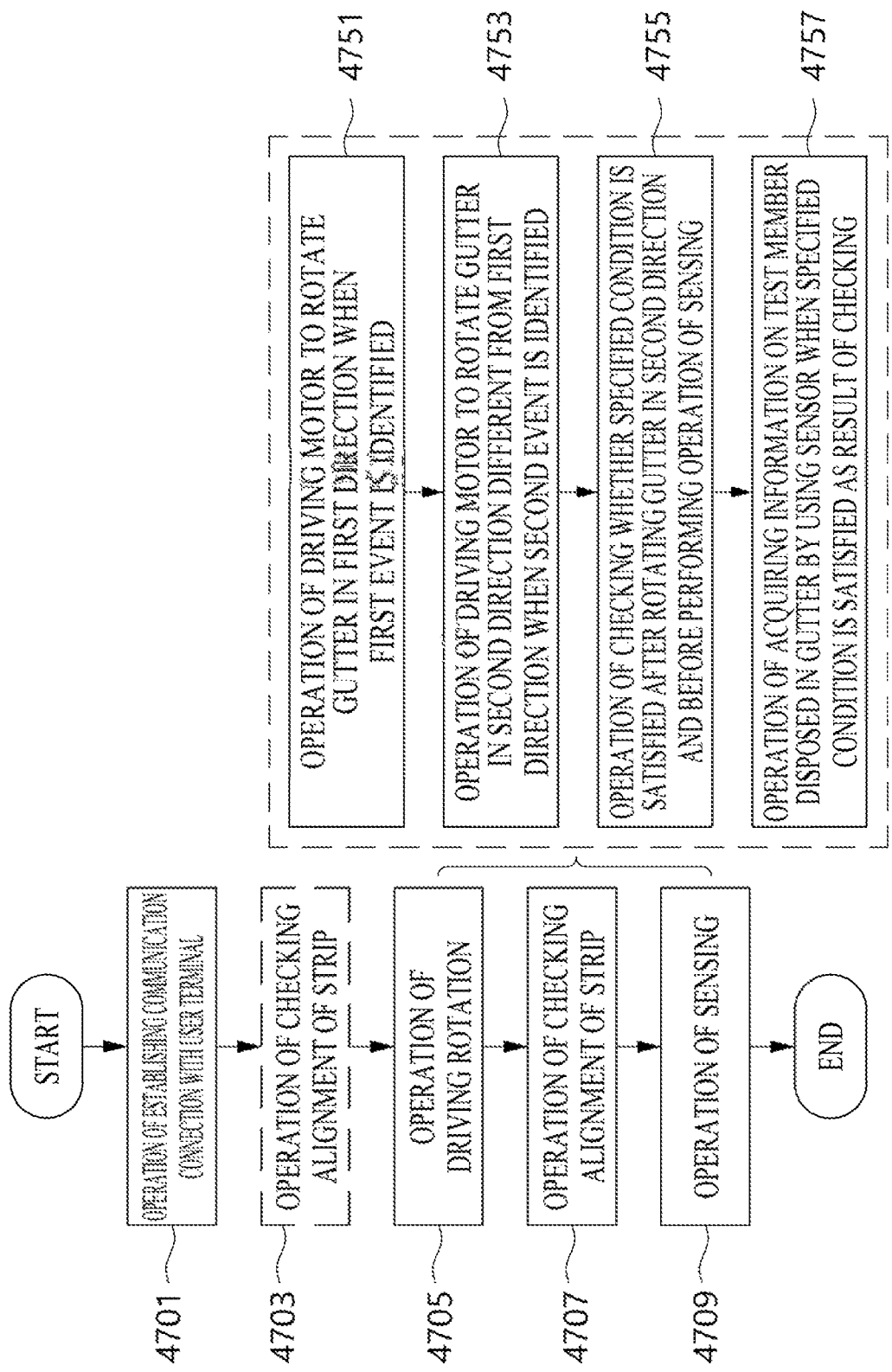
FIG. 47 is a diagram illustrating in detail an operation of acquiring urine information that is performed by an electronic device, according to various embodiments.

FIG. 47 is a diagram illustrating in detail an operation of acquiring urine information that is performed by an electronic device, according to various embodiments.

Referring to FIG. 47, an electronic device (e.g., at least one processor included in the electronic device for the urine test) may perform an operation of establishing a communication connection with a user terminal (4701).

In addition, the electronic device may check whether the strip is properly mounted in the gutter by performing operation 4703 of checking the alignment of the strip. In this case, operation 4703 may be selectively performed or may be performed along with an operation of determining a first event for performing an operation of driving rotation, which will be described below.

In addition, the electronic device may perform the operation 4705 of driving rotation of the gutter, may perform operation 4707 of checking alignment of the strip to determine whether to perform an operation of sensing after the preset operation of driving rotation is completed, and may perform the preset operation 4709 of sensing to acquire a color value of at least one reagent item included in the strip after the checking of the alignment of the strip.

Operations 4705 to 4709 may be performed as follows.

When a first event is identified, the electronic device may perform operation 4751 of driving the motor to rotate the gutter in a first direction. In this case, the first event may be a condition that is set in advance for rotational driving of the gutter in the first direction. For example, the first event may include an event for recognizing that the strip is mounted in the gutter. In addition, for example, the first event may include an event of a lapse of a predetermined time from a point of time when the communication connection with the user terminal has been established. In addition, for example, the first event may include an event of reception of an operation input from the user. Further, for example, the first event may include an event of alignment checking for the strip according to operation 4703. The example of the first event is not limited to the above examples, and the first event may be understood as a concept encompassing all types of events implying that preparation for the urine test has been completed. In addition, the motor may provide power to the coupling portion of the gutter to rotate the gutter. Further, the first direction may refer to a rotation direction from the first position P1 to the second position P2 in FIG. 43.

In addition, when the second event is identified, the electronic device may perform operation 4753 of driving the motor to rotate the gutter in a second direction different from the first direction. In this case, the second event may be a condition that is set in advance for rotational driving of the gutter in the second direction. For example, the second event may include an event of sensing completion of detection for urine excretion by the user. Further, for example, the second event may include an event of a lapse of a predetermined time from a point of time when the gutter is positioned at a second position (see P2 in FIG. 43) for receiving urine. In addition, for example, the second event may include an event of reception of an driving input from the user. In addition, for example, the second event may include an event of a lapse of a predetermined time from a point of time when the first event has been ended. The example of the second event is not limited to the above examples, and the second event may be understood as a concept encompassing all types of events implying that urine excretion of the user has been completed. Further, the second direction may refer to a rotation direction from the second position P2 to the first position P1 in FIG. 43.

In addition, the electronic device may perform operation 4755 of checking whether a specified condition is satisfied after rotating the gutter in the second direction and before performing the operation of sensing. Details of operation 4755 will be described with reference to FIG. 48.

In addition, when the specified condition is satisfied as a result of the checking, the electronic device may perform operation 4757 of acquiring information on a test member (e.g., the strip or at least one reagent item included in the strip) disposed in the gutter by using at least one sensor. Details of the operation 4757 will be described with reference to FIG. 49.

Figure 48:
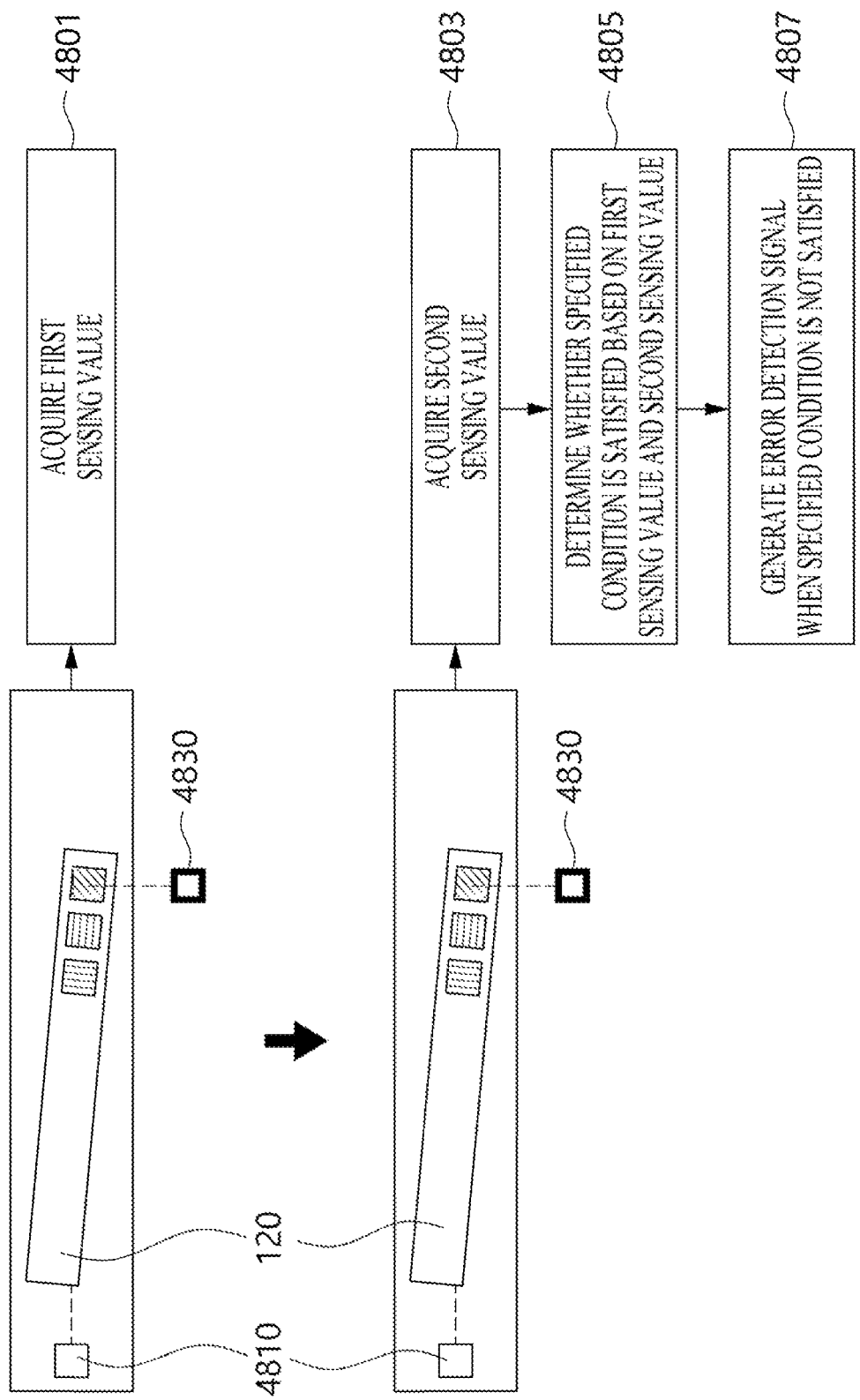
FIG. 48 is a flowchart illustrating a first embodiment of an operation of checking whether to satisfy a specified condition before an electronic device performs a sensing operation, according to various embodiments.

FIG. 48 is a flowchart illustrating a first embodiment of an operation of checking whether to satisfy a specified condition before an electronic device performs a sensing operation, according to various embodiments.

The operations according to a first embodiment may include operations of checking whether the alignment of the strip is normal by checking whether the strip 120 is normally moved by the first motor 4810 for moving the strip 120.

Referring to FIG. 48, the electronic device may acquire a first sensing value by using the first sensor 4830 after the operation 4705 of driving rotation described above is completed (4801).

In addition, the electronic device may acquire a second sensing value by using the first sensor 4830 after supplying power to move the strip 120 by using the first motor 4810 (4803).

In addition, the electronic device may determine whether a specified condition is satisfied based on the first sensing value and the second sensing value (4805). Specifically, it may be checked whether a difference between the first sensing value and the second sensing value is equal to or greater than a preset threshold value (e.g., a minimum value difference set assuming that color values are acquired from different reagent items).

Accordingly, when the specified condition is not satisfied, the electronic device may generate an error detection signal (4807). In addition, the electronic device may output an alarm for transferring an error regarding the alignment of the strip to the user based on the error detection signal.

In the operations according to the above-described first embodiment, when the strip 120 is not properly aligned in the gutter, a problem may occur in that the strip is not moved by the first motor 4810, and accordingly, the purpose of the operations is to check the alignment of the strip based on the difference between the continuously acquired sensing values.

Further, the electronic device is not limited thereto, and may determine whether to perform the sensing operation based on operations according to a second embodiment. In this case, the operations according to the second embodiment may include at least one operation for checking whether the gutter is positioned at a position required to normally perform the sensing operation (e.g., the first position P1 in FIG. 43) by the rotational driving of the gutter.

Specifically, the electronic device may further include a second sensor for detecting a rotation state of the gutter. Further, the electronic device may check whether the rotation state of the gutter is normal based on sensing information acquired by using the second sensor. For example, the second sensor may be a photo sensor and may be disposed adjacent to a specified position (first position) of a gutter required for a sensing operation, and it may be checked whether the gutter is present at the specified position (first position) by using the second sensor.

Further, the electronic device is not limited thereto, and may determine whether to perform the sensing operation based on operations according to a third embodiment. In this case, like the operations according to the second embodiment, the operations according to the third embodiment may include at least one operation for checking whether the gutter is positioned at a position required to normally perform the sensing operation (e.g., the first position P1 in FIG. 43) by the rotational driving of the gutter.

Specifically, the electronic device may acquire a third sensing value by using the first sensor 4830 after the operation 4705 of driving rotation according to FIG. 47 is completed. In addition, the electronic device may check whether the third sensing value is within a preset range (e.g., a maximum range of color values that the first reagent item of the strip may have). As described above, when the sensing value initially acquired by the first sensor is not within a normal range, the electronic device may determine that an operation error where the gutter does not reach the specified position has occurred.

Figure 49:
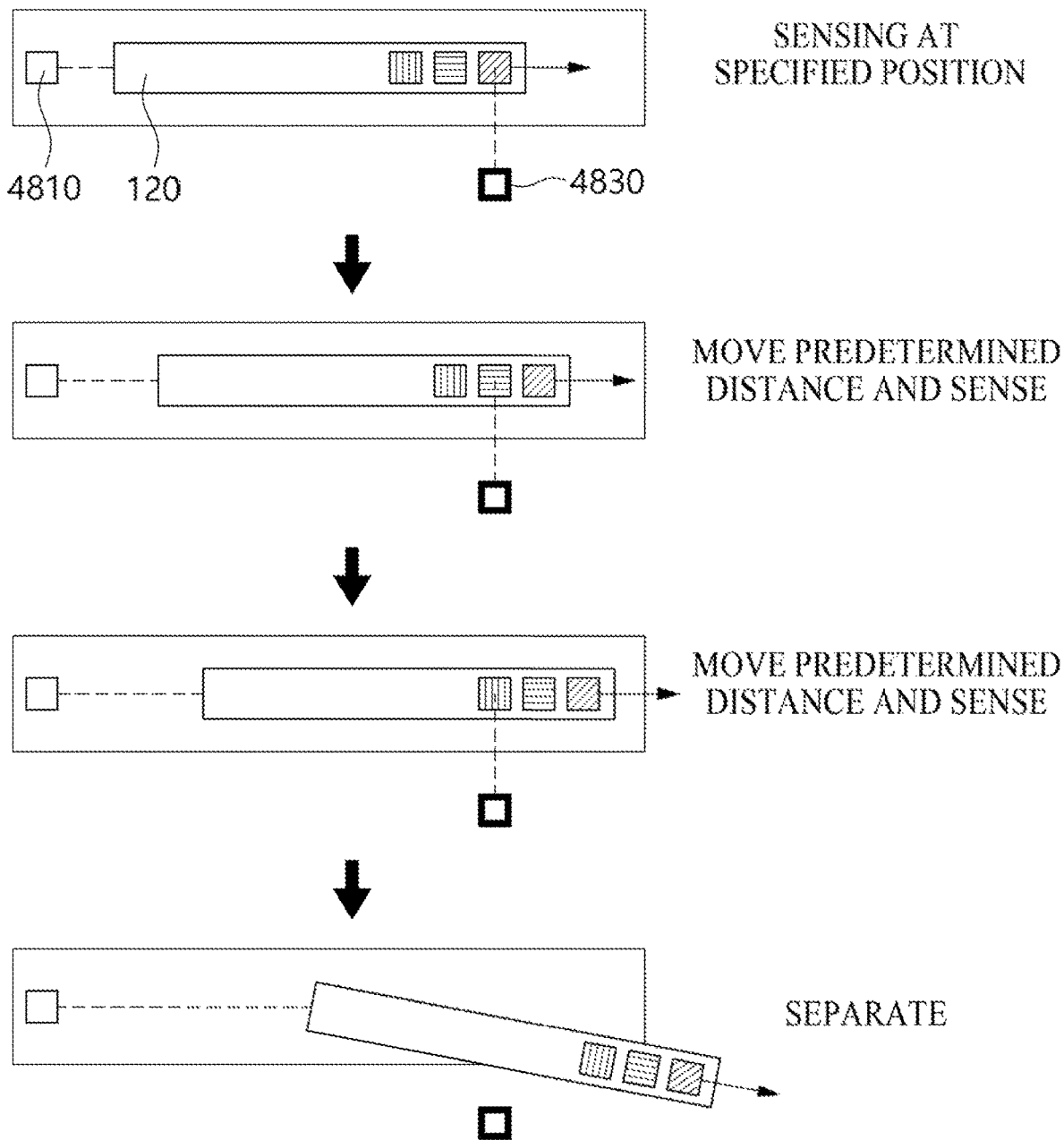
FIG. 49 is a flowchart illustrating a first embodiment in which an electronic device performs a sensing operation, according to various embodiments.

FIG. 49 is a flowchart illustrating a first embodiment in which an electronic device performs a sensing operation, according to various embodiments.

Operations according to the first embodiment may include operations of acquiring sensing information using at least one sensor by moving at least one reagent item included in the strip to a sensing position sensed by the at least one sensor.

Referring to FIG. 49, after the above-described operation of checking the alignment of the strip (see 4707 in FIG. 47) is completed, the electronic device may position the strip at a specified position by using the first motor 4810, and then acquire sensing information by using the first sensor 4830. In this case, the specified position may be set to coincide with the position of the strip at a point of time when the operation of checking the alignment of the strip is completed, but is not limited thereto, and may be set so that a position where the strip 120 for which the operation of checking has been completed may be moved to the specified position by using the first motor 4810. In this case, the first sensor 4830 may be a color sensor, and the electronic device may acquire a color value of at least one reagent item included in the strip 120 by using the color sensor.

In addition, the electronic device may acquire sensing information using the first sensor 4830 after moving the strip a predetermined distance by using the first motor 4810. In this case, the predetermined distance may be determined based on a distance between neighboring reagent items included in the strip 120. In other words, the electronic device may acquire sensing information on one or more reagent items that are linearly disposed by moving the strip 120 by the distance between neighboring reagent items included in the strip 120 (the above is a moving and sensing mechanism of the electronic device).

In this case, the above-described moving and sensing mechanism may be performed corresponding to the number of at least one reagent item included in the strip 120.

In addition, after performing the above-described moving and sensing mechanism a predetermined number of times (e.g., determined based on the number of at least one reagent item), the electronic device may use the first motor 4810 to separate the strip 120 from the gutter. In this case, the first motor 4810 may separate the strip 120 from the gutter by supplying power greater than power supplied to move the strip 120.

Further, the electronic device is not limited thereto, and may perform the sensing operation based on operations according to a second embodiment. Specifically, an electronic device according to another embodiment may include a second motor (not shown) for moving the first sensor 4830. In this case, the electronic device may acquire color information on at least one reagent item included in the strip 120 by moving the first sensor 4830 using the second motor and then acquiring sensing information. In this case, the principle of the moving and sensing mechanism of the strip accompanying the sensing operation according to the first embodiment described above may be applied as it is to the principle of the moving and sensing mechanism of the first sensor 4830; however, when the first sensor 4830 senses the last reagent item, the first sensor 4830 may be returned to its original position instead of separating the first sensor 4830.

Further, the electronic device is not limited thereto, and may perform the sensing operation based on operations according to a third embodiment. Specifically, an electronic device according to another embodiment may include a second sensor (not shown) having a wide viewing angle. In this case, the electronic device may be implemented to acquire sensing information on a plurality of reagent items at once by using the second sensor. For example, the electronic device may acquire sensing information on a plurality of reagent items by using the second sensor, and accordingly, the number of times the moving and sensing mechanism is performed may be reduced.

Further, the electronic device is not limited thereto, and may perform the sensing operation based on operations according to a fourth embodiment. Specifically, an electronic device according to another embodiment may include a plurality of sensors for acquiring information on a plurality of reagent items included in the strip. In this case, the number of the plurality of sensors may correspond to the number of the plurality of reagent items. For example, when the number of the plurality of reagent items is three, the electronic device may include three color sensors corresponding to the disposition of the plurality of reagent items, and may acquire color values for the three reagent items by using the three color sensors. Further, for example, when the number of the plurality of reagent items is four, the electronic device may include two color sensors, and in this case, may acquire color values for the four reagent items by using the two color sensors by moving the plurality of sensors or the strip.

Hereinafter, an example of an operation of connecting a communication between the user terminal 130 and the electronic device 140 according to various embodiments will be described.

Figure 50:
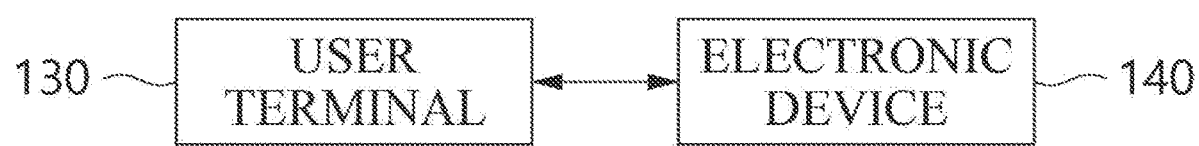
FIG. 50 is a diagram for describing an example of a communication connection between a user terminal and an electronic device, according to various embodiments.

FIG. 50 is a diagram for describing an example of a communication connection between the user terminal 130 and the electronic device 140, according to various embodiments. FIG. 51 is a diagram for describing an example of an operation of establishing and/or releasing the communication connection between the user terminal 130 and the electronic device 140, according to various embodiments.

According to various embodiments, the user terminal 130 may establish a communication connection with the electronic device 140, transmit a signal for controlling the electronic device 140 to perform the above-described urine test operation to the electronic device 140 based on the communication connection, and receive information associated with the urine test from the electronic device 140.

Referring to (a) of FIG. 51, in an embodiment, the user terminal 130 may receive a user input for selecting establishment and/or release of the communication connection (e.g., selecting graphical objects representing connection establishment and/or release) on a screen for establishing and/or releasing the communication connection provided based on the execution of the application 1441, and may establish the communication connection with the electronic device 140 and/or release the communication connection through the communication circuit 1430 based on the reception.

Referring to (b) of FIG. 51, in an embodiment, the electronic device 140 may be implemented to include a physical button for establishing and/or releasing the communication connection with the user terminal 130. The user terminal 130 may receive a signal for establishing and/or releasing the communication connection from the electronic device 140 when the physical button of the electronic device 140 is pressed by the user, and may establish or release the communication connection with the electronic device 140 based on the received signal.

Referring to (c) of FIG. 51, in an embodiment, the user terminal 130 and the electronic device 140 each may be implemented to include an NFC module 5101*a* or 5103*a* to exchange information for specific short-range communication (e.g., Bluetooth communication) with each other. When the user terminal 130 and the electronic device 140 approaches each other within a distance for NFC communication (e.g., contact each other), the user terminal 130 and the electronic device 140 may exchange information for Bluetooth communication with each other and establish a communication connection by using Bluetooth communication circuits 5101*b* and 5013*b*.

Further, although not shown, the electronic device 140 may be implemented to, when the user terminal 130 receives information associated with the urine test from the electronic device 140 while maintaining the communication connection with the electronic device 140, release the communication connection.

Hereinafter, an example of an operation of connecting a communication between the user terminal 130 and the electronic device 140 according to various embodiments will be described.

According to various embodiments, when the electronic device 140 is provided in an environment where a plurality of users reside (e.g., a bathroom in a house where families live), the electronic device 140 may establish a communication connection with the user terminals 130 of a plurality of users. In this case, the electronic device 140 and the user terminal 130 may be implemented to perform a communication connection setting operation so that a user who intends to perform a urine test among the plurality of users may use the urine test.

Figure 52:
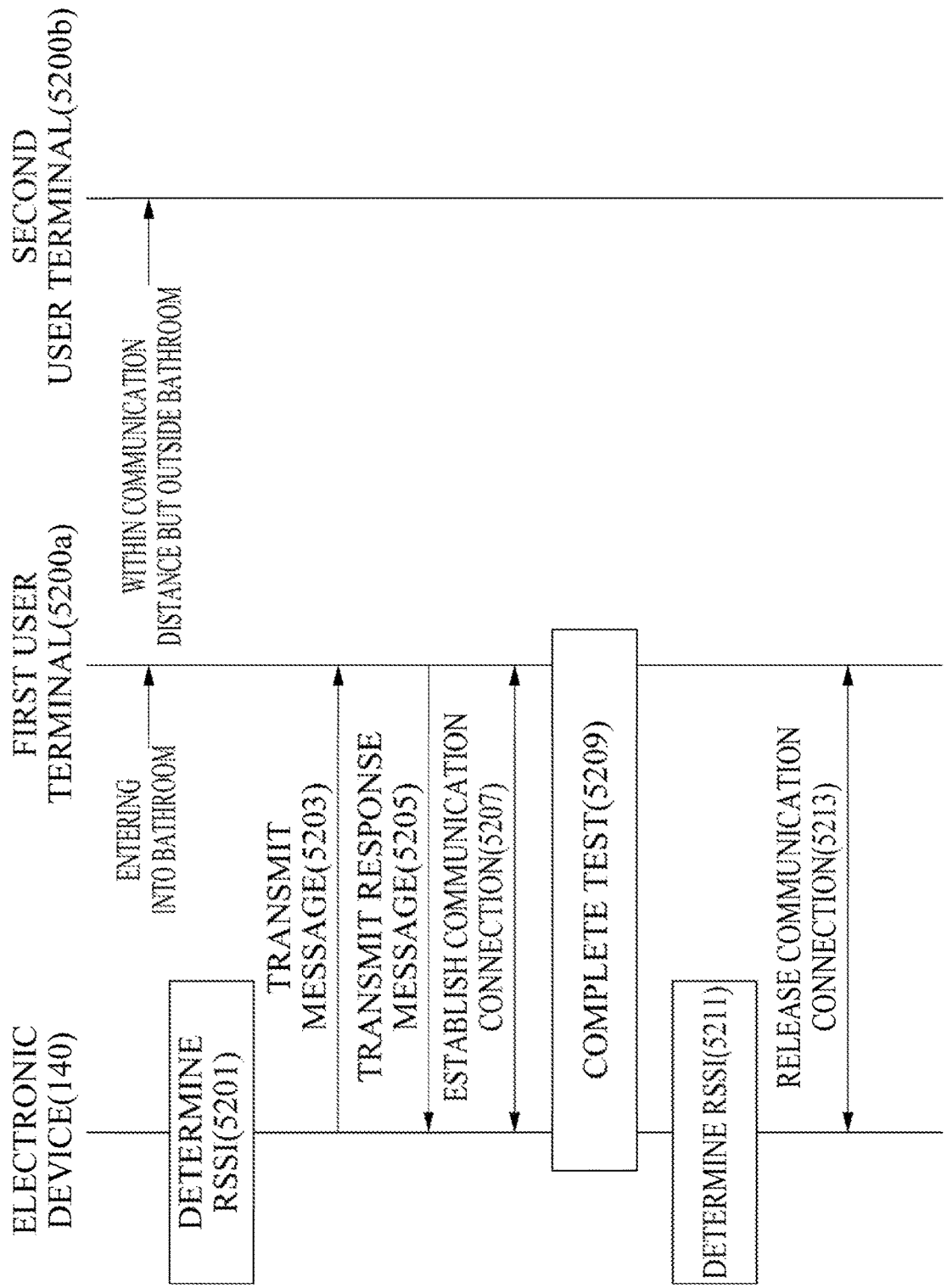
FIG. 52 is a flowchart illustrating an example of operations of a user terminal and an electronic device, according to various embodiments.

FIG. 52 is a flowchart illustrating an example of operations of the user terminal 130 and the electronic device 140, according to various embodiments. According to various embodiments, the operations shown in FIG. 52 are not limited to the order shown and may be performed in various orders. Further, according to various embodiments, at least one operation, but more than the operations shown in FIG. 52 or less than those shown in FIG. 52 may be performed. Hereinafter, a further description of FIG. 52 will be given with reference to FIG. 53.

Figure 53:
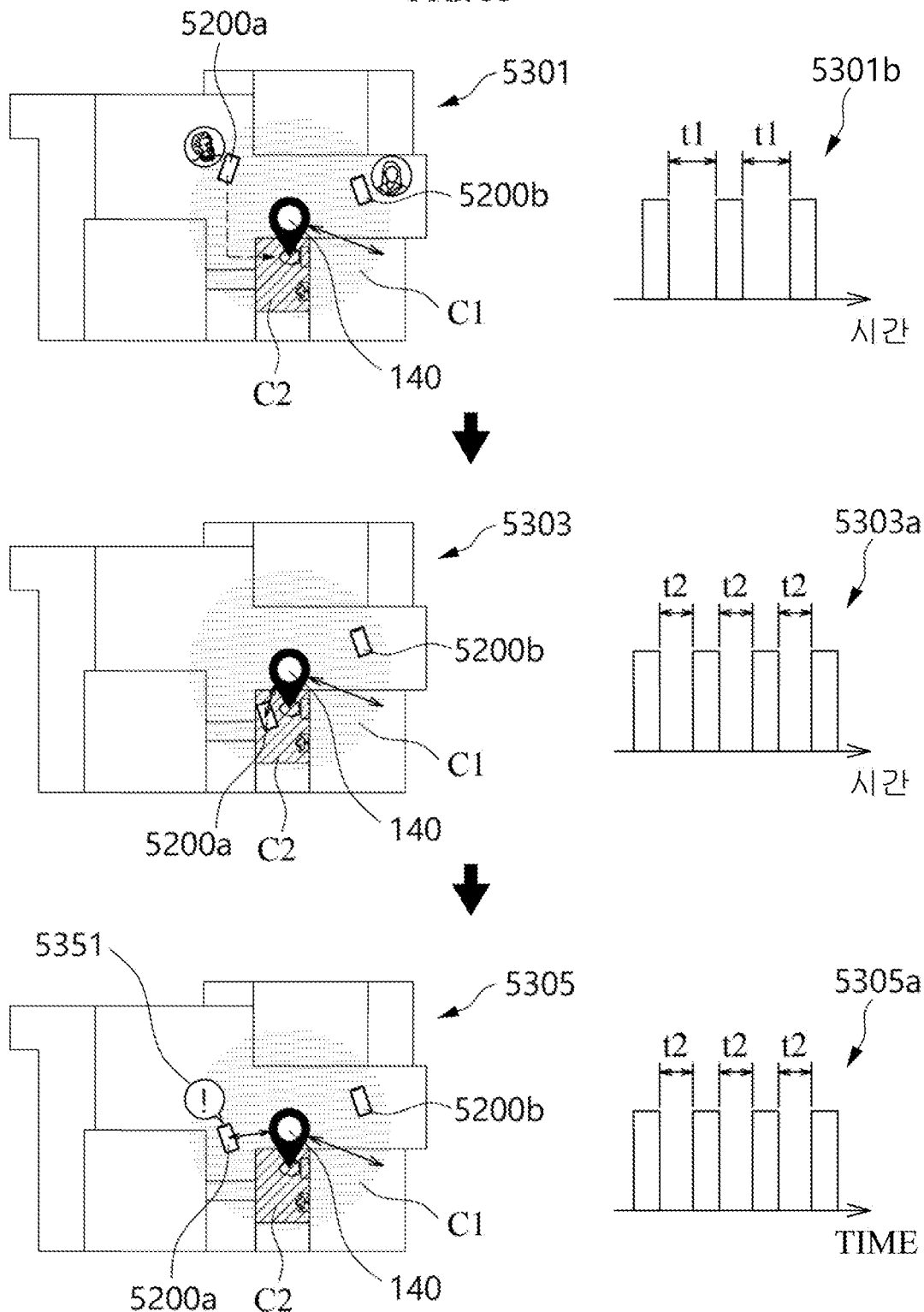
FIG. 53 is a diagram for describing an example of a communication connection operation between a user terminal and an electronic device, according to various embodiments.

FIG. 53 is a diagram for describing an example of an operation of connecting a communication between the user terminal 130 and the electronic device 140, according to various embodiments.

According to various embodiments, the electronic device 140 may determine a received signal strength indicator (RSSI) in operation 5201, and transmit a message to a first user terminal 5200*a* in operation 5203. For example, as shown in 5301*a* of FIG. 53, the electronic device 140 may identify the RSSI of a signal (e.g., advertising signal) received from a plurality of user terminals (e.g., the first user terminal 5200*a* and a second user terminal 5200*b*) based on performing the scan in a first period t1, and may transmit a message to a user terminal (e.g., the first user terminal 5200*a*) corresponding to the RSSI that satisfies a specific condition. For example, satisfaction of the specific condition may mean that the identified RSSI is equal to or greater than a specific strength and/or is included in a specific range. The specific strength and/or the specific range may be an strength corresponding to an average distance of the toilet space around on the position of a urinal where the electronic device 140 is disposed, and may be set to be greater than the strength corresponding to a communication connectable distance (e.g., a first distance C1) of a communication connection method (e.g., Bluetooth) that supports the communication connection between the electronic device 140 and the user terminal 130. Accordingly, as shown in 5301 to 5303 of FIG. 53, the electronic device 140 may be implemented to establish a communication connection with the user terminal (e.g., the first user terminal 5200*a*) of a user entering a space C2 in the bathroom for the urine test. Meanwhile, the user terminal 130 is not limited to the described example, and may perform an operation of identifying a pattern of the RSSI as at least a part of an operation of determining satisfaction of the specific condition, which will be further described with reference to FIGS. 54 and 55.

For example, referring to (a) of FIG. 53, each of the first user terminal 5200*a* and the second user terminal 5200*b* may be included within the first distance C1 from the electronic device 140 installed in the bathroom. The first distance C1 may correspond to a communication connection possible distance of a communication connection method (e.g., Bluetooth) that supports the communication connection between the electronic device 140 and the user terminal 130. In this case, the users of the first user terminal 5200*a* and the second user terminal do not have an intention to the urine test, and thus the specific strength to be compared with the identified RSSI described above may be set to be greater than the strength corresponding to the first distance C1 to prevent establishment of the communication connection between the electronic device 140 and each of the first user terminal 5200*a* and the second user terminal 5200*b*.

According to various embodiments, the user terminal 130 (e.g., the processor 1410) may provide a function for measuring the RSSI based on the application 1441 when the electronic device 140 is installed, and may perform an operation of determining a specific size to be compared with the aforementioned RSSI according to the measured RSSI. For example, when the user terminal 130 is positioned in a space outside the bathroom and when the user terminal 130 is positioned in the space C2 in the bathroom, the user terminal 130 may identify the RSSI calculated from the electronic device 140 based on transmitting a signal to the electronic device 140. The user terminal 130 may determine the RSSI that is greater than the RSSI when the user terminal 130 is positioned in the space outside the bathroom, and is in a range including the RSSI when the user terminal 130 is positioned in the space C2 in the bathroom and transmit the RSSI to the electronic device 140 so that the determined RSSI in the range is registered. The electronic device 140 may perform an operation of comparing the range of the registered RSSI with the RSSI of the received signal.

According to various embodiments, in operation 5205, the electronic device 140 may receive a response message from the first user terminal 5200*a*, may establish the communication connection in operation 5207, and may complete the test based on performing the urine test operation in operation 5209. For example, the electronic device 140 may perform the urine test operation and, upon completion, transmit information associated with the urine test to the user terminal 130 with which a communication connection is established.

According to various embodiments, the electronic device 140 may determine the RSSI in operation 5211 and release the communication connection with the first user terminal 5200*a* in operation 5213. For example, as shown in 5303*a* of FIG. 53, the electronic device 140 may identify the RSSI corresponding to the signal received from the first user terminal 5200*a* in communication connection in a second period t2. When the identified RSSI is less than a specific strength and/or out of the specific range, the electronic device 140 may transmit a message for releasing the communication connection with the user terminal 130 to the user terminal 130. The communication connection between the electronic device 140 and the user terminal 130 may be released based on the transmission of the message. Accordingly, when the user leaves the bathroom after completing the urine test, a communication connection between the user terminal 130 and another user terminal (e.g., the second user terminal 5200*b*) may be established for the urine test. Meanwhile, in order to smoothly release the establishment of the communication connection between the user terminal 130 and the electronic device 140, the second period t2 may be set to be shorter than the aforementioned first period t1, but is not limited to the described example.

Meanwhile, according to various embodiments, as shown in 5305 of FIG. 53, when the user terminal 130 is still present within the communication possible distance C1, the user terminal 130 may refrain from releasing the communication connection when the user terminal 130 does not receive information on the urine test result from the electronic device 140, even if the user terminal 130 receives the message for releasing the communication connection from the electronic device 140.

Meanwhile, the operations of determining the RSSI by the electronic device 140 and establishing and releasing the communication connection with the first user terminal 5200*a* may be made to be performed by the user terminal 130.

Hereinafter, an example of an operation of connecting a communication between the user terminal 130 and the electronic device 140 according to various embodiments will be described.

According to various embodiments, the electronic device 140 may perform an operation of identifying a pattern of RSSI in order to more accurately determine conditions for establishing and/or releasing the communication connection with the user terminal 130.

Figure 54:
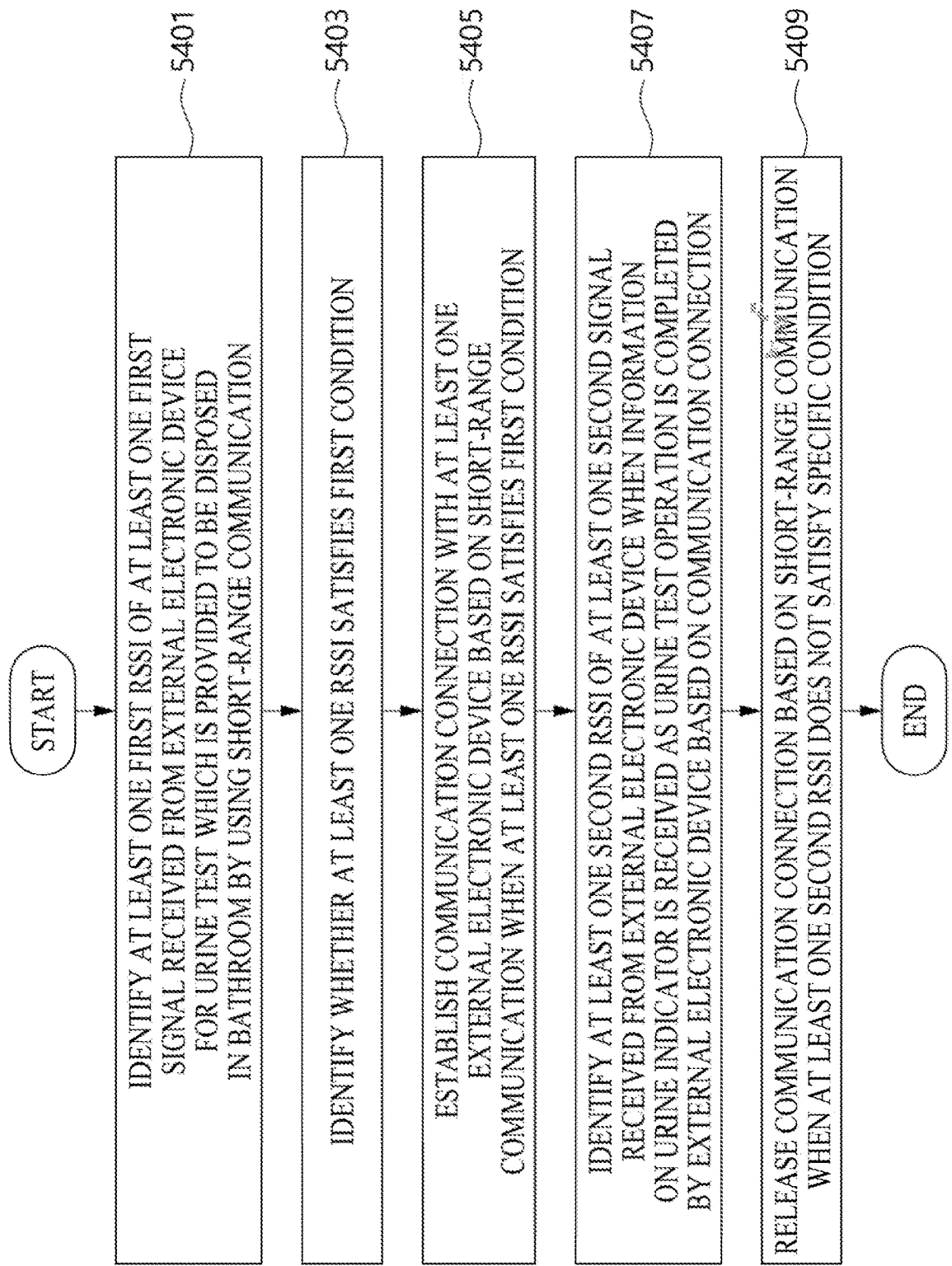
FIG. 54 is a flowchart illustrating an example of operations of an electronic device, according to various embodiments.

FIG. 54 is a flowchart illustrating an example of operations of the electronic device 140, according to various embodiments. According to various embodiments, the operations shown in FIG. 54 are not limited to the order shown and may be performed in various orders. Further, according to various embodiments, at least one operation, but more than the operations shown in FIG. 54 or less than those shown in FIG. 54 may be performed. Hereinafter, a further description of FIG. 54 will be given with reference to FIG. 55.

Figure 55:
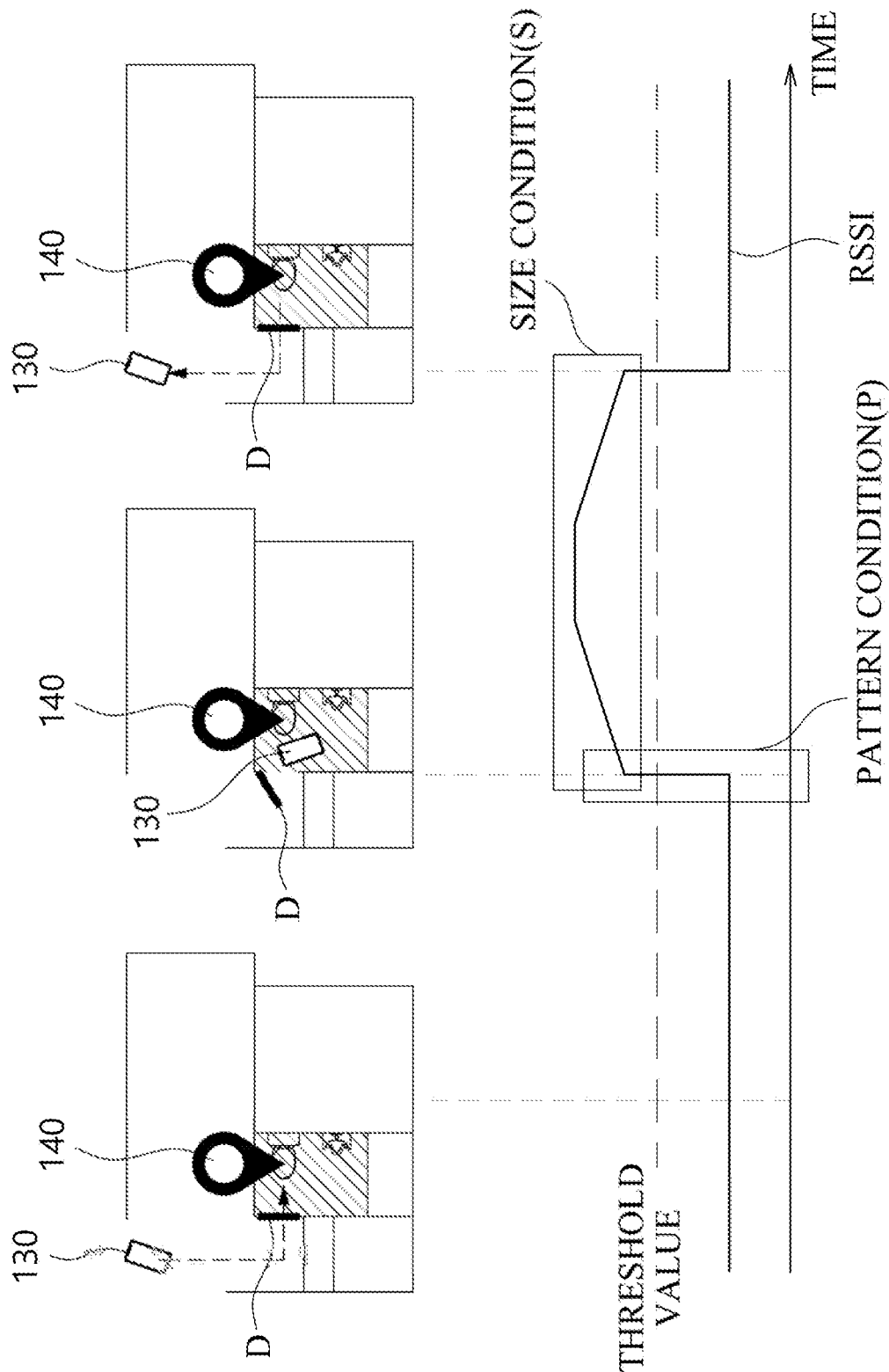
FIG. 55 is a diagram for describing an example of an operation of identifying a received signal strength indicator (RSSI) pattern of an electronic device, according to various embodiments.

FIG. 55 is a diagram for describing an example of an operation of identifying a RSSI pattern of the electronic device 140, according to various embodiments.

According to various embodiments, the electronic device 140 may identify at least one first RSSI of at least one first signal received from an external electronic device for the urine test which is provided to be disposed in a bathroom by using short-range communication in operation 5401, may identify whether the at least one RSSI satisfies a first condition in operation 5403, and may establish the communication connection with the at least one external electronic device based on the short-range communication when the at least one RSSI satisfies the first condition in operation 5405. For example, as described above with reference to FIGS. 52 and 53, as at least part of the operation of determining whether the RSSI satisfies the first condition, the electronic device 140 may determine whether the RSSI exceeds a specific value and/or is included within a specific numerical range. Further, for example, referring to FIG. 55, as at least part of the operation of determining whether the RSSI satisfies the first condition, the electronic device 140 may determine whether the RSSI satisfies a specific pattern P1. The pattern P1 may include an RSSI inflection point and/or RSSI sizes before and after the RSSI inflection point. As an example, referring to FIG. 55, the strength of RSSI is maintained within a certain range during a specific time before and/or after the time when the user terminal 130 enters or exits a bathroom D where the electronic device 140 is disposed, and at the time when the user terminal 130 enters or exits the bathroom D where the electronic device 140 is disposed, the RSSI pattern P1 may be generated in which the inflection point at which the strength of the RSSI is rapidly changed occurs. As the user opens and closes the door while entering and/or exiting the bathroom D, the patterns P1 and P2 may be generated. Accordingly, the electronic device 140 may be implemented to determine whether the pattern P1 is present, as at least part of the operation of determining whether the first condition is satisfied. For example, when the inflection point is identified, the electronic device 140 may perform an operation of comparing the RSSI waveform including the inflection point with a pre-stored pattern P1. For more example, when the inflection point is identified, the electronic device 140 may perform an operation of comparing the strength of the RSSI before the inflection point and the strength of the RSSI after the inflection point with the strength of the RSSI before the inflection point and the strength of the RSSI after the inflection point which are identified from the pre-stored pattern P1. The electronic device 140 may establish the communication connection with the user terminal 130 when the pattern P1 is identified based on the operation of identifying the pattern.

According to various embodiments, the electronic device 140 may identify at least one second RSSI of at least one second signal received from the external electronic device when information on the urine indicator is received as the urine test operation is completed by the external electronic device based on the communication connection in operation 5407, and may release the communication connection based on the short-range communication when the at least one second RSSI satisfies the specific condition in operation 5409. The electronic device 140 may release the communication connection with the user terminal 130 when the pattern P2 is identified while the communication connection is established. The operation of identifying the pattern P2 of the electronic device 140 may be performed in the same way as the operation of identifying the pattern P1, and thus repeated description thereof will be omitted.

Meanwhile, the operations of determining the RSSI by the electronic device 140 and establishing and releasing the communication connection with the user terminal 130 may be made to be performed by the user terminal 130.

Hereinafter, an example of an operation of connecting a communication between the user terminal 130 and the electronic device 140 according to various embodiments will be described.

According to various embodiments, the electronic device 140 may identify a size condition and a pattern condition of the RSSI in order to more accurately determine conditions for establishing and/or releasing the communication connection with the user terminal 130 and improve convenience.

Figure 56:
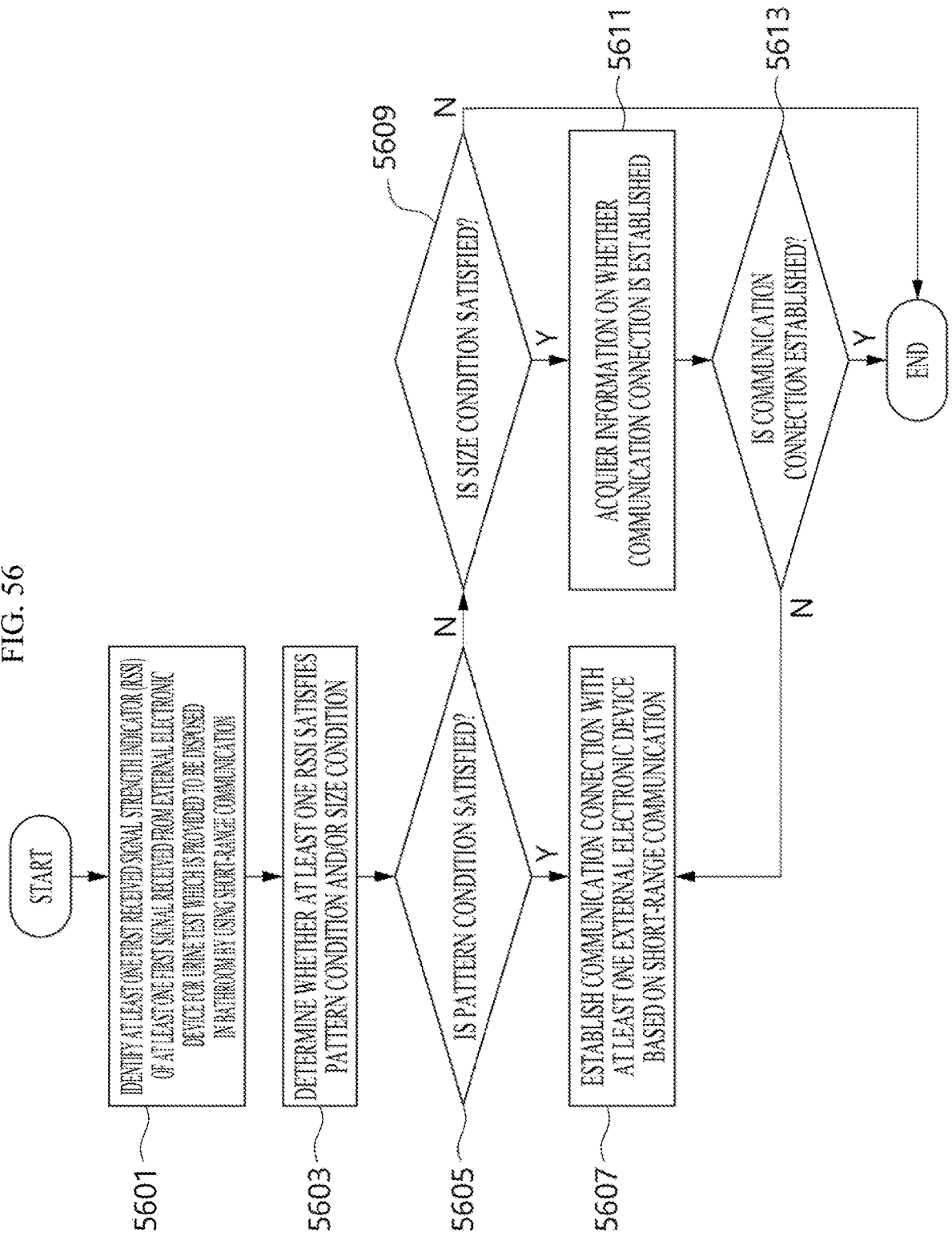
FIG. 56 is a flowchart illustrating an example of operations of an electronic device, according to various embodiments.

FIG. 56 is a flowchart illustrating an example of operations of the electronic device 140, according to various embodiments. According to various embodiments, the operations shown in FIG. 56 are not limited to the order shown and may be performed in various orders. Further, according to various embodiments, at least one operation, but more than the operations shown in FIG. 56 or less than those shown in FIG. 56 may be performed.

According to various embodiments, the electronic device 140 may identify at least one first RSSI of at least one first signal received from an external electronic device for the urine test which is provided to be disposed in a bathroom by using short-range communication in operation 5601, and may determine whether the at least one RSSI satisfies a pattern condition and/or a size condition in operation 5603. The operation of determining whether the RSSI of the electronic device 140 satisfies the pattern condition, may refer to the operation of determining whether the patterns P1 and P2 are identified based on the RSSI of the electronic device 140, which has been described above with reference to FIGS. 54 and 55. The operation of determining whether the RSSI of the electronic device 140 satisfies the size condition may refer to the operation of determining whether the RSSI of the electronic device 140 exceeds a specific value and/or is within a specific range, which has been described above with reference to FIGS. 52 and 53.

According to various embodiments, the electronic device 140 may determine whether the pattern condition is satisfied in operation 5605, and may establish the communication connection with the at least one external electronic device based on the short-range communication when the pattern condition is satisfied (Yes in 5605) in operation 5607. That is, the electronic device 140 may determine that the user intends to use the urine test from satisfaction of the pattern condition, and may immediately establish the communication connection with the corresponding user terminal 130.

According to various embodiments, the electronic device 140 may determine whether the size condition is satisfied when the pattern condition is unsatisfied (No in 5605) in operation 5609, may acquire information on whether the communication connection is established when the size condition is satisfied (Yes in 5609), may determine whether the communication connection is established in operation 5613, and may perform operation 5607 when the determination is made that the communication connection is established (Yes in 5613). For example, when the pattern condition is not satisfied but the size condition is satisfied, the electronic device 140 may transmit a message inquiring about whether the communication connection is established to the user terminal 130. The user terminal 130 may display a screen for inquiring about whether the communication connection is established based on the received message, and may receive an input for selecting establishment of the communication connection from the user on the screen. When the user input for the communication connection is received, the user terminal 130 may transmit a message for communication connection establishment to the electronic device 140. The electronic device 140 may determine that a communication connection is to be established based on the received message, and may establish the communication connection with the user terminal 130.

Hereinafter, an example of operations of the electronic device 140 according to various embodiments will be described.

According to various embodiments, the electronic device 140 may reduce power consumption by determining a scan operation period based on a toilet use pattern of the user. The scanning operation may include an operation of identifying an advertisement signal received from the user terminal 130.

Figure 57:
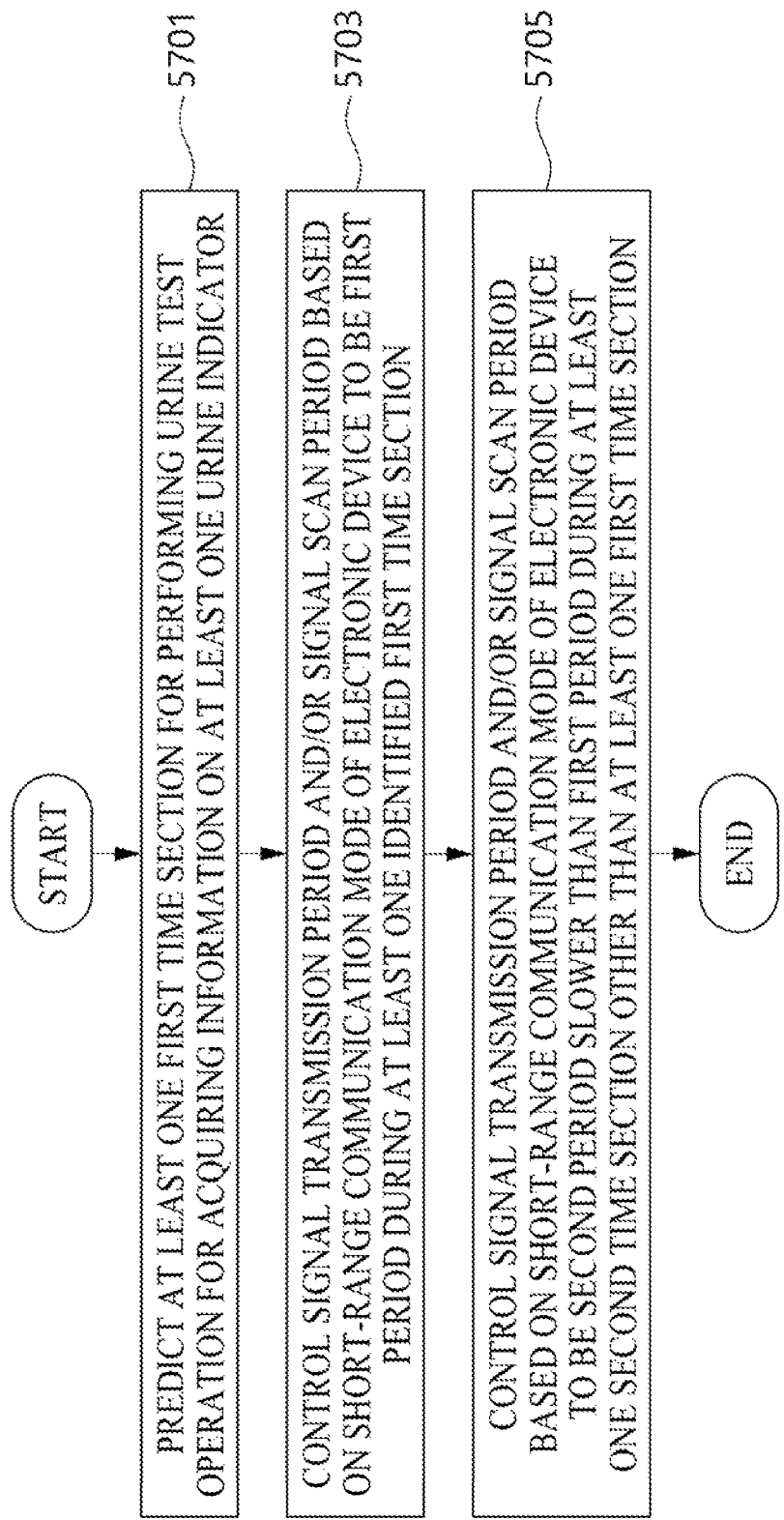
FIG. 57 is a flowchart illustrating an example of operations of an electronic device, according to various embodiments.

FIG. 57 is a flowchart illustrating an example of operations of the electronic device 140, according to various embodiments. According to various embodiments, the operations shown in FIG. 57 are not limited to the order shown and may be performed in various orders. Further, according to various embodiments, at least one operation, but more than the operations shown in FIG. 57 or less than those shown in FIG. 57 may be performed. Hereinafter, a further description will be given with reference to FIG. 58.

Figure 58:
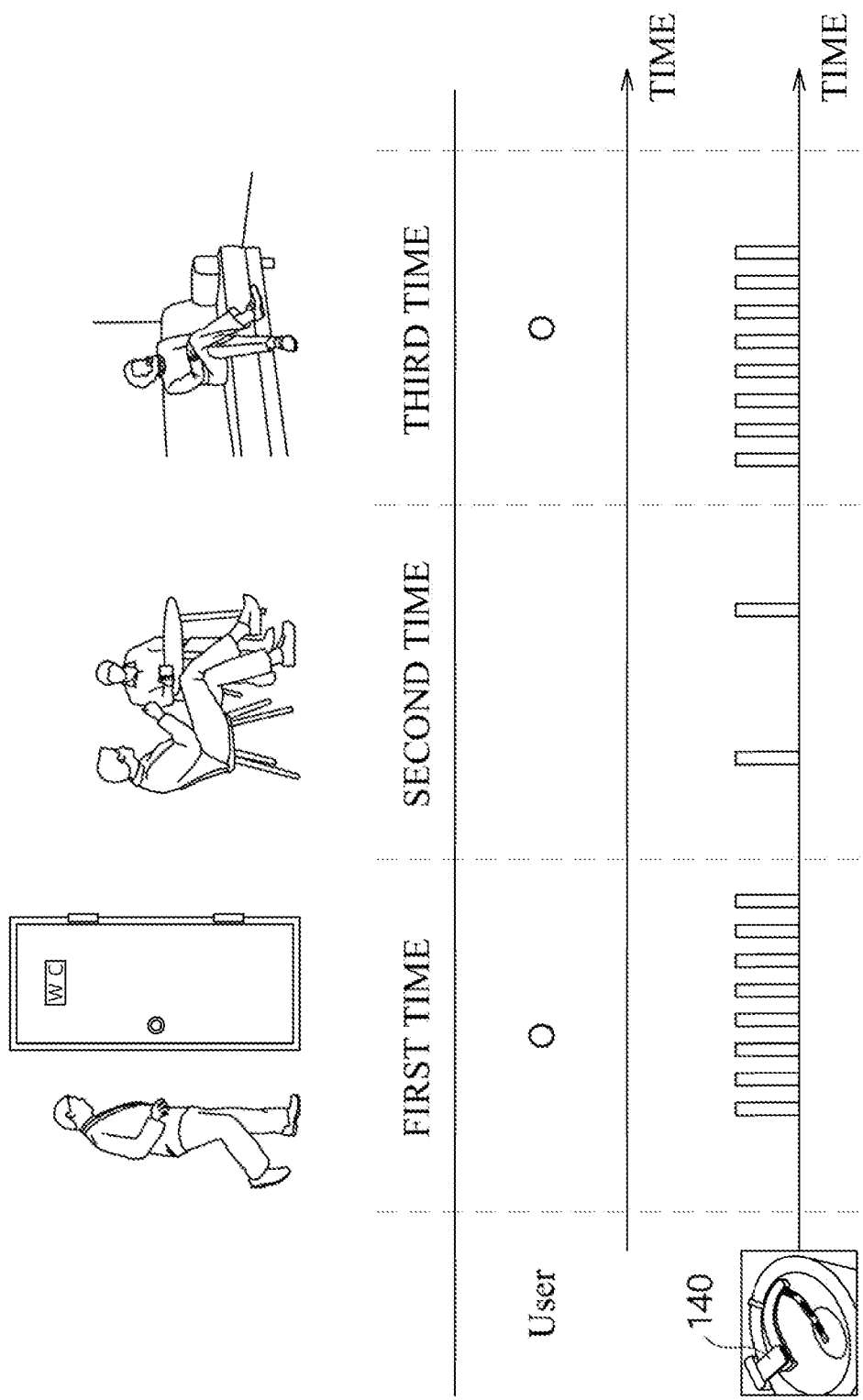
FIG. 58 is a diagram for describing an example of an operation of controlling a scan period by an electronic device based on a toilet use pattern, according to various embodiments.

FIG. 58 is a diagram for describing an example of an operation of controlling a scan period by the electronic device 140 based on the toilet use pattern, according to various embodiments.

According to various embodiments, in operation 5701, the electronic device 140 may predict at least one first time section for performing the urine test operation for acquiring information on at least one urine indicator. For example, the electronic device 140 may identify the toilet use pattern based on the number of times of establishing the communication connection with the user terminal 130 for each time section during a specified period. For example, as shown in FIG. 58, in the case of a single office worker household, time sections for using the toilet may be specified as morning and evening when the user lives at home. The electronic device 140 may store a communication connection setting history with the user terminal 130 in a state in which maintaining a constant scan period is maintained for a specified period after being installed in the toilet, and may identify time sections (e.g., first time, third time) of a specific number of times or more based on the number of times the communication connection is established for each time section, based on the stored history. For another example, the electronic device 140 may receive information about time sections (e.g., first time, third time) for using the toilet through the user terminal 130 and identify the time sections for using the toilet.

According to various embodiments, the electronic device 140 may control a signal transmission period and/or a signal scan period based on a short-range communication mode of the electronic device to be a first period during the at least one identified first time section in operation 5703 and may control the signal transmission period and/or the signal scan period based on the short-range communication mode of the electronic device to be a second period slower than the first period during at least one second time section other than the at least one first time section in operation 5705. For example, as shown in FIG. 58, the electronic device 140 may control the scan period with the first period that is relatively fast in the time section (e.g., first time, third time) in which the toilet is identified to be used, and may control the scan period with the second period that is slower than the first period in other time sections (e.g., the second time).

Hereinafter, an example of operations of the electronic device 140 according to various embodiments will be described.

According to various embodiments, the electronic device 140 may perform control so that the urine test is performed based on a urine analysis algorithm customized for a specific time section when the urine test is performed during the specific time section.

Figure 59A:
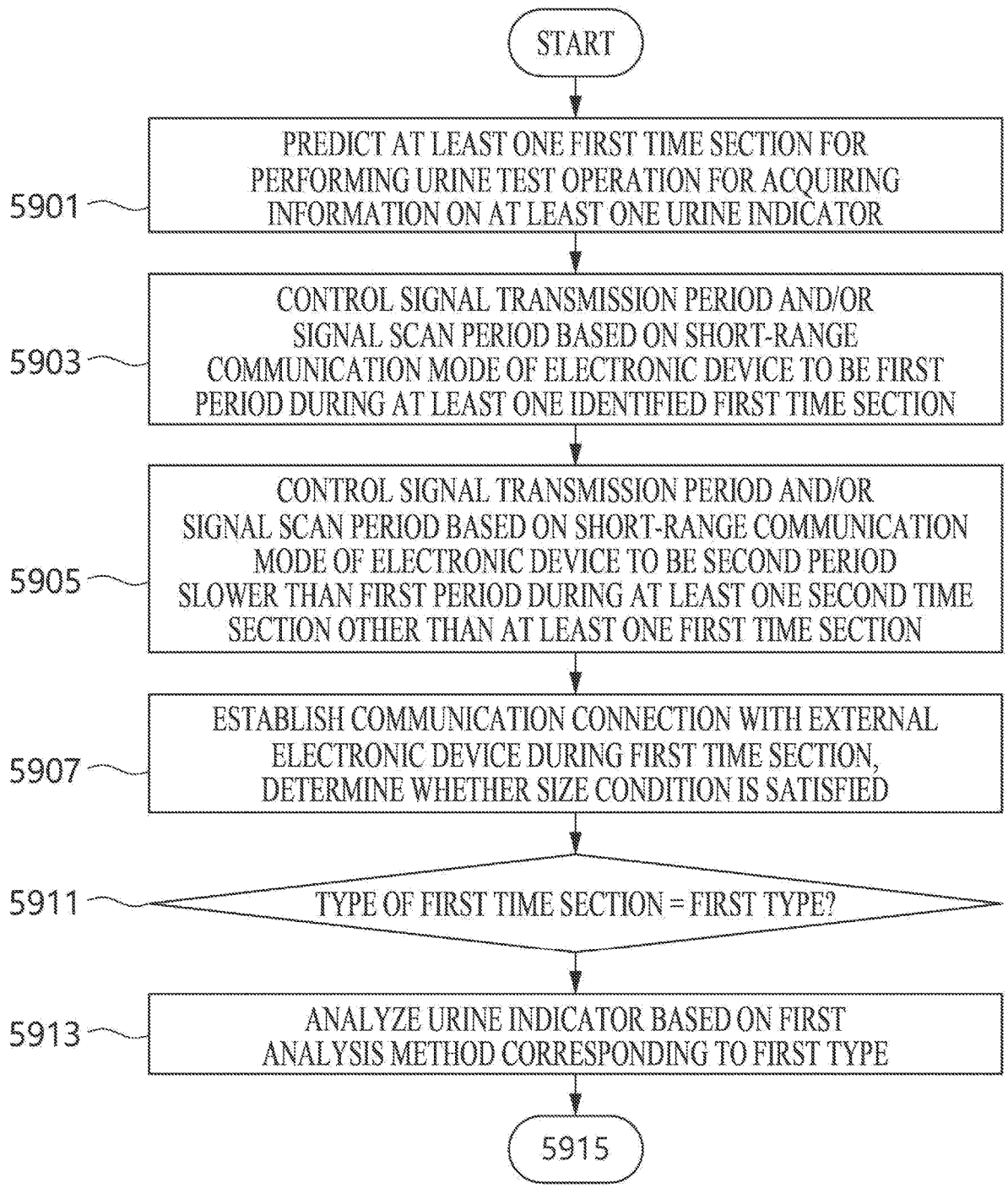
FIGS. 59A and 59B are flowcharts illustrating an example of operations of an electronic device, according to various embodiments.
Figure 59B:
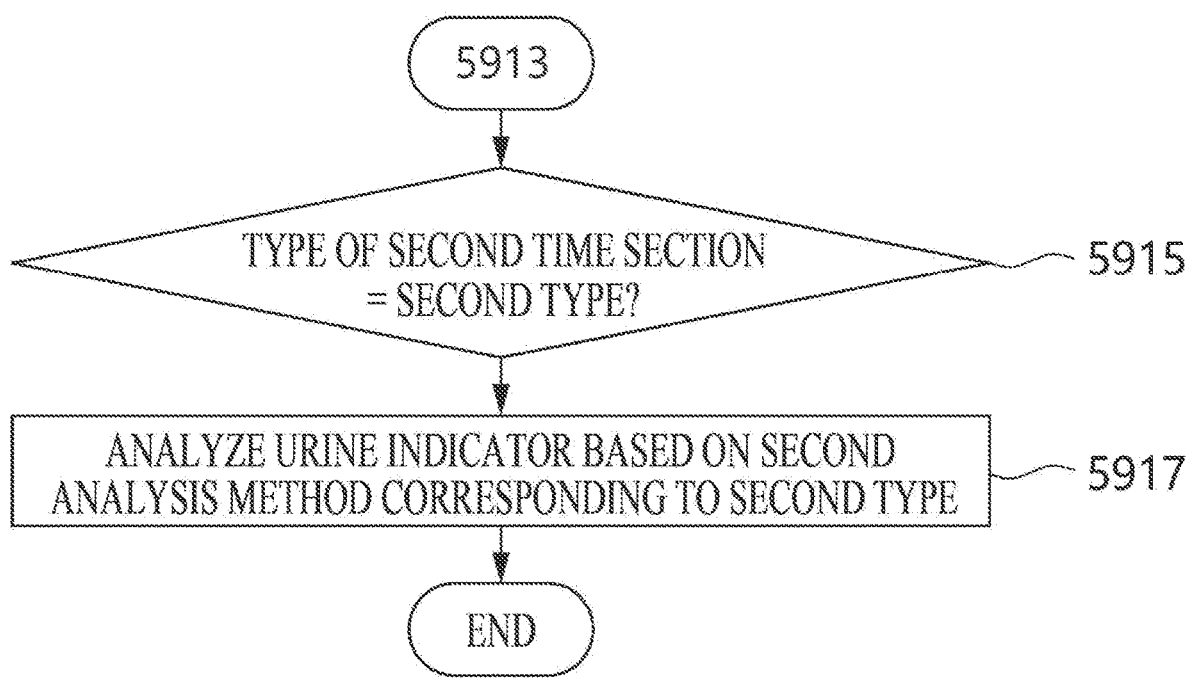

FIGS. 59A and 59B are flowcharts illustrating an example of operations of the electronic device 140, according to various embodiments. According to various embodiments, the operations shown in FIGS. 59A and 59B are not limited to the order shown and may be performed in various orders. Further, according to various embodiments, at least one operation, but more than the operations shown in FIGS. 59A and 59B or less than those shown in FIGS. 59A and 59B may be performed.

According to various embodiments, the electronic device 140 may predict at least one first time section for performing the urine test operation for acquiring information on at least one urine indicator in operation 5901, may control a signal transmission period and/or a signal scan period based on a short-range communication mode of the electronic device 140 to be a first period during the at least one identified first time section in operation 5903, and may control the signal transmission period and/or the signal scan period based on the short-range communication mode of the electronic device 140 to be a second period slower than the first period during at least one second time section other than the at least one first time section in operation 5905. Operations 5901 to 5905 of the electronic device 140 may be performed in the same manner as operations 5701 to 5703 of the electronic device 140 described above, and thus repeated description thereof will be omitted.

According to various embodiments, the electronic device 140 may determine whether the first time section in which the communication connection with an external electronic device (e.g., the user terminal 130) is established is the first type in operation 5911, may analyze the urine indicator based on a first analysis method corresponding to the first type when the first time section is the first type (Yes in 5911), may determine whether the first time section in which the communication connection is established is the second type in operation 5915, and may analyze the urine indicator based on a second analysis method corresponding to the second type when the first time section is the second type (Yes in 5915) in operation 5917.

For example, there are characteristics of each urine as shown in [Table 3] below for each time section in which urine is acquired, and based on the characteristics, a corresponding urine test algorithm may be set.

TABLE 3

| Time section | Urine characteristics | Algorithm |
|---|---|---|
| Morning | Highly acidic contaminants present | First urine test algorithm |
| Medium | Acid average | Second urine test algorithm |

For example, the electronic device 140 may perform control so that the urine test is performed based on a first urine test correction algorithm for reducing the effects of high acidity and contaminants in the first urine when the first time section is the morning time section, and may perform control so that the urine test is performed based on a second normal urine test algorithm when the first time section is not the morning. Meanwhile, the urine test operations based on the aforementioned urine test algorithms may be performed by the user terminal 130 and/or the server 150 instead of the electronic device 140. As an example, the electronic device 140 may transmit information indicating a time section in which the urine test is performed to the user terminal 130 and perform control so that the urine test is performed based on the urine test algorithm corresponding to the time section, but the control is not limited to the described example, and the user terminal 130 may identify the time section in which information is received from the electronic device 140 and perform control so that the urine test is performed based on the identified time section.

Hereinafter, an example of operations of the server 150 according to various embodiments will be described.

According to various embodiments, the server 150 (e.g., the processor) may perform an operation of recommending a lifestyle to the user based on evaluation of various types of life information for the user based on the urine test result. Accordingly, the user using the urine test system 1 may perform various types of health promotion through the urine test.

FIG. 60 is a flowchart illustrating an example of operations of the server 150, according to various embodiments. According to various embodiments, the operations shown in FIG. 60 are not limited to the order shown and may be performed in various orders. Further, according to various embodiments, at least one operation, but more than the operations shown in FIG. 60 or less than those shown in FIG. 60 may be performed. Hereinafter, a further description of FIG. 61 will be given with reference to FIGS. 61 and 62.

Figure 62:
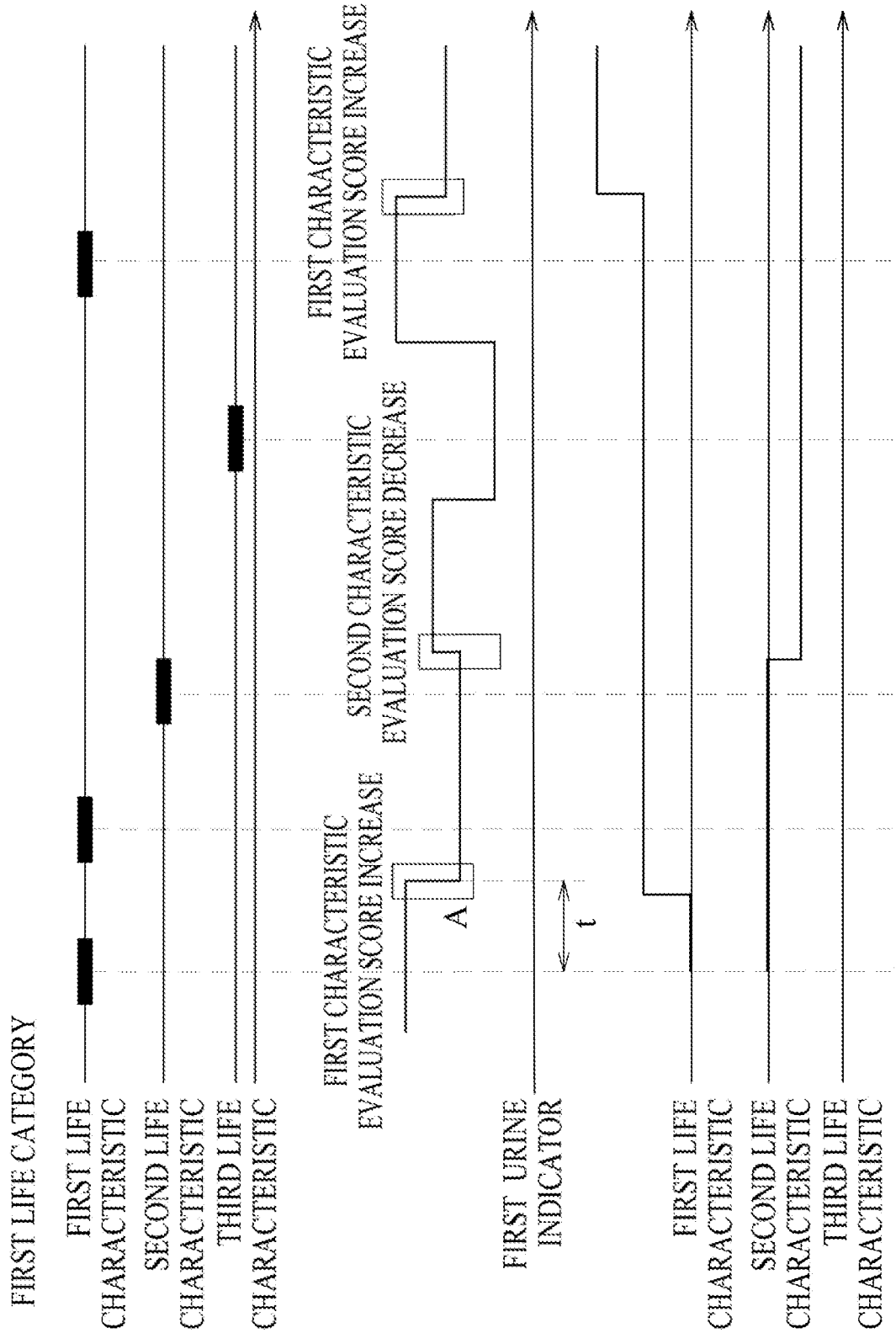
FIG. 62 is a diagram for describing an example of an operation of evaluating a life characteristic for each life category based on a change in a urine indicator, by a server, according to various embodiments.

FIG. 61 is a diagram for describing an example of an operation of collecting information about life characteristics for each life category by the server 150, according to various embodiments. FIG. 62 is a diagram for describing an example of an operation of evaluating a life characteristic for each life category based on a change in a urine indicator, by the server 150, according to various embodiments.

According to various embodiments, in operation 6001, the server 150 (e.g., the processor) may acquire, from the electronic device 140 and/or the user terminal 130, a plurality of pieces of first information associated with urine indicators of the user. For example, as the user performs the urine test by using the electronic device 140 and/or the user terminal 130, the server 150 may acquire information for each of a plurality of urine indicators (e.g., occult blood, bilirubin, bilogen, ketone body, protein, nitrite, glucose, PH, specific gravity, and/or white blood cells) associated with the user.

According to various embodiments, in operation 6003, the server 150 (e.g., the processor) may acquire a plurality of pieces of second information for each of a plurality of characteristics associated with the life of the user from an external electronic device. The plurality of pieces of second information for each of the plurality of characteristics associated with the life of the user may include information for each life characteristic included for each life category as described in [Table 4] and information about a time at which the life category for the specific life characteristic is performed by the user.

TABLE 4

| Life category | Life characteristics | Information |
|---|---|---|
| Exercise | Type | Jogging |
|  |  | Health |
|  | Strength | First strength |
|  |  | Second strength |
| Diet | Diet ratio | First diet ratio |
|  |  | Second diet ratio |
|  | Total calories | First calorie |
|  |  | Second calorie |

For example, the life category may include various types of categories related to the user's health, including food, clothing, and shelter, and may further include not only exercise and diet, but also other life categories such as sleep time related to health of the user, as described in [Table 4]. The life characteristics may include various types of subcategories associated with the life category, and in addition to the life characteristics, may further include various types of life characteristics collectable by a wearable device, a medicine and pharmacy server, an IOT device, and the like, as described in [Table 4]. As an example, information on the characteristics of each life category may be collected from different types of devices at different times. For example, as shown in (a) of FIG. 61, the server 150 may information on the first type of exercise (e.g., home training) performed by the user among exercise categories from an IOT device (e.g., a smart mirror 6111) provided in the home at a first time, and may receive information on the second type of exercise (e.g., jogging) performed by the user from a wearable device 6113 at a second time.

As an example, information on the characteristics of each life category may be collected from the same device at different times. As shown in (b) of FIG. 61, the server 150 may receive first meal information (e.g., a first calorie ratio) about a meal consumed by the user among diet categories from the user terminal 130 provided in the home at a first time, and may receive information about second meal information (e.g., a second calorie ratio) from the user terminal 130 at a second time.

According to various embodiments, the server 150 (e.g., the processor) may identify at least one time when a change associated with the urine indicator occurs from the plurality of pieces of first information in operation 6005, may identify a specific category having information associated with the at least one time among the plurality of categories in operation 6007, may assign a score to the specific category based on the size of change associated with the urine indicator in operation 6009, and may provide recommendation information associated with the plurality of second categories based on the assignment of the score in operation 6011. For example, when the user selects a specific life category requiring recommendation for health promotion (e.g., a first life category) (e.g., select a specific characteristic of a specific life category through the user terminal 130), the server 150 may perform evaluation for each characteristic (e.g., first to third life characteristics) of the selected category (e.g., the first life category) based on the size of change associated with the urine indicator, as shown in FIG. 62. For example, the server 150 may perform evaluation for each life characteristic based on a change amount A of the urine indicator (e.g., the first urine indicator), and/or a different t between a point of time when the change of the urine indicator (e.g., the first urine indicator) has occurred and a point of time when the life characteristic has been performed, as shown in Equation 1 below.

$$\text{Evaluation score for each life characteristic} = \alpha \pm \beta \cdot \frac{A}{t} \quad \text{[Equation 1]}$$

In Equation 1, $\alpha$ is an initial score, $\beta$ is a proportional constant, A is a change amount of urine indicator, t is a difference between a point of time when the change in urine indicator has occurred and a time when the life characteristic has been performed, and it is obvious to those skilled in the art that an additional expression may be further reflected in Equation 1.

In Equation 1, ± may be determined as + when the change amount is negative or as − when the change amount is positive, but is not limited thereto, and may be determined in the opposite way, and may be determined differently for each urine indicator. For example, for a urine indicator determined to require a decrease, the sign may be determined as + when the change amount is negative or as − when the change amount is positive, but for the urine indicator determined to require an increase, the sign may be determined as − when the change amount is negative or as + when the change amount is positive.

Accordingly, as a result, the server 150 may determine the life characteristic (e.g., the first life characteristic) having the highest score at the current point of time, and may provide (e.g., provide and display the determined life characteristic to the user terminal 130) as the recommended characteristic of the specific life category (e.g., first life category).

According to various embodiments, as at least part of the operation of performing the operation of evaluating, the server 150 may perform an operation of determining a specific range including a urine indicator for evaluation for each of a plurality of urine indicators and assigning an evaluation score based on the specific range. For example, the server 150 may determine the value of the proportional constant $\beta$ of the above Equation 1 for each specific range including the urine indicator. As an example, the value of the proportional constant $\beta$ may be determined to be larger in the danger range than in the normal range. In addition, for example, the server 150 may perform the above-described operation of evaluating when the specific range included in the urine indicator corresponds to the normal range, but may perform an operation of deducting an evaluation score by a pre-set value, instead of the operation of evaluating, when the specific range falls within a risk range.

According to various embodiments, the server 150 may determine a specific urine indicator to evaluate characteristics for each life category based on specific information. In an embodiment, the server 150 may determine a specific urine indicator requiring improvement based on the user input and/or information about the user (e.g., job). In another embodiment, the server 150 may be implemented to select the specific urine indicator (e.g., the first urine indicator) corresponding to the selected life category.

Meanwhile, without being limited to the described example, similar to that described in FIGS. 24 and 25, an artificial intelligence model is implemented to output recommended life characteristics in response to receiving information on the change amount of the urine indicator and information on life characteristics for each life category, and thus the operation of recommending life characteristics, which has been described above, may be performed based on the artificial intelligence model.

Hereinafter, an example of operations of the server 150 according to various embodiments will be described.

According to various embodiments, the server 150 (e.g., the processor) may perform an operation of evaluating based on a weight for each of a plurality of urine indicators as at least part of the operation of evaluating based on a change in the urine indicator.

Figure 63:
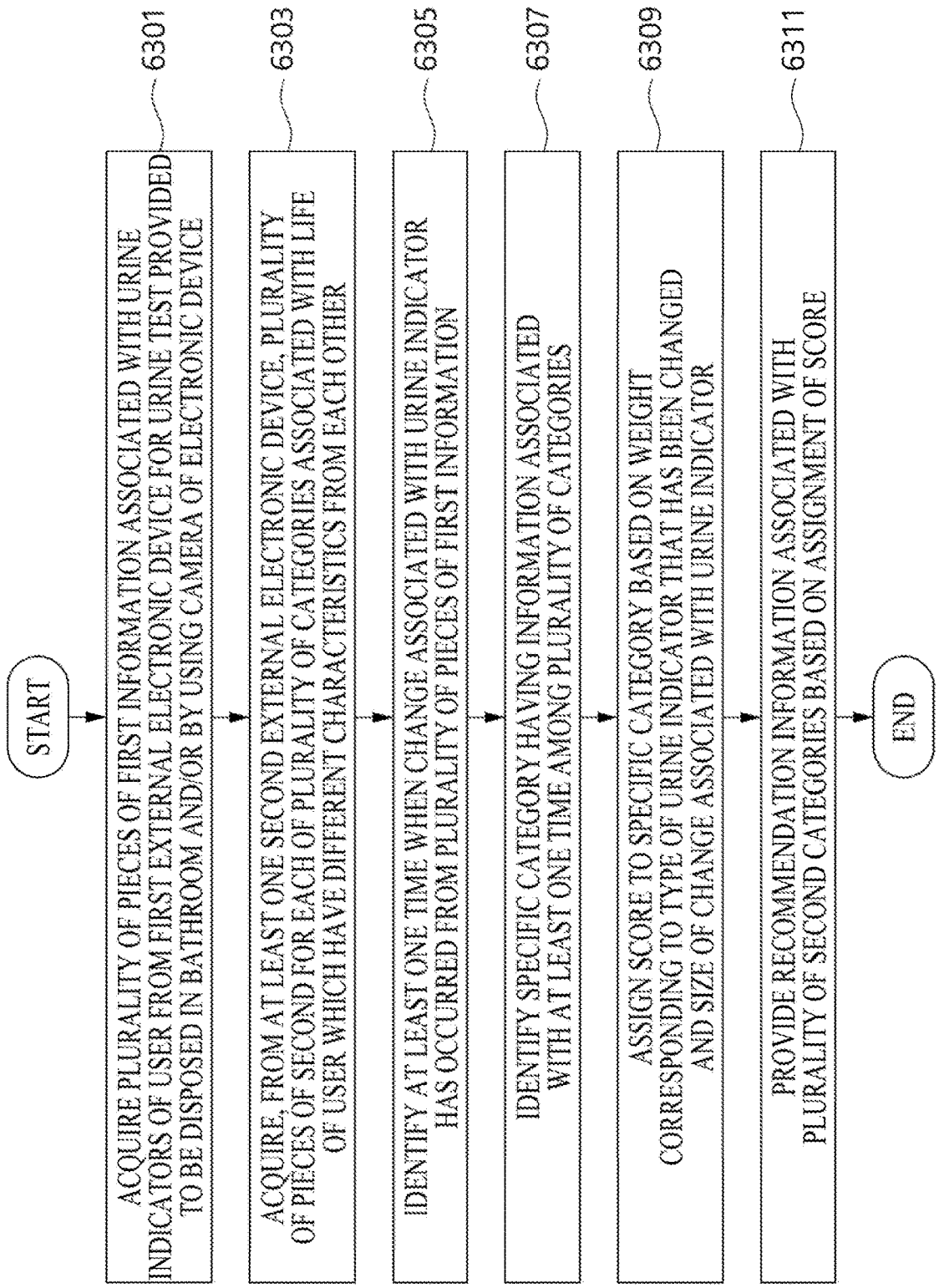
FIG. 63 is a flowchart illustrating an example of operations of an electronic device, according to various embodiments.

FIG. 63 is a flowchart illustrating an example of operations of the electronic device 140, according to various embodiments. According to various embodiments, the operations shown in FIG. 63 are not limited to the order shown and may be performed in various orders. Further, according to various embodiments, at least one operation, but more than the operations shown in FIG. 63 or less than those shown in FIG. 63 may be performed.

According to various embodiments, as at least part of the operation of evaluating based on the change in urine indicators described above, the server 150 may select a plurality of urine indicators for evaluation in operation 6301, and may assign a score to a specific category based on a weight for each of the plurality of urine indicators and a change for each of the plurality of urine indicators in operation 6303. For example, when the life category and life characteristic to be evaluated are determined, the server 150 may determine a plurality of urine indicators (e.g., the first urine indicator and a second urine indicator) for evaluating the life category and life characteristic. In this case, according to a relevance of the determined life characteristic and the plurality of urine indicators, weights β1 and β2 of Equation 2 for each of the plurality of urine indicators (e.g., the first urine indicator and the second urine indicator) may be determined. For example, when the relevance is high, the weight may be determined to be high, but it may be determined conversely without being limited to the described example.

Evaluation score for each life characteristic = [Equation 2]
$$\alpha \pm \beta1 \cdot \frac{A1}{t1} \pm \beta2 \cdot \frac{A2}{t2}$$

In Equation 2, A1 is a change amount of the first urine indicator, t1 is a difference between a point of time when the amount change of the first urine indicator has occurred and a time when the life characteristic has been performed, A2 is a change amount of the second urine indicator, and t2 is a difference between a point of time when the amount change of the second urine indicator has occurred and a time when the life characteristic has been performed, and it is obvious to those skilled in the art that an additional expression may be further reflected in Equation 2.

Hereinafter, an example of operations of the user terminal 130 according to various embodiments will be described.

According to various embodiments, the user terminal 130 (e.g., the processor 1410) may transmit information for security of the urine test, encrypting the information associated with the urine test analyzed by the electronic device 140, which makes it possible to perform control so that personal information is protected when the information associated with the urine test is stolen.

Figure 64:
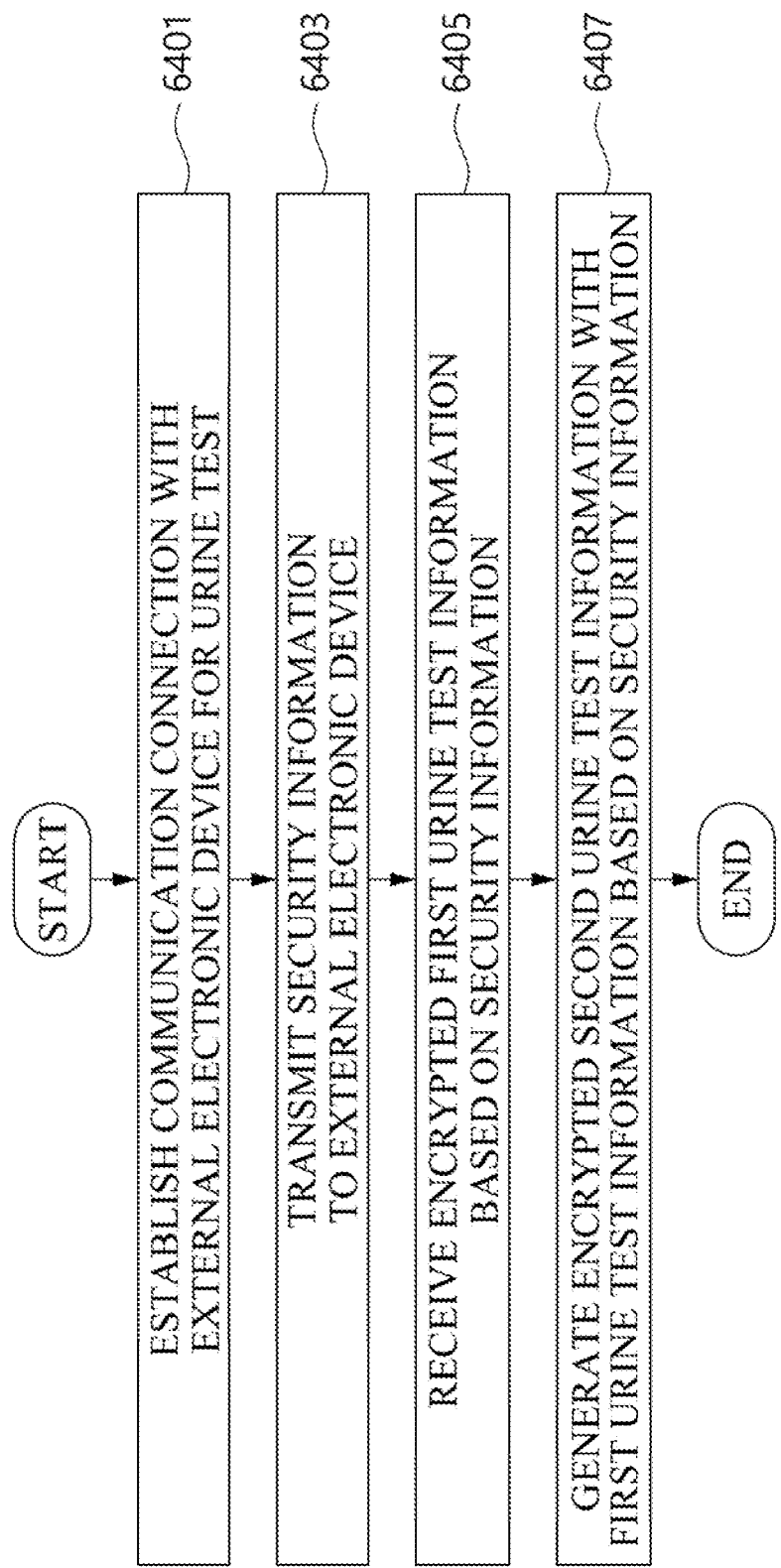
FIG. 64 is a flowchart illustrating an example of operations of a user terminal, according to various embodiments.

FIG. 64 is a flowchart illustrating an example of operations of the user terminal 130, according to various embodiments. According to various embodiments, the operations shown in FIG. 64 are not limited to the order shown and may be performed in various orders. Further, according to various embodiments, at least one operation, but more than the operations shown in FIG. 64 or less than those shown in FIG. 64 may be performed. Hereinafter, a further description of FIG. 64 will be given with reference to FIG. 65.

FIG. 65 is a diagram for describing an example of performing a urine test in an environment in which a plurality of electronic devices 140 are provided, according to various embodiments.

According to various embodiments, the user terminal 130 (e.g., the processor 1410) may establish a communication connection with an external electronic device for the urine test in operation 6401, and may transmit security information to the external electronic device in operation 6403. For example, the electronic device 140 may be provided for each of a plurality of toilets so that the urine test for a plurality of users is possible. In this case, information on urine test results may be stolen by the users, and thus a first user terminal 6501a may transmit a private key as security information to the electronic device 140 so that information (e.g., color value) analyzed by the electronic device 140 is encrypted based on the private key, as shown in (b) of FIG. 65, or the first user terminal 6501a may transmit an ID to the electronic device 140 so that information (e.g., color value) analyzed by the electronic device 140 is managed to be associated with the transmitted ID, as shown in (c) of FIG. 65.

Hereinafter, an example of a color sensor algorithm applicable to the above analysis system according to various embodiments will be described. A description overlapping with the various embodiments described above will be omitted. For example, the operation of the electronic device 6610 including the analysis device 6700 described below may be an example of the operation of the electronic device 140 described above.

Figure 66:
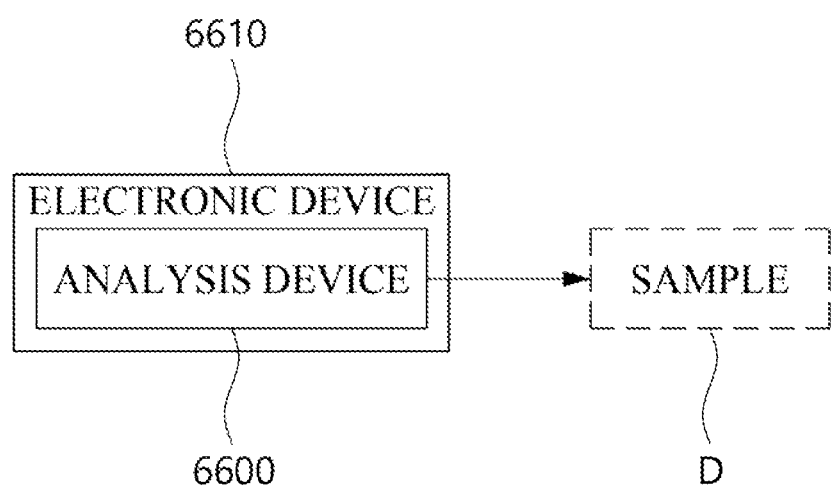
FIG. 66 is a diagram illustrating an example of a configuration of an analysis system according to various embodiments.
Figure 67:
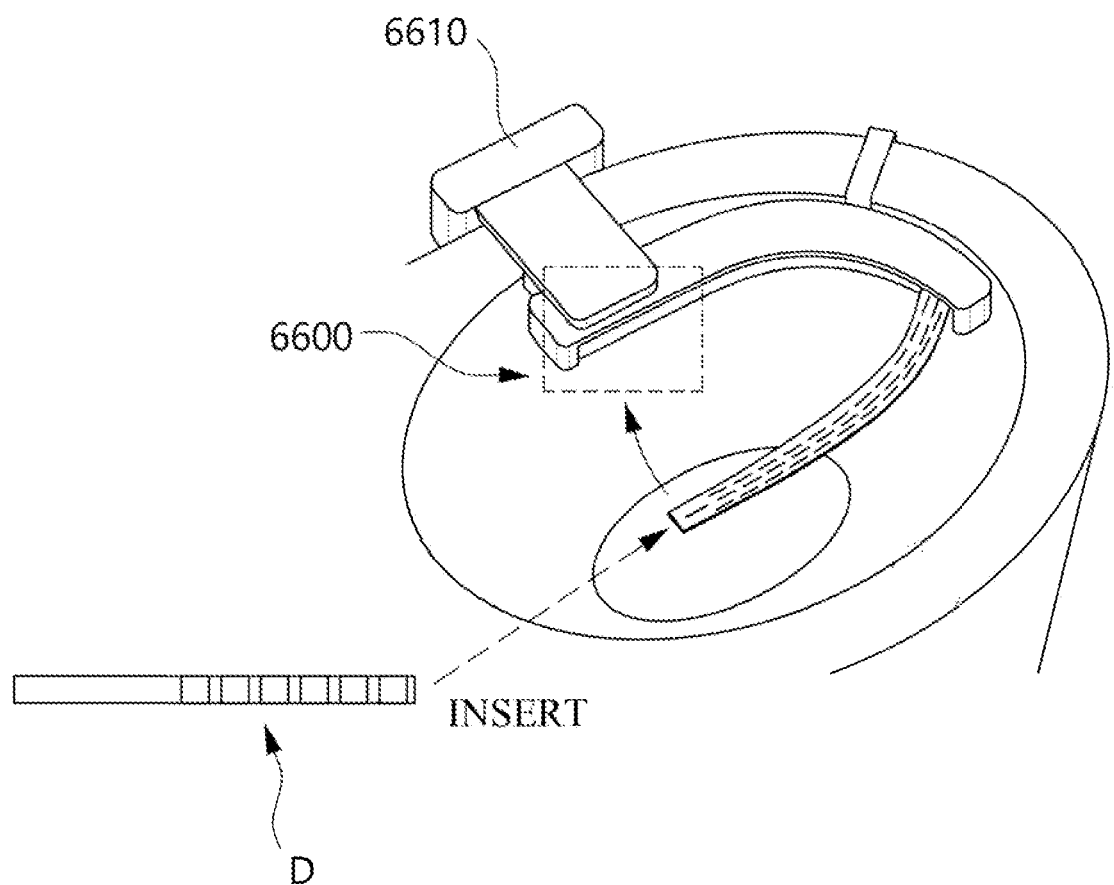
FIG. 67 is a diagram illustrating an example of an electronic device including an analysis device and a sample D according to various embodiments.

FIG. 66 is a diagram illustrating an example of a configuration of an analysis system according to various embodiments. FIG. 67 is a diagram illustrating an example of an electronic device 6610 including an analysis device 6700 and a sample D according to various embodiments. Below, with reference to FIG. 67, FIG. 66 is further described.

According to various embodiments, referring to FIG. 66, the analysis system includes an electronic device 6610 including an analysis device 6600 and a sample, analyzed by the electronic device 6610 (e.g., the analysis device 6600). D) may be included. The electronic device 6610 may be an example of the electronic device 140 described above.

According to various embodiments, the electronic device 6610 may be configured as various types of devices. For example, referring to FIG. 67, the electronic device 6610 is a device for analyzing a sample D and can be installed in a toilet bowl, while the sample D (e.g., a urine strip), is placed on or inserted to a gutter 6700 capable of reciprocating in the direction. When the gutter 6700 is moved in the direction of the analysis device 6600 while the sample D (e.g., urine strip) is seated on a part (e.g., end part) of the gutter 6700, an analysis of a part (e.g., a test item (or color item)) of a sample (e.g., a urine strip (D)) may be performed by the analysis device 6600. Meanwhile, the electronic device 6610 is not limited to the examples described and/or illustrated. The electronic device may include various types of medical devices for analyzing the above-described various types of samples (D) and personal electronic devices such as smart phones.

According to various embodiments, the analysis device 6600, as will be described later, is configured to obtain a plurality of different color values measured from the sample D, and obtain result information corresponding to the obtained plurality of color values. The result information may mean values of substances related to living organisms, such as the concentration of biologically derived substances. As shown in FIG. 66, the analysis device 6600 may be provided in the electronic device 6610 as a single number, but is not limited to the examples described and/or illustrated and may be provided in the electronic device 6610 in a plurality of pieces. When a plurality of analysis devices 6600 are implemented, the plurality of analysis devices 6600 may be disposed on a specific substrate (e.g., a printed circuit board (PCB)). That is, the analysis device 660 may be a kind of electronic component disposed inside the aforementioned electronic device 140, but is not limited to the described example.

Hereinafter, examples of configurations of the electronic device 6610 according to various embodiments will be described.

Figure 68:
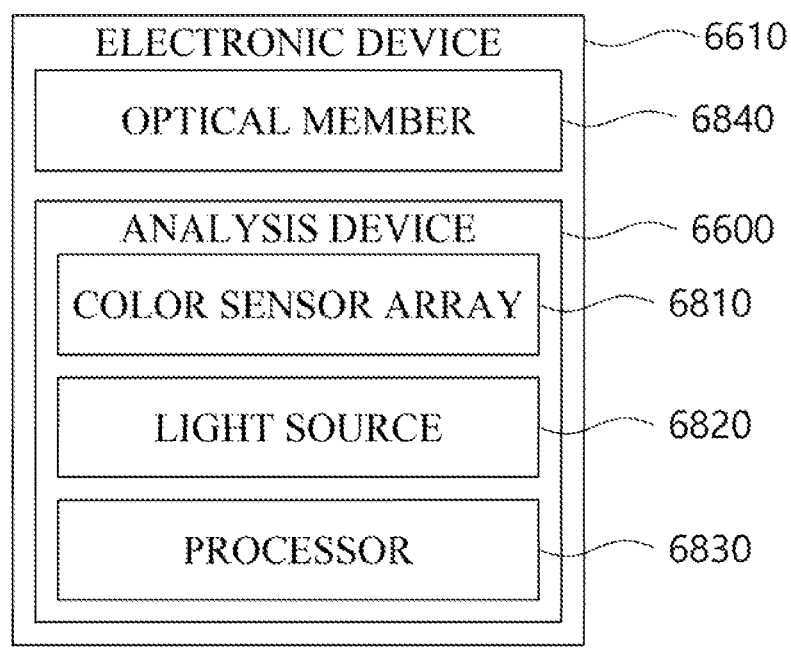
FIG. 68 is a diagram illustrating an example of a configuration of an electronic device 6610 according to various embodiments.
Figure 69:
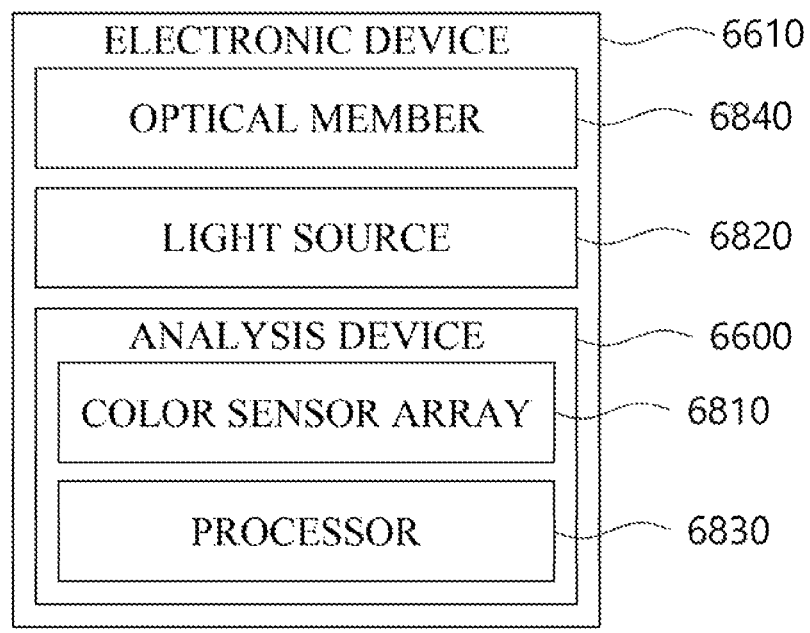
FIG. 69 is a diagram illustrating another example of a configuration of an electronic device according to various embodiments.

FIG. 68 is a diagram illustrating an example of a configuration of an electronic device 6610 according to various embodiments. FIG. 69 is a diagram illustrating another example of a configuration of an electronic device 6610 according to various embodiments.

Figure 70:
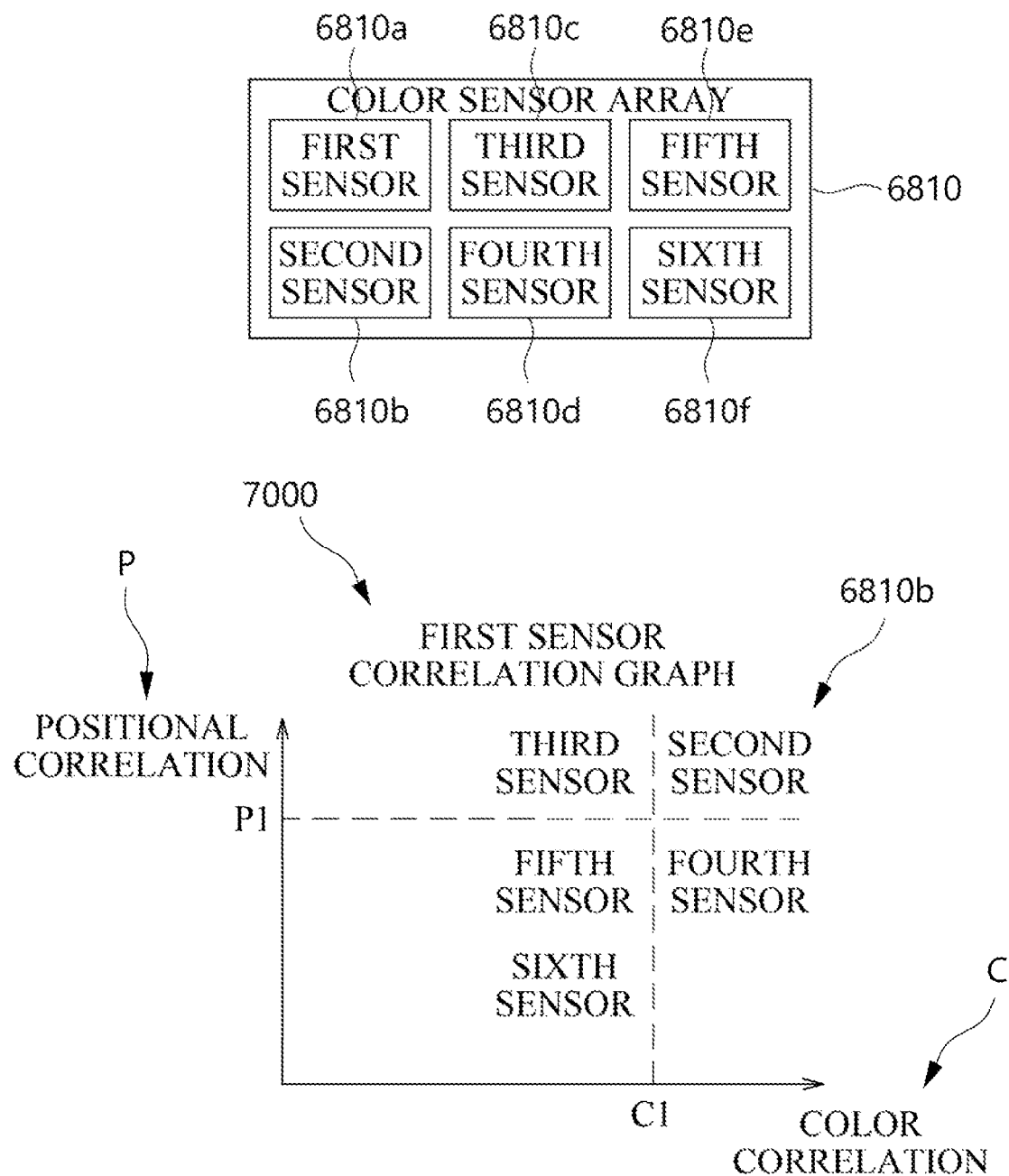
FIG. 70 is a graph for explaining a correlation between a color sensor array and a color sensor (or color value), according to various embodiments.

FIG. 70 is a graph for explaining a correlation between a color sensor array 6810 and a color sensor (or color value), according to various embodiments.

According to various embodiments, referring to FIGS. 68 and 69, an electronic device 6610 includes a color sensor array 6810, a light source 6820, a processor 6830, and an optical member 6840. However, not limited to the described and/or illustrated examples, the electronic device 6610 may be implemented to include more devices and/or fewer devices. For example, the electronic device 6610 may be implemented to further include a communication circuit and/or a communication interface for communicating with other external electronic devices, and may be implemented to include the components of FIG. 42 described above, but it is not limited to the examples described. the color sensor 6810 may be an example of the first sensor 4509, and the processor 6830 may be an example of the processor 4515.

According to one embodiment, referring to FIG. 68, an analysis device 6600 including a color sensor array 6810, a light source 6820, and a processor 6830 may be provided. According to one embodiment, referring to FIG. 69, an analysis device 6600 including a color sensor array 6810 and a processor 6830 separately from a light source 6820 may be provided. In other words, the light source 6820 may be provided separately from the analysis device 6600. The analysis device 6600 is implemented to a single board (e.g., a printed circuit board (PCB)) on which the aforementioned components (e.g., the color sensor array 6810) the light source 6820, and/or the processor 6830, are disposed, but it is not limited to the described and/or illustrated examples, and the analysis device 6600 may be configured in various types of forms.

According to various embodiments, as shown in FIG. 70, the color sensor array 6810 includes a plurality of sensors (e.g., a first sensor 6810*a*, a second sensor 6810*b*, a third sensor 6810*c*, a fourth sensor 6810*d*, a fifth sensor 6810*e*, and a sixth sensor 6810*f*) for measuring a plurality of color values of the sample D. Each of the plurality of sensors (e.g., first sensor 6810*a*, second sensor 6810*b*, third sensor 6810*c*, fourth sensor 6810*d*, fifth sensor 6810*e*, sixth sensor 6810*f*) may be positioned at a predetermined different portion on a predetermined substrate (not shown) included in the sensor array 6810. For example, each of the plurality of sensors (e.g., a first sensor 6810*a*, a second sensor 6810*b*, a third sensor 6810*c*, a fourth sensor 6810*d*, a fifth sensor 6810*e*, and a sixth sensor 6810*f*) may be a photo diode configured to detect (or sense) a specific color. The specific color may include green (G), orange (O), yellow (Y), violet (V), blue (B), and/or red (R). However, the sensor may be configured to detect more colors without being limited to the described examples. Meanwhile, the number of sensors included in the sensor array 6810 is not limited to the number of sensors shown in FIG. 70 and may be configured in various numbers. For example, the number of sensors may be three (e.g., R, G, B).

According to various embodiments, at least some of the plurality of color values measured by the color sensor array 6810 may be associated with each other. For example, the color values associated with each other may include sensors (e.g., a first sensor 6810*a*, a second sensor 6810*b*, a third sensor 6810*c*, a fourth sensor 6810*d*, a fifth sensor 6810*e*) It may mean that the positional correlation (P) and the color correlation (C) of the sixth sensor 6810*f* are greater than preset values (e.g., P1 and C1).

For example, the positional correlation (P) may be associated with a distance between sensors (e.g., a first sensor 6810*a*, a second sensor 6810*b*, a third sensor 6810*c*, a fourth sensor 6810*d*, and the fifth sensor 6810*e* and the sixth sensor 6810*f*) on the sensor array 6810. For example, it may be defined that the closer the distance between the sensors is, the higher the positional relevance P is, and the larger the distance between the sensors is, the smaller the positional relevance P is.

Also, for example, the color correlation C is associated with wavelength bands of color values detected from each of the sensors (e.g., a first sensor 6810*a*, a second sensor 6810*b*, a third sensor 6810*c*, a fourth sensor 6810*d*, a fifth sensor 6810*e* and the sixth sensor 6810*f*). For example, the degree of color correlation (C) may be determined according to the degree of overlap between each wavelength band. For example, when the degree of overlap is large or the degree of overlap is small, the degree of color correlation (C) may be defined as high. For example, as shown in Equation 3 below, if the difference between the overlapping band (or degree) (a) of the wavelength bands of the color values detected by the color sensors and the non-overlapping band (b) is large, the color correlation (C) is small, and if the difference between the overlapping band (a) and the non-overlapping band (b) is large, the color correlation (C) is small. That is, when the overlapping bands are large, the color correlation (C) is understood to be high because the interference effect is large, and when the overlapping bands are small, the color correlation (C) is high because it can be used for amplification.

$$\text{color correlation}(C) = \alpha \cdot |a - b| \qquad [\text{Equation 3}]$$

where $\alpha$ is the coefficient.

Alternatively, it is not limited to what is described in above Equation 3, and when each of a or b is large, it may be understood that the color correlation (C) is large.

Accordingly, referring to the first sensor correlation graph 7000 of FIG. 70, a sensor having the greatest correlation with the first sensor 6810*a* may be defined as the second sensor 6810*b*. For example, referring to 7000 of FIG. 70, the positional correlation P with the first sensor 6810*a* is greater than the first threshold value P1 and the color correlation C is greater than the second threshold value C1. The larger second sensor 6810*b* may be defined as a sensor having the greatest correlation with the first sensor 6810*a*. At this time, the sensor having the greatest correlation with the second sensor 6810*b* may be naturally determined as the first sensor 6810*a*.

According to various embodiments, a plurality of sensors exist in which the positional correlation (P) and the color correlation (C) with respect to a specific sensor (e.g., the first sensor 6810*a*) exceed threshold values (P1, C1). In this case, among the plurality of sensors, the sensor having the greatest sum of the positional correlation (P) and the color correlation (C) can be selected as the greatest correlation with the specific sensor (e.g., the first sensor 6810*a*).

For example, when the first sensor 6810*a* is a sensor for detecting red (R) and the second sensor 6810*b* is a sensor for detecting blue (B), the first sensor 6810*a* and the second sensor 6810, since the positional correlation (P) and the color correlation (C) between the two sensors 6810*b* are above the threshold value.

Meanwhile, without being limited to the illustrated and/or described examples, a sensor having the greatest correlation with the first sensor 6810*a* may be defined as a sensor other than the second sensor 6810*b*.

According to various embodiments, the values of the sensors (e.g., the first sensor 6810*a* and the second sensor 6810*b*) determined to have the greatest degree of correlation is using for correcting each other's values (e.g., It can be used to reduce interference from values and/or amplify the size of the value) and a specific method will be described later.

According to various embodiments, the light source 6820 may be implemented to provide light to the sample D. The sample D receiving light from the light source 6820 may output light associated with a plurality of colors. Accordingly, the sensor array 6810 (e.g., the plurality of sensors 6810*a*, 6810*b*, 6810*c*, 6810*d*, 6810*e*, and 6810*f*) may obtain a plurality of color values corresponding to the plurality of colors from the light output from the sample D. For example, the light source 6820 may include a light emitting diode (LED), a laser, and the like, and may be implemented in a form capable of providing light to the sample D without being limited to the examples described above.

According to various embodiments, the processor 6830 may execute software to control at least one other component (e.g., hardware or software component) of the electronic device 6610 connected to the processor 6830, and can perform various data processing or calculations. An example of the operation of the processor 6830 will be described later. According to one embodiment, as at least part of the data processing or operation, the processor 6830 loads instructions or data received from other components into volatile memory, processes the instructions or data stored in the volatile memory, and outputs the resulting data. It can be stored in non-volatile memory. According to one embodiment, the processor 6830 includes a main processor (e.g., a central processing unit or application processor) and a secondary processor (e.g., a graphics processing unit, an image signal processor, a sensor hub processor, or communication processor). Additionally or alternatively, the secondary processor may be configured to use less power than the main processor or to be specialized for a designated function. A secondary processor may be implemented separately from, or as part of, the main processor.

For example, the processor 6830 may be implemented to process a plurality of color values output from the color sensor array 6810 and obtain result information based on the processing of the plurality of color values.

For example, the processor 6830 may obtain a plurality of color values output from the color sensor array 6810, and transfer the obtained the plurality of color values to a processor (not shown) such that the result information is obtained based on the plurality of color values being analyzed by a processor (not shown) of an electronic device 6610 implemented outside the analysis device 6600.

For example, the processor 6830 may obtain a plurality of color values output from the color sensor array 6810, and transfer the obtained plurality of color values to another external electronic device (e.g., a server) such that the result information is obtained based on the plurality of color values being analyzed by a the external electronic device (e.g., a server).

According to various embodiments, an optical member 6840 may be provided to change characteristics of light. For example, the optical member 6840 may include a mirror member configured to reflect light, a refractive member configured to control a refractive index of light, and the like. For example, the characteristics of light output from the light source 6820 may be changed by the optical member 6840 and transmitted to the sample D. For example, light output from the light source 6820 may be reflected and/or refracted at least once by the optical member 6840 and transmitted to the sample D. Also, for example, the characteristics of light output from the sample D may be changed by the optical member 6840 and transmitted to the color sensor array 6810. For example, light output from the sample D may be reflected and/or refracted at least once by the optical member 6840 and transmitted to the color sensor array 6810.

Hereinafter, an example of an operation of the electronic device 6610 according to various embodiments will be described.

Hereinafter, unless otherwise specified, an operation of the electronic device 6610 may be understood as an operation of the electronic device 6610 performed based on computer code (or instructions) being executed by the processor 6830. At this time, as described above, the operation of obtaining result information by analyzing a plurality of values is performed by a processor implemented separately from the analysis device 6600, rather than the processor 6830 of the analysis device 6600, and/or an external electronic device (e.g., server), it is obvious to those skilled in the art.

Figure 71:
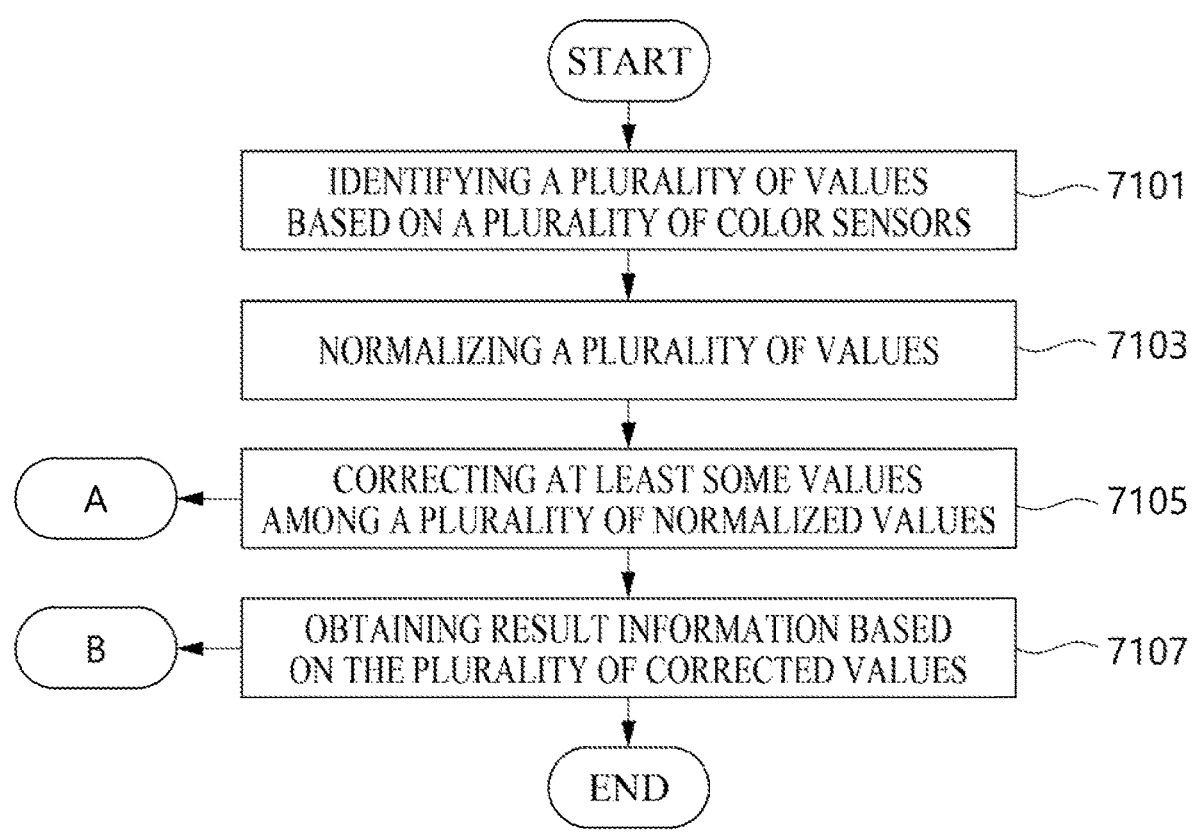
FIG. 71 is a flowchart for explaining an example of an operation of color value correction and result information acquisition of the electronic device, according to various embodiments.

FIG. 71 is a flowchart for explaining an example of an operation of color value correction and result information acquisition of the electronic device 6610, according to various embodiments. According to various embodiments, the operations shown in FIG. 71 are not limited to the shown order and may be performed in various orders. Also, according to various embodiments, more operations than the operations shown in FIG. 71 may be performed, or at least one operation less than that shown in FIG. 71 may be performed.

Figure 72:
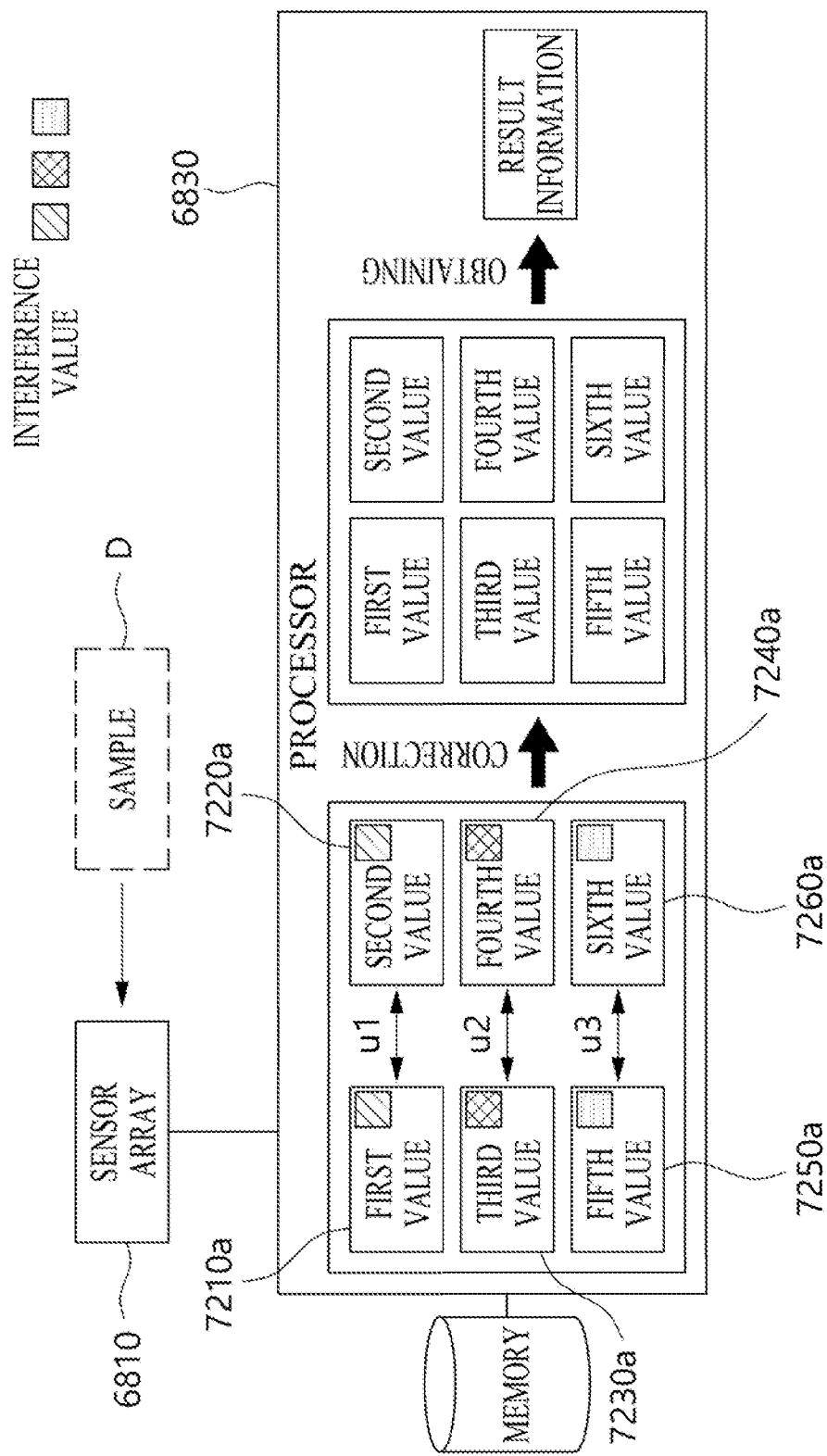
FIG. 72 is a diagram for explaining an example of an operation of obtaining result information by correcting color values associated with each other of the electronic device, according to various embodiments.

FIG. 72 is a diagram for explaining an example of an operation of obtaining result information by correcting color values associated with each other of the electronic device 6610, according to various embodiments. Hereinafter, FIG. 71 will be further described with reference to FIG. 72.

According to various embodiments, in operation 7101, the electronic device 6610 (e.g., the processor 6830) may identify a plurality of values based on a plurality of color sensors. For example, referring to FIG. 72, the electronic device 6610 may obtain a plurality of values 7200 detected by a plurality of sensors (e.g., a first sensor 6810*a*, a second sensor 6810*b*, a third sensor 6810*c*, a fourth sensor 6810*d*, a fifth sensor 6810*e*, a sixth sensor 6810*f*) included in the sensor array 6810, based on receiving light output from the sample D using the sensor array 6810 included in the analysis device 6600. The plurality of values may correspond to a plurality of sensors (e.g., a first sensor 6810*a*, a second sensor 6810*b*, a third sensor 6810*c*, a fourth sensor 6810*d*, a fifth sensor 6810*e*, and a sixth sensor 6810*e*) since the plurality of values correspond to colors detected by the plurality of sensors (e.g., a first sensor 6810*a*, a second sensor 6810*b*, a third sensor 6810*c*, a fourth sensor 6810*d*, a fifth sensor 6810*e*, and a sixth sensor 6810*f*). For example, the n-th value corresponds to the n-th sensor and may correspond to a color detected by the n-th sensor (n=1, 2, 3, 4, 5, or 6). Meanwhile, it is obvious to those skilled in the art that sensors may be implemented with various numbers without being limited to the numbers described and/or shown.

According to various embodiments, in operation 7103, the electronic device 6610 (e.g., the processor 6830) may normalize a plurality of values. For example, the electronic device 6610 includes a plurality of sensors (e.g., a first sensor 6810*a*, a second sensor 6810*b*, a third sensor 6810*c*, a fourth sensor 6810*d*, and a fifth sensor 6810*e*, sixth sensor 6810*f*). A normalization operation for comparatively analyzing the plurality of values 7200 may be performed based on at least one normalization value measured by each of the plurality of sensors (e.g., a first sensor 6810*a*, a second sensor 6810*b*, a third sensor 6810*c*, a fourth sensor 6810*d*, and a fifth sensor 6810*e*, and the sixth sensors 6810*f*). In one embodiment, the normalization operation may include a max-min normalization operation. For example, the at least one normalization value may be applied to a plurality of sensors (e.g., a first sensor 6810a, a second sensor 6810b, a third sensor 6810c, a fourth sensor 6810d, a fifth sensor 6810e, and the sixth sensor 6810f) may include a maximum value (max value) and a minimum value (min value) measured by each. For example, the electronic device 6610, by using the plurality of sensors (e.g., a first sensor 6810a, a second sensor 6810b, a third sensor 6810c, a fourth sensor 6810d, a fifth sensor 6810e, and sixth sensor 6810f) may obtain a white portion of the electronic device 100 disposed in front of the analysis device 6600 as the maximum value (e.g., a frame inside the electronic device 6610, and/or a gutter) and obtain a value a value in a state in which the sample D is not present as a minimum value. Accordingly, the electronic device 6610 may perform normalization on each of the plurality of values as shown in Equation 4 below.

$$\text{normalization value of specific sensor} = \frac{\text{valu of specific sensor} - \text{min value}}{\text{max value} - \text{min value}} \quad \text{[Equation 4]}$$

According to various embodiments, in operation 7105, the electronic device 6610 (e.g., the processor 6830) may correct at least some values among a plurality of normalized values. For example, referring to FIG. 72, at least some of the plurality of values 7200 (e.g., a first value 7210a and a second value 7220a, a third value 7230a and a fourth value 7240a, a fifth value 7250a, and a sixth value 7260a) may be associated with each other. The being associated with means that the degree of association (u1, u2, u3) between each values is greater than or equal to the threshold value, and as described above with reference to FIG. 70, each degree (C) may mean values between sensors that are equal to or greater than a threshold value. Alternatively, it may mean values of sensors for which the sum of the positional relevance (P) and the color relevance (C) is greater than or equal to a threshold value. In this case, as shown in FIG. 72, associated values may be used to reduce interference with each other and/or to amplify each other. The electronic device 6610 may obtain a plurality of corrected values by performing correction on another value (e.g., a first value, using one value (e.g., a second value)) among values associated with each other. This will be described later in more detail with reference to FIG. 73.

According to various embodiments, as at least part of an operation of identifying at least some of the plurality of values 7200 (e.g., a first value 7210a, a second value 7220a, a third value 7230a, the fourth value 7240a, the fifth value 7250a, and the sixth value 7260a), the electronic device 6610 may determine information on sensors (or values) having a high correlation pre-stored in the memory 70 An operation of comparing information about the identified values 7200 and identifying values associated with each other based on the comparison result may be performed. For example, the positional relevance (P) and/or the color relevance (C) between the sensors is calculated in advance, and the most related sensors are determined in advance, thereby providing values corresponding to the sensors associated with each other and/or the sensors associated with each other. Information on may be stored in the memory 70 in advance. Without being limited to the described example, the electronic device 6610 calculates the positional correlation (P) and the color correlation (C) whenever a plurality of values 7200 are acquired from the sensor array 6810, thereby related to each other. It can also be implemented to identify values.

According to various embodiments, in operation 7107, the electronic device 6610 (e.g., the processor 6830) may obtain result information based on the plurality of corrected values. For example, the electronic device 6610 may be implemented to obtain specific result information based on comparing a pre-stored plurality of values of a plurality of sensors with a plurality of corrected values, this may be described later in more detail with reference to FIG. 74.

Figure 73:
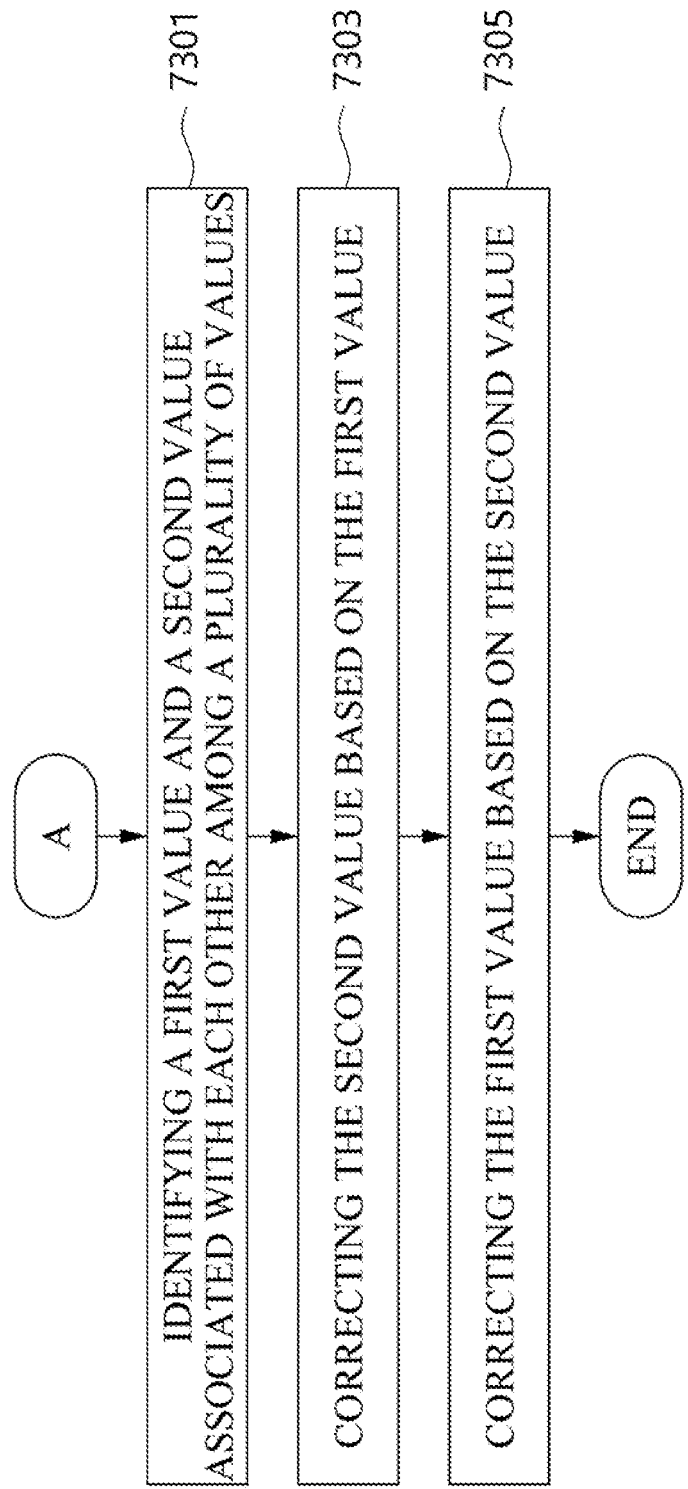
FIG. 73 is a flowchart for explaining an example of a correction operation based on values associated with each other of the electronic device, according to various embodiments.

FIG. 73 is a flowchart for explaining an example of a correction operation based on values associated with each other of the electronic device 6610, according to various embodiments. According to various embodiments, the operations shown in FIG. 73 are not limited to the shown order and may be performed in various orders. Also, according to various embodiments, more operations than the operations shown in FIG. 73 may be performed, or at least one operation less than that shown in FIG. 73 may be performed.

According to various embodiments, in operation 7301, the electronic device 6610 (e.g., the processor 6830). may identify a first value and a second value associated with each other among a plurality of values. Since operation 7301 of the electronic device 6610 may be performed in the same manner as at least a part of operation 7203 of the electronic device 6610 described above, duplicate descriptions will be omitted.

According to various embodiments, the electronic device 6610 (e.g., the processor 6830) may correct the second value based on the first value and correct in operation 7303, may correct the first value based on the second value in operation 7305. The correction, as described above, is for removing interfere each other between related values and/or amplifying related values.

In one embodiment, as at least part of an operation of correcting a specific value (e.g., a first value) as like below Equation 5, the electronic device 6610 may identify a value (e.g., a second value, associated with a specific value, and dividing the specific value (e.g., the first value) by the identified associated value (e.g., the second value).

$$\text{corrected specific first value} = \frac{\text{first value}}{\text{second value}} \quad \text{[Equation 5]}$$

In one embodiment, as at least part of an operation of correcting a specific value (e.g., a first value) as like below Equation 6, the electronic device 6610 may identify a value (e.g., a second value) associated with a specific value, and subtract the identified related value (e.g., the second value) from the specific value (e.g., the first value).

$$\text{corrected specific first value} = \text{first value} - \text{second value} \quad \text{[Equation 6]}$$

In one embodiment, as at least part of an operation of correcting a specific value (e.g., a first value) as like below Equation 7, the electronic device 6610 may identify a value (e.g., a second value) associated with a specific value, and divide a specific value (e.g., the first value, by not only the identified related value (e.g., the second value) but also the remaining values (e.g., the third value to the sixth value).

$$\text{corrected specific first value} = \frac{\text{first value}}{\text{first value} + \cdots + \text{sixth value}} \quad \text{[Equation 7]}$$

Meanwhile, it is obvious to those skilled in the art that predetermined four arithmetic operations may be further added to the above-described equations (e.g., equations 5 to 7).

According to various embodiments, the electronic device 6610 may vary the degree of correction according to the degree of correlation between values. Referring to Equation 5, for example, the electronic device 6610 may set the size of β larger as the correlation between values in Equation 8 below increases, and set the size of β smaller as the correlation decreases.

$$\text{corrected specific first value} = \frac{\text{first value}}{\beta \cdot \text{second value}}, (1 \le \beta) \quad [\text{Equation 8}]$$

Accordingly, the electronic device 6610 can perform an operation of correcting more accurately for related values that cause more interference or require more amplification because the degree of correlation is high.

Figure 74:
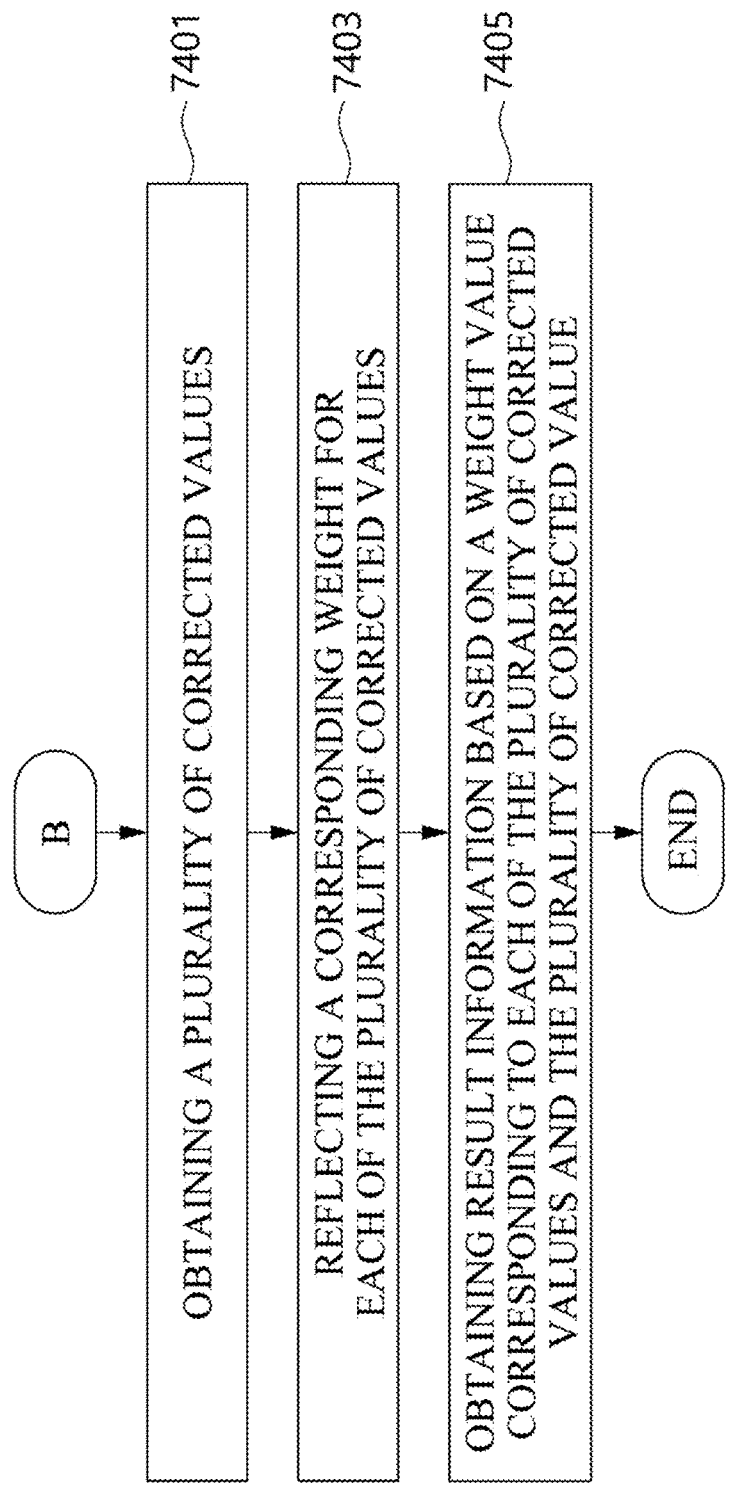
FIG. 74 is a flowchart for explaining an example of an operation of obtaining result information of the electronic device according to various embodiments.

FIG. 74 is a flowchart for explaining an example of an operation of obtaining result information of the electronic device 6610 according to various embodiments. According to various embodiments, the operations shown in FIG. 74 are not limited to the order shown and may be performed in various orders. Also, according to various embodiments, more operations than the operations shown in FIG. 74 or at least one operation less may be performed.

According to various embodiments, in operation 7401, the electronic device 6610 (e.g., the processor 6830) may obtain a plurality of corrected values. Since operation 7401 of the electronic device 6610 may be performed in the same manner as operations 7105 and 7303 to 7305 of the electronic device 6610 described above, duplicate descriptions are omitted.

According to various embodiments, in operation 7403, the electronic device 6610 (e.g., the processor 6830) may reflect a corresponding weight for each of the plurality of corrected values.

According to various embodiments, in operation 7405, the electronic device 6610 (e.g., the processor 6830) may obtain result information based on a weight value corresponding to each of the plurality of corrected values and the plurality of corrected values. For example, the electronic device 6610 may pre-store a plurality of result information (e.g., the concentration of bio-derived material) and values for each colors corresponding to the plurality of result information in a memory (not shown). The electronic device 6610 may obtain specific result information from among a plurality of pieces of result information based on comparing the previously stored value for each color with the identified corrected value for each color. For example, the electronic device 6610 may subtracts the pre-stored value for each color and the identified corrected color for specific result information (e.g., specific concentration of a bio-derived material) and may select the smallest sum of the subtracted values as the result information. At this time, referring to Equation 9 below, for each specific result information (e.g., specific concentration of a bio-derived material) a greater weight (δ) is applied to the subtracted value for a specific color with high accuracy in order to analyze the result information, and/or may reflect a smaller weight (δ) to the subtracted value for a specific color with low accuracy.

$$\text{difference} \cdot \text{value} \cdot \text{of} \cdot \text{sepcific} \cdot \text{color} = \quad [\text{Equation 9}]$$
$$\delta \cdot (\text{pre} \cdot \text{stored} \cdot \text{value} \cdot \text{of} \cdot \text{specific} \cdot \text{value} -$$
$$\text{corrected} \cdot \text{value} \cdot \text{of} \cdot \text{specific} \cdot \text{value})$$

Meanwhile, the electronic device 6610 is not limited to the described example, and the electronic device 6610 may be implemented to perform an operation of determining whether the corrected value and the pre-stored corresponding value correspond to each other by applying a weight to each of the identified corrected values and then subtracting them.

Figure 75:
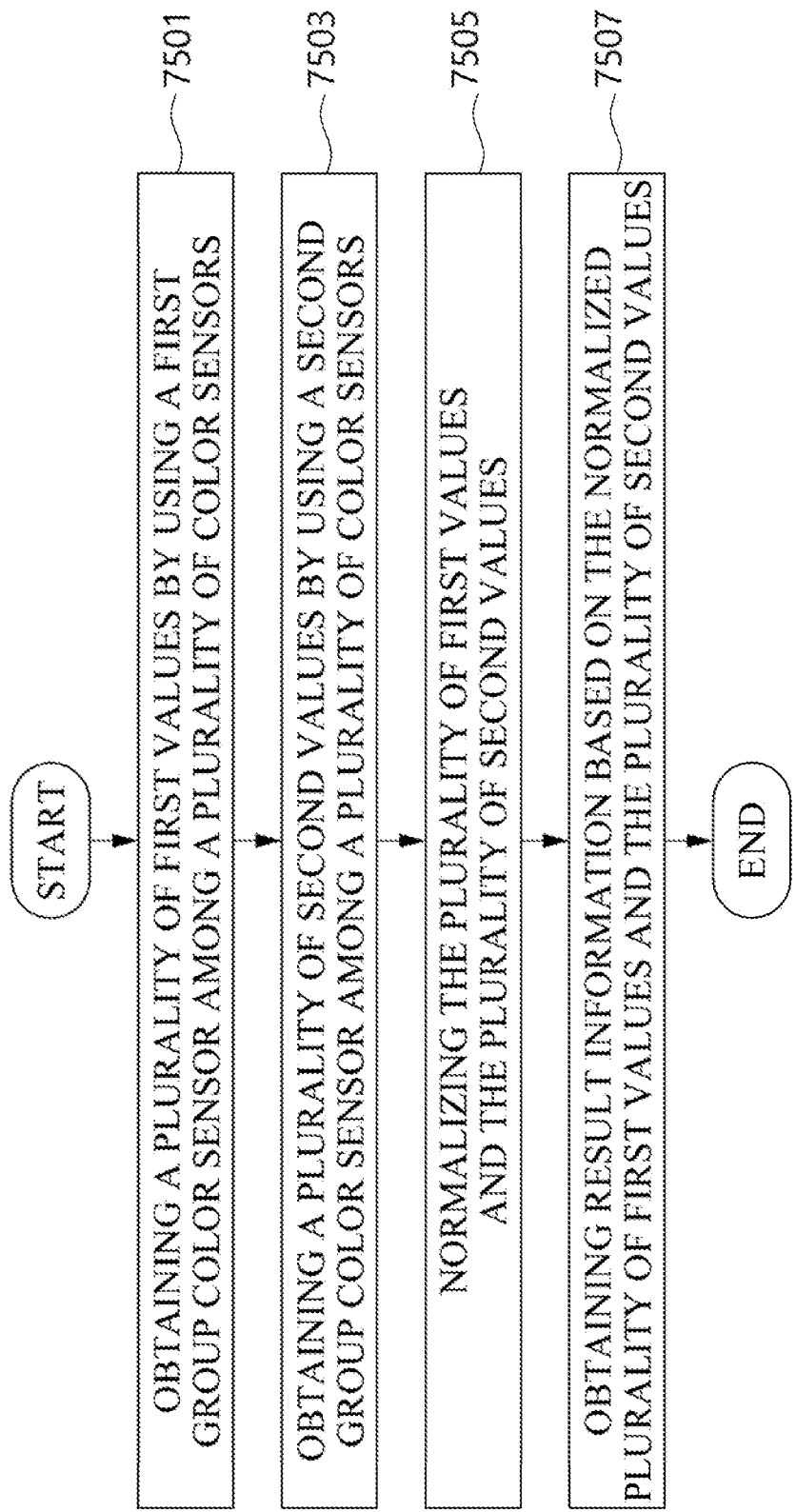
FIG. 75 is a flowchart for explaining an example of an operation of sequentially detecting values having a low degree of relevance of the electronic device according to various embodiments.

FIG. 75 is a flowchart for explaining an example of an operation of sequentially detecting values having a low degree of relevance of the electronic device 6610 according to various embodiments. According to various embodiments, the operations shown in FIG. 75 are not limited to the order shown and may be performed in various orders. Also, according to various embodiments, more operations than the operations shown in FIG. 75 may be performed, or at least one less operation may be performed.

Figure 76:
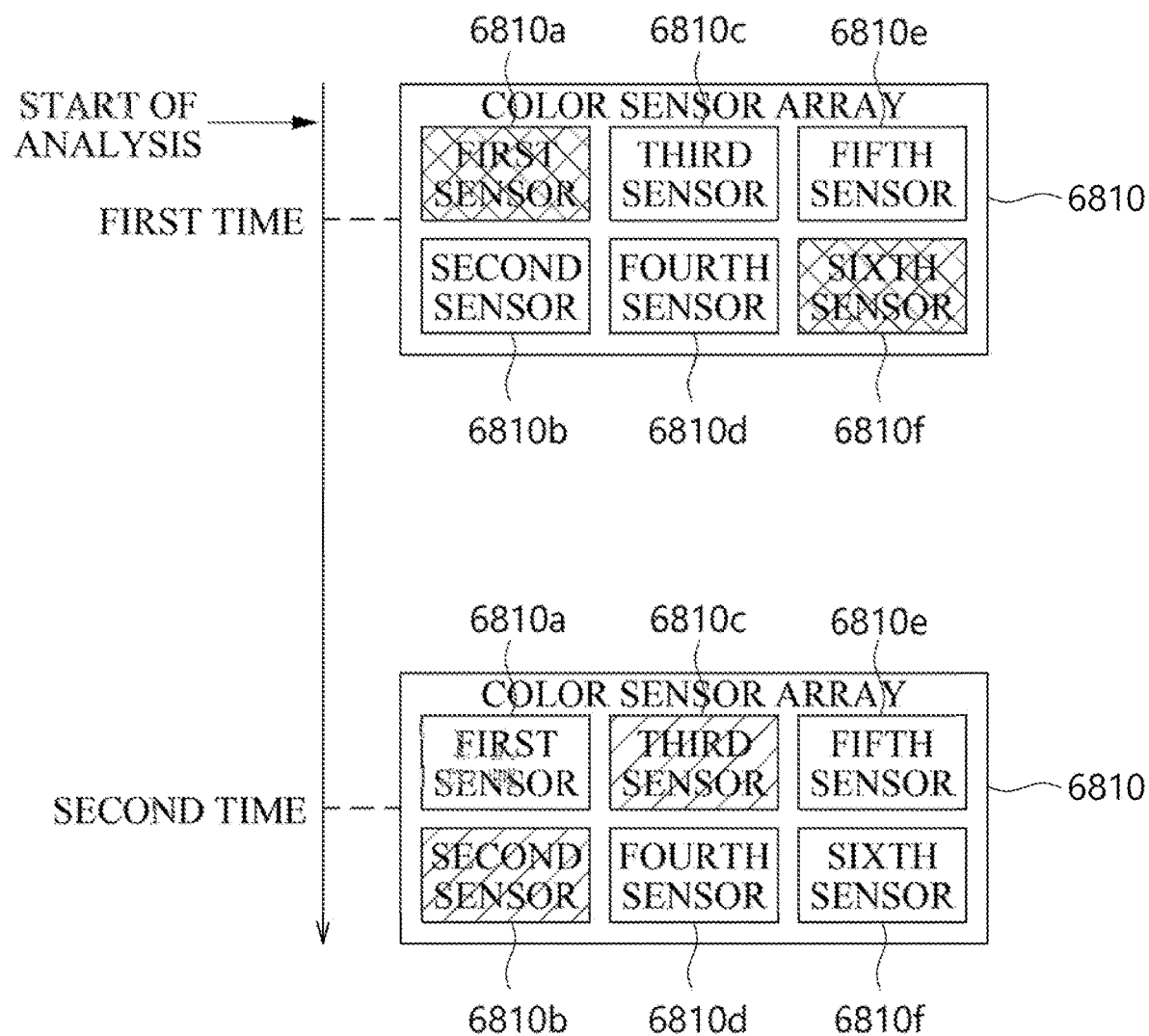
FIG. 76 is a flowchart for explaining an example of an operation of sequentially measuring values having a low degree of correlation using the sensor array of the electronic device, according to various embodiments.

FIG. 76 is a flowchart for explaining an example of an operation of sequentially measuring values having a low degree of correlation using the sensor array 6810 of the electronic device 6610, according to various embodiments. Below, with reference to FIG. 76, FIG. 75 is further demonstrated.

According to various embodiments, the electronic device 6610 may obtain a plurality of first values by using a first group color sensor among a plurality of color sensors in operation 7501, and the plurality of color sensors in operation 7503. Among them, a plurality of second values may be obtained by using a second group of color sensors. For example, referring to FIG. 76, after the analysis of the sample D is started, the electronic device 6610 may operate sensors with low correlation, the first sensor 6810*a* and the sixth sensor 6810*f*, and/or the second sensor 6810*b* and the third sensor 6810*c*, at different times (e.g., a first time and a second time). For example, among the plurality of sensors 6810*a*, 6810*b*, 6810*c*, 6810*d*, 6810*e*, and 6810*f*, sensors having a correlation lower than a threshold may be selected as a group. The threshold at this time may be set to be different from the threshold for selecting sensors associated with each other (e.g., may be set lower). Accordingly, the electronic device 6610 sequentially selects a specific group of sensors (e.g., the first sensor 6810*a* and the sixth sensor 6810*f*, and/or the second sensor 6810*b* and the third sensor 6810*c*), and perform an operation of measuring a value of the sample D. In other words, values may be measured using different groups of sensors at different times.

According to an embodiment, as at least part of the operation of measuring values using sensors of different groups at different times, the electronic device 6610 may turn on (or activate) only the sensors of the same group at each time.

According to another embodiment, as at least part of the operation of measuring values using sensors of different groups at different times, the electronic device 6610 may guide the light output from the sample D to a different group of sensors using an optical member at different times, while turning on (or activate) all sensors at different times.

According to various embodiments, the electronic device 6610 may normalize the plurality of first values and the plurality of second values in operation 7505, and obtain result information based on the normalized plurality of first values and the plurality of second values in operation 7507. Operations 7505 and 7507 of the electronic device 6610 may be performed in the same manner as the above-described operation of the electronic device 6610, and therefore, duplicate descriptions are omitted.

Figure 77:
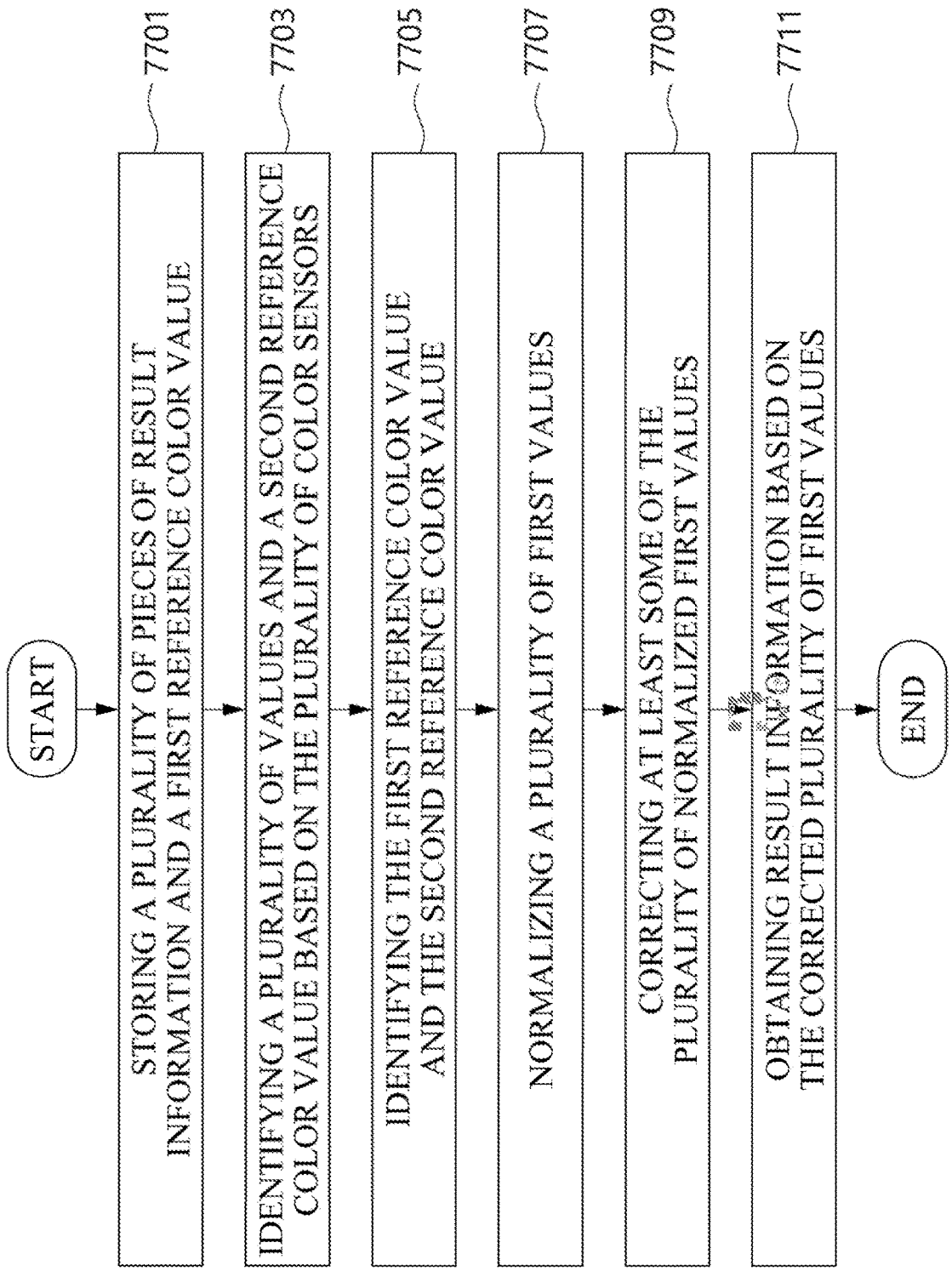
FIG. 77 is a flowchart for explaining an example of a calibration operation based on a reference value for each measurement environment of the electronic device according to various embodiments.

FIG. 77 is a flowchart for explaining an example of a calibration operation based on a reference value for each measurement environment of the electronic device 6610 according to various embodiments. According to various embodiments, the operations shown in FIG. 77 are not limited to the shown order and may be performed in various orders. Also, according to various embodiments, more operations than the operations shown in FIG. 77 may be performed, or at least one operation less than that shown in FIG. 77 may be performed.

FIG. 78 is a flowchart for explaining an example of an operation of measuring a reference value for each environment of the electronic device 6610 according to various embodiments. Below, with reference to FIG. 78, FIG. 77 is further demonstrated.

According to various embodiments, in operation 7701, the electronic device 6610 may store a plurality of pieces of result information and a first reference color value. For example, referring to FIG. 78, since a photographing deviation may occur for each environment 7801 and 7802 in which a sample D is measured, different values are measured for each environment 7801 and 7802 even for the same sample D. It can be, so it needs to be corrected. Therefore, as described above, the electronic device 6610 may pre-store result information (e.g., the concentration of bio-derived material), and values for each color of each result information along with information about reference color value (e.g., the first reference color value 7811), as information related to the environment in which the result information is measured. Referring to FIG. 78, the reference color value is a value or an average value detected, by all or at least some of the plurality of sensors 6810a to 6810f, from the portion of the sample D whose color does not change (e.g., in the board of a urine strip) the substrate of the urine strip portion, a frame inside the electronic device 6610, and/or a portion of the gutter 200, or the like.

According to various embodiments, the electronic device 6610 may identify a plurality of values and a second reference color value based on the plurality of color sensors in operation 7703, and may identify the first reference color value and the second reference color value in operation 7705. Based on the difference between the two reference color values, the plurality of values may be corrected into the plurality of first values. For example, the electronic device 6610 may use the sensor array 6810 to obtain a plurality of values for each of the plurality of sensors 6810a to 6810f as well as a reference color associated with the current environment (e.g., the second environment 1302). A value (e.g., the second reference color value 7812) may be measured. The electronic device 6610 may reflect the difference between the pre-stored first reference color value 7811 and the measured second reference color value 7812 to the measured values of the plurality of sensors 6810a to 6810f. For example, the electronic device 6610 may increase the measured color values by the difference when the currently measured second reference color value 7812 is higher than the first reference color value 7811, or decrease the measured color value when the currently measured second reference color value 7812 is lower than the first reference color value 7811. For example, the electronic device 6610 may reflect the ratio of the pre-stored first reference color value 7811 and the measured second reference color value 7812 to the measured values, but is not limited to the described example. The difference between the reference color values 7811 and 7812 may be reflected in various ways.

According to various embodiments, the electronic device 6610 may normalize a plurality of first values in operation 7707, may correct at least some of the plurality of normalized first values in operation 7709, and may obtain result information based on the corrected plurality of first values in operation 7711. Operations 7707 to 7711 of the electronic device 6610 may be performed in the same manner as operations 7103 to 7107 of the electronic device 6610 described above, and thus duplicate descriptions are omitted.

Meanwhile, without being limited to the example described above, the electronic device 6610 does not perform an operation of reflecting the difference between the pre-stored first reference color value 7811 and the measured second reference color value 7812 before the normalization. Alternatively, it may be implemented to reflect the difference between the pre-stored first reference color value 7811 and the measured second reference color value 7812 in the corrected plurality of values.

Figure 79:
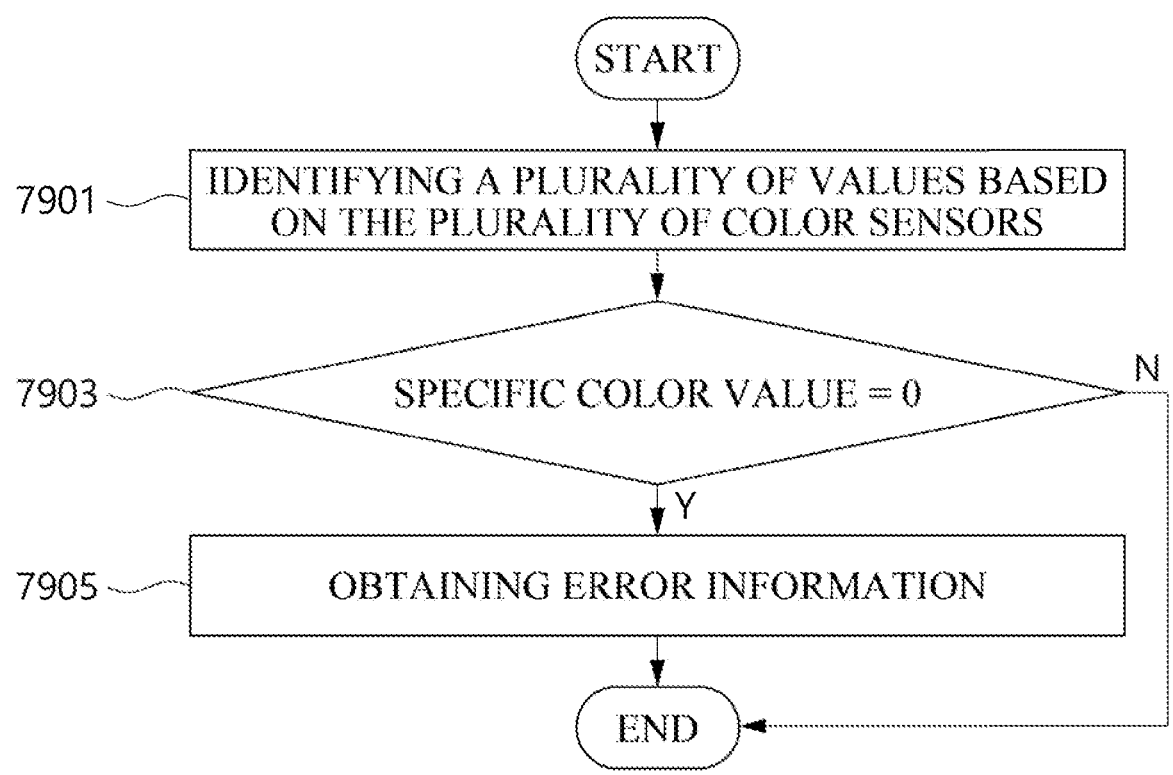
FIG. 79 is a flowchart for explaining an example of a calibration operation based on a reference value for each measurement environment of the electronic device according to various embodiments.

FIG. 79 is a flowchart for explaining an example of a calibration operation based on a reference value for each measurement environment of the electronic device 6610 according to various embodiments. According to various embodiments, the operations shown in FIG. 79 are not limited to the shown order and may be performed in various orders. Also, according to various embodiments, more operations than the operations shown in FIG. 79 may be performed, or at least one operation less than that shown in FIG. 79 may be performed.

According to various embodiments, in operation 7901, the electronic device 6610 may identify a plurality of values based on the plurality of color sensors 6810a to 6810f.

According to various embodiments, in operation 7903, the electronic device 6610 determines whether a specific color value corresponds to 0, and if the specific color value is 0 (1403-Y), in operation 7905, error information is provided, can be obtained. The electronic device 6610 refrains from an analysis operation based on the obtained error information, or outputs visual, auditory, and/or tactile content indicating an error through an output device (e.g., LED, display, speaker, haptic module, etc.) may be provided, and/or information may be transmitted to an external electronic device through a communication circuit (not shown) so that the content is provided through the external electronic device. According to various embodiments, the user terminal 130 (e.g., the processor 1410) may receive encrypted first urine test information based on the security information in operation 6405, and may generate encrypted second urine test information with the first urine test information based on the security information in operation 6407. For example, the first user terminal 6501a may decrypt the urine test information based on the private key. However, the second user terminal 6501b does not store the private key used for the encryption, thus the decryption may fail and stealing of the urine test information may be prevented.

According to various embodiments, an electronic device may include a first housing having a bottom surface formed to be disposed on a specific portion of a top surface of a toilet, a second housing connected to one side of the first housing, a third housing connected to another side of the first housing and having a shape extending from a point connected to the first housing by a specific length in a direction associated with a first curvature, and a detection unit having a shape of a second curvature corresponding to the first curvature, and the detection unit may be rotatably coupled to at least a portion of the third housing.

According to various embodiments, the electronic device may further include at least one motor and at least one processor, and the at least one processor may be configured to rotate the detection unit based on at least a portion of the third housing by using the at least one motor.

According to various embodiments, the electronic device may further include at least one sensor, and the at least one processor may be configured to rotate the detection unit between a first position and a second position by using the at least one motor, and acquire sensing information by using the at least one sensor when the detection unit is positioned in the first position.

According to various embodiments, the detection unit may include a strip mounting portion for mounting a urine test strip.

According to various embodiments, the detection unit may include a sensing device for electrically analyzing components of urine.

According to various embodiments, the electronic device may further include at least one mounting member connected to at least a portion of the third housing, and the at least one mounting member may include a first member for applying force to a specific portion of a side surface of the toilet to fix the electronic device to the toilet.

According to various embodiments, an electronic device may include at least one processor, at least one motor; a first housing having a bottom surface formed to be disposed on a specific portion of a top surface of a toilet, a second housing connected to one side of the first housing, a third housing connected to another side of the first housing and having a shape extending from a point connected to the first housing by a specific length in a direction associated with a first curvature, and a gutter having a shape of a second curvature corresponding to the first curvature, the gutter may include a strip mounting portion having an inner space for mounting a strip, and the at least one processor may provide power to the strip mounting portion by using the at least one motor to move the strip mounted on the strip mounting portion.

According to various embodiments, the electronic device may further include at least one sensor disposed at a first position of the third housing, and the at least one processor may be configured to move the strip to a second position corresponding to the first position by using the at least one motor, and acquire sensing information about at least a portion of the strip by using the at least one sensor.

The invention claimed is:

1. An operation method of an electronic device comprising:
obtaining, by at least one processor of the electronic device, using a plurality of color sensors included in a color sensor array of the electronic device, a plurality of color values associated with a specimen including a bio-derived material, wherein each of the plurality of color sensors are configured to obtain a value of a different respective color from the other ones of the plurality of color sensors;
normalizing, by the at least one processor, the plurality of color values;
obtaining, by the at least one processor, a plurality of corrected color values based on applying at least a first portion of the normalized plurality of color values to at least a second portion of the normalized plurality of color values, the at least first portion and the at least second portion having a correlation with each other above a predetermined value,
wherein the correlation is determined based on a location correlation and a color correlation,
wherein the location correlation is based on a distance between a location of at least one first sensor for obtaining the at least first portion of the normalized plurality of color values and a location of at least one second sensor for obtaining the at least second portion of the normalized plurality of color values; and
wherein the color correlation is based on a degree of overlap and a degree of non-overlap between a first wavelength band of a color corresponding to the at least first portion of the normalized plurality of color values and a second wavelength band of a color corresponding to the at least second portion of the normalized plurality of color values, and
obtaining, by the at least one processor, a specific result information associated with the plurality of corrected color values among a plurality of result information.

2. The operation method of claim 1,
wherein a distance between the at least one first sensor and the at least one second sensor is greater than or equal to a first threshold.

3. The operation method of claim 2,
wherein the color correlation between the first wavelength band and the second wavelength band is greater than or equal to a second threshold.

4. The operation method of claim 1, wherein obtaining the plurality of calibration color values comprises:
dividing the at least first portion by the at least second portion; and
dividing the at least first portion into the at least second portion; comprising.

5. The operation method of claim 1, wherein the obtaining the plurality of color values associated with the specimen including the bio-derived material, further comprises:
storing, in the electronic device, a plurality of values corresponding to the plurality of colors for each of the plurality of result information.

6. The operation method of claim 5, wherein the obtaining the result information comprises:
subtracting the plurality of corrected color values from the plurality of values corresponding to the plurality of colors to obtain a plurality of result values, and reflecting a weight on each of the plurality of result values; and
obtaining the result information corresponding to one of the plurality of result values, wherein a sum of the one of the plurality of result values weighted is the smallest.

7. The operation method of claim 1, wherein the normalizing the plurality of color values comprises,
obtaining a maximum value and a minimum value for each of the plurality of color sensors; and
normalizing the plurality of color values based on the maximum value and the minimum value.

8. An electronic device, comprising
a color sensor array comprising a plurality of color sensors, wherein each of the plurality of color sensors are configured to obtain a value of a different respective color from the other ones of the plurality of color sensors; and
at least one processor; wherein the at least one processor is configured to:
using the plurality of color sensors included in the color sensor array, obtain a plurality of color values associated with a specific target associated with a specimen comprising a bio-derived material, normalize the plurality of color values, obtain a plurality of corrected color values based on at least a first portion of the normalized plurality of color values and at least a second portion of the normalized plurality of color values, the at least first portion and the at least second portion having a correlation with each other above a predetermined value, wherein the correlation is determined based on a location correlation and a color correlation, wherein the location correlation is based on a distance between a location of at least one first sensor for obtaining to the at least first portion of the normalized plurality of color values and a location of at least one second sensor for obtaining the at least second portion of the normalized plurality of color values, and wherein the color correlation is based on a degree of overlap and a degree of non-overlap between a first wavelength band of a color corresponding to the at least first portion of the normalized plurality of color values and a second wavelength band of a color corresponding to the at least second portion of the normalized plurality of color values, and obtain a specific result information associated with the plurality of corrected color values among a plurality of result information.

9. An electronic device, comprising a color sensor array comprising a plurality of color sensors, wherein each of the plurality of color sensors are configured to obtain a value of a different respective color from the other ones of the plurality of color sensors; and at least one processor, wherein the at least one processor is configured to:

using the plurality of color sensors included in the color sensor array, obtain a plurality of color values associated with a specific target associated with a specimen comprising a bio-derived material, when a specific color value among the plurality of color values corresponds to zero, obtain error information, and when none of the plurality of color values has a color value corresponding to 0:

normalize the plurality of color values, obtain a plurality of corrected color values based on at least a first portion of the normalized plurality of color values and at least a second portion of the normalized plurality of color values, the at least first portion and the at least second portion are having a correlation with each other above a predetermined value, wherein the correlation is determined based on a location correlation and a color correlation, wherein the location correlation is based on a distance between a location of at least one first sensor for obtaining the at least first portion of the normalized plurality of color values and a location of at least one second sensor for obtaining the at least second portion of the normalized plurality of color values, and wherein the color correlation is based on a degree of overlap and a degree of non-overlap between a first wavelength band of a color corresponding to the at least first portion of the normalized plurality of color values and a second wavelength band of a color corresponding to the at least second portion of the normalized plurality of color values, and obtain a specific result information associated with the plurality of corrected color values among a plurality of result information.

* * * * *